US010941415B2

(12) United States Patent
Bogaert et al.

(10) Patent No.: US 10,941,415 B2
(45) Date of Patent: Mar. 9, 2021

(54) DOWN-REGULATING GENE EXPRESSION IN INSECT PLANTS

(71) Applicant: DEVGEN NV, Zwijnaarde (BE)

(72) Inventors: Thierry Bogaert, Kortrijk (BE); Romaan Raemaekers, Ghent (BE); Yann Naudet, Ghent (BE)

(73) Assignee: DEVGEN NV, Zwijnaarde (BE)

( * ) Notice: Subject to any disclaimer, the term of this patent is extended or adjusted under 35 U.S.C. 154(b) by 157 days.

(21) Appl. No.: 15/869,336

(22) Filed: Jan. 12, 2018

(65) Prior Publication Data

US 2018/0148737 A1 May 31, 2018

Related U.S. Application Data

(62) Division of application No. 13/881,792, filed as application No. PCT/EP2011/068910 on Oct. 27, 2011, now Pat. No. 9,944,948.

(60) Provisional application No. 61/407,212, filed on Oct. 27, 2010.

(51) Int. Cl.
*C12N 15/82* (2006.01)
*C12N 15/113* (2010.01)

(52) U.S. Cl.
CPC ........ *C12N 15/8286* (2013.01); *C12N 15/113* (2013.01); *C12N 2310/14* (2013.01); *C12N 2310/51* (2013.01); *C12N 2310/531* (2013.01); *C12N 2330/51* (2013.01)

(58) Field of Classification Search
CPC ....................... C12N 2310/14; C12N 15/8218; C12N 15/11; C12N 15/8286
See application file for complete search history.

(56) References Cited

U.S. PATENT DOCUMENTS

| | | | | |
|---|---|---|---|---|
| 2005/0245475 | A1 | 11/2005 | Khvorova et al. | |
| 2006/0021087 | A1 | 1/2006 | Baum et al. | |
| 2006/0178292 | A1* | 8/2006 | Ruvkun | C07K 14/4354 435/7.22 |
| 2007/0124836 | A1 | 5/2007 | Baum | |
| 2009/0149401 | A1 | 6/2009 | MacLachlan et al. | |
| 2009/0285784 | A1 | 11/2009 | Raemaekers et al. | |
| 2009/0306189 | A1 | 12/2009 | Raemaekers | |

FOREIGN PATENT DOCUMENTS

| | | | |
|---|---|---|---|
| EP | 1752531 | A1 | 2/2007 |
| WO | 2006129204 | A2 | 12/2006 |
| WO | 2007074405 | A2 | 7/2007 |
| WO | 2007080126 | A2 | 7/2007 |
| WO | 2007080127 | A2 | 7/2007 |
| WO | 2007083193 | A2 | 7/2007 |
| WO | 2009091864 | A2 | 7/2009 |
| WO | 2009116037 | A2 | 9/2009 |

OTHER PUBLICATIONS

Lebedeva, I.V. et al.: "Phosphorothioate oligodeoxynucleotides as inhibitors of gene expression: antisense and non-antisense effects", Applications of antisense therapies to restenosis, pp. 99-118, 1999. p. 101.
Richards, S. et al.: "Ribosomal protein L19", UniProtKB/TrEMBL, Accession No. D6WLJ5, Oct. 5, 2010.
International Search Report for International Patent Application PCT/EP2011/068910 dated Jun. 12, 2012.
Elomaa et al., 1996, Molecular Breeding, 2, 41-50.
Emery et al., 2003, Current Biology, 13, 1768-1774.
Tribolium Genome Sequencing Consortium Nature, 2008, 452, 949-955.
Salvador et al., 2013, JR948101, GenBank Submission.
Extended European Search Report for EP 19185681.4, dated Nov. 18, 2019.
E. Todres et al: "The tetraspanin superfamily in insects", in: Insect Molecular Biology, vol. 9, No. 6, Dec. 1, 2000, pp. 581-590.

* cited by examiner

*Primary Examiner* — Weihua Fan
(74) *Attorney, Agent, or Firm* — BakerHostetler; Toni-Junell Herbert

(57) ABSTRACT

The present invention relates to the prevention and/or control of infestation by insect pest species. In particular, the invention relates to down-regulation of expression of target genes in insect pests using interfering ribonucleic acid (RNA) molecules. Also described are transgenic plants that (i) express or are capable of expressing interfering RNAs of the invention and (ii) are resistant to infestation by insect pest species. Compositions containing the interfering RNAs of the invention are also provided.

26 Claims, 18 Drawing Sheets

Figure 1:
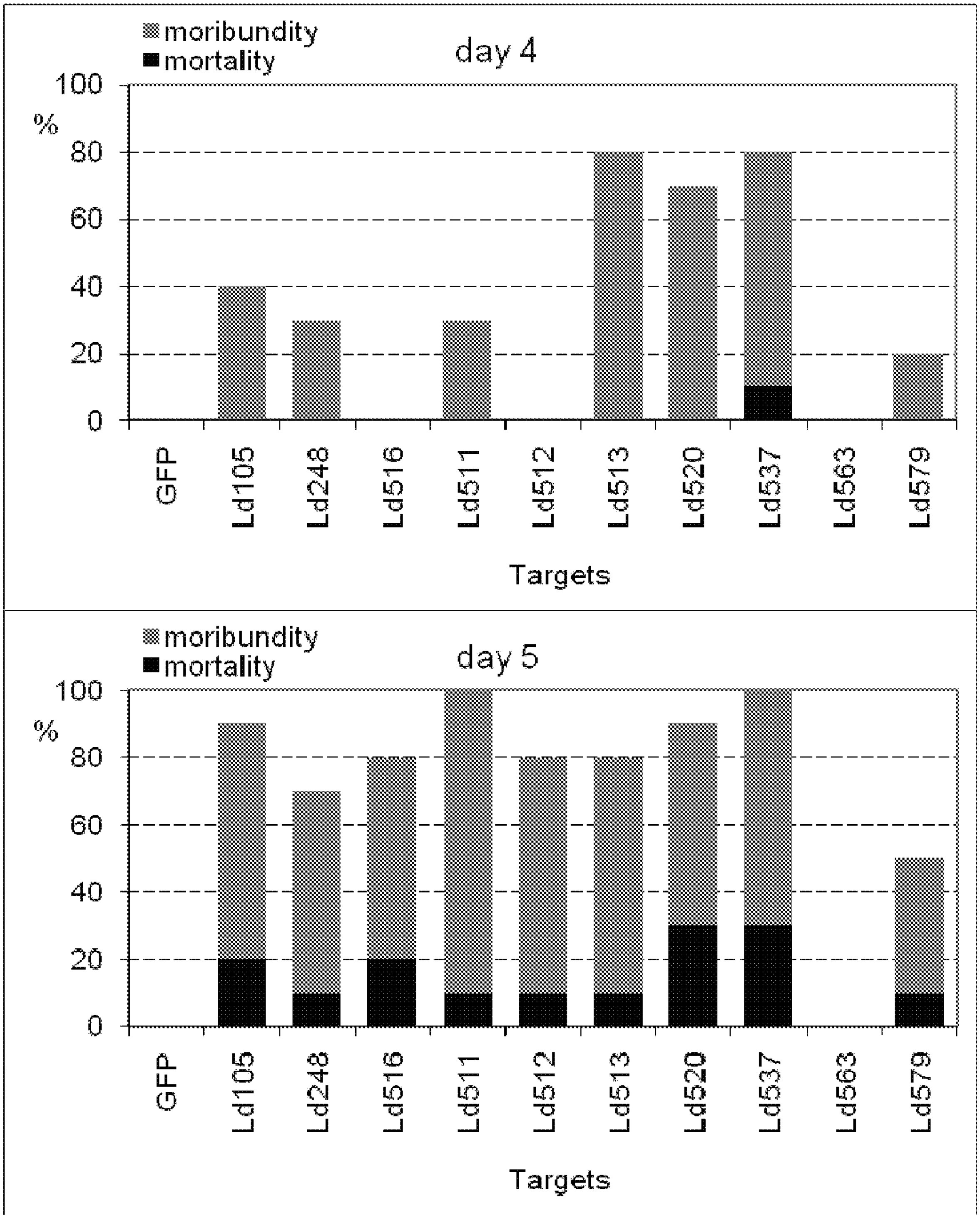
Figure 1:
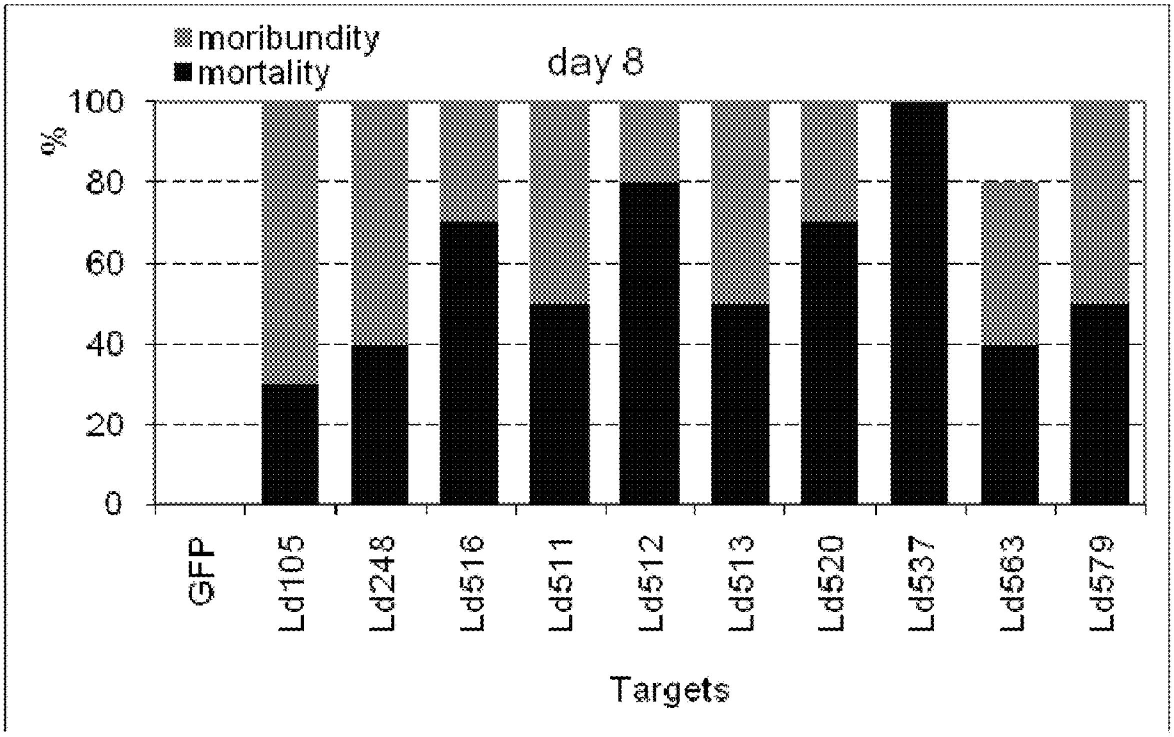
Figure 1:
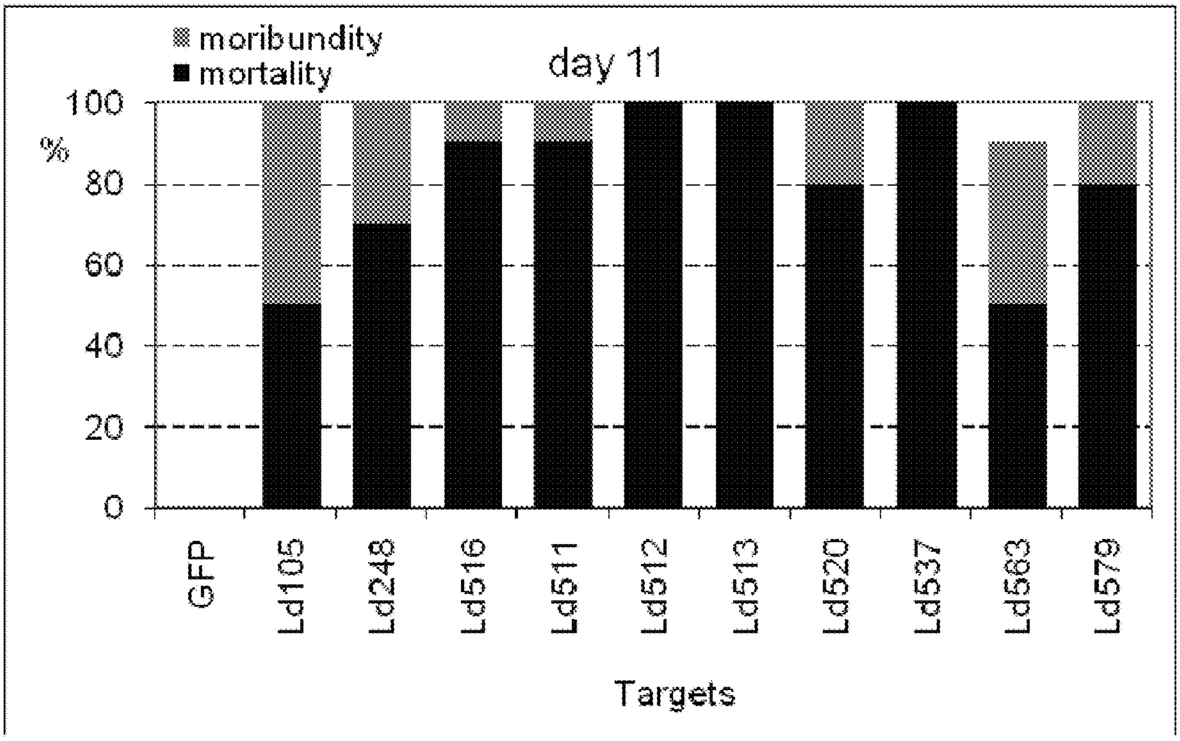
Figure 1:
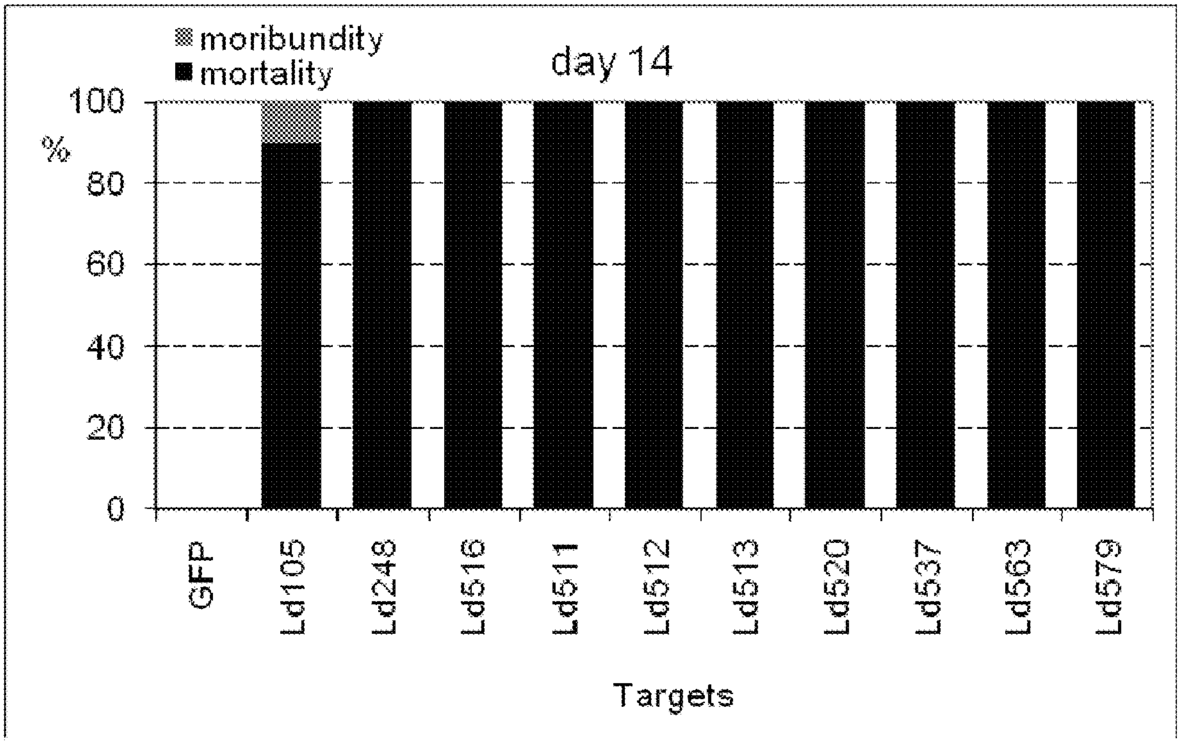

Specification includes a Sequence Listing.

(c)

(d)

C

D

DOWN-REGULATING GENE EXPRESSION IN INSECT PLANTS

RELATED APPLICATIONS

This application claims priority to U.S. application Ser. No. 13/811,792, filed on Jul. 15, 2013, which is a National Stage Entry of PCT/EP11/68910, filed Oct. 27, 2011, and which further claims priority under 35 U.S.C. § 371 from U.S. Provisional Application No. 61/407,212, filed Oct. 27, 2010. The disclosures of the priority applications are incorporated by reference herein in their entirety.

FIELD OF THE INVENTION

The present invention relates generally to genetic control of infestation by insect pest species, particularly prevention and/or control of pest infestation of plants. More specifically, the invention relates to down-regulation of expression of target genes in insect pest species by interfering ribonucleic acid (RNA) molecules. Also provided are transgenic plants that (i) express or are capable of expressing interfering RNAs of the invention and (ii) are resistant to infestation by insect pest species. Compositions containing the interfering RNA molecules of the invention for use in topical application onto plants or into the environment surrounding plants are also described.

BACKGROUND TO THE INVENTION

There exists an abundance of insect pest species that can infect or infest a wide variety of environments and host organisms. Insect pests include a variety of species from the insect Orders Hemiptera (true bugs), Coleoptera (beetles), Siphonaptera (fleas), Dichyoptera (cockroaches and mantids), Lepidoptera (moths and butterflies), Orthoptera (e.g. grasshoppers) and Diptera (true flies). Pest infestation can lead to significant damage. Insect pests that infest plant species are particularly problematic in agriculture as they can cause serious damage to crops and significantly reduce plant yields. A wide variety of different types of plant are susceptible to pest infestation including commercial crops such as rice, cotton, soybean, potato and corn.

Traditionally, infestation with insect pests has been prevented or controlled through the use of chemical pesticides. However, these chemicals are not always suitable for use in the treatment of crops as they can be toxic to other species and can cause significant environmental damage. Over more recent decades, researchers have developed more environmentally-friendly methods of controlling pest infestation. For example, microorganisms such as *Bacillus thuringiensis* bacteria that naturally express proteins toxic to insect pests have been used. Scientists have also isolated the genes encoding these insecticidal proteins and used them to generate transgenic crops resistant to insect pests e.g. corn and cotton plants genetically engineered to produce proteins of the Cry family.

Although bacterial toxins have been highly successful in controlling certain types of pest, they are not effective against all pest species. Researchers have therefore looked for other more targeted approaches to pest control and in particular to RNA interference or 'gene silencing' as a means to control pests at the genetic level.

RNA interference or 'RNAi' is a process whereby the expression of genes in the context of a cell or whole organism is down-regulated in a sequence-specific manner. RNAi is now a well-established technique in the art for inhibiting or down-regulating gene expression in a wide variety of organisms including pest organisms such as fungi, nematodes and insects. Furthermore, previous studies have shown that down-regulation of target genes in insect pest species can be used as a means to control pest infestation.

WO2007/074405 describes methods of inhibiting expression of target genes in invertebrate pests including Colorado potato beetle. WO2005/110068 describes methods of inhibiting expression of target genes in invertebrate pests including in particular Western corn rootworm as a means to control insect infestation. Furthermore, WO2009/091864 describes compositions and methods for the suppression of target genes from insect pest species including pests from the *Lygus* genus.

Although the use of RNAi for down-regulating gene expression in pest species is known in the art, the success of this technique for use as a pest control measure depends on selection of the most appropriate target genes, namely those wherein loss of function results in significant disruption of an essential biological process and/or death of the organism. The present invention is thus directed towards the down-regulation of particular target genes in insect pests as a means to achieve more effective prevention and/or control of insect pest infestation, particularly of plants.

SUMMARY OF THE INVENTION

The current inventors sought to identify improved means for preventing and/or controlling insect pest infestation using genetic approaches. In particular, they investigated the use of RNAi to down-regulate genes in such a way as to impair the ability of the insect pest to survive, grow, colonize specific environments and/or infest host organisms and thus limit the damage caused by the pest.

It has now been found by the inventors that RNAi-mediated down-regulation of specific target genes singly or in combination within insect pest species can be used as an effective means to control pest infestation.

In one embodiment, the present invention relates to an interfering ribonucleic acid (RNA or double stranded RNA) that inhibits or downregulates the expression of a target gene that encodes an insect ribosomal protein such as the ribosomal protein L19 (e.g. an insect orthologue of the CG2746 Dm protein), the ribosomal protein L40 (e.g. an insect orthologue of the CG2960 Dm protein) or the ribosomal protein S27A (e.g. an insect orthologue of the CG5271 Dm protein).

According to another embodiment the present invention relates to an interfering ribonucleic acid (RNA or double stranded RNA) that inhibits or downregulates the expression of a target gene that encodes an insect proteasome subunit such as the Rpn6 protein (e.g. an insect orthologue of the CG10149 Dm protein), the Pros 25 protein (e.g. an insect orthologue of the CG5266 Dm protein), the Rpn2 protein (e.g. an insect orthologue of the CG11888 Dm protein), the proteasome beta 1 subunit protein (e.g. an insect orthologue of the CG8392 Dm protein) or the Pros beta 2 protein (e.g. an insect orthologue of the CG3329 Dm protein).

According to still another embodiment the present invention relates to an interfering ribonucleic acid (RNA or double stranded RNA) that inhibits or downregulates the expression of a target gene that encodes an insect β-coatomer of the COPI vesicle (e.g. an insect orthologue of the CG6223 Dm protein), the γ-coatomer of the COPI vesicle (e.g. an insect orthologue of the 1528 Dm protein), the β'-coatomer protein (e.g. an insect orthologue of the CG6699 Dm protein) or the ζ-coatomer of the COPI vesicle (e.g. an insect orthologue of the CG3948 Dm protein).

According to still another embodiment the present invention relates to an interfering ribonucleic acid (RNA or double stranded RNA) that inhibits or downregulates the expression of a target gene that encodes an insect Tetraspanine 2 A protein which is a putative transmembrane domain protein (e.g. an insect orthologue of the CG11415 Dm protein).

According to still another embodiment the present invention relates to an interfering ribonucleic acid (RNA or double stranded RNA) that inhibits or downregulates the expression of a target gene that encodes an insect protein belonging to the actin family (e.g. an insect orthologue of the CG5409 Dm protein) such as Actin 5C (e.g. an insect orthologue of the CG4027 Dm protein).

According to still another embodiment the present invention relates to an interfering ribonucleic acid (RNA or double stranded RNA) that inhibits or downregulates the expression of a target gene that encodes an insect ubiquitin-5E protein (e.g. an insect orthologue of the CG32744 Dm protein).

According to still another embodiment the present invention relates to an interfering ribonucleic acid (RNA or double stranded RNA) that inhibits or downregulates the expression of a target gene that encodes an insect Sec23 protein which is a GTPase activator involved in intracellular protein transport (e.g. an insect orthologue of the CG1250 Dm protein).

According to still another embodiment the present invention relates to an interfering ribonucleic acid (RNA or double stranded RNA) that inhibits or downregulates the expression of a target gene that encodes an insect crinkled protein which is an unconventional myosin which is involved in motor activity (e.g. an insect orthologue of the CG7595 Dm protein).

According to still another embodiment the present invention relates to an interfering ribonucleic acid (RNA or double stranded RNA) that inhibits or downregulates the expression of a target gene that encodes an insect crooked neck protein which is involved in the regulation of nuclear alternative mRNA splicing (e.g. an insect orthologue of the CG3193 Dm protein).

According to still another embodiment the present invention relates to an interfering ribonucleic acid (RNA or double stranded RNA) that inhibits or downregulates the expression of a target gene that encodes an insect vacuolar H+-ATPase G-subunit protein (e.g. an insect orthologue of the CG6213 Dm protein).

According to still another embodiment the present invention relates to an interfering ribonucleic acid (RNA or double stranded RNA) that inhibits or downregulates the expression of a target gene that encodes an insect Tbp-1; Tat-binding protein (e.g. an insect orthologue of the CG10370 Dm protein).

Therefore, in accordance with a first aspect of the invention, there is provided an interfering ribonucleic acid (RNA or double stranded RNA) that functions upon uptake by an insect pest species to down-regulate expression of a target gene in said insect pest, wherein the target gene (i) is selected from the group of genes having a nucleotide sequence comprising any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or having a nucleotide sequence that, when the two sequences are optimally aligned and compared, is at least 75%, preferably at least 80%, 85%, 90%, 95%, 98% or 99% identical to any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or (ii) is selected from the group of genes having a nucleotide sequence consisting of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or (iii) is selected from the group of genes having a nucleotide sequence comprising a fragment of at least 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or having a nucleotide sequence that, when said gene comprising said fragment is optimally aligned and compared with any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, said nucleotide sequence is at least 75% preferably at least 80%, 85%, 90%, 95%, 98% or 99% identical to any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or (iv) is selected from the group of genes having a nucleotide sequence comprising a fragment of at least 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, and wherein when said fragment is optimally aligned and compared with the corresponding fragment in any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, said nucleotide sequence of said fragment is at least 75% preferably at least 80%, 85%, 90%, 95%, 98% or 99% identical to said corresponding fragment of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or (v) is an insect pest orthologue of a gene having a nucleotide sequence comprising any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or (vi) is selected from the group of genes having a nucleotide sequence encoding an amino acid sequence that, when the two amino acid sequences are optimally aligned and compared, is at least 70% preferably at least 75%, 80%, 85%, 90%, 95%, 98% or 99% identical to the amino acid sequence encoded by the nucleotide sequence represented in any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or (vii) is selected from the group of genes having a nucleotide sequence encoding an amino acid sequence that, when the two amino acid sequences are optimally aligned and compared, is at least 70% preferably at least 75%, 80%, 85%, 90%, 95%, 98% or 99% identical to the amino acid sequence represented in any of SEQ ID NOs 285, 242, 271, 226, 227, 281, 228, 282, 229, 230 to 233, 234, 283, 235, 236, 237, 238, 239, 240, 284, 241, 243, 244, 286, 269, 270, 287, 288, 206 to 225.

In a particular aspect of the invention, interfering RNA molecules of the current invention comprise at least one double-stranded region, typically the silencing element of the interfering RNA, comprising a sense RNA strand annealed by complementary basepairing to an antisense RNA strand wherein the sense strand of the dsRNA molecule comprises a sequence of nucleotides complementary to a sequence of nucleotides located within the RNA transcript of the target gene.

In one embodiment, the present invention relates to an interfering RNA molecule which comprises at least one double-stranded region, typically the silencing element of the interfering RNA molecule, comprising a sense RNA strand annealed by complementary basepairing to an antisense RNA strand wherein the sense strand of the dsRNA molecule comprises a sequence of at least 17, 18, 19, 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides, that is at least 75% preferably at least 80%, 85%, 90%, 95%, 98%, 99% or 100% complementary to a sequence of nucleotides located within the RNA transcript of a target gene that encodes an insect ribosomal protein such as the ribosomal protein L19 (e.g. an insect orthologue of the CG2746 Dm protein), the ribosomal protein L40 (e.g. an insect orthologue of the CG2960 Dm protein) or the ribosomal protein S27A (e.g. an insect orthologue of the CG5271 Dm protein).

According to another embodiment the present invention relates to an interfering RNA molecule which comprises at least one double-stranded region, typically the silencing element of the interfering RNA molecule, comprising a sense RNA strand annealed by complementary basepairing to an antisense RNA strand wherein the sense strand of the dsRNA molecule comprises a sequence of at least 17, 18, 19, 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides, that is at least 75% preferably at least 80%, 85%, 90%, 95%, 98%, 99% or 100% complementary to a sequence of nucleotides located within the RNA transcript of a target gene that encodes an insect proteasome subunit such as the Rpn6 protein (e.g. an insect orthologue of the CG10149 Dm protein), the Pros 25 protein (e.g. an insect orthologue of the CG5266 Dm protein), the Rpn2 protein (e.g. an insect orthologue of the CG11888 Dm protein), the proteasome beta 1 subunit protein (e.g. an insect orthologue of the CG8392 Dm protein) or the Pros beta 2 protein (e.g. an insect orthologue of the CG3329 Dm protein).

According to still another embodiment the present invention relates to an interfering RNA molecule which comprises at least one double-stranded region, typically the silencing element of the interfering RNA molecule, comprising a sense RNA strand annealed by complementary basepairing to an antisense RNA strand wherein the sense strand of the dsRNA molecule comprises a sequence of at least 17, 18, 19, 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides, that is at least 75% preferably at least 80%, 85%, 90%, 95%, 98%, 99% or 100% complementary to a sequence of nucleotides located within the RNA transcript of a target gene that encodes an insect β-coatomer of the COPI vesicle (e.g. an insect orthologue of the CG6223 Dm protein), the γ-coatomer of the COPI vesicle (e.g. an insect orthologue of the 1528 Dm protein), the β'-coatomer protein (e.g. an insect orthologue of the CG6699 Dm protein) or the ζ-coatomer of the COPI vesicle (e.g. an insect orthologue of the CG3948 Dm protein).

According to still another embodiment the present invention relates to an interfering RNA molecule which comprises at least one double-stranded region, typically the silencing element of the interfering RNA molecule, comprising a sense RNA strand annealed by complementary basepairing to an antisense RNA strand wherein the sense strand of the dsRNA molecule comprises a sequence of at least 17, 18, 19, 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides, that is at least 75% preferably at least 80%, 85%, 90%, 95%, 98%, 99% or 100% complementary to a sequence of nucleotides located within the RNA transcript of a target gene that encodes an insect Tetraspanine 2 A protein which is a putative transmembrane domain protein (e.g. an insect orthologue of the CG11415 Dm protein).

According to still another embodiment the present invention relates to an interfering RNA molecule which comprises at least one double-stranded region, typically the silencing element of the interfering RNA molecule, comprising a sense RNA strand annealed by complementary basepairing to an antisense RNA strand wherein the sense strand of the dsRNA molecule comprises a sequence of at least 17, 18, 19, 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides, that is at least 75% preferably at least 80%, 85%, 90%, 95%, 98%, 99% or 100% complementary to a sequence of nucleotides located within the RNA transcript of a target gene that encodes an insect protein belonging to the actin family (e.g. an insect orthologue of the CG5409 Dm protein) such as Actin 5C (e.g. an insect orthologue of the CG4027 Dm protein).

According to still another embodiment the present invention relates to an interfering RNA molecule which comprises at least one double-stranded region, typically the silencing element of the interfering RNA molecule, comprising a sense RNA strand annealed by complementary basepairing to an antisense RNA strand wherein the sense strand of the dsRNA molecule comprises a sequence of at least 17, 18, 19, 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides, that is at least 75% preferably at least 80%, 85%, 90%, 95%, 98%, 99% or 100% complementary to a sequence of nucleotides located within the RNA transcript of a target gene that encodes an insect ubiquitin-5E protein (e.g. an insect orthologue of the CG32744 Dm protein).

According to still another embodiment the present invention relates to an interfering RNA molecule which comprises at least one double-stranded region, typically the silencing element of the interfering RNA molecule, comprising a sense RNA strand annealed by complementary basepairing to an antisense RNA strand wherein the sense strand of the dsRNA molecule comprises a sequence of at least 17, 18, 19, 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides, that is at least 75% preferably at least 80%, 85%, 90%, 95%, 98%, 99% or 100% complementary to a sequence of nucleotides located within the RNA transcript of a target gene that encodes an insect Sec23 protein which is a GTPase activator involved in intracellular protein transport (e.g. an insect orthologue of the CG1250 Dm protein).

According to still another embodiment the present invention relates to an interfering RNA molecule which comprises at least one double-stranded region, typically the silencing element of the interfering RNA molecule, comprising a sense RNA strand annealed by complementary basepairing to an antisense RNA strand wherein the sense strand of the dsRNA molecule comprises a sequence of at least 17, 18, 19, 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides, that is at least 75% preferably at least 80%, 85%, 90%, 95%, 98%, 99% or 100% complementary to a sequence of nucleotides located within the RNA transcript of a target gene that encodes an insect crinkled protein which is an unconventional myosin which is involved in motor activity (e.g. an insect orthologue of the CG7595 Dm protein).

According to still another embodiment the present invention relates to an interfering RNA molecule which comprises at least one double-stranded region, typically the silencing element of the interfering RNA molecule, comprising a sense RNA strand annealed by complementary basepairing to an antisense RNA strand wherein the sense strand of the dsRNA molecule comprises a sequence of at least 17, 18, 19, 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides, that is at least 75% preferably at least 80%, 85%, 90%, 95%, 98%, 99% or 100% complementary to a sequence of nucleotides located within the RNA transcript of a target gene that encodes an insect crooked neck protein which is involved in the regulation of nuclear alternative mRNA splicing (e.g. an insect orthologue of the CG3193 Dm protein).

According to still another embodiment the present invention relates to an interfering RNA molecule which comprises at least one double-stranded region, typically the silencing element of the interfering RNA molecule, comprising a sense RNA strand annealed by complementary basepairing to an antisense RNA strand wherein the sense strand of the dsRNA molecule comprises a sequence of at least 17, 18, 19, 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides, that is at least 75% preferably at least 80%, 85%, 90%, 95%, 98%, 99% or 100% complementary to a sequence of nucleotides located within the RNA transcript of a target gene that encodes an insect vacuolar H+-ATPase G-subunit protein (e.g. an insect orthologue of the CG6213 Dm protein).

According to still another embodiment the present invention relates to an interfering RNA molecule which comprises at least one double-stranded region, typically the silencing element of the interfering RNA molecule, comprising a sense RNA strand annealed by complementary basepairing to an antisense RNA strand wherein the sense strand of the dsRNA molecule comprises a sequence of at least 17, 18, 19, 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides, that is at least 75% preferably at least 80%, 85%, 90%, 95%, 98%, 99% or 100% complementary to a sequence of nucleotides located within the RNA transcript of a target gene that encodes an insect Tbp-1; Tat-binding protein (e.g. an insect orthologue of the CG10370 Dm protein).

In accordance with a second aspect of the invention, there is provided an isolated polynucleotide selected from the group consisting of:

(i) a polynucleotide which comprises at least 21, preferably at least 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100 or 1115 contiguous nucleotides of a nucleotide sequence as represented by any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120, or the complement thereof, or (ii) a polynucleotide which consists of at least 21, preferably at least 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100 or 1115 contiguous nucleotides of a nucleotide sequence as represented by any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120, or the complement thereof, or (iii) a polynucleotide which comprises at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100 or 1115 contiguous nucleotides of a nucleotide sequence as represented in any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120, or the complement thereof, that, when the two sequences are optimally aligned and compared, said polynucleotide is at least 75% preferably at least 80%, 85%, 90%, 95%, 98% or 99% identical to any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120, or the complement thereof, or (iv) a polynucleotide which comprises a fragment of at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100 or 1115 contiguous nucleotides of a nucleotide as represented in any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120, or the complement thereof, and wherein said fragment or said complement has a nucleotide sequence that, when said fragment is optimally aligned and compared with the corresponding fragment in any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120, said nucleotide sequence is at least 75% preferably at least 80%, 85%, 90%, 95%, 98% or 99% identical to said corresponding fragment of any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120 or the complement thereof, or (v) a polynucleotide which consists of a fragment of at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100 or 1115 contiguous nucleotides of a nucleotide as represented in any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120, or the complement thereof, and wherein said fragment or said complement has a nucleotide sequence that, when said fragment is optimally aligned and compared with the corresponding fragment in any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120, said nucleotide sequence is at least 75% preferably at least 80%, 85%, 90%, 95%, 98% or 99% identical to said corresponding fragment of any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120 or the complement thereof, or (vi) a polynucleotide encoding an amino acid sequence that, when the two amino acid sequences are optimally aligned and compared, is at least 70% preferably at least 75%, 80%, 85%, 90%, 95%, 98% or 99% identical to the amino acid sequence encoded by the nucleotide sequence represented in any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120, or (vii) a polynucleotide encoding an amino acid sequence that, when the two amino acid sequences are optimally aligned and compared, is at least 70% preferably at least 75%, 80%, 85%, 90%, 95%, 98% or 99% identical to the amino acid sequence represented in any of SEQ ID NOs 285, 242, 271, 226, 227, 281, 228, 282, 229, 230 to 233, 234, 283, 235, 236, 237, 238, 239, 240, 284, 241, 243, 244, 286, 269, 270, 287, 288, 206 to 225, and wherein said polynucleotide is no longer than 10000, 9000, 8000, 7000, 6000, 5000, 4000, 3000, 2000 or 1500 nucleotides.

In a particular aspect of the invention, the isolated polynucleotide is part of an interfering RNA molecule, typically part of the silencing element, comprising at least one double-stranded region comprising a sense RNA strand annealed by complementary basepairing to an antisense RNA strand wherein the sense strand of the dsRNA molecule comprises a sequence of nucleotides complementary to a sequence of nucleotides located within the RNA transcript of the target gene. More particularly, the isolated polynucleotide is cloned in a DNA construct in a sense and antisense orientation so that upon transcription of the sense and antisense polynucleotide a dsRNA molecule is formed, which functions upon uptake by a pest to inhibit or down-regulate the expression of a target gene within said pest.

In one embodiment, the present invention relates to an isolated polynucleotide that is cloned in a DNA construct in a sense and antisense orientation so that upon transcription of the sense and antisense polynucleotide a dsRNA molecule is formed, which functions upon uptake by an insect to inhibit or down-regulate the expression of a target gene that encodes an insect ribosomal protein such as the ribosomal protein L19 (e.g. an insect orthologue of the CG2746 Dm protein), the ribosomal protein L40 (e.g. an insect orthologue of the CG2960 Dm protein) or the ribosomal protein S27A (e.g. an insect orthologue of the CG5271 Dm protein).

According to another embodiment the present invention relates to an isolated polynucleotide that is cloned in a DNA construct in a sense and antisense orientation so that upon transcription of the sense and antisense polynucleotide a dsRNA molecule is formed, which functions upon uptake by an insect to inhibit or down-regulate the expression of a target gene that encodes an insect proteasome subunit such as the Rpn6 protein (e.g. an insect orthologue of the CG10149 Dm protein), the Pros 25 protein (e.g. an insect orthologue of the CG5266 Dm protein), the Rpn2 protein (e.g. an insect orthologue of the CG11888 Dm protein), the proteasome beta 1 subunit protein (e.g. an insect orthologue of the CG8392 Dm protein) or the Pros beta 2 protein (e.g. an insect orthologue of the CG3329 Dm protein).

According to still another embodiment the present invention relates to an isolated polynucleotide that is cloned in a DNA construct in a sense and antisense orientation so that upon transcription of the sense and antisense polynucleotide a dsRNA molecule is formed, which functions upon uptake by an insect to inhibit or down-regulate the expression of a target gene that encodes an insect β-coatomer of the COPI vesicle (e.g. an insect orthologue of the CG6223 Dm protein), the γ-coatomer of the COPI vesicle (e.g. an insect orthologue of the 1528 Dm protein), the β'-coatomer protein (e.g. an insect orthologue of the CG6699 Dm protein) or the ζ-coatomer of the COPI vesicle (e.g. an insect orthologue of the CG3948 Dm protein).

According to still another embodiment the present invention relates to an isolated polynucleotide that is cloned in a DNA construct in a sense and antisense orientation so that upon transcription of the sense and antisense polynucleotide a dsRNA molecule is formed, which functions upon uptake by an insect to inhibit or down-regulate the expression of a target gene that encodes an insect Tetraspanine 2 A protein which is a putative transmembrane domain protein (e.g. an insect orthologue of the CG11415 Dm protein).

According to still another embodiment the present invention relates to an isolated polynucleotide that is cloned in a DNA construct in a sense and antisense orientation so that upon transcription of the sense and antisense polynucleotide a dsRNA molecule is formed, which functions upon uptake by an insect to inhibit or down-regulate the expression of a target gene that encodes an insect protein belonging to the actin family (e.g. an insect orthologue of the CG5409 Dm protein) such as Actin 5C (e.g. an insect orthologue of the CG4027 Dm protein).

According to still another embodiment the present invention relates to an isolated polynucleotide that is cloned in a DNA construct in a sense and antisense orientation so that upon transcription of the sense and antisense polynucleotide a dsRNA molecule is formed, which functions upon uptake by an insect to inhibit or down-regulate the expression of a target gene that encodes an insect ubiquitin-5E protein (e.g. an insect orthologue of the CG32744 Dm protein).

According to still another embodiment the present invention relates to an isolated polynucleotide that is cloned in a DNA construct in a sense and antisense orientation so that upon transcription of the sense and antisense polynucleotide a dsRNA molecule is formed, which functions upon uptake by an insect to inhibit or down-regulate the expression of a target gene that encodes an insect Sec23 protein which is a GTPase activator involved in intracellular protein transport (e.g. an insect orthologue of the CG1250 Dm protein).

According to still another embodiment the present invention relates to an isolated polynucleotide that is cloned in a DNA construct in a sense and antisense orientation so that upon transcription of the sense and antisense polynucleotide a dsRNA molecule is formed, which functions upon uptake by an insect to inhibit or down-regulate the expression of a target gene that encodes an insect crinkled protein which is an unconventional myosin which is involved in motor activity (e.g. an insect orthologue of the CG7595 Dm protein).

According to still another embodiment the present invention relates to an isolated polynucleotide that is cloned in a DNA construct in a sense and antisense orientation so that upon transcription of the sense and antisense polynucleotide a dsRNA molecule is formed, which functions upon uptake by an insect to inhibit or down-regulate the expression of a target gene that encodes an insect crooked neck protein which is involved in the regulation of nuclear alternative mRNA splicing (e.g. an insect orthologue of the CG3193 Dm protein).

According to still another embodiment the present invention relates to an isolated polynucleotide that is cloned in a DNA construct in a sense and antisense orientation so that upon transcription of the sense and antisense polynucleotide a dsRNA molecule is formed, which functions upon uptake by an insect to inhibit or down-regulate the expression of a target gene that encodes an insect vacuolar H+-ATPase G-subunit protein (e.g. an insect orthologue of the CG6213 Dm protein).

According to still another embodiment the present invention relates to an isolated polynucleotide that is cloned in a DNA construct in a sense and antisense orientation so that upon transcription of the sense and antisense polynucleotide a dsRNA molecule is formed, which functions upon uptake by an insect to inhibit or down-regulate the expression of a target gene that encodes an insect Tbp-1; Tat-binding protein (e.g. an insect orthologue of the CG10370 Dm protein).

In accordance with a third aspect of the invention there is provided a composition for preventing and/or controlling insect pest infestation comprising at least one interfering ribonucleic acid (RNA) and at least one suitable carrier, excipient or diluent, wherein the interfering RNA functions upon uptake by the pest to down-regulate the expression of a target gene within said pest, wherein the target gene (i) is selected from the group of genes having a nucleotide sequence comprising any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or having a nucleotide sequence that, when the two sequences are optimally aligned and compared, is at least 75%, preferably at least 80%, 85%, 90%, 95%, 98% or 99% identical to any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or (ii) is selected from the group of genes having a nucleotide sequence consisting of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or (iii) is selected from the group of genes having a nucleotide sequence comprising a fragment of at least 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or having a nucleotide sequence that, when said gene comprising said fragment is optimally aligned and compared with any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, said nucleotide sequence is at least 75% preferably at least 80%, 85%, 90%, 95%, 98% or 99% identical to any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or (iv) is selected from the group of genes having a nucleotide sequence comprising a fragment of at least 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, and wherein when said fragment is optimally aligned and compared with the corresponding fragment in any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, said nucleotide sequence of said fragment is at least 75% preferably at least 80%, 85%, 90%, 95%, 98% or 99% identical to said corresponding fragment of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or (v) is an insect pest orthologue of a gene having a nucleotide sequence comprising any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or (vi) is selected from the group of genes having a nucleotide sequence encoding an amino acid sequence that, when the two amino acid sequences are optimally aligned and compared, is at least 70% preferably at least 75%, 80%, 85%, 90%, 95%, 98% or 99% identical to the amino acid sequence encoded by the nucleotide sequence represented in any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or (vii) is selected from the group of genes having a nucleotide sequence encoding an amino acid sequence that, when the two amino acid sequences are optimally aligned and compared, is at least 70% preferably at least 75%, 80%, 85%, 90%, 95%, 98% or 99% identical to the amino acid sequence represented in any of SEQ ID NOs 285, 242, 271, 226, 227, 281, 228, 282, 229, 230 to 233, 234, 283, 235, 236, 237, 238, 239, 240, 284, 241, 243, 244, 286, 269, 270, 287, 288, 206 to 225.

In accordance with a fourth aspect of the invention, there is provided a method for down-regulating expression of a target gene in an insect pest species comprising contacting said insect pest species with an effective amount of at least one interfering ribonucleic acid (RNA) or an effective amount of a composition comprising at least one interfering ribonucleic acid (RNA) and at least one suitable carrier, excipient or diluent, wherein the interfering RNA functions upon uptake by the pest to down-regulate the expression of a target gene within said pest, and wherein the target gene (i) is selected from the group of genes having a nucleotide sequence comprising any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or having a nucleotide sequence that, when the two sequences are optimally aligned and compared, is at least 75%, preferably at least 80%, 85%, 90%, 95%, 98% or 99% identical any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or (ii) is selected from the group of genes having a nucleotide sequence consisting of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or (iii) is selected from the group of genes having a nucleotide sequence comprising a fragment of at least 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or having a nucleotide sequence that, when said gene comprising said fragment is optimally aligned and compared with any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, said nucleotide sequence is at least 75% preferably at least 80%, 85%, 90%, 95%, 98% or 99% identical to any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or (iv) is selected from the group of genes having a nucleotide sequence comprising a fragment of at least 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, and wherein when said fragment is optimally aligned and compared with the corresponding fragment in any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, said nucleotide sequence of said fragment is at least 75% preferably at least 80%, 85%, 90%, 95%, 98% or 99% identical to said corresponding fragment of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or (v) is an insect pest orthologue of a gene having a nucleotide sequence comprising any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or (vi) is selected from the group of genes having a nucleotide sequence encoding an amino acid sequence that, when the two amino acid sequences are optimally aligned and compared, is at least 70% preferably at least 75%, 80%, 85%, 90%, 95%, 98% or 99% identical to the amino acid sequence encoded by the nucleotide sequence represented in any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or (vii) is selected from the group of genes having a nucleotide sequence encoding an amino acid sequence that, when the two amino acid sequences are optimally aligned and compared, is at least 70% preferably at least 75%, 80%, 85%, 90%, 95%, 98% or 99% identical to the amino acid sequence represented in any of SEQ ID NOs 285, 242, 271, 226, 227, 281, 228, 282, 229, 230 to 233, 234, 283, 235, 236, 237, 238, 239, 240, 284, 241, 243, 244, 286, 269, 270, 287, 288, 206 to 225.

Preferably, the method of the invention finds practical application in the prevention and/or control of insect pest infestation, in particular, control of pest infestation of crop plants such as but not limited to rice, cotton, strawberries, seed crops such as alfalfa, soy, potato, tomato, canola, sunflower, sorghum, pearl millet, corn, eggplant, pepper and tobacco. In addition, the interfering RNA of the invention may be introduced into the plants to be protected by routine genetic engineering techniques.

Therefore, in accordance with a fifth aspect of the invention, there is provided a method for generating a transgenic plant resistant to infestation by an insect pest species comprising:

(a) transforming a plant cell with a DNA construct comprising a polynucleotide sequence encoding an interfering ribonucleic acid (RNA) that functions upon uptake by an insect pest species to down-regulate expression of a target gene in said insect pest species, wherein the target gene (i) is selected from the group of genes having a nucleotide sequence comprising any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or having a nucleotide sequence that, when the two sequences are optimally aligned and compared, is at least 75%, preferably at least 80%, 85%, 90%, 95%, 98% or 99% identical any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or (ii) is selected from the group of genes having a nucleotide sequence consisting of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or (iii) is selected from the group of genes having a nucleotide sequence comprising a fragment of at least 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or having a nucleotide sequence that, when said gene comprising said fragment is optimally aligned and compared with any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, said nucleotide sequence is at least 75% preferably at least 80%, 85%, 90%, 95%, 98% or 99% identical to any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or (iv) is selected from the group of genes having a nucleotide sequence comprising a fragment of at least 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, and wherein when said fragment is optimally aligned and compared with the corresponding fragment in any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, said nucleotide sequence of said fragment is at least 75% preferably at least 80%, 85%, 90%, 95%, 98% or 99% identical to said corresponding fragment of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or (v) is an insect pest orthologue of a gene having a nucleotide sequence comprising any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or (vi) is selected from the group of genes having a nucleotide sequence encoding an amino acid sequence that, when the two amino acid sequences are optimally aligned and compared, is at least 70% preferably at least 75%, 80%, 85%, 90%, 95%, 98% or 99% identical to the amino acid sequence encoded by the nucleotide sequence represented in any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or (vii) is selected from the group of genes having a nucleotide sequence encoding an amino acid sequence that, when the two amino acid sequences are optimally aligned and compared, is at least 70% preferably at least 75%, 80%, 85%, 90%, 95%, 98% or 99% identical to the amino acid sequence represented in any of SEQ ID NOs 285, 242, 271, 226, 227, 281, 228, 282, 229, 230 to 233, 234, 283, 235, 236, 237, 238, 239, 240, 284, 241, 243, 244, 286, 269, 270, 287, 288, 206 to 225;

(b) regenerating a plant from the transformed plant cell; and (c) growing the transformed plant under conditions suitable for the expression of the interfering RNA from the recombinant DNA construct, said plant thus being resistant to said pest as compared with an untransformed plant.

In accordance with a sixth aspect of the invention, there is provided a transgenic plant, or reproductive or propagation material for a transgenic plant or a cultured transgenic plant cell, which expresses or is capable of expressing at least one interfering ribonucleic acid (RNA) that functions upon uptake by an insect pest species to down-regulate the expression of a target gene within said pest, wherein the target gene (i) is selected from the group of genes having a nucleotide sequence comprising any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or having a nucleotide sequence that, when the two sequences are optimally aligned and compared, is at least 75%, preferably at least 80%, 85%, 90%, 95%, 98% or 99% identical any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or (ii) is selected from the group of genes having a nucleotide sequence consisting of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or (iii) is selected from the group of genes having a nucleotide sequence comprising a fragment of at least 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or having a nucleotide sequence that, when said gene comprising said fragment is optimally aligned and compared with any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, said nucleotide sequence is at least 75% preferably at least 80%, 85%, 90%, 95%, 98% or 99% identical to any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or (iv) is selected from the group of genes having a nucleotide sequence comprising a fragment of at least 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, and wherein when said fragment is optimally aligned and compared with the corresponding fragment in any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, said nucleotide sequence of said fragment is at least 75% preferably at least 80%, 85%, 90%, 95%, 98% or 99% identical to said corresponding fragment of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or (v) is an insect pest orthologue of a gene having a nucleotide sequence comprising any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or (vi) is selected from the group of genes having a nucleotide sequence encoding an amino acid sequence that, when the two amino acid sequences are optimally aligned and compared, is at least 70% preferably at least 75%, 80%, 85%, 90%, 95%, 98% or 99% identical to the amino acid sequence encoded by the nucleotide sequence represented in any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or (vii) is selected from the group of genes having a nucleotide sequence encoding an amino acid sequence that, when the two amino acid sequences are optimally aligned and compared, is at least 70% preferably at least 75%, 80%, 85%, 90%, 95%, 98% or 99% identical to the amino acid sequence represented in any of SEQ ID NOs 285, 242, 271, 226, 227, 281, 228, 282, 229, 230 to 233, 234, 283, 235, 236, 237, 238, 239, 240, 284, 241, 243, 244, 286, 269, 270, 287, 288, 206 to 225.

In one embodiment, the present invention relates to a transgenic plant or plant cell comprising an interfering nucleic acid (RNA or double stranded RNA) that is at least 75% preferably at least 80%, 85%, 90%, 95%, 98%, 99% or 100% complementary to a part of at least 17, 18, 19, 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides of or all of a mRNA encoding an insect ribosomal protein such as the ribosomal protein L19 (e.g. an insect orthologue of the CG2746 Dm protein), the ribosomal protein L40 (e.g. an insect orthologue of the CG2960 Dm protein) or the ribosomal protein S27A (e.g. an insect orthologue of the CG5271 Dm protein), and wherein the interfering nucleic acid inhibits or interferes with the translation of said mRNA and wherein the plant or plant cell is resistant to the insect as compared with an untransformed plant.

According to another embodiment the present invention relates to a transgenic plant or plant cell comprising an interfering nucleic acid (RNA or double stranded RNA) that is at least 75% preferably at least 80%, 85%, 90%, 95%, 98%, 99% or 100% complementary to a part of at least 17, 18, 19, 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides of or all of a mRNA encoding an insect proteasome subunit such as the Rpn6 protein (e.g. an insect orthologue of the CG10149 Dm protein), the Pros 25 protein (e.g. an insect orthologue of the CG5266 Dm protein), the Rpn2 protein (e.g. an insect orthologue of the CG11888 Dm protein), the proteasome beta 1 subunit protein (e.g. an insect orthologue of the CG8392 Dm protein) or the Pros beta 2 protein (e.g. an insect orthologue of the CG3329 Dm protein), and wherein the interfering nucleic acid inhibits or interferes with the translation of said mRNA and wherein the plant or plant cell is resistant to the insect as compared with an untransformed plant.

According to still another embodiment the present invention relates to a transgenic plant or plant cell comprising an interfering nucleic acid (RNA or double stranded RNA) that is at least 75% preferably at least 80%, 85%, 90%, 95%, 98%, 99% or 100% complementary to a part of at least 17, 18, 19, 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides of or all of a mRNA encoding an insect β-coatomer of the COPI vesicle (e.g. an insect orthologue of the CG6223 Dm protein), the γ-coatomer of the COPI vesicle (e.g. an insect orthologue of the 1528 Dm protein), the β'-coatomer protein (e.g. an insect orthologue of the CG6699 Dm protein) or the ζ-coatomer of the COPI vesicle (e.g. an insect orthologue of the CG3948 Dm protein), and wherein the interfering nucleic acid inhibits or interferes with the translation of said mRNA and wherein the plant or plant cell is resistant to the insect as compared with an untransformed plant.

According to still another embodiment the present invention relates to a transgenic plant or plant cell comprising an interfering nucleic acid (RNA or double stranded RNA) that is at least 75% preferably at least 80%, 85%, 90%, 95%, 98%, 99% or 100% complementary to a part of at least 17, 18, 19, 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides of or all of a mRNA encoding an insect Tetraspanine 2 A protein which is a putative transmembrane domain protein (e.g. an insect orthologue of the CG11415 Dm protein), and wherein the interfering nucleic acid inhibits or interferes with the translation of said mRNA and wherein the plant or plant cell is resistant to the insect as compared with an untransformed plant.

According to still another embodiment the present invention relates to a transgenic plant or plant cell comprising an interfering nucleic acid (RNA or double stranded RNA) that is at least 75% preferably at least 80%, 85%, 90%, 95%, 98%, 99% or 100% complementary to a part of at least 17, 18, 19, 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides of or all of a mRNA encoding an insect protein belonging to the actin family (e.g. an insect orthologue of the CG5409 Dm protein) such as Actin 5C (e.g. an insect orthologue of the CG4027 Dm protein), and wherein the interfering nucleic acid inhibits or interferes with the translation of said mRNA and wherein the plant or plant cell is resistant to the insect as compared with an untransformed plant.

According to still another embodiment the present invention relates to a transgenic plant or plant cell comprising an interfering nucleic acid (RNA or double stranded RNA) that is at least 75% preferably at least 80%, 85%, 90%, 95%, 98%, 99% or 100% complementary to a part of at least 17, 18, 19, 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides of or all of a mRNA encoding an insect ubiquitin-5E protein (e.g. an insect orthologue of the CG32744 Dm protein), and wherein the interfering nucleic acid inhibits or interferes with the translation of said mRNA and wherein the plant or plant cell is resistant to the insect as compared with an untransformed plant.

According to still another embodiment the present invention relates to a transgenic plant or plant cell comprising an interfering nucleic acid (RNA or double stranded RNA) that is at least 75% preferably at least 80%, 85%, 90%, 95%, 98%, 99% or 100% complementary to a part of at least 17, 18, 19, 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides of or all of a mRNA encoding an insect Sec23 protein which is a GTPase activator involved in intracellular protein transport (e.g. an insect orthologue of the CG1250 Dm protein), and wherein the interfering nucleic acid inhibits or interferes with the translation of said mRNA and wherein the plant or plant cell is resistant to the insect as compared with an untransformed plant.

According to still another embodiment the present invention relates to a transgenic plant or plant cell comprising an interfering nucleic acid (RNA or double stranded RNA) that is at least 75% preferably at least 80%, 85%, 90%, 95%, 98%, 99% or 100% complementary to a part of at least 17, 18, 19, 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides of or all of a mRNA encoding an insect crinkled protein which is an unconventional myosin which is involved in motor activity (e.g. an insect orthologue of the CG7595 Dm protein), and wherein the interfering nucleic acid inhibits or interferes with the translation of said mRNA and wherein the plant or plant cell is resistant to the insect as compared with an untransformed plant.

According to still another embodiment the present invention relates to a transgenic plant or plant cell comprising an interfering nucleic acid (RNA or double stranded RNA) that is at least 75% preferably at least 80%, 85%, 90%, 95%, 98%, 99% or 100% complementary to a part of at least 17, 18, 19, 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides of or all of a mRNA encoding an insect crooked neck protein which is involved in the regulation of nuclear alternative mRNA splicing (e.g. an insect orthologue of the CG3193 Dm protein), and wherein the interfering nucleic acid inhibits or interferes with the translation of said mRNA and wherein the plant or plant cell is resistant to the insect as compared with an untransformed plant.

According to still another embodiment the present invention relates to a transgenic plant or plant cell comprising an interfering nucleic acid (RNA or double stranded RNA) that is at least 75% preferably at least 80%, 85%, 90%, 95%, 98%, 99% or 100% complementary to a part of at least 17, 18, 19, 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides of or all of a mRNA encoding an insect vacuolar H+-ATPase G-subunit protein (e.g. an insect orthologue of the CG6213 Dm protein), and wherein the interfering nucleic acid inhibits or interferes with the translation of said mRNA and wherein the plant or plant cell is resistant to the insect as compared with an untransformed plant.

According to still another embodiment the present invention relates to a transgenic plant or plant cell comprising an interfering nucleic acid (RNA or double stranded RNA) that is at least 75% preferably at least 80%, 85%, 90%, 95%, 98%, 99% or 100% complementary to a part of at least 17, 18, 19, 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides of or all of a mRNA encoding an insect Tbp-1; Tat-binding protein (e.g. an insect orthologue of the CG10370 Dm protein), and wherein the interfering nucleic acid inhibits or interferes with the translation of said mRNA and wherein the plant or plant cell is resistant to the insect as compared with an untransformed plant.

BRIEF DESCRIPTION OF THE TABLES AND FIGURES

Table 1 Polynucleotide sequences of target genes identified in *Leptinotarsa decemlineata* (Colorado potato beetle, CPB).

Table 2 Amino acid sequences of target genes identified in *Leptinotarsa decemlineata* (Colorado potato beetle, CPB).

Table 3 Polynucleotide sequences of target genes identified in *Lygus hesperus*.

Table 4 Amino acid sequences of target genes identified in *Lygus hesperus*.

Table 5 dsRNAs (sense strand represented by equivalent DNA sequence) corresponding to *Leptinotarsa decemlineata* target genes.

Table 6 dsRNAs (sense strand represented by equivalent DNA sequence) corresponding to *Lygus hesperus* target genes.

Table 7 Effects of dsRNAs derived from different target genes on time taken to kill 50% ($LT_{50}$) of CPB larvae expressed as ratios versus the effect of a dsRNA derived from reference target gene Ld248 (SEQ ID NO 40).

Table 8 Effects of dsRNAs derived from different target genes on time taken to kill 50% ($LT_{50}$) of CPB adults expressed as ratios versus the effect of a dsRNA derived from reference target gene Ld248 (SEQ ID NO 40).

Table 9 Effects of dsRNAs derived from different target genes on CPB egg production.

Abbreviations: EM, normal egg masses; SE, single eggs; YS, yellow smear; none, no eggs.

Table 10 Survival analyses of target dsRNAs versus GFP dsRNA in the presence of tRNA in a *Lygus hesperus* nymph feeding assay. Log-rank test used to test the differences between the survival curves of the target dsRNA (or diet only) and GFP dsRNA generated using Kaplan-Meier estimates.

Table 11 Ranking of different target genes according to potency.

Table 12 Comparison of survival curves of test targets at 0.1, 0.05, or 0.025 μg/μL with GFP dsRNA at 0.1 μg/μL. Statistics were performed on data graphically represented in FIG. 5. *: P-value≤0.001; : 0.001<P-value≤0.01; *: 0.01<P-value≤0.05; ns: not significant, P-value>0.05.

Table 13 *Lygus* targets for which full length cDNAs were cloned.

Table 14 Full length polynucleotide sequences of target genes identified in *Lygus hesperus*.

Table 15 Corresponding amino acid sequences to full length cDNAs of target genes identified in *Lygus hesperus*.

FIG. 1 Effects of dsRNAs derived from different target genes on survival and fitness of CPB adults. For each target gene investigated, 10 young adult beetles were individually fed target dsRNA-treated potato leaf discs (total of 10 μg dsRNA) for the first 24 hours and thereafter placed together on untreated potato foliage. The numbers of dead or moribund insects were assessed over a 14-day period. Data are presented as percentage mortality or moribundity. GFP dsRNA (SEQ ID NO 245) was used as a control. Ld105 dsRNA (SEQ ID NO 39), Ld248 dsRNA (SEQ ID NO 40), Ld516 dsRNA (SEQ ID NO 29), Ld511 dsRNA (SEQ ID NO 36), Ld512 dsRNA (SEQ ID NO 37), Ld513 dsRNA (SEQ ID NO 22), Ld520 dsRNA (SEQ ID NO 24), Ld537 dsRNA (SEQ ID NO 25), Ld563 dsRNA (SEQ ID NO 38), Ld579 dsRNA (SEQ ID NO 30).

Figure 2:
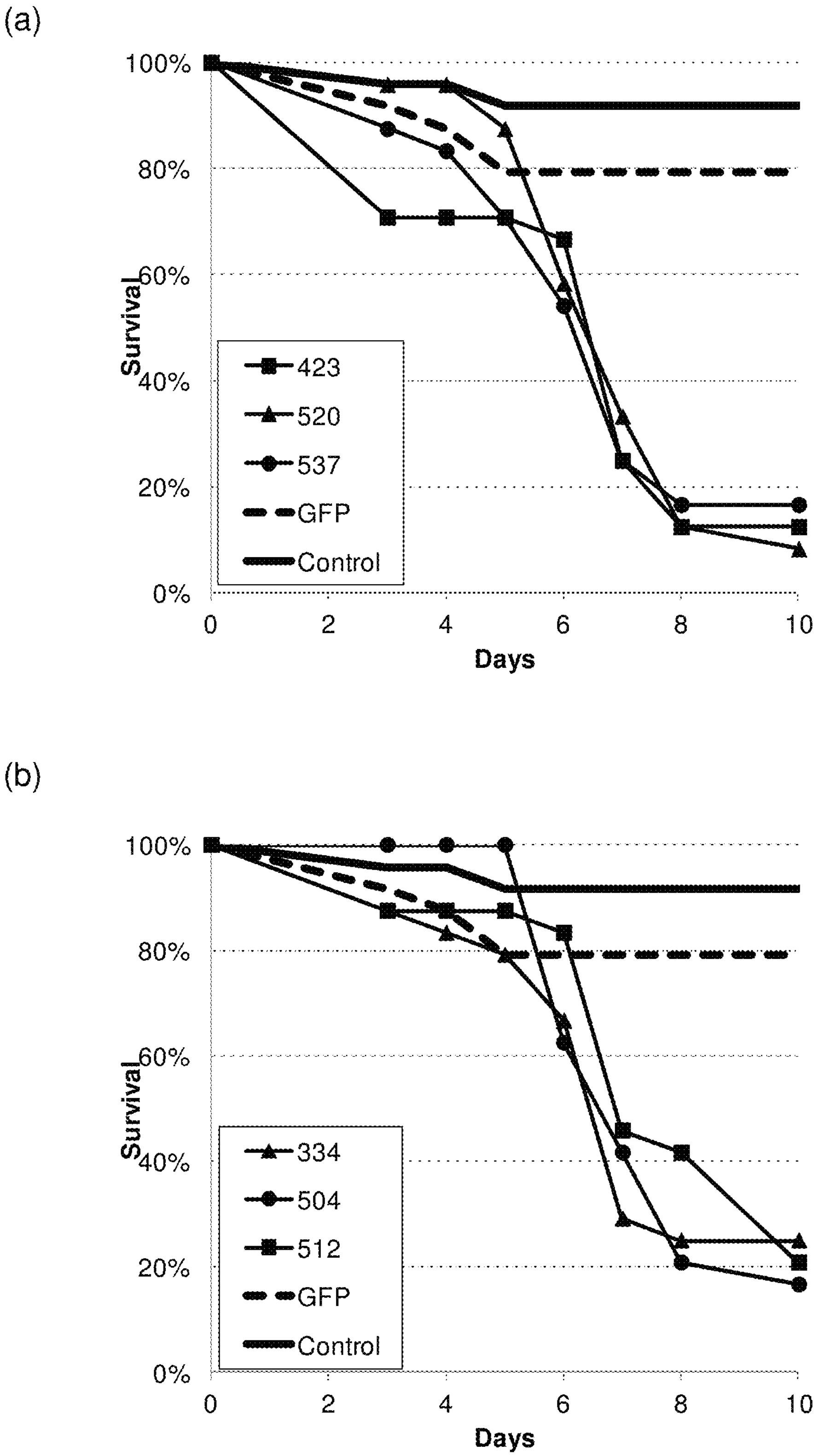
Figure 2:
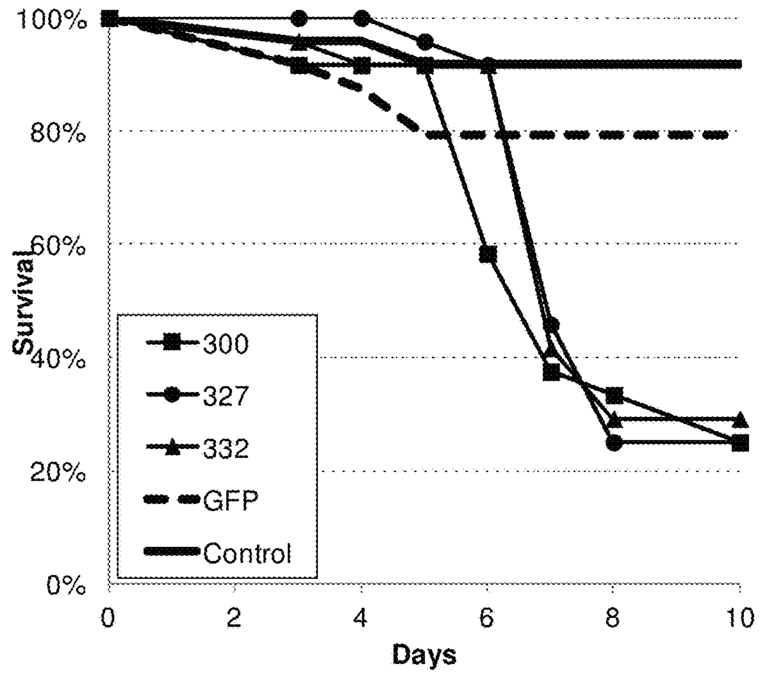
Figure 2:
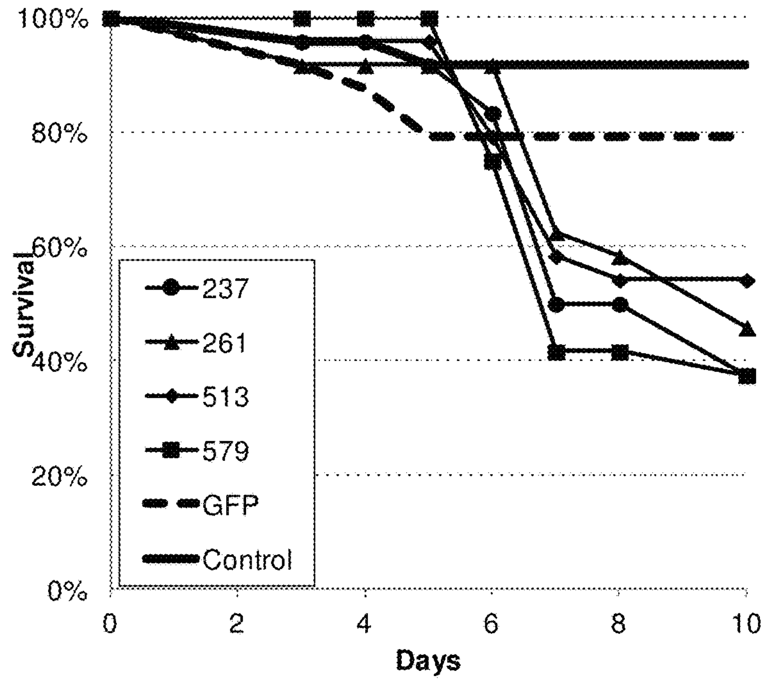

FIG. 2 Survival curves for *Lygus hesperus* nymphs exposed to 0.5 μg/μL target dsRNA in the presence of 5 μg/μL yeast tRNA in a feeding assay. (a) Targets: Lh520 (SEQ ID NO 143), Lh423 (SEQ ID NO 152), Lh537 (SEQ ID NO 144), (b) Targets: Lh504.2 (SEQ ID NO 142), Lh512 (SEQ ID NO 153), Lh334 (SEQ ID NO 145), (c) Targets: Lh300.1 (SEQ ID NO 151), Lh327 (SEQ ID NO 146), Lh332 (SEQ ID NO 148), (d) Targets: Lh237 (SEQ ID NO 149), Lh579 (SEQ ID NO 147), Lh261 (SEQ ID NO 150), Lh513 (SEQ ID NO 141). GFP dsRNA plus yeast tRNA at the same concentrations, respectively, and diet-only treatments were used as controls. Young nymphs were each exposed to 25 μL of 15% sucrose diet with or without incorporated test components for three days prior to transferring them on to 50 μL Biosery diet. Complex diet was refreshed on day 7. For all treatments, n=24.

Figure 3:
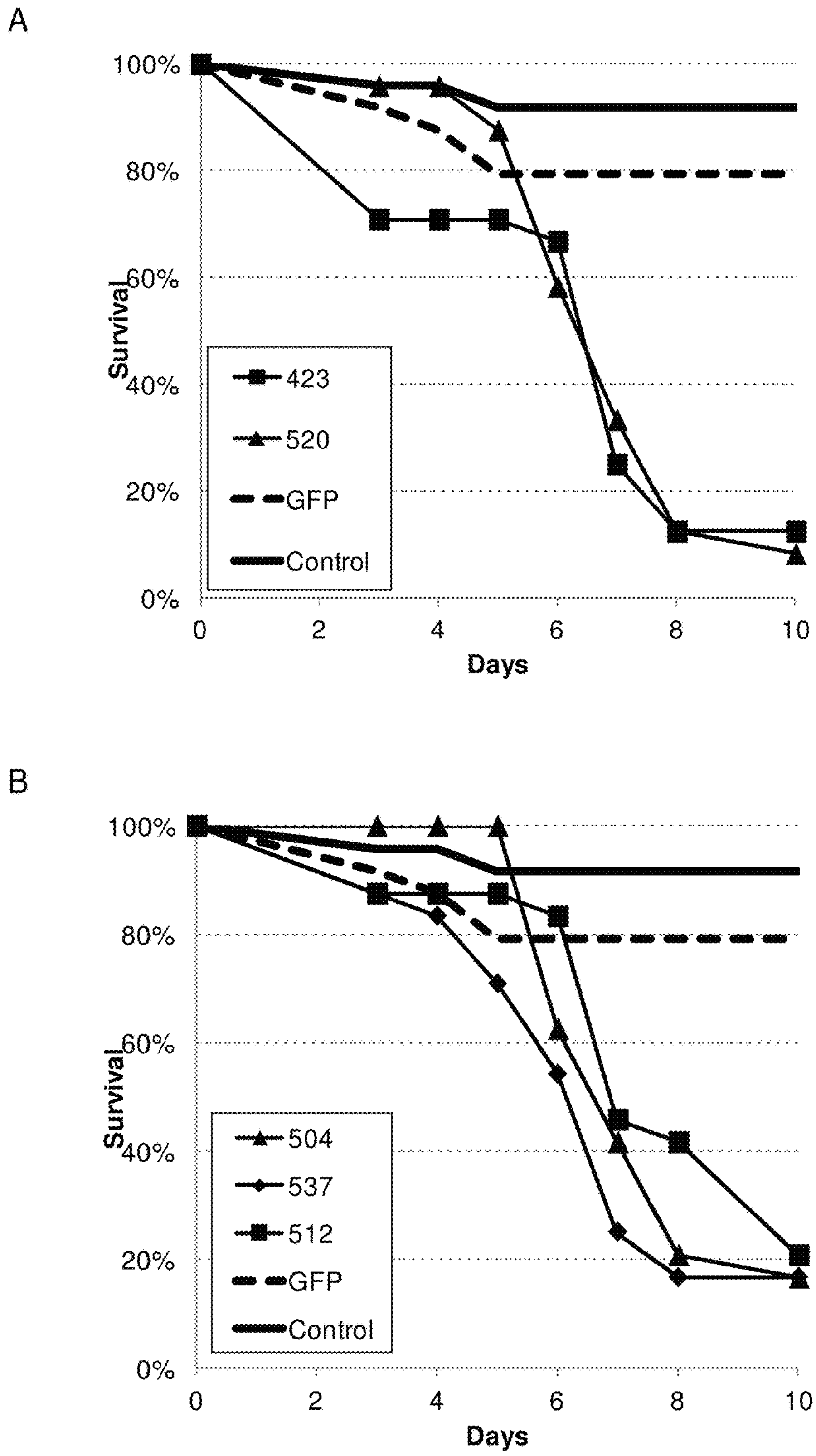
Figure 3:
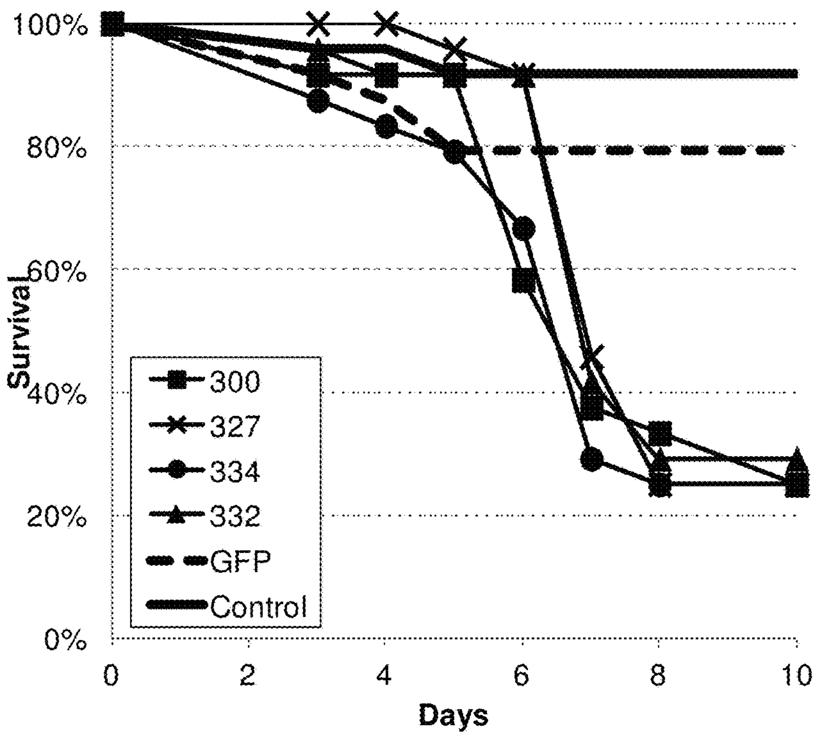
Figure 3:
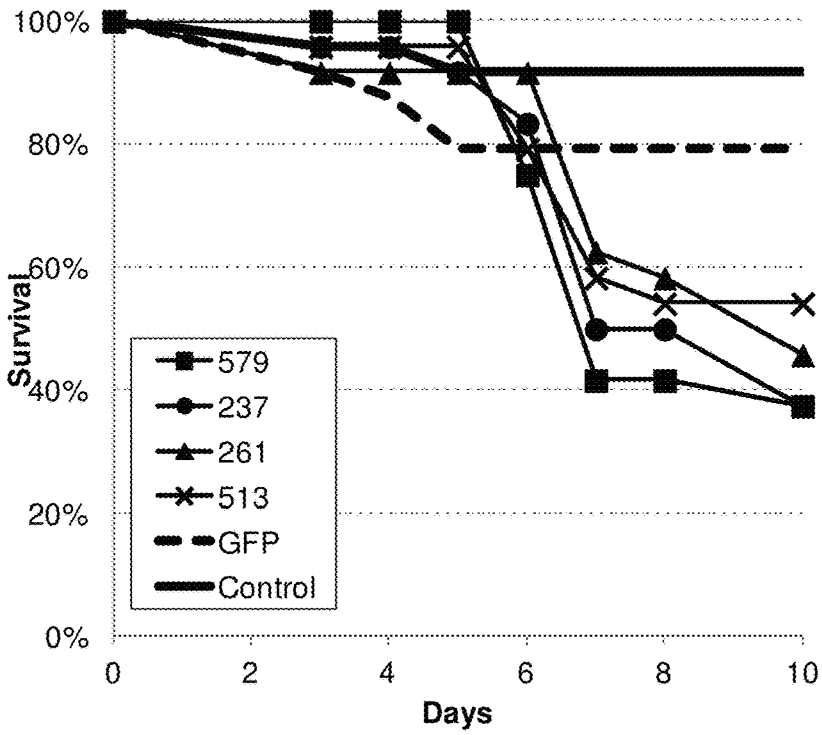

FIG. 3 Survival curves for *Lygus hesperus* nymphs exposed to 0.5 μg/μL target dsRNA in the presence of 5 μg/μL yeast tRNA in a feeding assay, wherein the targets are grouped in A, B, C, D according to potency. Set-up described as in FIG. 2.

Figure 4:
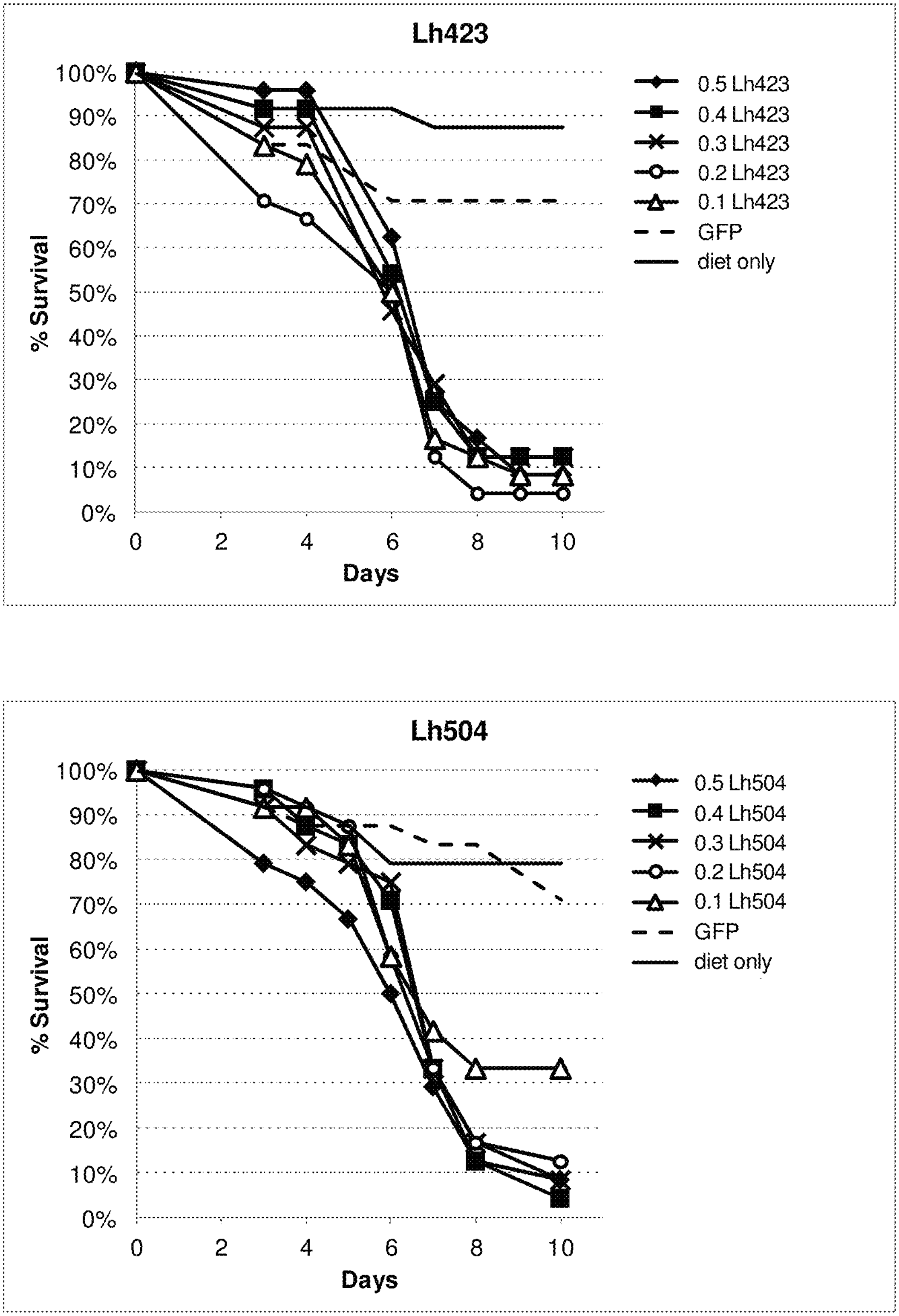
Figure 4:
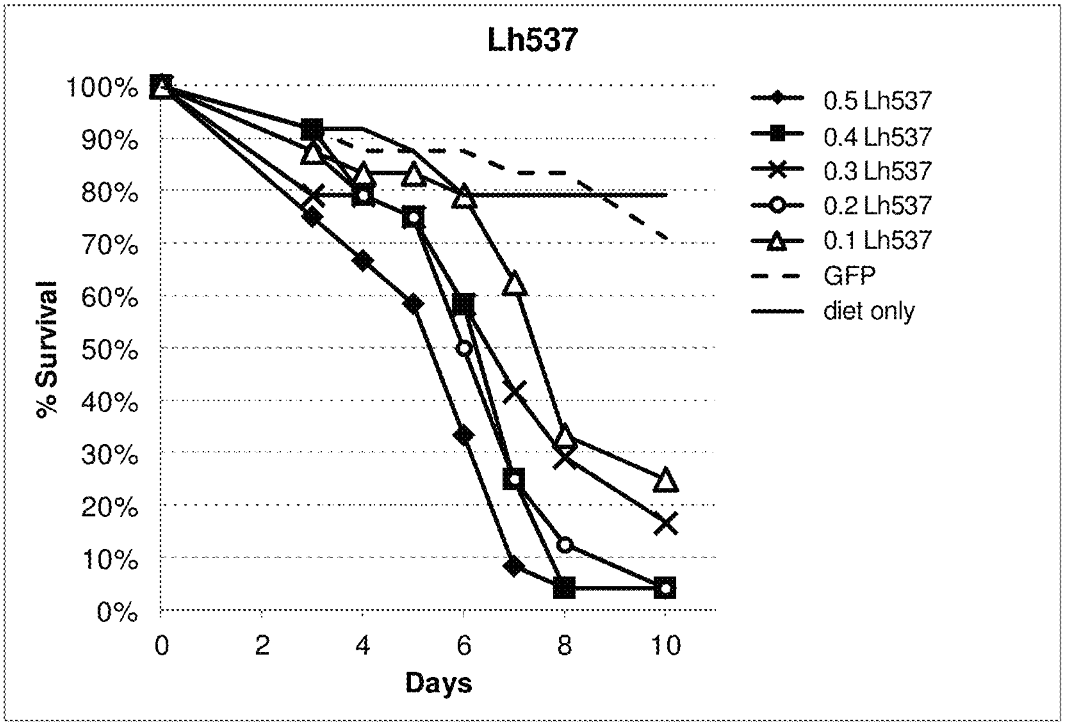
Figure 4:
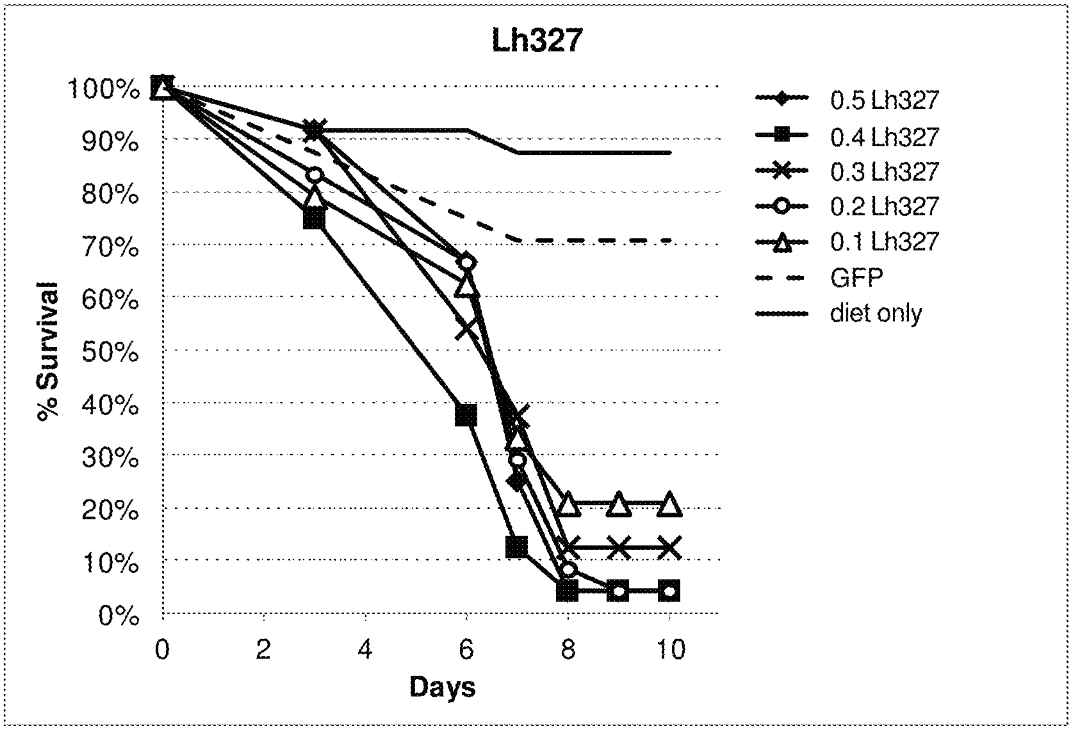
Figure 4:
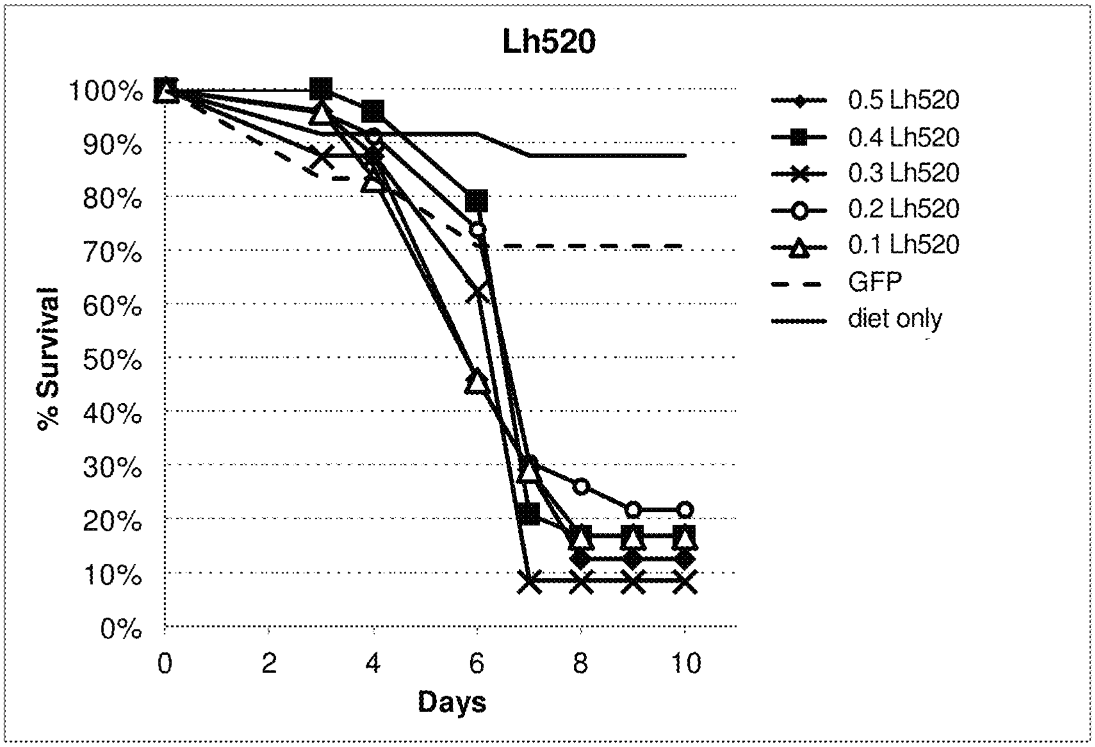
Figure 4:
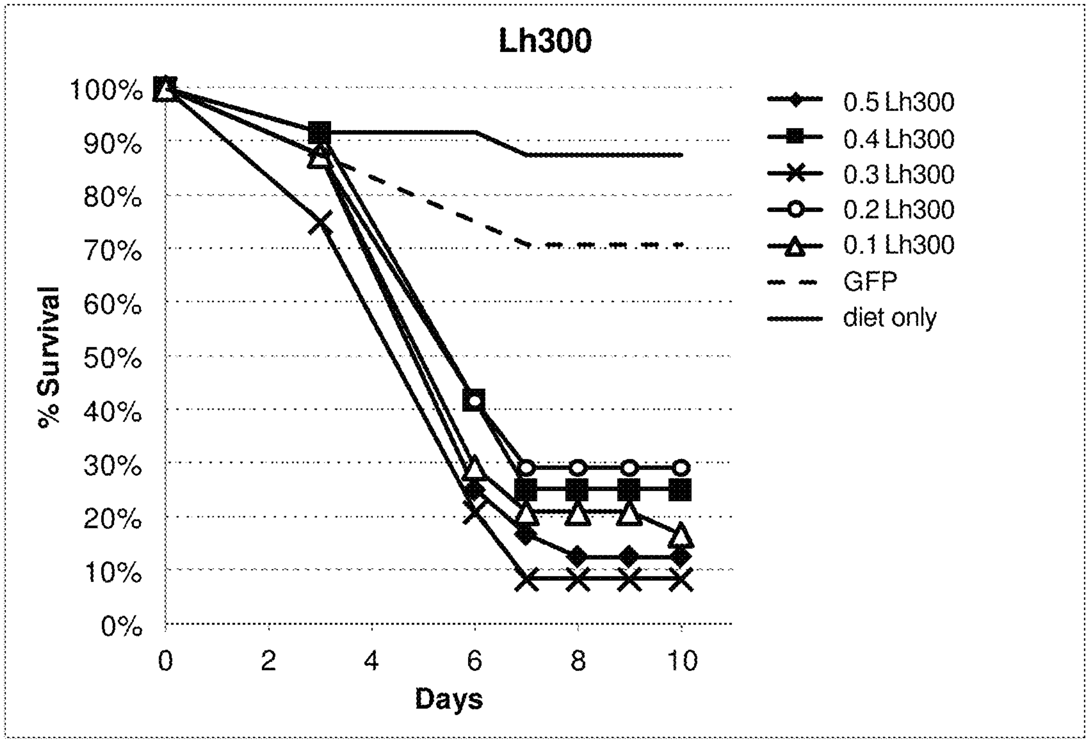

FIG. 4 Survival curves over time of *Lygus hesperus* nymphs exposed to lowering concentrations (from 0.5 to 0.1 μg/μL) of novel target dsRNA in the presence of yeast transfer RNA (5 μg/μL) in feeding bioassays. Each treatment in a bioassay consisted of 24 one-day-old nymphs placed individually in every well of a 24-well plate. Each nymph was exposed to a parafilm sachet containing the ribonucleic acids in a solution of 15% sucrose for a duration of 3 days. On days 3 and 7, the diets were replaced with fresh rearing (Bioserv) diet. The following controls were included in the assays: GFP dsRNA and diet only.

Figure 5:
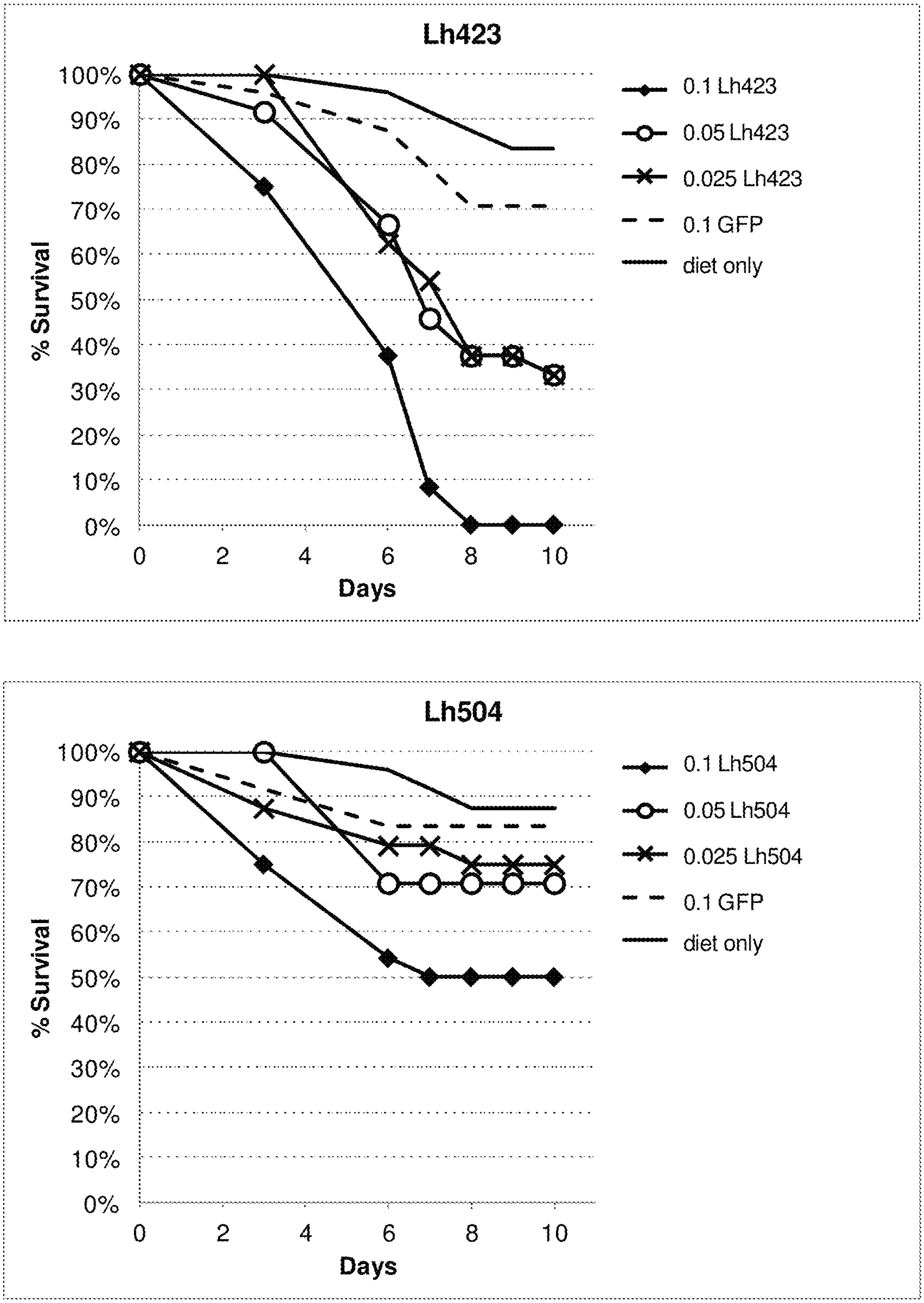
Figure 5:
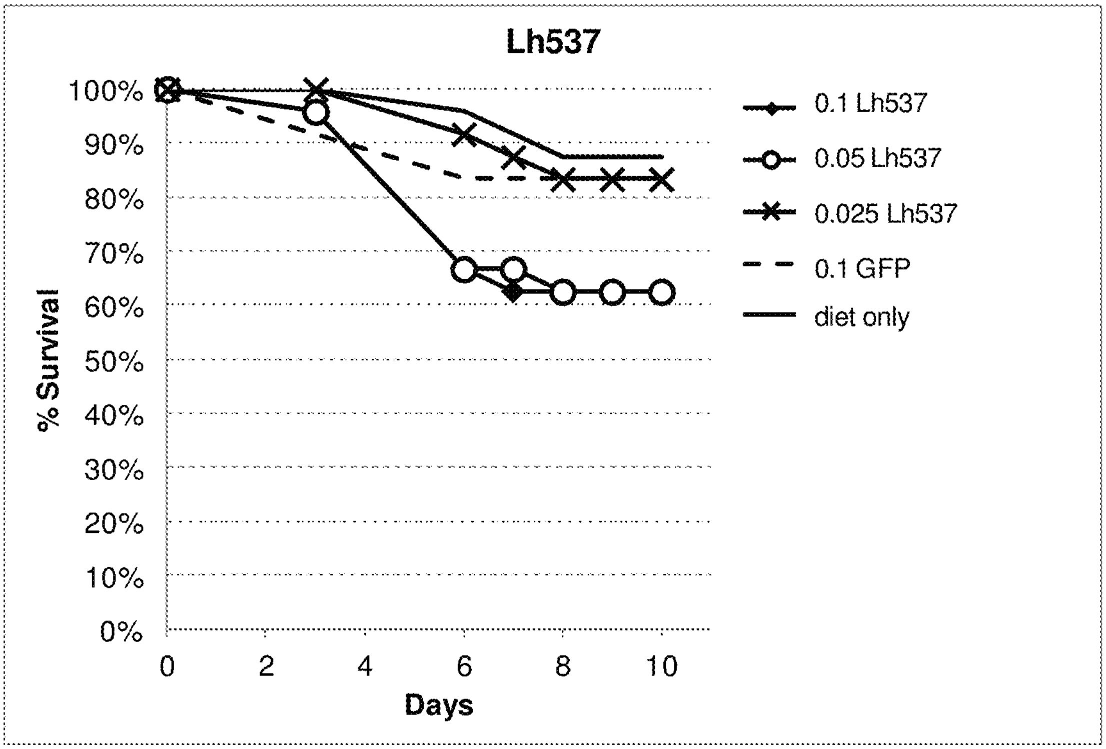
Figure 5:
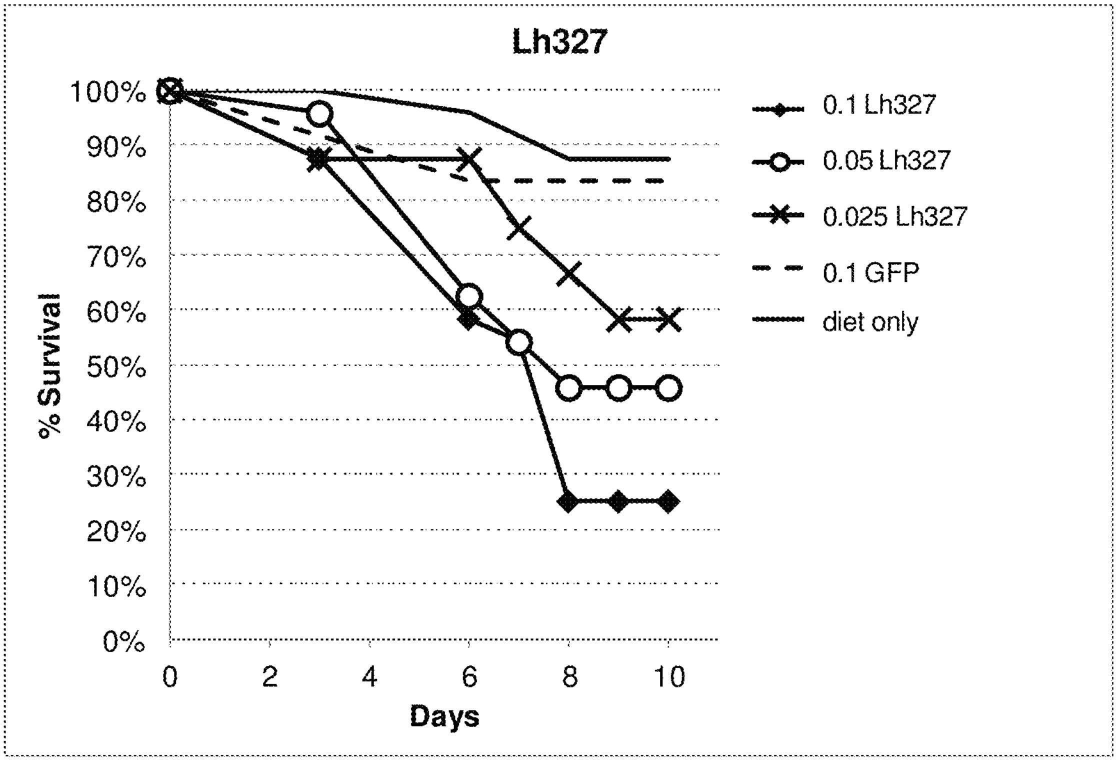
Figure 5:
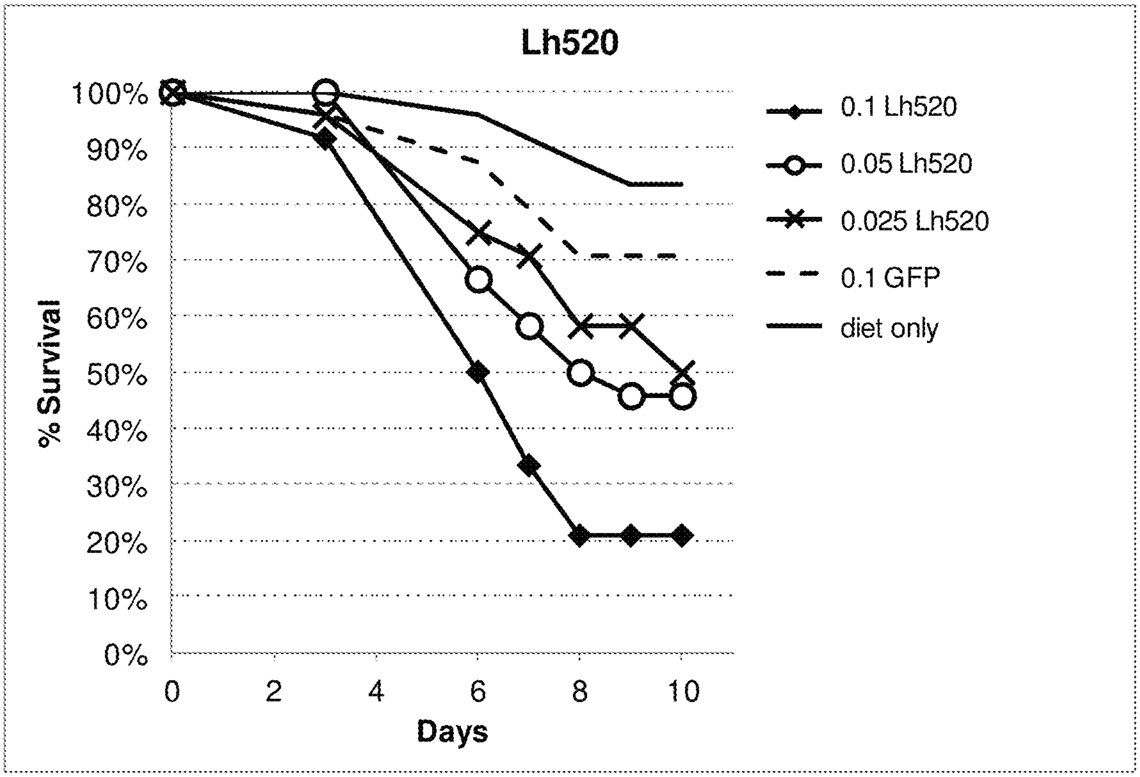
Figure 5:
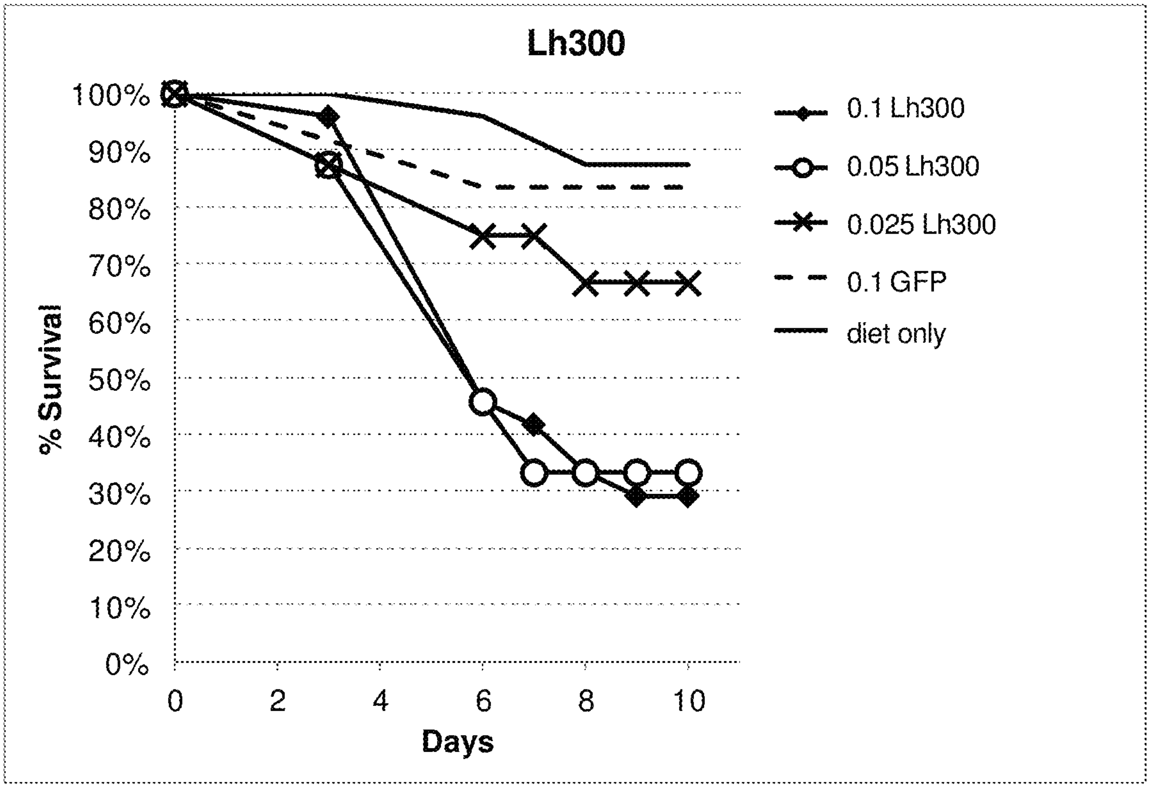

FIG. 5 Survival curves over time of *Lygus hesperus* nymphs exposed to lowering concentrations (from 0.1 to 0.025 μg/μL) of novel target dsRNA in the presence of yeast transfer RNA (5 μg/μL) in feeding bioassays. Set-up described similarly as in FIG. 4.

Figure 6:
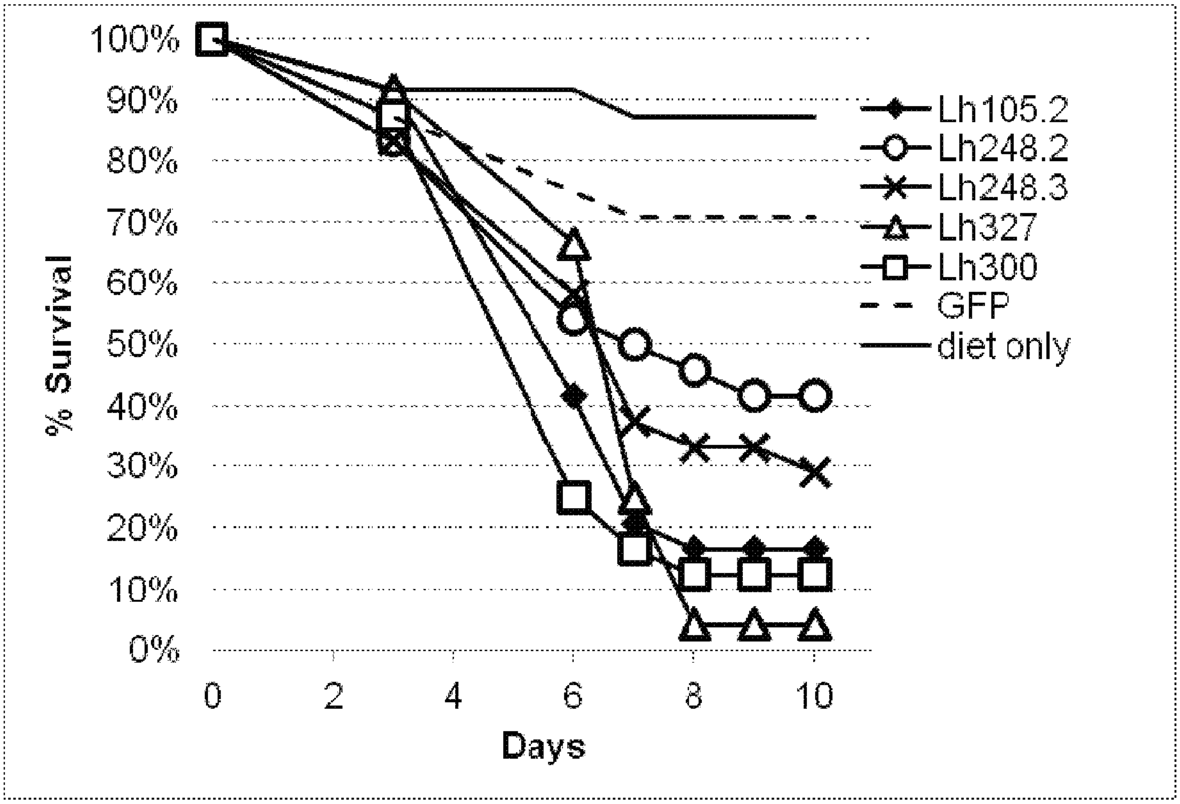

FIG. 6 Survival curves over time of *Lygus hesperus* nymphs exposed to 0.5 μg/μL of target dsRNA in the presence of yeast transfer RNA (5 μg/μL) in feeding bioassays. Target dsRNA tested: Lh105.2 (SEQ ID NO 254), Lh248.2 (SEQ ID NO 255), Lh248.3 (SEQ ID NO 256), Lh327 (SEQ ID NO 146) and Lh300 (SEQ ID NO 151). Set-up described similarly as in FIG. 4.

Figure 7:
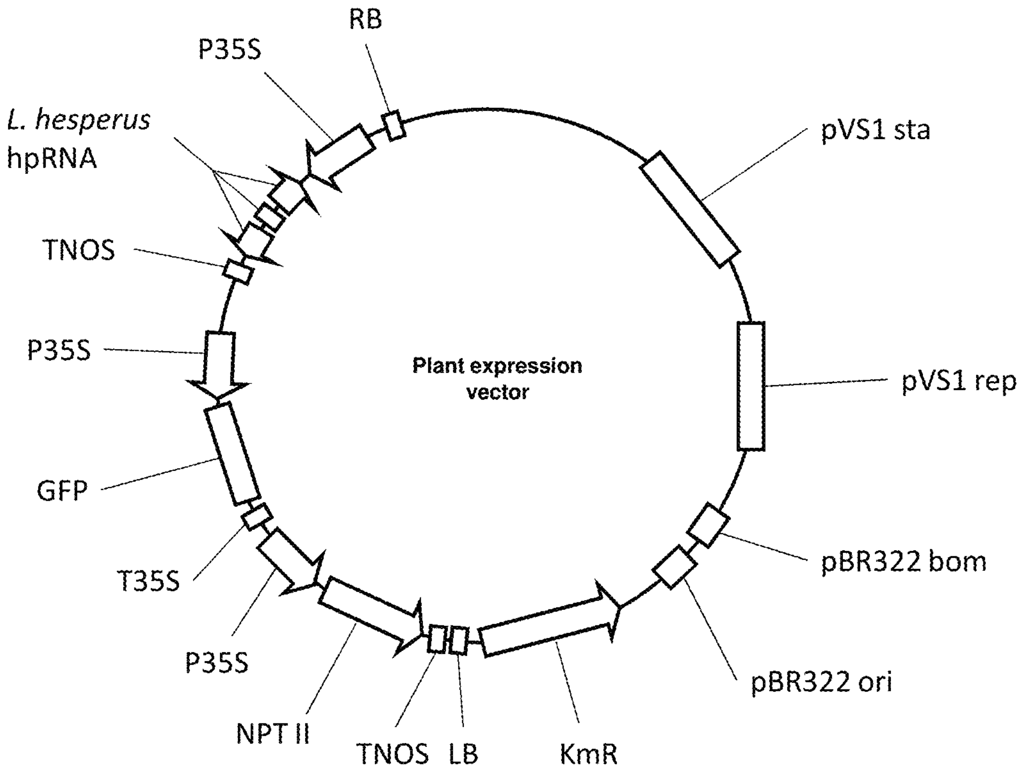

FIG. 7 Schematic representation of the plant expression vector harbouring the *Lygus hesperus* hpRNA cassette. RB: right border; LB: left border; P35S: Cauliflower Mosaic Virus 35S promoter; T35S: Cauliflower Mosaic Virus 35S terminator; TNOS: nopaline synthase terminator; GFP: green fluorescent reporter gene; NPT II: coding sequence of neomycin phosphotransferase II gene; KmR: Kanamycin resistance gene; pBR322 ori: pBR322 origin of replication; pBR322 bom: pBR322 mobilization; pVS1 rep: pVS1 replicon; pVS1 sta: pVS1 stability element.

Figure 8:
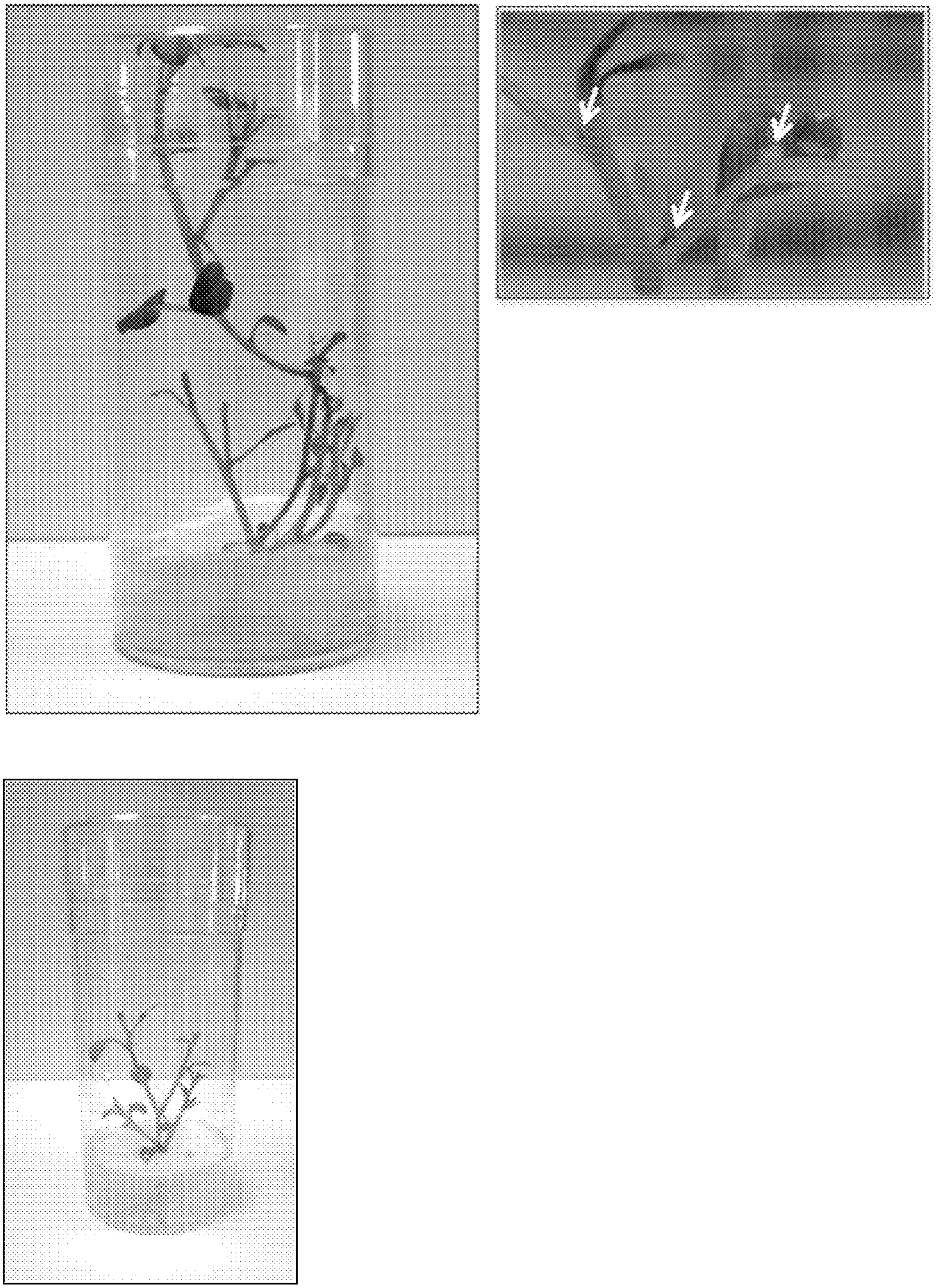

FIG. 8: Potato-*Lygus* in planta assay set up. White arrows indicate insect damage.

Figure 9:
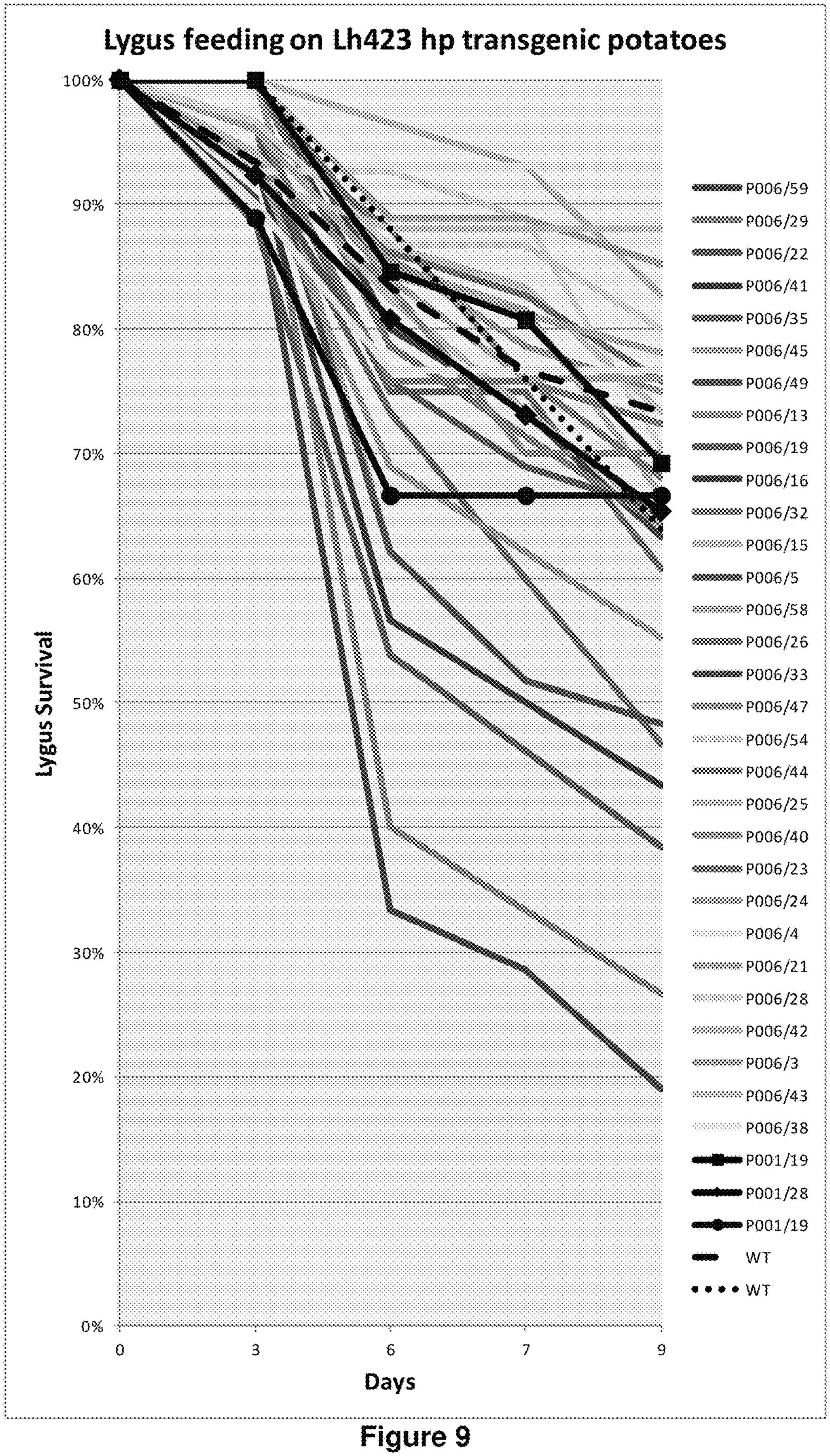

FIG. 9 *Lygus* feeding assays on transgenic potatoes, expressing Lh423 hairpin. Survival rate of *Lygus* nymphs feeding on transgenic potatoes carrying Lh423 hairpin (P006/XX) or a GUS hairpin (P001/XX). Wild type (WT) potatoes were also used as control.

Figure 10:
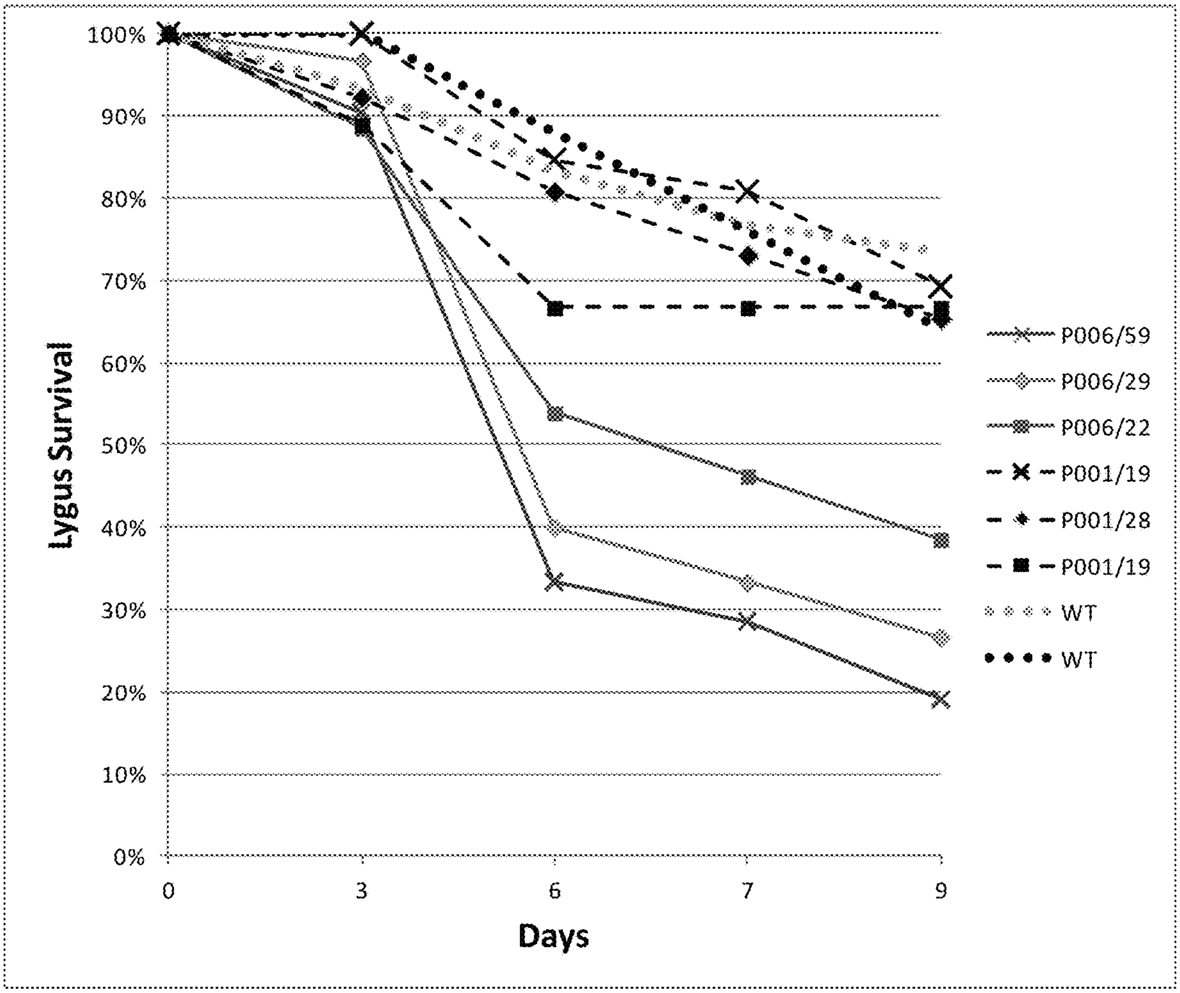

FIG. 10 *Lygus* feeding assays on positive transgenic potatoes, expressing Lh423 hairpin. Survival rate of *Lygus* nymphs feeding on transgenic potatoes carrying Lh423 hairpin (P006/59, P006/29 and P006/22) or a GUS hairpin (P001/19, P001/28). Wild type (WT) potatoes were also used as control. Statistical analysis results, based on Graph Pad survival curve analysis: ***=P<0.001; *=0.01<P<0.05.

DETAILED DESCRIPTION OF THE INVENTION

The present inventors have discovered that down-regulating the expression of particular target genes in insect pest species by RNAi can be used to effectively prevent and/or control infestation by said insect pest. As used herein, the term "control" of pest infestation refers to any effect on a pest that serves to limit and/or reduce either the numbers of pest organisms and/or the damage caused by the pest. Preferred target genes are therefore essential genes that control or regulate one or more essential biological functions within the insect pest, for example, cell division, reproduction, energy metabolism, digestion, neurological function and the like. Down-regulation of these essential genes by RNAi techniques can lead to death of the insect, or otherwise significantly retard growth and development or impair the ability of the pest to colonize an environment or infest host organisms.

Thus, in a first aspect, the invention provides an interfering ribonucleic acid (RNA) that functions upon uptake by an insect pest species to down-regulate expression of a target gene in said insect pest.

As used herein, a "target gene" comprises any gene in the insect pest which one intends to down-regulate. In a preferred embodiment, the target gene is down-regulated so as to control pest infestation, for example by disrupting an essential biological process occurring in the pest, or by decreasing the pathogenicity of the pest. Preferred target genes therefore include but are not limited to those that play key roles in regulating feeding, survival, growth, development, reproduction, infestation and infectivity. According to one embodiment, the target gene is such that when its expression is down-regulated or inhibited, the insect pest is killed. According to another embodiment, the target gene is such that when its expression is down-regulated or inhibited, growth of the pest is prevented or retarded or stunted or delayed or impeded or pest reproduction is prevented. According to yet another embodiment of the invention, the target gene is such that when its expression is down-regulated or inhibited, the damage caused by the pest and/or the ability of the pest to infect or infest environments, surfaces and/or plant or crop species is reduced; or the pest stops feeding from its natural food resources such as plants and plant products. The terms "infest" and "infect" or "infestation" and "infection" are generally used interchangeably throughout.

The target genes may be expressed in all or some of the cells of the insect pest. Furthermore, the target genes may only be expressed by the insect pest at a particular stage of its life-cycle, for example, the mature adult phase, immature nymph or larval phase or egg phase.

In specific embodiments, the present invention provides target genes which encode proteins involved in the function of a proteasome (subunit or regulatory particle), ribosomal protein, intracellular protein transport, COPI vesicle (coat protein complex), protein modification process, cytoskeleton, ATPase or GTPase activator activity (specified in Tables 7 and 8).

In preferred embodiments, the present invention provides target genes selected from the group of genes having a nucleotide sequence comprising any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or having a nucleotide sequence that, when the two sequences are optimally aligned and compared, is at least 75%, preferably at least 80%, 85%, 90%, 95%, 98% or 99% identical any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or having a nucleotide sequence consisting of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or having a nucleotide sequence comprising a fragment of at least 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or having a nucleotide sequence that, when said gene comprising said fragment is optimally aligned and compared with any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, said nucleotide sequence is at least 75% preferably at least 80%, 85%, 90%, 95%, 98% or 99% identical to any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or having a nucleotide sequence comprising a fragment of at least 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, and wherein when said fragment is optimally aligned and compared with the corresponding fragment in any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, said nucleotide sequence of said fragment is at least 75% preferably at least 80%, 85%, 90%, 95%, 98% or 99% identical to said corresponding fragment of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or which gene is an insect pest orthologue of a gene having a nucleotide sequence comprising any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or having a nucleotide sequence encoding an amino acid sequence that, when the two amino acid sequences are optimally aligned and compared, is at least 70% preferably at least 75%, 80%, 85%, 90%, 95%, 98% or 99% identical to the amino acid sequence encoded by the nucleotide sequence represented by any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40 or having a nucleotide sequence encoding an amino acid sequence that, when the two amino acid sequences are optimally aligned and compared, is at least 70% preferably at least 75%, 80%, 85%, 90%, 95%, 98% or 99% identical to the amino acid sequence represented in any of SEQ ID NOs 285, 242, 271, 226, 227, 281, 228, 282, 229, 230 to 233, 234, 283, 235, 236, 237, 238, 239, 240, 284, 241, 243, 244, 286, 269, 270, 287, 288, 206 to 225; and wherein the nucleotide sequence of said gene is no longer than 5000, 4000, 3000, 2000 or 1500 nucleotides.

As used herein, the term "sequence identity" is used to describe the sequence relationship between two or more nucleotide or amino acid sequences. The percentage of "sequence identity" between two sequences is determined by comparing two optimally aligned sequences over a comparison window (a defined number of positions), wherein the portion of the sequence in the comparison window may comprise additions or deletions (i.e. gaps) as compared to the reference sequence in order to achieve optimal alignment. The percentage sequence identity is calculated by determining the number of positions at which the identical nucleotide base or amino acid residue occurs in both sequences to yield the number of 'matched' positions, dividing the number of matched positions by the total number of positions in the comparison window and multiplying the result by 100. For comparison of two optimally aligned sequences, the comparison window will be determined by the full length of the aligned regions. Methods and software for determining sequence identity are available in the art and include the Blast software and GAP analysis. For nucleic acids, the percent identity is calculated preferably by the BlastN alignment tool whereby the percent identity is calculated over the entire length of the query nucleotide sequence.

A person skilled in the art will recognise that homologues or orthologues (homologues existing in different species) of the target genes represented by any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40 can be identified. These pest homologues and/or orthologues are also within the scope of the current invention. Preferred homologues and/or orthologues are genes similar in sequence to such a degree that when the two genes are optimally aligned and compared, the homologue and/or orthologue has a sequence that is at least 75%, preferably at least 80% or 85%, more preferably at least 90% or 95%, and most preferably at least about 99% identical to any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40 or the complement thereof.

Other homologues are genes which are alleles of a gene comprising a sequence as represented by any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40. Further preferred homologues are genes comprising at least one single nucleotide polymorphism (SNP) compared to a gene comprising a sequence as represented by any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40.

The 'interfering ribonucleic acid (RNA)' of the current invention encompasses any type of RNA molecule capable of down-regulating or 'silencing' expression of a target gene, including but not limited to sense RNA, antisense RNA, short interfering RNA (siRNA), microRNA (miRNA), double-stranded RNA (dsRNA), short hairpin RNA (shRNA) and the like. Methods to assay for functional interfering RNA molecules are well known in the art and are disclosed elsewhere herein.

The interfering RNA molecules of the current invention effect sequence-specific down-regulation of expression of a target gene by binding to a target nucleotide sequence within the target gene. Binding occurs as a result of base pairing between complementary regions of the interfering RNA and the target nucleotide sequence. As used herein, the term 'silencing element' refers to the portion or region of the interfering RNA comprising or consisting of a sequence of nucleotides which is complementary, or at least partially complementary, to a target nucleotide sequence within the target gene, and which functions as the active portion of the interfering RNA to direct down-regulation of expression of said target gene. In one embodiment of the invention, the silencing element comprises or consists of a sequence of at least 17 contiguous nucleotides, preferably at least 18 or 19 contiguous nucleotides, more preferably at least 21 contiguous nucleotides, even more preferably at least 22, 23, 24 or 25 contiguous nucleotides complementary to a target nucleotide sequence within the target gene.

As used herein, "expression of a target gene" refers to the transcription and accumulation of the RNA transcript encoded by a target gene and/or translation of the mRNA into protein. The term 'down-regulate' is intended to refer to any of the methods known in the art by which interfering RNA molecules reduce the level of primary RNA transcripts, mRNA or protein produced from a target gene. In certain embodiments, down-regulation refers to a situation whereby the level of RNA or protein produced from a gene is reduced by at least 10%, preferably by at least 33%, more preferably by at least 50%, yet more preferably by at least 80%. In particularly preferred embodiments, down-regulation refers to a reduction in the level of RNA or protein produced from a gene by at least 80%, preferably by at least 90%, more preferably by at least 95%, and most preferably by at least 99% within cells of the insect pest as compared with an appropriate control insect pest which has for example, not been exposed to an interfering RNA or has been exposed to a control interfering RNA molecule. Methods for detecting reductions in RNA or protein levels are well known in the art and include RNA solution hybridization, Northern hybridization, reverse transcription (e.g. quantitative RT-PCR analysis), microarray analysis, antibody binding, enzyme-linked immunosorbent assay (ELISA) and Western blotting. In another embodiment of the invention, down-regulation refers to a reduction in RNA or protein levels sufficient to result in a detectable change in a phenotype of the pest as compared with an appropriate pest control, for example, cell death, cessation of growth, or the like. Down-regulation can thus be measured by phenotypic analysis of the insect pest using techniques routine in the art.

In a preferred embodiment of the invention, the interfering RNA down-regulates gene expression by RNA interference or RNAi. RNAi is a process of sequence-specific gene regulation typically mediated by double-stranded RNA molecules such as short interfering RNAs (siRNAs). siRNAs comprise a sense RNA strand annealed by complementary basepairing to an antisense RNA strand. The sense strand or 'guide strand' of the siRNA molecule comprises a sequence of nucleotides complementary to a sequence of nucleotides located within the RNA transcript of the target gene. The sense strand of the siRNA is therefore able to anneal to the RNA transcript via Watson-Crick-type basepairing and target the RNA for degradation within a cellular complex known as the RNAi-induced silencing complex or RISC. Thus, in the context of preferred interfering RNA molecules of the current invention, the silencing element as referred to herein may be a double-stranded region comprising annealed complementary strands, at least one strand of which comprises or consists of a sequence of nucleotides which is complementary or at least partially complementary to a target nucleotide sequence within a target gene. In one embodiment the double-stranded region has a length of at least 21, 22, 23, 24, 25, 30, 35, 40, 50, 55, 60, 70, 80, 90, 100, 125, 150, 175, 200 base pairs.

Longer double-stranded RNA (dsRNA) molecules comprising one or more functional double-stranded silencing elements as described elsewhere herein, and capable of RNAi-mediated gene silencing are also contemplated within the scope of the current invention. Such longer dsRNA molecules comprise at least 80, 200, 300, 350, 400, 450, 500, 550, 600, 700, 800, 900, 1000 or 1100 base pairs. These dsRNA molecules may serve as precursors for the active siRNA molecules that direct the RNA transcript to the RISC complex for subsequent degradation. dsRNA molecules present in the environment surrounding an organism or the cells thereof may be taken up by the organism and processed by an enzyme called Dicer to yield siRNA molecules. Alternatively, the dsRNA may be produced in vivo i.e. transcribed from a polynucleotide or polynucleotides encoding the same present within a cell, for instance a bacterial cell or a plant cell, and subsequently processed by Dicer either within the host cell or preferably within the insect pest cells following uptake of the longer precursor dsRNA. The dsRNA may be formed from two separate (sense and antisense) RNA strands that anneal by virtue of complementary basepairing. Alternatively, the dsRNA may be a single strand that is capable of folding back on itself to form a short hairpin RNA (shRNA) or stem-loop structure. In the case of a shRNA, the double-stranded region or 'stem' is formed from two regions or segments of the RNA that are essentially inverted repeats of one another and possess sufficient complementarity to allow the formation of a double-stranded region. One or more functional double-stranded silencing elements may be present in this 'stem region' of the molecule. The inverted repeat regions are typically separated by a region or segment of the RNA known as the 'loop' region. This region can comprise any nucleotide sequence conferring enough flexibility to allow self-pairing to occur between the flanking complementary regions of the RNA. In general, the loop region is substantially single-stranded and acts as a spacer element between the inverted repeats.

All the interfering RNA molecules of the invention effect sequence-specific down-regulation of expression of a target gene by binding to a target nucleotide sequence within the target gene. Binding occurs as a result of complementary base pairing between the silencing element of the interfering RNA and the target nucleotide sequence. In one embodiment of the current invention, the target nucleotide sequence comprises a sequence of nucleotides as represented by the RNA transcript of the target gene, or a fragment thereof wherein the fragment is preferably at least 17 nucleotides, more preferably at least 18, 19 or 20 nucleotides, or most preferably at least 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000 or 1100 nucleotides. In a preferred embodiment of the current invention, the target nucleotide sequence comprises a sequence of nucleotides equivalent to the RNA transcript encoded by any of the polynucleotides selected from the group consisting of (i) a polynucleotide which comprises at least 21, preferably at least 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100 or 1115 contiguous nucleotides of a nucleotide sequence as represented by any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120, or the complement thereof, or (ii) a polynucleotide which consists of at least 21, preferably at least 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100 or 1115 contiguous nucleotides of a nucleotide sequence as represented by any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120, or the complement thereof, Or (iii) a polynucleotide which comprises at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100 or 1115 contiguous nucleotides of a nucleotide sequence as represented in any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120, or the complement thereof, that, when the two sequences are optimally aligned and compared, said polynucleotide is at least 75% preferably at least 80%, 85%, 90%, 95%, 98% or 99% identical to any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120, or the complement thereof, or (iv) a polynucleotide which comprises a fragment of at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100 or 1115 contiguous nucleotides of a nucleotide as represented in any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120, or the complement thereof, and wherein said fragment or said complement has a nucleotide sequence that, when said fragment is optimally aligned and compared with the corresponding fragment in any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120, said nucleotide sequence is at least 75% preferably at least 80%, 85%, 90%, 95%, 98% or 99% identical to said corresponding fragment of any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120 or the complement thereof, or (v) a polynucleotide which consists of a fragment of at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100 or 1115 contiguous nucleotides of a nucleotide as represented in any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120, or the complement thereof, and wherein said fragment or said complement has a nucleotide sequence that, when said fragment is optimally aligned and compared with the corresponding fragment in any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120, said nucleotide sequence is at least 75% preferably at least 80%, 85%, 90%, 95%, 98% or 99% identical to said corresponding fragment of any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120 or the complement thereof, or (vi) a polynucleotide encoding an amino acid sequence that, when the two amino acid sequences are optimally aligned and compared, is at least 70% preferably at least 75%, 80%, 85%, 90%, 95%, 98% or 99% identical to the amino acid sequence encoded by the nucleotide sequence represented in any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120, or (vii) a polynucleotide encoding an amino acid sequence that, when the two amino acid sequences are optimally aligned and compared, is at least 70% preferably at least 75%, 80%, 85%, 90%, 95%, 98% or 99% identical to the amino acid sequence represented in any of SEQ ID NOs 285, 242, 271, 226, 227, 281, 228, 282, 229, 230 to 233, 234, 283, 235, 236, 237, 238, 239, 240, 284, 241, 243, 244, 286, 269, 270, 287, 288, 206 to 225. In a more preferred embodiment of the above, said polynucleotide is no longer than 10000, 9000, 8000, 7000, 6000, 5000, 4000, 3000, 2000 or 1500 nucleotides.

Preferably, the interfering RNA molecules of the current invention comprise at least one double-stranded region, typically the silencing element of the interfering RNA, comprising a sense RNA strand annealed by complementary basepairing to an antisense RNA strand wherein the sense strand of the dsRNA molecule comprises a sequence of nucleotides complementary to a sequence of nucleotides located within the RNA transcript of the target gene.

The silencing element, or at least one strand thereof wherein the silencing element is double-stranded, may be fully complementary or partially complementary to the target nucleotide sequence of the target gene. As used herein, the term "fully complementary" means that all the bases of the nucleotide sequence of the silencing element are complementary to or 'match' the bases of the target nucleotide sequence. The term "at least partially complementary" means that there is less than a 100% match between the bases of the silencing element and the bases of the target nucleotide sequence. The skilled person will understand that the silencing element need only be at least partially complementary to the target nucleotide sequence in order to mediate down-regulation of expression of the target gene. It is known in the art that RNA sequences with insertions, deletions and mismatches relative to the target sequence can still be effective at RNAi. According to the current invention, it is preferred that the silencing element and the target nucleotide sequence of the target gene share at least 80% or 85% sequence identity, preferably at least 90% or 95% sequence identity, or more preferably at least 97% or 98% sequence identity and still more preferably at least 99% sequence identity. Alternatively, the silencing element may comprise 1, 2 or 3 mismatches as compared with the target nucleotide sequence over every length of 24 partially complementary nucleotides.

It will be appreciated by the person skilled in the art that the degree of complementarity shared between the silencing element and the target nucleotide sequence may vary depending on the target gene to be down-regulated or depending on the insect pest species in which gene expression is to be controlled.

In another embodiment of the current invention, the silencing element comprises a sequence of nucleotides that is the RNA equivalent of any of the polynucleotides selected from the group consisting of a polynucleotide which comprises at least 21, preferably at least 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100 or 1115 contiguous nucleotides of a nucleotide sequence as represented by any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120, or the complement thereof, or (ii) a polynucleotide which comprises at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100 or 1115 contiguous nucleotides of a nucleotide sequence as represented in any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120, or the complement thereof, that, when the two sequences are optimally aligned and compared, said polynucleotide is at least 75% preferably at least 80%, 85%, 90%, 95%, 98% or 99% identical to any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120, or the complement thereof, or (iii) a polynucleotide which comprises a fragment of at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100 or 1115 contiguous nucleotides of a nucleotide as represented in any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120, or the complement thereof, and wherein said fragment or said complement has a nucleotide sequence that, when said fragment is optimally aligned and compared with the corresponding fragment in any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120, said nucleotide sequence is at least 75% preferably at least 80%, 85%, 90%, 95%, 98% or 99% identical to said corresponding fragment of any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120 or the complement thereof, wherein said polynucleotide is no longer than 10000, 9000, 8000, 7000, 6000, 5000, 4000, 3000, 2000 or 1500 nucleotides. It will be appreciated that in such embodiments the silencing element may comprise or consist of a region of double-stranded RNA comprising annealed complementary strands, one strand of which, the sense strand, comprises a sequence of nucleotides at least partially complementary to a target nucleotide sequence within a target gene.

The target nucleotide sequence may be selected from any suitable region or nucleotide sequence of the target gene or RNA transcript thereof. For example, the target nucleotide sequence may be located within the 5'UTR or 3'UTR of the target gene or RNA transcript or within exonic or intronic regions of the gene.

The skilled person will be aware of methods of identifying the most suitable target nucleotide sequences within the context of the full-length target gene. For example, multiple silencing elements targeting different regions of the target gene can be synthesised and tested. Alternatively, digestion of the RNA transcript with enzymes such as RNAse H can be used to determine sites on the RNA that are in a conformation susceptible to gene silencing. Target sites may also be identified using in silico approaches, for example, the use of computer algorithms designed to predict the efficacy of gene silencing based on targeting different sites within the full-length gene.

The interfering RNAs of the current invention may comprise one silencing element or multiple silencing elements, wherein each silencing element comprises or consists of a sequence of nucleotides which is at least partially complementary to a target nucleotide sequence within a target gene and that functions upon uptake by an insect pest species to down-regulate expression of said target gene. Concatemeric RNA constructs of this type are described in WO2006/046148 as incorporated herein by reference. In the context of the present invention, the term 'multiple' means at least two, at least three, at least four, etc and up to at least 10, 15, 20 or at least 30. In one embodiment, the interfering RNA comprises multiple copies of a single silencing element i.e. repeats of a silencing element that binds to a particular target nucleotide sequence within a specific target gene. In another embodiment, the silencing elements within the interfering RNA comprise or consist of different sequences of nucleotides complementary to different target nucleotide sequences. It should be clear that combinations of multiple copies of the same silencing element combined with silencing elements binding to different target nucleotide sequences are within the scope of the current invention.

The different target nucleotide sequences may originate from a single target gene in an insect pest species in order to achieve improved down-regulation of a specific target gene in an insect pest species. In this case, the silencing elements may be combined in the interfering RNA in the original order in which the target nucleotide sequences occur in the target gene, or the silencing elements may be scrambled and combined randomly in any rank order in the context of the interfering RNA as compared with the order of the target nucleotide sequences in the target gene.

Alternatively, the different target nucleotide sequences are representing a single target gene but originating from different insect pest species.

Alternatively, the different target nucleotide sequences may originate from different target genes. If the interfering RNA is for use in preventing and/or controlling pest infestation, it is preferred that the different target genes are chosen from the group of genes regulating essential biological functions of insect pest species, including but not limited to survival, growth, development, reproduction and pathogenicity. The target genes may regulate the same or different biological pathways or processes. In one embodiment, at least one of the silencing elements comprises or consists of a sequence of nucleotides which is at least partially complementary to a target nucleotide sequence within a target gene wherein the target gene is selected from the group of genes having a nucleotide sequence comprising any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or having a nucleotide sequence that, when the two sequences are optimally aligned and compared, is at least 75%, preferably at least 80%, 85%, 90%, 95%, 98% or 99% identical to any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or (ii) is selected from the group of genes having a nucleotide sequence comprising a fragment of at least 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or having a nucleotide sequence that, when said gene comprising said fragment is optimally aligned and compared with any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, said nucleotide sequence is at least 75% preferably at least 80%, 85%, 90%, 95%, 98% or 99% identical to any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or (iii) is selected from the group of genes having a nucleotide sequence comprising a fragment of at least 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, and wherein when said fragment is optimally aligned and compared with the corresponding fragment in any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, said nucleotide sequence of said fragment is at least 75% preferably at least 80%, 85%, 90%, 95%, 98% or 99% identical to said corresponding fragment of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or (iv) is an insect pest orthologue of a gene having a nucleotide sequence comprising any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or (v) is selected from the group of genes having a nucleotide sequence encoding an amino acid sequence that, when the two amino acid sequences are optimally aligned and compared, is at least 70% preferably at least 75%, 80%, 85%, 90%, 95%, 98% or 99% identical to the amino acid sequence encoded by the nucleotide sequence represented in any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or (vi) is selected from the group of genes having a nucleotide sequence encoding an amino acid sequence that, when the two amino acid sequences are optimally aligned and compared, is at least 70% preferably at least 75%, 80%, 85%, 90%, 95%, 98% or 99% identical to the amino acid sequence represented in any of SEQ ID NOs 285, 242, 271, 226, 227, 281, 228, 282, 229, 230 to 233, 234, 283, 235, 236, 237, 238, 239, 240, 284, 241, 243, 244, 286, 269, 270, 287, 288, 206 to 225. Preferably, the nucleotide sequence of the target gene is no longer than 5000, 4000, 3000, 2000 or 1500 nucleotides.

In a further embodiment of the invention, the different genes targeted by the different silencing elements originate from the same insect pest species. This approach is designed to achieve enhanced attack against a single insect pest species. In particular, the different target genes may be expressed differentially in the different stages of the insect's life cycle, for example, the mature adult, immature larval and egg stages. The interfering RNA of the invention may thus be used to prevent and/or control insect pest infestation at more than one stage of the insect's life cycle.

In an alternative embodiment of the invention, the different genes targeted by the different silencing elements originate from different insect pest species. The interfering RNA of the invention can thus be used to prevent and/or control infestation by more than one insect pest species simultaneously.

The silencing elements may be arranged as one contiguous region of the interfering RNA or may be separated by the presence of linker sequences. The linker sequence may comprise a short random nucleotide sequence that is not complementary to any target nucleotide sequences or target genes. In one embodiment, the linker is a conditionally self-cleaving RNA sequence, preferably a pH-sensitive linker or a hydrophobic-sensitive linker. In one embodiment, the linker comprises a sequence of nucleotides equivalent to an intronic sequence. Linker sequences of the current invention may range in length from about 1 base pair to about 10,000 base pairs, provided that the linker does not impair the ability of the interfering RNA to down-regulate the expression of target gene(s).

In addition to the silencing element(s) and any linker sequences, the interfering RNA of the invention may comprise at least one additional polynucleotide sequence. In different embodiments of the invention, the additional sequence is chosen from (i) a sequence capable of protecting the interfering RNA against RNA processing, (ii) a sequence affecting the stability of the interfering RNA, (iii) a sequence allowing protein binding, for example to facilitate uptake of the interfering RNA by cells of the insect pest species, (iv) a sequence facilitating large-scale production of the interfering RNA, (v) a sequence which is an aptamer that binds to a receptor or to a molecule on the surface of the insect pest cells to facilitate uptake, or (v) a sequence that catalyses processing of the interfering RNA within the insect pest cells and thereby enhances the efficacy of the interfering RNA. Structures for enhancing the stability of RNA molecules are well known in the art and are described further in WO2006/046148 as incorporated herein by reference.

The length of the interfering RNA of the invention needs to be sufficient for uptake by the cells of an insect pest species and down-regulation of target genes within the pest as described elsewhere herein. However, the upper limit on length may be dependent on (i) the requirement for the interfering RNA to be taken up by cells of the pest and (ii) the requirement for the interfering RNA to be processed in the cells of the pest to mediate gene silencing via the RNAi pathway. The length may also be dictated by the method of production and the formulation for delivery of the interfering RNA to cells. Preferably, the interfering RNA of the current invention will be between 21 and 10,000 nucleotides in length, preferably between 50 and 5000 nucleotides or between 100 and 2500 nucleotides, more preferably between 80 and 2000 nucleotides in length.

The interfering RNA may contain DNA bases, non-natural bases or non-natural backbone linkages or modifications of the sugar-phosphate backbone, for example to enhance stability during storage or enhance resistance to degradation by nucleases. Furthermore, the interfering RNA may be produced chemically or enzymatically by one skilled in the art through manual or automated reactions.

Alternatively, the interfering RNA may be transcribed from a polynucleotide encoding the same. Thus, provided herein is an isolated polynucleotide encoding any of the interfering RNAs of the current invention.

Also provided herein is an isolated polynucleotide selected from the group consisting of (i) a polynucleotide which comprises at least 21, preferably at least 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100 or 1115 contiguous nucleotides of a nucleotide sequence as represented by any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120, or the complement thereof, or (ii) a polynucleotide which consists of at least 21, preferably at least 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100 or 1115 contiguous nucleotides of a nucleotide sequence as represented by any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120, or the complement thereof, or (iii) a polynucleotide which comprises at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100 or 1115 contiguous nucleotides of a nucleotide sequence as represented in any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120, or the complement thereof, that, when the two sequences are optimally aligned and compared, said polynucleotide is at least 75% preferably at least 80%, 85%, 90%, 95%, 98% or 99% identical to any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120, or the complement thereof, or (iv) a polynucleotide which comprises a fragment of at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100 or 1115 contiguous nucleotides of a nucleotide as represented in any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120, or the complement thereof, and wherein said fragment or said complement has a nucleotide sequence that, when said fragment is optimally aligned and compared with the corresponding fragment in any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120, said nucleotide sequence is at least 75% preferably at least 80%, 85%, 90%, 95%, 98% or 99% identical to said corresponding fragment of any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120 or the complement thereof, or (v) a polynucleotide which consists of a fragment of at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100 or 1115 contiguous nucleotides of a nucleotide as represented in any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120, or the complement thereof, and wherein said fragment or said complement has a nucleotide sequence that, when said fragment is optimally aligned and compared with the corresponding fragment in any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120, said nucleotide sequence is at least 75% preferably at least 80%, 85%, 90%, 95%, 98% or 99% identical to said corresponding fragment of any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120 or the complement thereof, or (vi) a polynucleotide encoding an amino acid sequence that, when the two amino acid sequences are optimally aligned and compared, is at least 70% preferably at least 75%, 80%, 85%, 90%, 95%, 98% or 99% identical to the amino acid sequence encoded by the nucleotide sequence represented in any of SEQ ID NOs 277, 138, 253, 152, 198 to 201, 121, 122, 141, 154 to 157, 273, 123, 142, 158 to 161, 274, 124, 143, 162 to 165, 125 to 129, 144, 166 to 169, 130, 145, 170 to 173, 275, 131, 146, 174 to 177, 132, 133, 147, 178 to 181, 134, 148, 182 to 185, 135, 149, 186 to 189, 136, 150, 190 to 193, 276, 137, 151, 194 to 197, 139, 140, 153, 202 to 205, 278, 251, 254, 257 to 260, 279, 252, 255, 256, 261 to 268, 280, 1, 21, 41 to 44, 2, 22, 45 to 48, 3, 23, 49 to 52, 4, 24, 53 to 56, 5, 25, 57 to 60, 6, 26, 61 to 64, 7, 27, 65 to 68, 8, 28, 69 to 72, 9, 29, 73 to 76, 10, 30, 77 to 80, 11, 31, 81 to 84, 12, 32, 85 to 88, 13, 33, 89 to 92, 14, 34, 93 to 96, 15, 35, 97 to 100, 16, 36, 101 to 104, 17, 37, 105 to 108, 18, 38, 109 to 112, 19, 39, 113 to 116, 20, 40, 117 to 120, or (vii) a polynucleotide encoding an amino acid sequence that, when the two amino acid sequences are optimally aligned and compared, is at least 70% preferably at least 75%, 80%, 85%, 90%, 95%, 98% or 99% identical to the amino acid sequence represented in any of SEQ ID NOs 285, 242, 271, 226, 227, 281, 228, 282, 229, 230 to 233, 234, 283, 235, 236, 237, 238, 239, 240, 284, 241, 243, 244, 286, 269, 270, 287, 288, 206 to 225, and wherein said polynucleotide is no longer than 10000, 9000, 8000, 7000, 6000, 5000, 4000, 3000, 2000 or 1500 nucleotides.

In preferred embodiments, the isolated polynucleotide is part of an interfering RNA molecule, typically part of the silencing element, comprising at least one double-stranded region comprising a sense RNA strand annealed by complementary basepairing to an antisense RNA strand wherein the sense strand of the dsRNA molecule comprises a sequence of nucleotides complementary to a sequence of nucleotides located within the RNA transcript of the target gene. The sense strand of the dsRNA is therefore able to anneal to the RNA transcript and target the RNA for degradation within the RNAi-induced silencing complex or RISC.

The polynucleotides of the invention may be inserted via routine molecular cloning techniques into DNA constructs or vectors known in the art. Therefore, according to one embodiment, a DNA construct comprising any of the polynucleotides of the current invention is provided. Preferably, provided herein is a DNA construct comprising a polynucleotide encoding any of the interfering RNAs of the current invention. The DNA construct may be a recombinant DNA vector, for example a bacterial or yeast vector or plasmid. In a preferred embodiment of the invention, the DNA construct is an expression construct and the polynucleotide is operably linked to at least one regulatory sequence capable of driving expression of the polynucleotide sequence. The term 'regulatory sequence' is to be taken in a broad context and is intended to refer to any nucleotide sequence capable of effecting expression of polynucleotides to which it is operably linked including but not limited to promoters, enhancers and other naturally-occurring or synthetic transcriptional activator elements. The regulatory sequence may be located at the 5' or 3' end of the polynucleotide sequence. The term 'operably linked' refers to a functional linkage between the regulatory sequence and the polynucleotide sequence such that the regulatory sequence drives expression of the polynucleotide. Operably linked elements may be contiguous or non-contiguous.

Preferably, the regulatory sequence is a promoter selected from the group comprising but not limited to constitutive promoters, inducible promoters, tissue-specific promoters and growth/developmental stage-specific promoters. In one embodiment, the polynucleotide is placed under the control of a strong constitutive promoter such as any selected from the group comprising the CaMV35S promoter, doubled CaMV35S promoter, ubiquitin promoter, actin promoter, rubisco promoter, GOS2 promoter, Figwort mosaic virus 34S promoter. In another embodiment, the regulatory sequence is a plant promoter for use in regulating expression of the polynucleotide in plants. Plant promoters, in particular, tissue-specific plant promoters encompassed within the scope of the current invention are described in more detail elsewhere herein.

Optionally, one or more transcription termination sequences may be incorporated in the expression construct of the invention. The term 'transcription termination sequence' encompasses a control sequence at the end of a transcriptional unit, which signals termination of transcription, 3' processing and poly-adenylation of a primary transcript. Additional regulatory sequences including but not limited to transcriptional or translational enhancers may be incorporated in the expression construct, for instance as with the double enhanced CaMV35S promoter.

The present invention also encompasses a method for generating any of the interfering RNAs of the invention comprising the steps of (i) contacting a polynucleotide encoding said interfering RNA or a DNA construct comprising the same with cell-free components; or (ii) introducing (e.g. by transformation, transfection or injection) a polynucleotide encoding said interfering RNA or a DNA construct comprising the same into a cell. Accordingly, also provided herein is a host cell comprising any of the interfering RNAs of the current invention, any of the polynucleotides of the current invention or a DNA construct comprising the same. The host cell may be a prokaryotic cell including but not limited to gram-positive and gram-negative bacterial cells, or an eukaryotic cell including but not limited to yeast cells or plant cells. Preferably, said host cell is a bacterial cell or a plant cell. The bacterial cell can be chosen from the group comprising, but not limited to, Gram positive and Gram negative cells comprising *Escherichia* spp. (e.g. *E. coli*), *Bacillus* spp. (e.g. *B. thuringiensis*), *Rhizobium* spp., *Lactobacilllus* spp., *Lactococcus* spp., *Pseudomonas* spp. and *Agrobacterium* spp. The polynucleotide or DNA construct of the invention may exist or be maintained in the host cell as an extra-chromosomal element or may be stably incorporated into the genome of the host cell. Characteristics of particular interest in selecting a host cell for the purposes of the current invention include the ease with which the polynucleotide or DNA construct encoding the interfering RNA can be introduced into the host, the availability of compatible expression systems, the efficiency of expression, and the stability of the interfering RNA in the host.

The DNA construct of the invention may further include an origin of replication which is required for maintenance and/or replication in a specific cell type or host cell. One example is when an expression construct is required to be maintained in a bacterial cell as an extra-chromosomal or episomal genetic element (e.g. a plasmid or cosmid molecule) in a cell. Preferred origins of replication include but are not limited to f1-ori, pBR322 ori (pMB1) and colE1 ori.

The recombinant construct may optionally comprise a selectable marker gene. As used herein, the term 'selectable marker gene' includes any gene, which confers a phenotype on a cell in which it is expressed to facilitate the identification and/or selection of cells, which are transfected or transformed with an expression construct of the invention. Examples of suitable selectable markers include resistance genes against ampicillin (Ampr), tetracycline (Tcr), kanamycin (Kanr), phosphinothricin, and chloramphenicol (CAT). Other suitable marker genes provide a metabolic trait, for example manA. Visual marker genes may also be used and include for example beta-glucuronidase (GUS), luciferase and Green Fluorescent Protein (GFP).

In situations wherein the interfering RNA is expressed within a host cell and/or is used to prevent and/or control pest infestation of a host organism, it is preferred that the interfering RNA does not exhibit significant 'off-target' effects i.e. the interfering RNA does not affect expression of genes within the host. Preferably, the silencing element does not exhibit significant complementarity with nucleotide sequences other than the intended target nucleotide sequence of the target gene. In one embodiment of the invention, the silencing element shows less than 30%, more preferably less than 20%, more preferably less than 10% and even more preferably less than 5% sequence identity with any gene of the host cell or organism. If genomic sequence data is available for the host organism, one can cross-check identity with the silencing element using standard bioinformatics tools. In one embodiment, there is no sequence identity between the silencing element and a gene from the host cell or host organism over a region of 17, more preferably over a region of 18 or 19 and most preferably over a region of 20 or 21 contiguous nucleotides.

Any of the interfering RNA molecules or DNA constructs encoding the interfering RNA molecule or host cells comprising the interfering RNA molecule as herein described may be used for the prevention and/or control of insect pest infestation. As such, the interfering RNAs or DNA constructs or host cells comprising the same may be referred to as pesticides or insecticides. Preferably, the interfering RNA molecules and/or DNA constructs or host cells of the present invention are used to treat plants as a means to prevent and/or control pest infestation thereof. In particular, the interfering RNA molecules and/or DNA constructs or host cells may be provided as a kit for the purposes of preventing and/or controlling pest infestation, preferably pest infestation of plants.

Furthermore, in accordance with another aspect of the invention, there is provided herein a composition for preventing and/or controlling insect pest infestation comprising at least one interfering ribonucleic acid (RNA) and optionally at least one suitable carrier, excipient or diluent, wherein the interfering RNA functions upon uptake by the pest to down-regulate the expression of a target gene within said pest. The interfering RNA may be any of those as disclosed elsewhere herein. Preferably, the interfering RNA comprises or consists of at least one silencing element and said silencing element is a region of double-stranded RNA comprising annealed complementary strands, one strand of which (the sense strand) comprises a sequence of nucleotides which is at least partially complementary to a target nucleotide sequence within a target gene. The 'target gene' may be any of the pest target genes as disclosed elsewhere herein including but not limited to genes involved in regulating pest survival, growth, development, reproduction and pathogenicity. Alternatively, the composition comprises at least one host cell comprising at least one interfering RNA molecule or DNA construct encoding the same and optionally at least one suitable carrier, excipient or diluent, wherein the interfering RNA functions upon uptake of the host cell by the insect pest to down-regulate the expression of a target gene within said pest.

In the practical application of the invention, the composition may be used for the prevention and/or control of any insect pest belonging to the Orders Coleoptera, Lepidoptera, Diptera, Dichyoptera, Orthoptera, Hemiptera and Siphonaptera. The composition may therefore be in any suitable form for application to insect pests or for application to substrates and/or organisms, in particular plants, susceptible to infestation by said insect pest. In one embodiment, the composition is for use in preventing and/or controlling pest infestation of plants or propagation or reproductive material of plants and is thus directed towards insect pest species that infest plants. The composition of the present invention is particularly effective when the insect pest belongs to the category of 'chewing' insects that cause considerable damage to plants by eating plant tissues such as roots, leaves, flowers, buds, twigs and the like. Examples from this large insect category include beetles and their larvae. In a preferred embodiment of the invention, the insect pest is selected from the *Leptinotarsa* genus. More preferably, the target insect pest species is *Leptinotarsa decemlineata.*

The composition of the present invention is also effective against species of insects that pierce and/or suck the fluids from the cells and tissues of plants. Thus, in a further preferred embodiment of the invention, the insect pest is selected from the *Lygus* genus. Preferably, the target insect pest species is selected from the group comprising *Lygus adspersus, Lygus alashanensis, Lygus borealis, Lygus elisus, Lygus gemellatus, Lygus hesperus, Lygus lineolaris* or *Lygus rugulipennis*. More preferably, the target insect pest species is *Lygus hesperus*. The composition of the invention may be used to control insect pests at all stages of their life cycle, for example, the mature adult stage, the larval and egg stages.

In the context of the composition of the invention, the interfering RNA may be produced from a DNA construct, in particular an expression construct as described elsewhere herein, comprising a polynucleotide encoding the same. Furthermore, the interfering RNA may be produced inside a host cell or organism engineered to express said interfering RNA from a polynucleotide encoding the same. Suitable host organisms for use in the compositions of the current invention include but are not limited to microorganisms that are known to colonize the environment on and/or around plants or crops of interest i.e. plants or crops susceptible to infestation by insect pest species. Such microorganisms include but are not limited to those that occupy the phylloplane (the surface of plant leaves) and/or the rhizosphere (the soil surrounding plant roots). These microorganisms are selected so as to be capable of successfully competing with any wild-type organisms present in the plant environment. Suitable microorganisms for use as hosts include various species of bacteria, algae and fungi. It is clear that the chosen microorganisms must not be toxic to plants.

Host organisms that do not naturally colonize plants and/or their environment are also within the scope of the current invention. In one embodiment, the interfering RNA is fermented in a bacterial host, and the resulting dead bacteria are processed and used as an insecticidal spray in the same manner that *Bacillus thuringiensis* strains have been used as an insecticide for a spray application.

Wherein the composition of the invention is for use in preventing and/or controlling pest infestation of a plant, the composition can contain an agriculturally suitable carrier. Such a carrier may be any material that the plant to be treated can tolerate, which does not cause undue damage to the environment or other organisms therein and, which allows the interfering RNA to remain effective against the insect pest species. In particular, the compositions of the invention may be formulated for delivery to plants in accordance with routine agricultural practices used in the bioinsecticide industry. The composition may contain further components capable of performing other functions including but not limited to (i) enhancement or promotion of uptake of the interfering RNA by cells of the pest and (ii) stabilization of the active components of the composition. Specific examples of such further components contained in the composition comprising the interfering RNA, are yeast tRNA or yeast total RNA.

The compositions may be formulated for direct application or as a concentration of a primary composition that requires dilution prior to use. Alternatively, the composition may be supplied as kit comprising the interfering RNA or the host cell comprising or expressing the same in one container and the suitable diluent or carrier for the RNA or host cell in a separate container. In the practical application of the invention, the composition may be applied to a plant or any part of a plant at any stage of the plant's development. In one embodiment, the composition is applied to the aerial parts of a plant, for example during cultivation of plant crops in a field. In a further embodiment, the composition is applied to the seeds of a plant either while they are in storage or once they are planted in the soil. It is generally important to obtain good control of pests in the early stages of plant growth as this is the time when the plant can be most severely damaged by pest species.

The composition may be applied to the environment of an insect pest by various techniques including but not limited to spraying, atomizing, dusting, scattering, pouring, coating of seeds, seed treatment, introduction into the soil, and introduction into irrigation water. In the treatment of plants susceptible to pest infestation, the composition may be delivered to the plant or part of a plant before the appearance of the pest (for the purposes of prevention), or once signs of pest infestation begin to appear (for the purposes of pest control).

In a further embodiment of the invention, the composition is formulated so as to contain at least one further agronomical agent, for example a herbicide or an additional pesticide. As used herein, a 'second pesticide' or 'additional pesticide' refers to a pesticide other than the first or original interfering RNA molecule of the composition. Alternatively, the composition of the invention may be delivered in combination with at least one other agronomical agent, for a example a herbicide or a second pesticide. In one embodiment, the composition is provided in combination with a herbicide selected from any known in the art, for instance glyphosate, imidazolinone, sulphonylurea and bromoxynil. In a further embodiment, the composition is provided in combination with at least one additional pesticide. The additional pesticide may be selected from any pesticides known in the art and/or may comprise an interfering ribonucleic acid that functions upon uptake by a pest to down-regulate expression of a target gene in said pest species. In one embodiment, the target pest is an insect pest species and the interfering RNA is selected from any of the interfering RNAs as described herein. In a further embodiment, the additional pesticide comprises an interfering RNA that functions to down-regulate expression of a known gene in any target pest species, not limited to insect pests. The original interfering RNA molecule of the composition and the second or additional pesticide(s) may target the same insect pest species or may be intended to target different insect pest species. For example, the original interfering RNA and the second pesticide may target different species of insect pest or may target different families or classes of pest organisms, for example, fungi or nematodes or insects. It will be apparent to one skilled in the art how to test combinations of interfering RNA molecules and other agronomical agents for synergistic effects. In a preferred embodiment, the composition contains a first interfering RNA molecule described elsewhere herein and one or more additional pesticides, each toxic to the same insect pest, wherein the one or more additional pesticides are selected from a patatin, a *Bacillus thuringiensis* insecticidal protein, a *Xenorhabdus* insecticidal protein, a *Photorhabdus* insecticidal protein, a *Bacillus laterosporous* insecticidal protein, a *Bacillus spaericus* insecticidal protein, and a lignin, and wherein said *Bacillus thuringiensis* insecticidal protein is selected from the group consisting of a Cry1Ab, a Cry1C, a Cry2Aa, a Cry3, a TIC851, a CryET70, a Cry22, a VIP, a TIC901, a TIC1201, a TIC407, a TIC417, a binary insecticidal protein selected from CryET33 and CryET34, CryET80 and CryET76, TIC100 and TIC101, and PS149B1, and insecticidal chimeras of any of the preceding insecticidal proteins.

The different components of the combinations described herein may be administered, for example to a host organism susceptible to infestation by pest, in any order. The components may be delivered simultaneously or sequentially to the area or organism to be treated.

According to a further aspect of the current invention, there is provided herein a method for down-regulating expression of a target gene in an insect pest species comprising contacting said pest with an effective amount of at least one interfering ribonucleic acid (RNA), wherein the interfering RNA functions upon uptake by the pest to down-regulate the expression of a target gene within said pest.

The target gene may be any of the pest genes as described elsewhere herein. In particular, the target gene may be selected from the group of genes having a nucleotide sequence comprising any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or having a nucleotide sequence that, when the two sequences are optimally aligned and compared, is at least 75%, preferably at least 80%, 85%, 90%, 95%, 98% or 99% identical any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or is selected from the group of genes having a nucleotide sequence consisting of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or is selected from the group of genes having a nucleotide sequence comprising a fragment of at least 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or having a nucleotide sequence that, when said gene comprising said fragment is optimally aligned and compared with any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, said nucleotide sequence is at least 75% preferably at least 80%, 85%, 90%, 95%, 98% or 99% identical to any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or is selected from the group of genes having a nucleotide sequence comprising a fragment of at least 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, and wherein when said fragment is optimally aligned and compared with the corresponding fragment in any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, said nucleotide sequence of said fragment is at least 75% preferably at least 80%, 85%, 90%, 95%, 98% or 99% identical to said corresponding fragment of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof.

The target gene may also be an insect pest orthologue of a gene having a nucleotide sequence comprising any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40. Preferably the nucleotide sequence of said target gene is no longer than 5000, 4000, 3000, 2000 or 1500 nucleotides.

The interfering RNA for use in the present method may be any of the interfering RNA molecules as described elsewhere herein. In one embodiment, the interfering RNA mediates down-regulation of gene expression by the process of RNA interference or RNAi, and the interfering RNA is selected from the group of regulatory RNA molecules capable of effecting RNAi or 'gene silencing' including but not limited to short interfering RNAs (siRNA), microRNAs (miRNA), double-stranded RNAs (dsRNA) and hairpin RNAs (shRNA).

In preferred embodiments, the interfering RNA molecules for use in the present method comprise at least one silencing element wherein the silencing element is a region of double-stranded RNA comprising a sense RNA strand annealed by complementary basepairing to an antisense RNA strand wherein the sense strand of the dsRNA molecule comprises a sequence of nucleotides complementary to a sequence of nucleotides located within the RNA transcript of the target gene. The sense strand of the dsRNA is therefore able to anneal to the RNA transcript and target the RNA for degradation within the RNAi-induced silencing complex or RISC.

In the present method, the insect pest is treated with at least one interfering RNA. In one embodiment of the method, the insect pest species may be contacted with multiple interfering RNA molecules. Wherein the pest is contacted with multiple interfering RNAs, the different RNAs may function to down-regulate the same target gene or different target genes.

The interfering RNA to be delivered to the insect pest species may be formulated as a composition comprising at least one suitable carrier, excipient or diluent. Furthermore, the interfering RNA may be transcribed from a polynucleotide encoding the same or a DNA construct comprising said polynucleotide. In one embodiment, the interfering RNA is expressed inside a host cell or organism including a prokaryotic or eukaryotic host. The host cell or organism may be a host susceptible to infestation by an insect pest wherein the interfering RNA functions to down-regulate expression of a target gene in said pest. In a preferred embodiment, the host organism is a plant susceptible to infestation by the targeted insect pest species.

As used in the context of the present method, the term 'contacting' refers to any means by which the insect pest species or a cell thereof is exposed to the interfering RNA and which allows for uptake of the interfering RNA by cells of the pest. Thus, 'contacting' encompasses for example, the processes of cell transformation, microinjection and feeding. These techniques may be carried out in respect of isolated cells grown in vitro or cells within the intact body of the insect pest species. Wherein the intact insect pest is contacted with the interfering RNA of the method, the RNA may be microinjected into an extracellular space and subsequently taken up by cells of the body by natural processes such as endocytosis or transcytosis. In a preferred embodiment of the invention, the interfering RNA is provided to the pest in the form of or included in foodstuff to be ingested by the pest. Once ingested, the interfering RNA may pass from the insect's digestive tract into the cells of the body by natural processes such as endocytosis or transcytosis. In one embodiment, the insect pest is exposed to a plant that has been treated with an interfering RNA or a composition comprising the same, and the interfering RNA is taken up as the pest feeds on the plant tissue. The interfering RNA may be present on the surface of a plant or a part thereof or may be present intracellularly in the plant or the plant tissue eaten by the insect pest.

In the context of a method for down-regulating expression of a target gene in an insect pest species, the phrase 'effective amount' should be taken to mean the quantity or concentration of interfering RNA required to down-regulate expression of the target gene by at least 10% or 20%, preferably by at least 33%, more preferably by at least 50%, yet more preferably by at least 80% or 90%. In particularly preferred embodiments, an 'effective amount' is the quantity or concentration required to down-regulate expression of the target gene by at least 60%, 70% or 80%, preferably by at least 90%, more preferably by at least 95%, and most preferably by at least 99% relative to expression in the absence of an interfering RNA or in the presence of a control RNA. As described elsewhere herein, down-regulation of gene expression can be measured by a reduction in the levels of either the RNA transcript or the protein ultimately produced from the target gene. Levels of RNA and/or protein can be measured using techniques routine in the art.

Also provided herein is a method for preventing and/or controlling pest infestation, comprising contacting an insect pest species with an effective amount of at least one interfering RNA wherein the RNA functions upon uptake by said pest to down-regulate expression of an essential pest target gene. The essential target gene may be any pest gene involved in the regulation of an essential biological process required by the pest to initiate or maintain infestation including but not limited to survival, growth, development, reproduction and pathogenicity. In particular, the target gene may be any of the pest genes as described elsewhere herein. Furthermore, there is provided herein a method for preventing and/or controlling insect pest infestation in a field of crop plants, said method comprising expressing in said plants an effective amount of an interfering RNA as described herein.

Wherein the method is for the control of pest infestation, the phrase 'effective amount' extends to the quantity or concentration of interfering RNA required to produce a phenotypic effect on the pest such that the numbers of pest organisms infesting a host organism are reduced and/or the amount of damage caused by the pest is reduced. In one embodiment, the phenotypic effect is death of the pest and the interfering RNA is used to achieve at least 20%, 30%, 40%, preferably at least 50%, 60%, 70%, more preferably at least 80% or 90% pest mortality as compared to control insect pests. In a further embodiment, the phenotypic effects include but are not limited to stunting of pest growth, cessation of feeding and reduced egg-laying. The total numbers of pest organisms infesting a host organism may thus be reduced by at least 20%, 30%, 40%, preferably at least 50%, 60%, 70%, more preferably at least 80% or 90% as compared with control pests. Alternatively, the damage caused by the insect pest may be reduced by at least 20%, 30%, 40%, preferably at least 50%, 60%, 70%, more preferably at least 80% or 90% as compared with control insect pests. Hence, the method of the invention can be used to achieve at least 20%, 30%, 40%, preferably at least 50%, 60%, 70%, more preferably at least 80% or 90% pest control. As used herein 'control pests' are pests not contacted with any pesticidal agent, or pests contacted with an interfering RNA targeting a non-essential gene i.e. a gene not required for the initiation or maintenance of pest infestation or pests contacted with an interfering RNA targeting a gene not found and/or not expressed in said pest.

Methods for down-regulating expression of a target gene in an insect pest species may be used to prevent and/or control pest infestation on a particular substrate or material susceptible to infestation by said insect pest. In one embodiment, the method is used to treat any plant susceptible to infestation by said pest. Plants of interest for use according to the methods of the current invention include but are not limited to rice, potato, cotton, tomato, canola, soy, sunflower, sorghum, pearl millet, corn, seed crops such as alfalfa, strawberries, eggplant, pepper and tobacco.

Furthermore, there is provided herein a method for increasing the yield of a plant crop comprising contacting said plants with an effective amount of an interfering RNA that functions upon uptake by an insect pest species to down-regulate expression of a target gene in said pest, wherein down-regulation of the target gene affects an essential biological function of the pest required for initiation and/or maintenance of infestation, such that the damage caused to the plant crop is reduced as compared with untreated crops.

Plants or plant crops to be treated according to the methods of the current invention may be treated externally with an interfering RNA or composition comprising the same. For example, the interfering RNA or host cells comprising or expressing the same may be applied to the surface of the plant or to the plant's environment by processes including but not limited to spraying, atomizing, dusting, scattering, pouring, coating of seeds, seed treatment, introduction into the soil and introduction into irrigation water. In one embodiment, the plant to be treated is engineered to express the interfering RNA intracellularly via transcription from a polynucleotide incorporated therein. As the pest feeds on tissues of the plant, the cells containing the interfering RNA will be broken down inside the insect's digestive tract and the interfering RNA will thus be distributed within the insect's body resulting in down-regulation of target genes.

Thus, in accordance with another aspect of the present invention is provided a method for generating a transgenic plant resistant to infestation by an insect pest species comprising the steps of (a) transforming a plant cell with a DNA construct comprising a polynucleotide sequence encoding an interfering ribonucleic acid (RNA) that functions upon uptake by an insect pest species to down-regulate expression of a target gene in said insect pest species, (b) regenerating a plant from the transformed plant cell; and (c) growing the transformed plant under conditions suitable for the expression of the interfering RNA from the recombinant DNA construct, said plant thus being resistant to said pest as compared with an untransformed plant.

The interfering RNA expressed by the plant or part thereof may be any of those as disclosed elsewhere herein. Preferably, the interfering RNA comprises or consists of at least one silencing element and said silencing element is a region of double-stranded RNA comprises annealed complementary strands, one strand of which (the sense strand) comprises a sequence of nucleotides which is at least partially complementary to a target nucleotide sequence within a target gene. Wherein part of the interfering RNA is double-stranded, the two strands of the molecule may be expressed from at least two separate polynucleotides or may be encoded by a single polynucleotide encoding an interfering RNA with for example, a stem-loop structure as described elsewhere herein.

The interfering RNA expressed by the plant or part thereof may target any of the pest genes as described elsewhere herein. In particular, the target gene may be selected from the group of genes having a nucleotide sequence comprising any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or having a nucleotide sequence that, when the two sequences are optimally aligned and compared, is at least 75%, preferably at least 80%, 85%, 90%, 95%, 98% or 99% identical any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or is selected from the group of genes having a nucleotide sequence consisting of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or is selected from the group of genes having a nucleotide sequence comprising a fragment of at least 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or having a nucleotide sequence that, when said gene comprising said fragment is optimally aligned and compared with any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, said nucleotide sequence is at least 75% preferably at least 80%, 85%, 90%, 95%, 98% or 99% identical to any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, or is selected from the group of genes having a nucleotide sequence comprising a fragment of at least 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100 or 1115 contiguous nucleotides of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, and wherein when said fragment is optimally aligned and compared with the corresponding fragment in any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, said nucleotide sequence of said fragment is at least 75% preferably at least 80%, 85%, 90%, 95%, 98% or 99% identical to said corresponding fragment of any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof. The target gene may also be an insect pest orthologue of a gene having a nucleotide sequence comprising any of SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 277, 138, 253, 152, 121, 122, 141, 273, 123, 142, 274, 124, 143, 125 to 129, 144, 130, 145, 275, 131, 146, 132, 133, 147, 134, 148, 135, 149, 136, 150, 276, 137, 151, 139, 140, 153, 278, 251, 254, 279, 252, 255, 256, 280, 1, 21, 2, 22, 3, 23, 4, 24, 5, 25, 6, 26, 7, 27, 8, 28, 9, 29, 10, 30, 11, 31, 12, 32, 13, 33, 14, 34, 15, 35, 16, 36, 17, 37, 18, 38, 19, 39, 20 or 40, Preferably the nucleotide sequence of said target gene is no longer than 5000, 4000, 3000, 2000 or 1500 nucleotides. Furthermore, it is important that the interfering RNA does not disrupt expression of any genes of the plant host.

As used herein, the term 'transgenic plant' or 'transgenic plant cell' refers to any plant or plant cell that has been genetically engineered or is descended from a plant that has been genetically engineered so as to carry an exogenous polynucleotide sequence. 'Exogenous' refers to the fact that the polynucleotide originates from outside the plant cell. Typically, the exogenous polynucleotide is non-native to the transgenic plant i.e. it is not found naturally within the genome of the plant.

As used herein, the term 'transformation' refers to the introduction of exogenous polynucleotide molecules into a plant or a cell thereof. Techniques for introducing polynucleotides into plants are known in the art. In one embodiment of the current invention, the plants are 'stably transformed' with a polynucleotide or DNA construct comprising the same, i.e. the polynucleotide or DNA construct introduced into the plant cell integrates into the genome of the plant and is capable of being inherited by the progeny thereof. Transformation protocols for introducing polynucleotides or DNA constructs into the cells of plants may vary depending on the type of plant concerned. Suitable transformation methods include but are not limited to microinjection, electroporation, *Agrobacterium*-mediated transformation, and ballistic particle acceleration. Methods are also known in the art for the targeted insertion of a polynucleotide or DNA construct at a specific location in the plant genome using site-specific recombination systems.

The DNA construct comprising the polynucleotide encoding the active interfering RNA molecule may be any vector suitable for transformation of plant cells. Suitable vectors include but are not limited to bacterial plasmids, for example the Ti plasmid of *Agrobacterium tumefaciens*, and viral vector systems. The DNA construct introduced into the cells of a plant must not be harmful or toxic to the plant and/or must not be harmful or toxic to any organisms higher up the food chain that feed on said plants.

In one embodiment, the DNA construct is an expression construct comprising a polynucleotide encoding an interfering RNA operably linked to a regulatory sequence capable of driving expression of the polynucleotide sequence in plants such as any selected from the group comprising the CaMV35S promoter, doubled CaMV35S promoter, ubiquitin promoter, actin promoter, rubisco promoter, GOS2 promoter, Figwort mosaic virus 34S promoter and the double enhanced CaMV35S promoter. Preferably, the regulatory sequence is a plant promoter selected from those known in the art. In some embodiments, it may be preferred that the plant produces interfering RNA molecules only in the parts of the plant which will come into contact with and/or are damaged by the insect pest species, for example, the aerial parts of the plant, the roots etc. This effect can be achieved through the use of tissue-specific plant promoters including but not limited to leaf-specific promoters, root-specific promoters, stem-specific promoters, flower-specific promoters and fruit-specific promoters known in the art. Suitable examples of a root specific promoter are PsMTA and the Class III Chitinase promoter. Examples of leaf- and stem-specific or photosynthetic tissue-specific promoters that are also photoactivated are promoters of two chlorophyll binding proteins (cab1 and cab2) from sugar beet, ribulose-bisphosphate carboxylase (Rubisco), encoded by rbcS, A (gapA) and B (gapB) subunits of chloroplast glyceraldehyde-3-phosphate dehydrogenase, promoter of the *Solanum tuberosum* gene encoding the leaf and stem specific (ST-LS1) protein, stem-regulated, defense-inducible genes, such as JAS promoters, flower-specific promoters such as chalcone synthase promoter and fruit-specific promoters such as that of RJ39 from strawberry.

In other embodiments, it may be preferred that the plant produces interfering RNA molecules only at a particular stage of its growth. This effect can be achieved through the use of development-specific plant promoters that drive expression only during certain periods of plant development. In particular, it is important to protect plants from pest infestation during the early stages of plant growth or during flowering (for instance in case of rice) or during fructification or fruit maturation or seed-filling, as this is the time when the plant can be most severely damaged.

The DNA construct for use in transformation of a plant according to the present method may comprise more than one polynucleotide encoding an interfering RNA molecule of the current invention. In one embodiment, the different polynucleotides may encode interfering RNA molecules targeting different nucleotide sequences within the same target gene. In a further embodiment, the different polynucleotides may encode interfering RNA molecules targeting different nucleotide sequences within different target genes, wherein the different target genes originate from the same or different insect pest species. Wherein the DNA construct encodes more than one interfering RNA, these RNAs may be expressed differentially within different tissues of the plant by virtue of being under the control of different tissue-specific promoter sequences as described elsewhere herein. In one embodiment, the plant is engineered to express an interfering RNA in the leaves which down-regulates expression of a target gene in an insect that feeds on the leaves, and to additionally express an interfering RNA in the roots which down-regulates expression of a target gene in an insect that colonizes the soil and feeds on the plant roots.

The DNA construct may also comprise at least one other polynucleotide of interest, for example a polynucleotide encoding an additional regulatory RNA molecule, a polynucleotide encoding a protein toxic to insect pest species and/or a polynucleotide encoding a protein conferring herbicide resistance.

In accordance with the present method, a plant is regenerated from a transformed plant cell using techniques known in the art. One such technique comprises enzymatic digestion of the plant cell wall to produce a plant protoplast, which can subsequently undergo multiple rounds of cell division and differentiation to produce an adult plant. Adult plants generated in such a way can be subsequently tested for resistance to pest infestation. 'Resistant' as used herein should be interpreted broadly and relates to the ability of the plant to defend against attack from a pest that is typically capable of inflicting damage or loss to the plant. Resistant may either be taken to mean that the plant is no longer susceptible to pest infestation or that any disease symptoms resulting from pest infestation are reduced by at least about 20%, preferably at least 30%, 40% or 50%, more preferably at least 60%, 70% or 80% and most preferably by at least 90%. Techniques to measure the resistance of a plant to insect pest species are commonly known in the art and include but are not limited to measuring over time the average lesion diameter, the pest biomass, and/or the overall percentage of decayed plant tissues.

In one embodiment, the present method of producing a transgenic plant also includes the step of generating offspring or progeny from the transgenic plant and testing the progeny for resistance to the insect pest. Two or more generations may be produced to ensure that expression of the resistance trait is stably maintained and inherited. Seeds may also be harvested from the parent transgenic plant and/or its progeny to test for resistance to an insect pest.

Also encompassed within the present invention is a method for generating transgenic plants resistant to infestation by an insect pest species comprising the steps of crossing a first transgenic plant carrying a DNA construct encoding an interfering RNA that functions to down-regulate expression of a pest target gene, with a second plant lacking said DNA construct, and selecting progeny resistant to said pest. Crossing may be carried out by any methods routinely used in the context of plant breeding. The progeny selected for pest resistance may additionally be self-pollinated or 'selfed' to produce a subsequent generation of pest resistant progeny. In one embodiment, multiple rounds of self pollination or selfing may be carried out to generate 2, 3, 4, 5 or more generations of progeny. The resultant progeny may be tested for pest resistance to ensure that expression of the resistance trait is stably maintained and inherited.

In a further embodiment, any pest resistant progeny plants derived from a cross between a first transgenic parent plant carrying a DNA construct of interest and a second parent plant lacking said DNA construct may be back-crossed to the second parent plant and subsequent progeny tested for resistance to pest infestation. Plants or their progeny may be tested for resistance to pest infestation either by phenotypic analysis as described elsewhere herein or by standard molecular techniques. For example, the pest resistant plants may be identified by the detection of the presence of a DNA construct comprising a polynucleotide sequence encoding an interfering RNA that functions upon uptake by an insect pest species to down-regulate expression of a target gene. Techniques for detecting the presence of specific polynucleotide sequences within cells are known in the art and include PCR, enzymatic digestion and SNP analysis.

The methods of the invention can be used to generate 'stacked transgenic' plants that are resistant to insect pest species and that optionally possess at least one other desirable trait. As used herein, a 'stacked' transgenic plant refers to a plant carrying more than one exogenous polynucleotide sequence. The phrase 'more than one' refers to the possibility of a plant carrying at least 2, at least 3, at least 4 exogenous polynucleotides. In one embodiment, the plant cell transformed with the DNA construct encoding the interfering RNA targeting a pest gene may have previously been engineered to carry a separate exogenous polynucleotide. Alternatively, the method for generating a transgenic plant from a plant cell as described herein may comprise a co-transformation protocol wherein the DNA construct encoding an interfering RNA of the invention is delivered to a plant cell simultaneously or sequentially with a separate exogenous polynucleotide.

Stacked transgenic plants demonstrating pest resistance may also be generated by standard plant breeding techniques. In one embodiment, a first pest-resistant transgenic plant is crossed with a second plant engineered to express an exogenous polynucleotide or heterologous gene conferring a desirable plant trait. Any progeny produced can be tested for pest resistance and acquisition of the additional desirable trait. Alternatively or in addition, any pest-resistant progeny produced from the cross may be back-crossed to the second parent in order to generate further progeny that can be selected for inheritance of the heterologous gene carried by the second parent and thus the additional desirable plant trait. The exogenous polynucleotides carried by a stacked transgenic plant of the invention may be expressed in the same parts of the plant or may be expressed differentially by virtue of the fact that expression of each is controlled by a different tissue-specific promoter.

In one embodiment, the exogenous polynucleotide or heterologous gene conferring a further desirable trait encodes another interfering RNA targeting the same or different insect pest species. In a further embodiment, the heterologous gene encodes a protein harmful or toxic to a plant insect pest species, for example an insecticidal protein selected from the group including but not limited to Cry1Ab, Cry1C, Cry2Aa, Cry3, CryET70, Cry22, CryET33, CryET34, CryET80, CryET76, TIC100, TIC101, TIC851, TIC900, TIC901, TIC1201, TIC407, TIC417, PS149B1 and VIP insecticidal proteins. In a yet further embodiment, the heterologous gene encodes a protein conferring herbicide resistance. Examples of genes conferring herbicide resistance include Bar, EPSPS which confers glyphosate resistance, ALS which confers imidazolinone and sulphonylurea resistance and bxn which confers bromoxynil resistance.

Also provided herein is a method for producing hybrid seed from any of the transgenic plants generated by the methods of the current invention, said method comprising the steps of (i) planting the seed obtained from a first inbred plant and the seed obtained from a second inbred plant, wherein at least one of the inbred plants is a transgenic plant resistant to pest infestation (ii) cultivating the seeds into plants that bear flowers, (iii) preventing self-pollination of at least one of the first or second adult plants, (iv) allowing cross-pollination to occur between the first and second plants; and (v) harvesting the seeds resulting from the cross-pollination. Hybrid seed produced by this method and hybrid plants produced by cultivating said seed are within the scope of the current invention. Hybrid plants produced by this method will typically be genetically uniform and are likely to exhibit heterosis or hybrid vigour. Thus, crops with the potential for increased yield may be generated by such a method.

According to another aspect of the current invention are provided transgenic plants resistant to infestation by insect pest species. In particular, provided herein are transgenic plants which express or are capable of expressing at least one interfering ribonucleic acid (RNA) that functions upon uptake by an insect pest species to down-regulate the expression of a target gene as described elsewhere herein within said pest. The interfering RNA may be any of those as disclosed elsewhere herein. Preferably, the interfering RNA comprises or consists of at least one silencing element and said silencing element is a region of double-stranded RNA comprises annealed complementary strands, one strand of which (the sense strand) comprises a sequence of nucleotides which is at least partially complementary to a target nucleotide sequence within a target gene. Down-regulation of a pest target gene can be used to disrupt an essential biological process or function in the pest, wherein 'essential' refers to the fact that the process or function is required for initiation or maintenance of pest infestation.

As used herein, the term 'plant' may include any reproductive or propagation material for a plant. Reference to a plant may also include plant cells, plant protoplasts, plant tissue cultures, plant calli, plant clumps and plant cells that are intact in plants or parts of plants such as embryos, pollen, ovules, seeds, leaves, flowers, branches, fruit, kernels, ears, cobs, husks, stalks, roots, root tips and the like. Progeny, variants and mutants of any of the transgenic plants described herein are within the scope of the current invention. Also included is seed produced from any of said transgenic plants.

Included within the group of transgenic plants of the current invention are transgenic plants produced by any of the methods described herein. Thus in one embodiment of the invention the transgenic plants comprise stacked transgenic traits carrying a first exogenous polynucleotide conferring pest resistance and at least one other exogenous polynucleotide or heterologous gene conferring an additional desirable plant trait. The additional heterologous genes may comprise genes encoding additional pesticidal agents, genes encoding proteins toxic or harmful to insect pest species and/or genes encoding proteins conferring herbicide resistance as described elsewhere herein.

Also provided herein is the use of the interfering ribonucleic acid (RNA) as described herein or the DNA construct as described herein for preventing and/or controlling insect pest infestation, preferably insect pest infestation of plants.

The invention will be further understood with reference to the following non-limiting examples.

EXAMPLES

Example 1 Identification of Target Genes in Insect Pest Species 1.1 Cloning of Partial Sequences of the *Leptinotarsa decemlineata* Genes Nucleic acids were isolated from the gut cells of Colorado potato beetle, CPB, (*Leptinotarsa decemlineata*) larvae and a cDNA library was prepared. The gut cDNAs were cloned into the pGN49A vector (as described in WO01/88121) such that they were flanked by chemically-inducible T7 promoters, oppositely oriented at each end of the cDNA duplex. The recombinant vector constructs were transformed into cells of *Escherichia coli* strain AB301-105 (DE3). The transformed cells were subsequently diluted and plated so as to obtain single colonies or clones. The clones were checked to ensure that clone redundancy for the library did not exceed 5%. Between 3000 and 4000 clones were generated.

1.2 Testing the Effect of Bacterially-Expressed dsRNA Molecules on the Survival of *Leptinotarsa decemlineata* Larvae Multiwell plates were pre-filled with LB (Luria-broth) medium and each well was inoculated with a separate clone of transformed bacterial cells taken from the CPB cDNA library. The bacteria were grown at 28° C. with shaking at 280 rpm, followed by a chemical induction step at 37° C. After centrifugation, the resulting bacterial pellet was washed with water and subjected to a heat treatment to inactivate the bacteria.

The bacterial suspensions were tested for their effects on CPB larvae survival using an artificial diet-based feeding assay. A bacterial suspension produced from a single bacterial clone was topically applied to solid artificial diet in the wells of a multiwell plate and the diet was dried in a laminar flow cabinet. The effects of each clone were tested in triplicate. A single 2nd stage CPB larva was subsequently added to each well. The plates were stored in an insect rearing chamber at 25±2° C., 60±5% relative humidity, with a 16:8 hours light:dark photoperiod. Bacterial cells transformed with an empty vector, pGN29 (WO01/88121), were used as controls. The survival of CPB larvae in each of the wells was assessed on day 14.

A number of bacterial clones exhibited high potency against CPB larvae indicating that the cDNAs encoding double-stranded RNAs contained therein are essential for pest survival and thus represent target genes of interest for the purposes of pest control. The DNA sequences and corresponding amino acid sequences of these target genes were therefore determined and are provided in Tables 1 and 2 respectively.

TABLE 1

| Target ID | cDNA Sequence (sense strand) 5' → 3' |
|---|---|
| Ld556 | SEQ ID NO 1 |
| Ld513 | SEQ ID NO 2 |
| Ld504.2 | SEQ ID NO 3 |
| Ld520 | SEQ ID NO 4 |
| Ld537 | SEQ ID NO 5 |
| Ld334 | SEQ ID NO 6 |
| Ld327 | SEQ ID NO 7 |
| Ld502 | SEQ ID NO 8 |
| Ld516 | SEQ ID NO 9 |
| Ld579 | SEQ ID NO 10 |
| Ld332 | SEQ ID NO 11 |
| Ld237 | SEQ ID NO 12 |

TABLE 1-continued

| Target ID | cDNA Sequence (sense strand) 5' → 3' |
|---|---|
| Ld261 | SEQ ID NO 13 |
| Ld300.1 | SEQ ID NO 14 |
| Ld423 | SEQ ID NO 15 |
| Ld511 | SEQ ID NO 16 |
| Ld512 | SEQ ID NO 17 |
| Ld563 | SEQ ID NO 18 |
| Ld105 | SEQ ID NO 19 |
| Ld248 | SEQ ID NO 20 |

TABLE 2

| Target ID | Corresponding amino acid sequence of cDNA clone as represented in Table 1 |
|---|---|
| Ld556 | SEQ ID NO 206 (frame + 2) |
| Ld513 | SEQ ID NO 207 (frame + 3) |
| Ld504.2 | SEQ ID NO 208 (frame + 2) |
| Ld520 | SEQ ID NO 209 (frame + 3) |
| Ld537 | SEQ ID NO 210 (frame + 1) |
| Ld334 | SEQ ID NO 211 (frame + 1) |
| Ld327 | SEQ ID NO 212 (frame + 3) |
| Ld502 | SEQ ID NO 213 (frame + 2) |
| Ld516 | SEQ ID NO 214 (frame + 3) |
| Ld579 | SEQ ID NO 215 (frame + 1) |
| Ld332 | SEQ ID NO 216 (frame + 3) |
| Ld237 | SEQ ID NO 217 (frame + 2) |
| Ld261 | SEQ ID NO 218 (frame + 3) |
| Ld300.1 | SEQ ID NO 219 (frame + 3) |
| Ld423 | SEQ ID NO 220 (frame + 1) |
| Ld511 | SEQ ID NO 221 (frame + 3) |
| Ld512 | SEQ ID NO 222 (frame + 3) |
| Ld563 | SEQ ID NO 223 (frame + 1) |
| Ld105 | SEQ ID NO 224 (frame + 1) |
| Ld248 | SEQ ID NO 225 (frame + 1) |

1.3 Design of Degenerate Primers for Cloning *Lygus hesperus* Orthologous Sequences A protein (blastp) search was performed for each target gene of interest by searching non-redundant protein databases of Arthropods using the protein sequence corresponding to each of the *Leptinotarsa decemlineata* targets. A selection of up to twenty protein sequences was made from the best hits which represented a diversity of insect species.

These sequences were first processed into blocks using the "Blockmaker" program (http://bioinfo.weizmann.ac.il/blockmkr-bin/makeblocks.pl) which generated multiple sequence alignments and analyses of the protein sequences for regions of conservation.

Blocks of conserved amino acid sequences were submitted to CodeHop (http://blocks.fhcrc.org/codehop.html). From the output of degenerate primers a selection of up to ten forward and ten reverse primers for each target was produced.

1.4 Cloning of Partial Sequences of the *Lygus hesperus* Genes by Family PCR

High quality, intact RNA was isolated from 1st instar nymphs of *Lygus hesperus*. Any genomic DNA present in the RNA preparation was removed by DNase treatment. cDNA was generated using Reverse Transcriptase. To isolate cDNA sequences comprising a segment of the Lh513, Lh504.2, Lh520, Lh537, Lh334, Lh327, Lh579, Lh332, Lh237, Lh261, Lh300.1, Lh423, Lh512, Lh105 and Lh248 genes, a series of PCR reactions with degenerate primers was performed.

The resulting PCR fragments were analyzed on agarose gel, purified and sequenced. The sequences of the resulting PCR products are represented by the respective SEQ ID NOs as provided in Table 3 and are referred to as the partial sequences. The corresponding partial amino acid sequences are represented by the respective SEQ ID NOs as provided in Table 4.

TABLE 3

| Target ID | cDNA Sequence (sense strand) 5' → 3' |
|---|---|
| Lh513.1 | SEQ ID NO 121 |
| Lh513.2 | SEQ ID NO 122 |
| Lh504.2 | SEQ ID NO 123 |
| Lh520 | SEQ ID NO 124 |
| Lh537.1 | SEQ ID NO 125 |
| Lh537.2 | SEQ ID NO 126 |
| Lh537.3 | SEQ ID NO 127 |
| Lh537.4 | SEQ ID NO 128 |
| Lh537.5 | SEQ ID NO 129 |
| Lh334 | SEQ ID NO 130 |
| Lh327 | SEQ ID NO 131 |
| Lh579.1 | SEQ ID NO 132 |
| Lh579.2 | SEQ ID NO 133 |
| Lh332 | SEQ ID NO 134 |
| Lh237 | SEQ ID NO 135 |
| Lh261 | SEQ ID NO 136 |
| Lh300.1 | SEQ ID NO 137 |
| Lh423 | SEQ ID NO 138 |
| Lh423.2 | SEQ ID NO 253 |
| Lh512.1 | SEQ ID NO 139 |
| Lh512.2 | SEQ ID NO 140 |
| Lh105 | SEQ ID NO 251 |
| Lh248 | SEQ ID NO 252 |

TABLE 4

| Target ID | Corresponding amino acid sequence of cDNA clone as represented in Table 3 |
|---|---|
| Lh513.1 | SEQ ID NO 226 |
| Lh513.2 | SEQ ID NO 227 |
| Lh504.2 | SEQ ID NO 228 |
| Lh520 | SEQ ID NO 229 |
| Lh537.1 | SEQ ID NO 230 |
| Lh537.2 and Lh537.3 | SEQ ID NO 231 |
| Lh537.4 | SEQ ID NO 232 |
| Lh537.5 | SEQ ID NO 233 |
| Lh334 | SEQ ID NO 234 |
| Lh327 | SEQ ID NO 235 |
| Lh579.1 | SEQ ID NO 236 |
| Lh579.2 | SEQ ID NO 237 |
| Lh332 | SEQ ID NO 238 |
| Lh237 | SEQ ID NO 239 |
| Lh261 | SEQ ID NO 240 |
| Lh300.1 | SEQ ID NO 241 |
| Lh423 | SEQ ID NO 242 |
| Lh423.2 | SEQ ID NO 271 |
| Lh512.1 | SEQ ID NO 243 |
| Lh512.2 | SEQ ID NO 244 |
| Lh105 | SEQ ID NO 269 |
| Lh248 | SEQ ID NO 270 |

1.5 Full Length cDNA Cloning by RACE (Rapid Amplification of cDNA Ends)

In order to clone full length cDNA, starting from a known clone of internal fragment from the most potent targets, the 5/3' RACE kit was used (Roche, Cat. No. 1 734 792; based on Sambrook, J. & Russell, D. M). The standard protocol, described in the *Instruction Manual*, was followed. Briefly, for a 5' RACE, a target sequence specific antisense primer was designed on the known sequence and used for a first strand cDNA synthesis, using *Lygus* RNA as template. A tail was added to the first strand cDNA and used as an anchor for the second strand synthesis and amplification of an unknown end portion of the transcript. For a 3' RACE, an oligo dT anchor primer was used for the first strand cDNA synthesis. For the 5' and 3' RACEs, nested primers, specific to the target sequence were used in a second PCR reaction. The PCR fragments were analysed on agarose gel, purified, cloned and sequenced for confirmation.

Full length cDNA sequences corresponding to the *Lygus* targets listed in Table 13 were assembled in VectorNTi, a fully integrated sequence analysis software package for DNA sequence analysis (Invitrogen). The nucleotide sequences resulting from the assemblies are provided in Table 14 and the corresponding amino acid sequences are provided in Table 15.

TABLE 13

| Target ID | Dm orthologue | NAME | SYMBOL |
|---|---|---|---|
| Lh049 | CG8055 | shrub-snf7 (vesicle trafficking) | shrb |
| Lh248 | CG6699 | beta'-coatomer protein | beta'Cop |
| Lh105 | CG1250 | sec23 | sec23 |
| Lh300 | CG6213 | vacuolar H[+] ATPase G-subunit | Vha13 |
| Lh327 | CG6223 | beta-coatomer protein | betaCop |
| Lh423 | CG2746 | ribosomal protein L19 | RpL19 |
| Lh504 | CG5271 | ribosomal protein 527A | RpS27A |
| Lh520 | CG2960 | ribosomal protein L40 | RpL40 |

TABLE 14

| Target ID | cDNA Sequence (sense strand) 5' → 3' |
|---|---|
| Lh049 | SEQ ID NO 280 |
| Lh248 | SEQ ID NO 279 |
| Lh105 | SEQ ID NO 278 |
| Lh300 | SEQ ID NO 276 |
| Lh327 | SEQ ID NO 275 |
| Lh423 | SEQ ID NO 277 |
| Lh504 | SEQ ID NO 273 |
| Lh520 | SEQ ID NO 274 |

TABLE 15

| Target ID | Corresponding amino acid sequence to cDNA, as respresented in Table 14 |
|---|---|
| Lh049 | SEQ ID NO 288 |
| Lh248 | SEQ ID NO 287 |
| Lh105 | SEQ ID NO 286 |
| Lh300 | SEQ ID NO 284 |
| Lh327 | SEQ ID NO 283 |
| Lh423 | SEQ ID NO 285 |
| Lh504 | SEQ ID NO 281 |
| Lh520 | SEQ ID NO 282 |

Example 2 In Vitro Production of Double-Stranded RNAs for Gene Silencing 2.1 Production of dsRNAs Corresponding to the Partial Sequences of the *Leptinotarsa decemlineata* and *Lygus hesperus* Target Genes Double-stranded RNA was synthesized in milligram quantities. First, two separate 5' T7 RNA polymerase promoter templates (a sense template and an antisense template) were generated by PCR. PCRs were designed and carried out so as to produce sense and antisense template polynucleotides, each having the T7 promoter in a different orientation relative to the target sequence to be transcribed.

For each of the target genes, the sense template was generated using a target-specific T7 forward primer and a target-specific reverse primer. The antisense templates were generated using target-specific forward primers and target-specific T7 reverse primers. The sequences of the respective primers for amplifying the sense and antisense templates via PCR for each of the target genes are provided in Table 5 (for *Leptinotarsa decemlineata* cDNAs) and in Table 6 (for *Lygus hesperus* cDNAs). The PCR products were analysed by agarose gel electrophoresis and purified. The resultant T7 sense and antisense templates were mixed and transcribed by the addition of T7 RNA polymerase. The single-stranded RNAs produced by transcription from the templates were allowed to anneal, were treated with DNase and RNase, and were purified by precipitation. The sense strand of the resulting dsRNA produced from each of the target genes is provided in Table 5 (for *Leptinotarsa decemlineata*) and in Table 6 (for *Lygus hesperus*).

TABLE 5

| Target ID | Primers Forward 5' → 3' | Primers Reverse 5' → 3' | dsRNA: sense strand represented by equivalent DNA Sequence 5' → 3' |
|---|---|---|---|
| Ld556 | SEQ ID NO 41<br>SEQ ID NO 43 | SEQ ID NO 42<br>SEQ ID NO 44 | SEQ ID NO 21 |
| Ld513 | SEQ ID NO 45<br>SEQ ID NO 47 | SEQ ID NO 46<br>SEQ ID NO 48 | SEQ ID NO 22 |
| Ld504.2 | SEQ ID NO 49<br>SEQ ID NO 51 | SEQ ID NO 50<br>SEQ ID NO 52 | SEQ ID NO 23 |
| Ld520 | SEQ ID NO 53<br>SEQ ID NO 55 | SEQ ID NO 54<br>SEQ ID NO 56 | SEQ ID NO 24 |
| Ld537 | SEQ ID NO 57<br>SEQ ID NO 59 | SEQ ID NO 58<br>SEQ ID NO 60 | SEQ ID NO 25 |
| Ld334 | SEQ ID NO 61<br>SEQ ID NO 63 | SEQ ID NO 62<br>SEQ ID NO 64 | SEQ ID NO 26 |
| Ld327 | SEQ ID NO 65<br>SEQ ID NO 67 | SEQ ID NO 66<br>SEQ ID NO 68 | SEQ ID NO 27 |
| Ld502 | SEQ ID NO 69<br>SEQ ID NO 71 | SEQ ID NO 70<br>SEQ ID NO 72 | SEQ ID NO 28 |
| Ld516 | SEQ ID NO 73<br>SEQ ID NO 75 | SEQ ID NO 74<br>SEQ ID NO 76 | SEQ ID NO 29 |
| Ld579 | SEQ ID NO 77<br>SEQ ID NO 79 | SEQ ID NO 78<br>SEQ ID NO 80 | SEQ ID NO 30 |
| Ld332 | SEQ ID NO 81<br>SEQ ID NO 83 | SEQ ID NO 82<br>SEQ ID NO 84 | SEQ ID NO 31 |
| Ld237 | SEQ ID NO 85<br>SEQ ID NO 87 | SEQ ID NO 86<br>SEQ ID NO 88 | SEQ ID NO 32 |
| Ld261 | SEQ ID NO 89<br>SEQ ID NO 91 | SEQ ID NO 90<br>SEQ ID NO 92 | SEQ ID NO 33 |
| Ld300.1 | SEQ ID NO 93<br>SEQ ID NO 95 | SEQ ID NO 94<br>SEQ ID NO 96 | SEQ ID NO 34 |
| Ld423 | SEQ ID NO 97<br>SEQ ID NO 99 | SEQ ID NO 98<br>SEQ ID NO 100 | SEQ ID NO 35 |
| Ld511 | SEQ ID NO 101<br>SEQ ID NO 103 | SEQ ID NO 102<br>SEQ ID NO 104 | SEQ ID NO 36 |
| Ld512 | SEQ ID NO 105<br>SEQ ID NO 107 | SEQ ID NO 106<br>SEQ ID NO 108 | SEQ ID NO 37 |
| Ld563 | SEQ ID NO 109<br>SEQ ID NO 111 | SEQ ID NO 110<br>SEQ ID NO 112 | SEQ ID NO 38 |
| Ld105 | SEQ ID NO 113<br>SEQ ID NO 115 | SEQ ID NO 114<br>SEQ ID NO 116 | SEQ ID NO 39 |
| Ld248 | SEQ ID NO 117<br>SEQ ID NO 119 | SEQ ID NO 118<br>SEQ ID NO 120 | SEQ ID NO 40 |

TABLE 6

| Target ID | Primers Forward 5' → 3' | Primers Reverse 5' → 3' | dsRNA: sense strand represented by equivalent DNA Sequence 5' → 3' |
|---|---|---|---|
| Lh513 | SEQ ID NO 154<br>SEQ ID NO 156 | SEQ ID NO 155<br>SEQ ID NO 157 | SEQ ID NO 141 |

TABLE 6-continued

| Target ID | Primers Forward 5' → 3' | Primers Reverse 5' → 3' | dsRNA: sense strand represented by equivalent DNA Sequence 5' → 3' |
|---|---|---|---|
| Lh504.2 | SEQ ID NO 158<br>SEQ ID NO 160 | SEQ ID NO 159<br>SEQ ID NO 161 | SEQ ID NO 142 |
| Lh520 | SEQ ID NO 162<br>SEQ ID NO 164 | SEQ ID NO 163<br>SEQ ID NO 165 | SEQ ID NO 143 |
| Lh537 | SEQ ID NO 166<br>SEQ ID NO 168 | SEQ ID NO 167<br>SEQ ID NO 169 | SEQ ID NO 144 |
| Lh334 | SEQ ID NO 170<br>SEQ ID NO 172 | SEQ ID NO 171<br>SEQ ID NO 173 | SEQ ID NO 145 |
| Lh327 | SEQ ID NO 174<br>SEQ ID NO 176 | SEQ ID NO 175<br>SEQ ID NO 177 | SEQ ID NO 146 |
| Lh579 | SEQ ID NO 178<br>SEQ ID NO 180 | SEQ ID NO 179<br>SEQ ID NO 181 | SEQ ID NO 147 |
| Lh332 | SEQ ID NO 182<br>SEQ ID NO 184 | SEQ ID NO 183<br>SEQ ID NO 185 | SEQ ID NO 148 |
| Lh237 | SEQ ID NO 186<br>SEQ ID NO 188 | SEQ ID NO 187<br>SEQ ID NO 189 | SEQ ID NO 149 |
| Lh261 | SEQ ID NO 190<br>SEQ ID NO 192 | SEQ ID NO 191<br>SEQ ID NO 193 | SEQ ID NO 150 |
| Lh300.1 | SEQ ID NO 194<br>SEQ ID NO 196 | SEQ ID NO 195<br>SEQ ID NO 197 | SEQ ID NO 151 |
| Lh423 | SEQ ID NO 198<br>SEQ ID NO 200 | SEQ ID NO 199<br>SEQ ID NO 201 | SEQ ID NO 152 |
| Lh512 | SEQ ID NO 202<br>SEQ ID NO 204 | SEQ ID NO 203<br>SEQ ID NO 205 | SEQ ID NO 153 |
| Lh105.2 | SEQ ID NO 257<br>SEQ ID NO 259 | SEQ ID NO 258<br>SEQ ID NO 260 | SEQ ID NO 254 |
| Lh248.2 | SEQ ID NO 261<br>SEQ ID NO 263 | SEQ ID NO 262<br>SEQ ID NO 264 | SEQ ID NO 255 |
| Lh248.3 | SEQ ID NO 265<br>SEQ ID NO 267 | SEQ ID NO 266<br>SEQ ID NO 268 | SEQ ID NO 256 |
| GFP | SEQ ID NO 246<br>SEQ ID NO 248 | SEQ ID NO 247<br>SEQ ID NO 249 | SEQ ID NO 245 |

Example 3 Down-Regulating Expression of Target Genes in *Leptinotarsa decemlineata* as a Means to Achieve Pest Control

3.1 Testing of In Vitro-Synthesized dsRNA Molecules for Activity Against *Leptinotarsa decemlineata* Larvae In vitro-synthesized dsRNAs transcribed from template polynucleotides derived from target genes identified according to the methods of Example 1 were tested for effects on the survival of CPB larvae using feeding assays. Briefly, artificial diet-based assays were carried out as follow. To each well of a 48-well plate was added 0.5 ml artificial diet pre-treated by topical application of 1000 ng/$cm^2$ synthetic dsRNA in 25 μL. A single L2 larva was added to each well. dsRNAs derived from a variety of target genes were tested using this method and 24 larvae were tested for each dsRNA. The total numbers of surviving larvae were counted at regular intervals up to 14 days after the start of feeding. The time taken for each dsRNA to kill 50% of treated larvae ($LT_{50}$) was calculated for each target gene investigated and compared to the $LT_{50}$ for a reference target gene (Ld248) previously described in WO2007/074405. The results are presented in Table 7.

TABLE 7

| Rank | Target | Dm[1] orthologue | Name/Description (FlyBase) | $LT_{50}$ target X/ $LT_{50}$ target Ld248 | dsRNA length (bp) |
|---|---|---|---|---|---|
| 1 | Ld556 | CG11415 | Tsp2A; Tetraspanin 2A, putative transmembrane domain protein | 0.60 | 558 |
| 2 | Ld513 | CG5409 & others | Protein belonging to the actin family; structural constituent of cytoskeleton | 0.67 | 320 |
| 3 | Ld504.2 | CG5271 | Ribosomal protein S27A; structural constituent of ribosome | 0.70 | 490 |
| 4 | Ld520 | CG2960 | Ribosomal protein L40; structural constituent of ribosome | 0.70 | 231 |
| 5 | Ld537 | CG32744 | Ubiquitin-5E; protein modification process | 0.77 | 571 |
| 6 | Ld334 | CG3948 | ζ-coatomer of COPI vesicle | 0.80 | 542 |
| 7 | Ld327 | CG6223 | β-coatomer of COPI vesicle | 0.83 | 747 |
| 8 | Ld105 | CG1250 | Sec23; GTPase activator involved in intracellular protein transport | 0.85 | 1504 |
| 9 | Ld502 | CG7595 | Crinkled protein; unconventional myosin involved in motor activity | 0.90 | 393 |
| 10 | Ld516 | CG11888 | Rpn2; proteasome regulatory particle | 0.90 | 779 |
| 11 | Ld579 | CG8392 | Proteasome β1 subunit | 0.90 | 392 |
| 12 | Ld332 | CG1528 | γ-coatomer of COPI vesicle | 0.90 | 178 |
| 13 | Ld237 | CG10149 | Rpn6; proteasome p44.5 subunit | 0.90 | 559 |
| 14 | Ld261 | CG5266 | Pros25; proteasome 25 kD subunit | 0.90 | 586 |
| 15 | Ld300.1 | CG6213 | Vacuolar $H^+$-ATPase G-subunit | 1.00 | 267 |
| 16 | Ld248 | CG6699 | β'-coatomer protein | 1.00 | 967 |
| 17 | Ld423 | CG2746 | Ribosomal protein L19 | 1.00 | 603 |
| 18 | Ld511 | CG3329 | Prosβ2; proteasome β2 subunit | 1.02 | 273 |

[1]*Drosophila melanogaster*

From these results, it can be concluded that dsRNAs targeting the CPB genes identified in Example 1 are more potent or at least as potent as reference CPB target genes that have been previously reported in WO2007/074405 i.e. in the majority of cases, the 'time-to-kill' CPB larvae was shorter than for the reference targets Ld105 and Ld248 (as previously described in WO2007/074405: Ld105=[Target ID NO LD010], Ld248=[Target ID NO LD027]). The efficacy against CPB larvae after dsRNA consumption differed depending on the nature of the gene targeted.

3.2 Testing of In Vitro-Synthesized dsRNA Molecules for Activity Against *Leptinotarsa decemlineata* Adults The data provided below exemplify the findings that ingested dsRNAs produced from template polynucleotides derived from a variety of CPB target genes adversely affected the survival, fitness, feeding behaviour, mating behaviour, egg production and offspring generation of CPB adults.

Various gene targets selected from the larvae gut cDNA expression library and as shown above in Example 3.1 to be effective for the purposes of killing CPB larvae, were tested in order to assess the effects of gene down-regulation in adult beetles. Gene targets identified as important in both CPB larvae and adult beetles are of particular interest since they may be used to control and/or prevent insect pest infestation at different stages of an insect's life-cycle.

Briefly, a leaf disc assay to test the effects of dsRNA molecules derived from various target genes, against adult beetles was set up as follows. A potato leaf disc, diameter 1.5 cm, treated with 5 μg of in vitro-synthesized target dsRNA provided in 20 μL, was placed in a well of a 6-well plate together with a week-old CPB adult. After a few hours, once the leaf disc had been entirely consumed by the insect, another leaf disc treated with 5 μg of in vitro-synthesized target dsRNA was presented to the adult. For each dsRNA to be tested, a total of ten young adult beetles (a mix of males and females) were exposed to treated leaf discs. The following day, after the second treated leaf disc had been entirely consumed, the ten adults in each treatment group were pooled in the same box and fed abundant untreated potato foliage. Adult beetles fed dsRNA derived from the GFP gene were used as controls in this assay.

The numbers of surviving and/or moribund adult insects were counted at regular intervals from day 4 up to 14 days after the start of the feeding assay. CPB adults were classified as moribund if they appeared sick and less mobile than healthy adults and were not able to right themselves when placed on their backs for longer than one minute. Effects on feeding, mating, egg production and hatching were also assessed at regular intervals from day 4.

Mortality and Moribundity

The percentage of moribund and/or dead CPB adults assessed over a 14-day period for each target gene tested are shown in FIG. 1. In addition, the time taken to achieve 50% mortality of adult beetles ($LT_{50}$) in each treatment group was calculated and the results shown in Table 8 are presented as a ratio based on the $LT_{50}$ calculated for a reference target gene previously described in WO2007/074405.

TABLE 8

| Rank | Target | Dm orthologue | Name/Description (FlyBase) | $LT_{50}$ target X/ $LT_{50}$ target Ld248 | dsRNA length (bp) |
|---|---|---|---|---|---|
| 1 | Ld537 | CG32744 | Ubiquitin-5E; protein modification process | 0.63 | 571 |

TABLE 8-continued

| Rank | Target | Dm orthologue | Name/Description (FlyBase) | $LT_{50}$ target X/ $LT_{50}$ target Ld248 | dsRNA length (bp) |
|---|---|---|---|---|---|
| 2 | Ld520 | CG2960 | Ribosomal protein L40; structural constituent of ribosome | 0.70 | 231 |
| 3 | Ld516 | CG11888 | Rpn2; proteasome regulatory particle | 0.74 | 779 |
| 4 | Ld512 | CG10370 | Tbp-1; Tat-binding protein | 0.74 | 310 |
| 5 | Ld511 | CG3329 | Prosβ2; proteasome β2 subunit | 0.77 | 273 |
| 6 | Ld579 | CG8392 | Proteasome β1 subunit | 0.87 | 392 |
| 7 | Ld513 | CG5409 & others | Protein belonging to the actin family; structural constituent of cytoskeleton | 0.88 | 320 |
| 8 | Ld248 | CG6699 | β'-coatomer protein | 1.00 | 967 |
| 9 | Ld563 | CG3193 | Crooked neck protein; involved in regulation of nuclear alternative mRNA splicing | 1.05 | 388 |
| 10 | Ld105 | CG1250 | Sec23; GTPase activator involved in intracellular protein transport | 1.06 | 1504 |

From these results, it can be concluded that dsRNAs targeting a variety of CPB genes identified in Example 1 are more potent or at least as potent as reference CPB target genes that have been previously reported in the WO2007/074405 i.e. in the majority of cases, the 'time-to-kill' CPB adults was shorter than for the reference targets Ld105 and Ld248 (as previously described in WO2007/074405: Ld105=[Target ID NO LD010], Ld248=[Target ID NO LD027]). The efficacy against CPB adults after dsRNA consumption differed depending on the nature of the gene targeted.

Feeding Inhibition

For all target genes of interest, complete cessation of feeding by CPB adults was observed from day 5 onwards of the assay (4 days after the treated potato foliage was replaced by untreated potato foliage). Control CPB adults fed as normal throughout the assay.

Mating, Egg Production, and Egg Hatching

Mating, egg production, and egg hatching were assessed throughout the 14-day time-course of the assay. The results are shown in Table 9.

TABLE 9

| Target | Day 4 | Day 5 | Day 6 | Day 7 | Day 8 | Day 14 |
|---|---|---|---|---|---|---|
| Ld105 | EM | SE | none | none | none | none |
| Ld248 | EM | YS | YS | none | none | none |
| Ld516 | EM | SE | none | none | none | none |
| Ld511 | EM & SE | YS | none | none | none | none |
| Ld512 | EM & SE | SE | SE | none | none | none |
| Ld513 | EM & SE | none | none | none | none | none |
| Ld520 | SE | none | none | none | none | none |
| Ld537 | EM & SE | SE | none | none | none | none |
| Ld563 | none | SE | none | none | none | none |
| Ld579 | EM | SE | SE | none | none | none |
| GFP | EM | EM | EM | EM | EM | EM |

From day 5 onwards, no mating was observed in CPB adults in the treated groups, however, mating of CPB adults in the GFP control group was as normal.

On day 4, normal egg masses (with 20-30 eggs per egg mass) were observed in groups treated with dsRNAs targeting Ld105, Ld248, Ld516, Ld579, and GFP. (These egg masses were laid between days 1 and 3 of the assay.) However, for the groups treated with dsRNAs targeting Ld511, Ld512, Ld513, and Ld537, a mixture of normal egg masses and single eggs were found. No normal egg masses were observed in the CPB group treated with dsRNA targeting Ld520; only individual single eggs were observed.

Eggs identified on day 4 were harvested and both hatching frequency and larval survival were assessed. In all treatment groups for which normal egg masses were harvested, hatching was 100% except for the Ld537 group in which only 50% of eggs in the single egg mass harvested went on to hatch. All larvae from these egg masses developed normally.

For groups in which Ld511 and Ld537 were the target genes of interest, less than 10% of the single eggs hatched and these larvae died within 7 days after hatching. For the groups in which the target genes were Ld512, Ld520 and Ld513, the hatching frequency was 30%, 70% and 100% respectively.

On day 5, no egg masses were observed in any of the treatment groups except for the GFP control. However, single eggs were present in the groups wherein the target genes were Ld105, Ld516, Ld512, Ld537, Ld563, and Ld579. A yellow smear (indicative of no intact eggs) was visible in the feeding chambers of insects in the groups treated with dsRNAs targeting Ld248 and Ld511. In the groups for which Ld513 and Ld520 were the target genes, no eggs were discovered.

Eggs identified on day 5 were harvested and both hatching frequency and larval survival were assessed. For groups with target genes Ld512, Ld516, and Ld563, hatching was between 20 and 50%, but all larvae in group Ld563 died within 7 days of hatching. For the group with Ld579 as the gene target, all eggs hatched and larvae developed as normal.

On day 6, only single eggs were identified in the treatment groups wherein the target genes were Ld512 and Ld579. A yellow smear was noted in the Ld248 target group. No eggs were present in any of the other treatment groups. From day 7 onwards, no eggs were laid by any of the treated adult beetles. However, GFP dsRNA-treated control females continued to lay normal egg masses throughout the assay.

Example 4 Down-Regulating Expression of Target Genes in *Lygus hesperus* by Ingestion of dsRNA as a Means to Achieve Pest Control 4.1 Modification of the *Lygus hesperus* Feeding Assay to Allow for More Effective Uptake of dsRNA Molecules Although the rearing diet from BioServ used in maintaining the *Lygus* cultures over many generations is effective, this diet may not be appropriate for testing candidate dsRNA molecules in a feeding assay. The oligidic diet includes ingredients which are not chemically defined and therefore some components may possibly interact with the molecules to be delivered to the nymphs. Therefore, the *Lygus* feeding assay has been modified such that it consists of two phases: an initial exposure of early instar nymphs to dsRNA molecules in a simplified diet (15% sucrose only) for three days followed by transfer of the nymphs to a normal oligidic *Lygus* diet for the remainder of the assay.

4.2 Effects of Various Target dsRNAs Plus Yeast tRNA on *Lygus hesperus* Survival

*Lygus hesperus* nymphs were exposed to 0.5 μg/μL dsRNA derived a number of *Lygus hesperus* target genes as described herein in the presence of 5 μg/μL yeast tRNA (Sigma) in a feeding assay (FIG. 2). Controls are GFP dsRNA plus yeast tRNA at the same concentrations, respectively, and diet only treatments. Young nymphs were each exposed to 25 μL of 15% sucrose diet with or without incorporated test components for three days prior to transferring them on to 50 μL complex (Bioserv) diet. Complex diet was refreshed on day 7.

In this assay, ingested dsRNA from all tested targets in combination with tRNA led to high mortalities of *L. hesperus* nymphs when compared to the GFP dsRNA or diet only control treatments (Table 10).

TABLE 10

| | | Log-rank test (versus GFP) | | |
|---|---|---|---|---|
| Target ID | DsRNA length (bp) | Chi square | P-value | Significant difference?† |
| Lh520 | 231 | 18.04 | <0.0001 | *** |
| Lh423 | 511 | 17.11 | <0.0001 | *** |
| Lh537 | 300 | 14.63 | 0.0001 | *** |
| Lh504.2 | 168 | 12.99 | 0.0003 | *** |
| Lh512 | 495 | 11.86 | 0.0006 | *** |
| Lh334 | 172 | 10.39 | 0.0013 | ** |
| Lh300.1 | 235 | 10.22 | 0.0014 | ** |
| Lh327 | 408 | 9.153 | 0.0025 | ** |
| Lh332 | 1041 | 7.972 | 0.0047 | ** |
| Lh237 | 710 | 5.793 | 0.0161 | * |
| Lh579 | 273 | 5.336 | 0.0209 | * |
| Lh261 | 368 | 3.928 | 0.0475 | * |
| Lh513 | 625 | 2.144 | 0.1432 | ns |
| diet only | / | 1.483 | 0.2233 | ns |

†survival curves significantly different?
*** = extremely significant,
** = very significant,
* = significant,
ns = not significant A table which ranks the targets according to potency is made based upon the results of this RNAi-by-feeding assay (Table 11 and FIG. 3).

TABLE 11

| Target | dsRNA length (bp) | *D. melanogaster* orthologue | Description (FlyBase) | % Survival range at day 10 | FIG. |
|---|---|---|---|---|---|
| Lh423 | 511 | CG2746 | Ribosomal protein L19 | 0-15 | 3 A |
| Lh520 | 231 | CG2960 | Ribosomal protein L40 | | |
| Lh504.2 | 168 | CG5271 | Ribosomal protein S27A | 16-30 | 3 B |
| Lh537 | 300 | CG32744 | Ubiquitin-5E | | |
| Lh512 | 495 | CG10370 | Tbp-1, Tat-binding protein | | |
| Lh300.1 | 235 | CG6213 | Vacuolar $H^+$-ATPase G subunit | | 3 C |
| Lh327 | 408 | CG6223 | β-coatomer of COPI vesicle | | |

TABLE 11-continued

| Target | dsRNA length (bp) | *D. melanogaster* orthologue | Description (FlyBase) | % Survival range at day 10 | FIG. |
|---|---|---|---|---|---|
| Lh334 | 172 | CG3948 | ζ-coatomer of COPI vesicle | | |
| Lh332 | 1041 | CG1528 | γ-coatomer of COPI vesicle | | |
| Lh579 | 273 | CG8392 | Proteasome β1 subunit | 31-45 | 3 D |
| Lh237 | 710 | CG10149 | Rpn6, proteasome p44.5 subunit | | |
| Lh261 | 368 | CG5266 | Pros25, proteasome 25 kD subunit | >45 | 3 D |
| Lh513 | 625 | CG4027 | Actin 5C | | |

In another RNAi-by-feeding assay under the same conditions as described hereabove, we tested the effects of Lh105 and Lh248 target dsRNA on *Lygus hesperus* nymphal survival. Double-stranded RNA from targets Lh105 and Lh248 at 0.5 μg/μL in the presence of 5 μg/μL of tRNA led to significant *L. hesperus* nymphal lethality at day 10 in a feeding assay (83% for Lh105.2 dsRNA and 58% for Lh248.2 dsRNA and 71% for Lh248.3 dsRNA) (FIG. 6). In the same assay, Lh327 and Lh300 dsRNA showed only 4% and 13% survivors, respectively, at the end of the bioassay (FIG. 6).

4.3 Dose-Response Relationship Over Time of Target dsRNA Against *Lygus hesperus* Nymphs in RNAi-by-Feeding Assays The dose-response relationship was studied to determine the *L. hesperus* nymphs' susceptibility to lowering dsRNA concentrations of test targets in RNAi-by-feeding assays. The data are graphically represented in FIGS. 4 and 5. The Kaplan-Meier estimated survival curves of the test targets at the low concentrations of 0.1, 0.05 and 0.025 μg/μL were compared with those of GFP dsRNA control at 0.1 μg/μL using the log rank test (Table 12).

TABLE 12

| Target dsRNA[1] | Dose (μg/μL) | $X^2$ | P-value | Significance |
|---|---|---|---|---|
| Lh423 | 0.1 | 30.36 | <0.0001 | *** |
| | 0.05 | 6.759 | 0.0093 | ** |
| | 0.025 | 6.239 | 0.0125 | * |
| Lh504.2 | 0.1 | 5.828 | 0.0158 | * |
| | 0.05 | 0.7283 | 0.3934 | ns |
| | 0.025 | 0.4834 | 0.4869 | ns |
| Lh537 | 0.1 | 2.150 | 0.1426 | ns |
| | 0.05 | 2.150 | 0.1426 | ns |
| | 0.025 | 0.007874 | 0.9293 | ns |
| Lh327 | 0.1 | 13.80 | 0.0002 | *** |
| | 0.05 | 6.176 | 0.0129 | * |
| | 0.025 | 3.000 | 0.0833 | ns |
| Lh520 | 0.1 | 12.65 | 0.0004 | *** |
| | 0.05 | 2.944 | 0.0862 | ns |
| | 0.025 | 1.893 | 0.1689 | ns |
| Lh300.1 | 0.1 | 12.24 | 0.0005 | *** |
| | 0.05 | 10.81 | 0.0010 | ** |
| | 0.025 | 1.615 | 0.2038 | ns |

[1]in the presence of 5 μg/μL of yeast transfer RNA

All targets tested were toxic towards *L. hesperus* nymphs at concentrations as low as 0.1 μg/μL. Target Lh423 dsRNA at this concentration yielded under 10% nymphal survival towards the end of the bioassays. At the lowest concentration tested, i.e. 0.025 μg/μL, target Lh423 still showed a significant drop in survival when compared to GFP. Double-stranded RNAs from targets Lh300.1 and Lh327 also demonstrated high potency at low concentrations with significant drops in survival at 0.05 μg/μL.

Example 5 Generation of Plants Resistant to Insect Pest Species

5.1 Assembly of Plant Expression Vectors Comprising a *Lygus hesperus* Hairpin Sequence or *Leptinotarsa decemlineata* Hairpin Sequence for Transformation of Potato or Cotton Since the mechanism of RNA interference operates through dsRNA fragments, the target polynucleotide sequences were cloned in anti-sense and sense orientation, separated by an intron (SEQ ID NO 250), to form a dsRNA hairpin construct. The dsRNA hairpin constructs encoding the *L. hesperus* dsRNA molecule derived from the target genes as mentioned herein were subcloned into a plant expression vector. Similarly a GUS dsRNA hairpin control construct, wherein the sense polynucleotide sequence encoding GUS (SEQ ID NO 272) was cloned in anti-sense and sense orientation, separated by the same intron (SEQ ID NO 250), was subcloned into a plant expression vector.

The plant expression vector comprises as well elements necessary for the maintenance of the plasmid in a bacterial cell. The dsRNA hairpin construct is located between the left border (LB) and right border (RB), 3' downstream from the Cauliflower Mosaic Virus 35S promoter (P35S) and 5' upstream from the TNOS terminator. A GFP reporter expression cassette comprising the GFP sequence flanked by the P35S promoter and terminator was subcloned into the plant transformation vector harbouring the *L. hesperus* hairpin cassette. The NPT II expression cassette comprising the NPT II sequence flanked by the P35S promoter and terminator is used for selecting plants that have been effectively transformed. Correct assembly of the genetic fragments in the plant expression vector was confirmed by sequencing (FIG. 7).

The plant expression vectors comprising the individual *L. hesperus* target hairpins were subsequently transformed into *Agrobacterium tumefaciens*. For all *L. hesperus* target genes mentioned herein, fragments can be selected and cloned as hairpins in a similar manner.

5.2 Transformation of Potato with a Plant Expression Vector Comprising a *Lygus hesperus* Hairpin Sequence or *Leptinotarsa decemlineata* Hairpin Sequence and Testing of the Transformed Potato Plants for Resistance Towards *L. hesperus* or *Leptinotarsa decemlineata*

The example provided below is an exemplification of the finding that transgenic potato plants expressing target gene-specific hairpin RNAs adversely affect survival and/or development of insect pest species.

*Lygus hesperus* RNAi-by-Feeding in Planta

Potato Transformation

Stably transformed potato plants were obtained using an adapted protocol received through Julie Gilbert at the NSF Potato Genome Project (http://www.potatogenome.org/nsf5). Stem internode explants of potato 'Line V' (originally obtained from the Laboratory of Plant Breeding at PRI Wageningen, the Netherlands) which was derived from the susceptible diploid *Solanum tuberosum* 6487-9 was used as starting material for transformation. In vitro-derived explants were inoculated with *Agrobacterium tumefaciens* $C58C_1Rif^R$ containing the hairpin constructs. After three days co-cultivation, the explants were put onto a selective medium containing 100 mg/L Kanamycin and 300 mg/L Timentin. After 6 weeks post-transformation, the first putative shoots were removed and rooted on selective medium. Shoots originating from different explants were treated as independent events, shoots originating from the same callus were termed 'siblings' until their clonal status could be verified by Southern blotting, and nodal cuttings of a shoot were referred to as 'clones'.

The transgenic status of the rooting shoots was checked either by GFP fluorescence and by plus/minus PCR for the inserted target sequence. Positive shoots were then clonally propagated in tissue culture to ensure enough replicates were available for the *Lygus hesperus* or *Leptinotarsa decemlineata* assays. These shoots were kept in tissue culture medium for greater flexibility to test for resistance towards *Lygus* nymphs/adults or *L. decemlineata* larvae/adults. The first plants were available to test fourteen weeks post transformation.

Bioassay

Following the positive results obtained in the dsRNA feeding experiments proof-of-principle in planta experiments were initiated.

The plantlets were analysed by PCR to confirm the integration of the T-DNA and the presence of the hairpin, before being propagated. Excess explants were produced with the aim of obtaining at least 30 independent events for each construct.

The in planta assay for *Lygus hesperus* was developed with in vitro potato plantlets which sustained insect survival at least 8 days, keeping background mortality low. *L. hesperus* nymphs survived and fed on wild type potato plantlets. This was supported by the visual damage caused by insects which was observed on the leaves and buds (FIG. 8).

In the assay, *L. hesperus* was fed with transgenic potato, expressing hairpin dsRNA targeting the *L. hesperus* targets identified herein. Plasmids carrying hairpin constructs and a GUS control were generated.

Young transgenic potato plants were kept in tissue culture medium in a plant growth room chamber with the following conditions: 25±1° C., 50±5% relative humidity, 16:8 hour light:dark photoperiod. Per construct, a number of events, in this case 30 (P006/XX), were generated with a suitable number of clones (more than 20) per event. A number of young *Lygus* nymphs/adults were placed on the individually caged young (for example, at the 4-5 unfolded leaf stage) potato plants and left for at least seven days. The resistance towards *Lygus hesperus* was assessed regularly over the period of the assay in terms of reduced nymph/adult survival, delayed development and stunted growth, and/or decreased plant feeding damage. FIG. 9 specifically shows *L. hesperus* nymph survival. The transgenic events were compared to the control GUS hairpin transformed events (P001/XX) and the wild type potatoes (FIG. 9 and FIG. 10).

A bioassay for testing transgenic plants, transformed with *L. decemlineata* specific hairpin constructs, for resistance against *L. decemlineata* larvae or adults is done in the same way as described for *L. hesperus*.

5.3 Transformation of Cotton with a Plant Expression Vector Comprising a *Lygus hesperus* Hairpin Sequence and Testing of the Transformed Cotton Callus Material or Plants for Resistance Towards *L. hesperus*

The example provided below is an exemplification of the finding that transgenic cotton plants or callus expressing target gene-specific hairpin RNAs adversely affect survival and/or development of insect pest species.

Cotton Transformation

Coker 312 seed is surface sterilized using first, a 5 minute wash in 70% ethanol and then shaking in a 20% bleach (Chlorox Co. USA, 1% available chlorine) solution plus 10 drops of the non-ionic detergent, Tween® 20, per litre. The seed is then rinsed 3 times in sterile distilled water before blotting dry on sterile filter papers. The sterile seed is germinated on Seed Germination (SG) medium for 4-6 days, and at this point the hypocotyls are harvested and cut into 0.5 cm lengths ready for *Agrobacterium* inoculation. The cut sections are placed on sterile filter papers overlaying a Murashige and Skoog based medium containing no phytohormones. The explants are incubated on a 16:8 hours day:night cycle at 28° C.+/−2° C. for 3 days prior to inoculation.

For the inoculation, an *Agrobacterium tumefaciens* liquid LB culture (10 ml), strain GV3101 (pMP90) Gent$^R$ or strain LBA4404 containing the RNA hairpin target of choice and a hygromycin resistance encoding plant selection cassette, is grown up overnight and 5 ml used to inoculate a 100 ml culture the evening prior to the inoculation. The culture is spun down, resuspended and diluted to an OD600 of 0.15 in the bacterial dilution medium.

The hypocotyl segments are inoculated with the *Agrobacterium* suspension for 5 minutes. After this the explants are blotted onto sterile filter paper to remove the excess bacterial suspension. The explants are incubated in the dark on Cotton Co-cultivation Medium (CCM) for 48 hours. The explants are then placed on Selective Callus Induction Medium (SCIM) containing 10 mg/l Hygromycin and 500 mg/l Cefotaxime and including the phytohormones 2, 4-dichlorophenoxyacetic acid (0.1 μg/ml) and kinetin (0.1 μg/ml). After 4-6 weeks the first resistant calli are observed, and these can be removed to fresh SCIM and further amplified for molecular assessment and insect bioassays. Plates are refreshed every 4-6 weeks to maintain nutrients and antibiotic selection.

Calli that are shown to give a positive result in the insect feeding bioassay are chosen for regeneration and callus is transferred to non-selective medium for the maturation of the somatic embryos, the recipe is based on the publication of Trolinder and Goodin, 1986. Once the embryos have reached 4 mm in length and have differentiated cotyledons and radicles (2-3 months after transfer to maturation medium), they can be transferred Elongation Rooting Medium. This consists of sterilized vermiculite in large test tubes soaked with a Stewart & Hsu (1977) based liquid medium supplemented with kinetin, giberellic acid both added at the final concentration of 0.1 mg/l. The embryos are incubated at 28° C. in a 16:8 day/night cycle, and once they reach the 2-3 leaf stage the plantlets can be hardened off in pots of vermiculite enclosed in a propagator to maintain humidity. Once the plants are fully hardened (4-6 true leaf stage) they can be potted into a 50:50 peat:loam mix and grown in a 14:10 light cycle at 30/20° C. day/night.

Bioassay

*Lygus* nymphs are placed in a Petri dish containing undifferentiated cotton callus tissue expressing target hairpin RNA. Per construct, a number of transformed cotton calli are generated and tested in a feeding bioassay for reduced nymph/adult survival and/or delayed development and stunted growth. Transgenic calli not expressing *Lygus* target hairpin RNA gene fragment serve as a negative control. Furthermore, young regenerated cotton plants from transgenic calli are grown in soil in a plant growth room chamber with the following conditions: 30/20° C. day/night, 50±5% relative humidity, 14:10 hour light:dark photoperiod. Per construct, a number of events (for example, twenty) are generated. A number of young *Lygus* nymphs/adults are placed on the individually caged young (for example, at the 4-5 unfolded leaf stage) plants and left for at least seven days before assessing resistance towards *Lygus hesperus* in terms of reduced nymph/adult survival, delayed development and stunted growth, and/or decreased plant feeding damage. Cotton plants not transformed with the *Lygus* target hairpin RNA gene fragment serve as a negative control.

It will be appreciated by persons skilled in the art that numerous variations and/or modifications may be made to the above mentioned assays without departing from the spirit or scope of this assay as generically described. Those skilled in the art will recognize, or be able to ascertain using no more than routine experimentation, many equivalents to the specific examples, and such equivalents are intended to be encompassed by the present invention. The present example, therefore, is to be considered in all respects as illustrative and not restrictive.

What is claimed:

1. An interfering ribonucleic acid (RNA) molecule which comprises at least one double-stranded region, wherein said double-stranded region comprises a sense RNA strand annealed by complementary basepairing to an antisense RNA strand, wherein the interfering RNA molecule is encoded by a nucleic acid molecule comprising:

(i) a nucleotide sequence that is at least 95% identical to any of SEQ ID NOs: 1, 21, or the complement thereof; or (ii) a nucleotide sequence comprising at least 21 contiguous nucleotides of any of SEQ ID NOs: 1, 21, or the complement thereof.

2. The interfering RNA of claim 1, wherein the RNA comprises at least one silencing element, wherein the silencing element comprises a sequence of nucleotides which is at least partially complementary to a target nucleotide sequence within a tetraspanin 2A protein target gene.

3. The interfering RNA of claim 2, wherein the silencing element comprises a sequence of at least 21 contiguous nucleotides which is at least partially complementary to a target nucleotide sequence within the tetraspanin 2A protein target gene.

4. The interfering RNA of claim 2, wherein the silencing element is a region of double-stranded RNA comprising annealed complementary strands, one strand of which comprises a sequence of nucleotides which is at least partially complementary to a target nucleotide sequence within the tetraspanin 2A protein target gene.

5. The interfering RNA of claim 2 wherein the RNA comprises at least two silencing elements, wherein each silencing element comprises a sequence of nucleotides which is at least partially complementary to a target nucleotide sequence within a tetraspanin 2A protein target gene.

6. The interfering RNA of claim 5 wherein each of the silencing elements comprises a different sequence of nucleotides which is complementary to a different target nucleotide sequence.

7. The interfering RNA of claim 6 wherein the different target nucleotide sequences originate from a single tetraspanin 2A protein target gene.

8. The interfering RNA of claim 6 wherein the different target nucleotide sequences originate from different target genes.

9. The interfering RNA of claim 8 wherein the different target genes originate from the same insect pest species.

10. The interfering RNA of claim 8 wherein the different target genes originate from different insect pest species.

11. An isolated polynucleotide encoding the interfering RNA of claim 1.

12. A DNA construct comprising the polynucleotide of claim 11.

13. The DNA construct of claim 12 wherein the construct is an expression construct and wherein the polynucleotide is operably linked to at least one regulatory sequence capable of driving expression of the polynucleotide.

14. A host cell comprising an interfering RNA of claim 1, a polynucleotide encoding the interfering RNA of claim 1, or a DNA construct comprising a polynucleotide encoding the interfering RNA of claim 1.

15. The host cell of claim 14 wherein the host cell is a prokaryotic or a eukaryotic cell.

16. The host cell of claim 15 wherein the host cell is a bacterial cell or a plant cell.

17. A composition comprising at least one interfering RNA of claim 1 and at least one suitable carrier, excipient or diluent.

18. The composition of claim 17 wherein the excipient is an agronomical excipient.

19. The composition of claim 17 further comprising a DNA construct comprising a polynucleotide encoding said interfering RNA, wherein the RNA is expressed from said DNA construct.

20. The composition of claim 17 comprising a host cell, wherein the RNA is expressed inside said host cell.

21. A transgenic plant, or reproductive or propagation material for a transgenic plant, or a cultured transgenic plant cell, which expresses or is capable of expressing an interfering RNA of claim 1.

22. Seed produced from the transgenic plant of claim 21, wherein said seed comprises said interfering RNA.

23. The transgenic plant of claim 21 wherein the transgenic plant or a cell thereof has previously been engineered to express a heterologous gene.

24. The transgenic plant of claim 21 wherein the heterologous gene encodes a protein toxic to a plant pest species.

25. The transgenic plant of claim 21 wherein the heterologous gene encodes a protein conferring herbicide resistance.

26. Hybrid seed produced by crossing a first inbred plant with a second distinct inbred plant wherein at least one of the inbred plants is a transgenic plant of claim 21, and wherein the plant is chosen from rice, cotton, canola, sunflower, sorghum, pearl millet, corn, strawberries, soy, and seed crops including alfalfa, potato, tomato, eggplant, pepper and tobacco, wherein the hybrid seed produces a plant that expresses or is capable of expressing the interfering RNA.

* * * * *

SEQUENCE LISTING

```
<160> NUMBER OF SEQ ID NOS: 288

<210> SEQ ID NO 1
<211> LENGTH: 1217
<212> TYPE: DNA
<213> ORGANISM: Leptinotarsa decemlineata

<400> SEQUENCE: 1

agtacgcggg gagtgttctc aatattacaa caaagtgcgg tttcgggtgg ctttaacacg     60

ttcagacggt tcagtgattg aggatattct tgtttgcttt gtcgtggaag atagcaggaa    120

agggagacgg agaaggtgag ggaaacatcc tcaagttgga gaatcaaatt gccgtcatca    180

agtatgtgct gatatttacg aatatcttgt catggtacat cggaactcaa gttgccggct    240

ttatattcgg tctgtctgga gcgtctgtac tgctggataa cagcgctaga gattcccatt    300

tccagcccag gatccgagaa agtatgcgac gacttatcat gaatgcccat cacgaggaat    360

ccagacaaac actcgccatg attcaggaga atattgcttg ctgtggagct gatggtgcac    420

atgattacct gtctttgcag caaccgctac caagcacttg cagagataca gttactggaa    480

atccctttta tcatggatgc gttgatgagc tgacttggtt tttcgaggag aaatgcggct    540
```

-continued gggtggccgg acttgtcatg atactttgct tgatccaagt aataaacaca gtcctgtcaa 600
ttatattcct tcaagctctc aagaaagaag agggacaagc tgatacatac agaaaatgaa 660
gtgcacattc gcttttacga tttttgttgt ttcatttttg catacttgca tattcaccat 720
agtcgtattt caaactgatt aatgtttgag tttgtagcgt aggtaatagt ttacttaaga 780
gtttcattca catttgttag caattccgtt agccgaagaa gaaatattct cgagttttgg 840
tgggtagtta ctgaaaagtt cattttatgt tcagcccgag ctaacgacat atatatatat 900
tatataaccc aacttatttt tttatcgaat cattcgcagt tgcagaactt gaaagcattt 960
ccagatatgc cgtaaatttc gattaacatt ataaaatcac tagtctgcat aatacataaa 1020
cattatattt cacctaatga tgtttgtcta tgatcatgtt atgcgcagaa taaatcgttt 1080
atcatatatg tatagcactg agtcaatccc atgatgaatg gtatgtggta tcatgattcc 1140
atgatcacaa tgtcatctag ctggatcatg caatttctag aattcactcg aatatattag 1200
ttgggcgtgt tccccag 1217

<210> SEQ ID NO 2
<211> LENGTH: 750
<212> TYPE: DNA
<213> ORGANISM: Leptinotarsa decemlineata

<400> SEQUENCE: 2
cgcccagcag tggtatcaac gcagagtacg cgggagacat tcaagtcttg tgatagtgca 60
ggcacggcag ttcaaataaa ctggtgcctt caatttattt atatatttat actttttttac 120 tagaaaccaa atactaacca atcaacatgt gtgacgaaga ggttgccgca ttagtcgtag 180
acaatggatc tggtatgtgc aaagctggat ttgctgggga tgatgccccc cgtgcagttt 240
tcccatccat tgttggtcgt ccaagacatc aaggagttat ggtaggaatg ggccaaaagg 300
actcgtatgt aggagatgaa gcccaaagca aaagaggtat ccttaccttg aaataccccca 360 ttgaacacgg tattgtcaca aactgggatg atatggagaa aatctggcac catacettct 420 acaatgaact tcgagttgcc cccgaagagc accctgtttt gttgacagag gcaccattga 480
accccaaagc caacagggag aagatgaccc agatcatgtt tgaaaccttc aatacccccg 540
ccatgtacgt cgccatccaa gctgtattgt ctctgtatgc ttctggtcgt acaactggta 600
ttgtgctgga ttctggagat ggtgtttctc acacagtacc aatctatgaa ggttatgccc 660
ttcctcatgc catccttcgt ttggacttgg ctggtagaga cttgactgat taccttatga 720
aaattctgac tgaacgtggt tactctttca 750

<210> SEQ ID NO 3
<211> LENGTH: 706
<212> TYPE: DNA
<213> ORGANISM: Leptinotarsa decemlineata

<400> SEQUENCE: 3
agtggggcgg aaacttggta agaatcgtct tttcgtcata tccactgtca aaaagtttct 60
ttttatgagc agcgtgtaat ggtggagtag aagttgtttc aactaacttc ccaagatgca 120
gatctttgtt aaaactttga ctggtaagac catcactctt gaggtcgaac cttcggatac 180
catcgaaaat gttaaggcta agattcaaga caaggaggga attccaccag accaactgcg 240
tttaattttt gctggtaaac aattggaaga tggacgtact ttgtcggact acaatataca 300
aaaggaatct actcttcacc ttgtattgcg attgagggga ggtgcaaaga aacgtaagaa 360

-continued

```
gaagaattac tccaccccaa aaaaaaatca agcataagaa gaagaaggtc aagctggctg    420

tattgaaatt ttataaagtc gaagacaatg gtaaaatcca caggttgagg cgtgagtgtc    480

ctgctgaaca atgcggagct ggtgtcttca tggcagccat ggaagacaga cattactgtg    540

gaaagtgtgg atacacactt gtcttctcta aaccagatga taagtaaact ccaaaccaga    600

tgagaactag tttagggttt aaaagtttat aaaaacttgt attatttcta aataaagtaa    660

tacaaggatt agacttgaaa aaaaaaaaaa aaaaaaaaaa aaaaaa                   706


<210> SEQ ID NO 4
<211> LENGTH: 313
<212> TYPE: DNA
<213> ORGANISM: Leptinotarsa decemlineata

<400> SEQUENCE: 4

gatgtaagta gatttcaccg ttgtattatt cactaatttt cttactgtaa tttaaccaaa     60

caagaaacgc cacgatgcaa attttcgtaa aaacactcac gggtaagacc atcaccctcg    120

aggtcgaacc ctctgacacc atcgaaaacg tcaaggctaa gatccaagac aaggaaggga    180

tccccccaga tcagcaaagg ttggtcttcg ctggaaaaca gctcgaagat ggtcgaactc    240

tttccgacta caatattcag aaggagtcca ccctccatct cgtcctcaga ttgaggggag    300

gtattatcga gcc                                                       313


<210> SEQ ID NO 5
<211> LENGTH: 792
<212> TYPE: DNA
<213> ORGANISM: Leptinotarsa decemlineata

<400> SEQUENCE: 5

agtacgcggg gaccaacaaa ggcttatctt cgctggaaaa caactggaag atggccgaac     60

cttatcagat tataacattc agaaagaatc tacacttcac ttggttcttc gtctccgtgg    120

tggtatgcag atctttgtca aaactctaac tggaaagacc attaccttag aagtggaacc    180

atccgatacc attgagaatg taaaagccaa aattcaggac aaggaaggaa ttcccccaga    240

ccaacaaaga ttgatcttcg ctggaaaaca acttgaagat ggccgaacct tgtcagatta    300

taacattcaa aaagaatcca cactccactt ggttcttcgt ctccgtggtg gtatgcagat    360

ctttgtcaaa actctaactg gaaagacaat taccttggaa gttgaaccat ccgacaccat    420

cgagaacgtg aaagctaaaa tccaagacaa agagggcatt cccccagacc aacaaagatt    480

gatcttcgct ggaaaacgac tggaagatgg ccgaaccttg tcagattata acattcagaa    540

agaatctacg cttcatttgg ttcttcgtct cagaggaggc aaatattgac tgattttttt    600

cacttattta tttcattaaa ttgtactact ttgaagcaaa tattttattt taaaataaat    660

attcctgttc tattatatta aggcttgaaa atgttttttt gatatgaaag gcttcgaatg    720

aaattatatt tggctgtttt aagataaata aatgaaggtg tagtaaaaaa aaaaaaaaaa    780

aaaaaaaaaa aa                                                        792


<210> SEQ ID NO 6
<211> LENGTH: 719
<212> TYPE: DNA
<213> ORGANISM: Leptinotarsa decemlineata

<400> SEQUENCE: 6

agagtttaag ccgcgtctta taataggtta tagaaatatt tttaattaaa aaataaactt     60

gtttgctcca gtctcgaaac tacgagaatt gaagccatgg aaggttcatt gttggaaccc    120
```

```
actttataca ccataaaagg gattttgatc ctggataatg atggaaacag aatcctggca    180

aaatattacg acaaaaccac attccccaca tcaaaagagc agaaggcatt tgagaaaaat    240

ctatttaaca aaacacatag agcaaatgca gaaatcatca tgctggatgg attaacctgc    300

ctctatagga gcaatgtgga tttatttttc tatgttatgg gcagctcaca cgaaaacgag    360

cttattctta tgagtattct caattgtctt tatgactcag ttagccaaat actgaggaaa    420

aatgtggaaa aacgagcagt actagagtcc ctggatatag ttatgttagc gctggatgag    480

atatgtgatg gaggaattat ccttgatgct gattcgaatt ctgctgtgtc aagggtagct    540

ttgaggaatg atgatatacc aattggagag cagaccgtag cccaggtctt tcaatctgca    600

aaagaacagc tgaaatggtc attattaaag taggtgattt ttataaattt aatgaaatgt    660

atgttctgaa actataagaa ttaaaatatt cgaaaaaaaa aaaaaaaaaa aaaaaaaaa     719
```

<210> SEQ ID NO 7
<211> LENGTH: 1079
<212> TYPE: DNA
<213> ORGANISM: Leptinotarsa decemlineata

<400> SEQUENCE: 7

```
gtactccgca tcattcagat attcacagag cgctgcggta gtttcatgac atgcttgtcg     60

ccatgagcag aagaggctcg atcgagacga aagagaaatt cgcatacgat caacagatga    120

ccgatagctc tcagctggag gccgacaaga atggagactt gcgaaaacgt atttgagacc    180

tcgctgtcgc aagccctcgt cggtggaaga ggcagcgcgg cagattctgc cacaggaaca    240

aataagttga acaagataac gcagttgaca ggttttcgga tcccgtttat tcagaagctt    300

atgtccacgt caaccagtat gatattgtgc tggacgtttt gatcgtcaat caaactaatg    360

atactctgca aaattgtact ttggagctgg cgacgttggg agatctgaaa cttgtcgaaa    420

aacctcagcc agtagttctt gctcccaaag acttctgtaa catcaaagcc cacgtaaagg    480

ttgcttccac tgaaaacgga atcatctttg gaaacatcgt ttatgacgtg acgggcgcgg    540

cctcagacag gaacgtagtc gtcctcaatg acatccacat cgacatcatg gactatattg    600

ttccagcgtc ttgtaccgat tcagaattta tgaggatgtg ggctgaattt gaatgggaaa    660

ataaggtgac tgtcaacaca cctttgacgg accttgcgga ctacttggag cacctcatta    720

agagcaccaa catgaaatgc ttgacgccag aaaaggcgct cagcggtcag tgtggtttca    780

tggcagccaa tatgtacgct aaatccatat ttggagaaga cgctttggcc aatttgagta    840

tagagaaacc gtttaacaaa ccagaagcac ctgtagctgg acacatcaga atcagggcta    900

agagtcaggg catggccttg agcttaggag acaaaataaa tatgactcaa aaaggcatac    960

caagtaagat tgttgcatct tgatttgtat gttaactata tttgttattt cgccatttca   1020

ttttataatc atgtctaata ttaaaatcta catagatttt gaataaaaag tatcgaatt    1079
```

<210> SEQ ID NO 8
<211> LENGTH: 506
<212> TYPE: DNA
<213> ORGANISM: Leptinotarsa decemlineata

<400> SEQUENCE: 8

```
acgcggggga aaaaccagca aacgaagaca tcgaatcacc ccgagatatt ataaacaaag     60

catttagaga aatttttgag gctgacgaaa acgggatcaa tgggtctctg gtggaaccac    120

caactccaac gcagaaaacg tttgatagac ctttccaaga agatctaagc gagttcaact    180
```

-continued

```
ttagaatata tgcagcaacg tattttacga acaatgccaa ctatcagttt tcaaagaaac    240

ctcttaagga atccctacat tatcttccga ccccagatga cgtgatcgcc gcacaagcct    300

tgtggataac catcctcagg ttcatgggag actatccgga gcccaaatac gacaattcga    360

cgaaagaaaa cgttcccatc atgcaaatca tctcagagtc gatcggcaaa agtttcacga    420

atcgtaaaga gtaccaggaa atactcaaag aagaaaaaaa tatgcctctg caacaaaatc    480

aagcaaaaaa aaaaaaaaaa aaaaaa                                          506
```

<210> SEQ ID NO 9
<211> LENGTH: 959
<212> TYPE: DNA
<213> ORGANISM: Leptinotarsa decemlineata

<400> SEQUENCE: 9

```
tgtacggacg tttggaggaa gccgacgctc tcatccaaca gctctcttcc gacaaggatc     60

ccatcctcag gcggtcgggc atgtacacta tcgccatggc ttactgcagc accggacaca    120

accaggcgat caggaagctg cttcacgttg ctgtatccga cgtaaatgat gacgtccgac    180

gagctgccgt cacggcgctg ggtttcctct tattcagaac tcctgaacaa tgcccaagcg    240

tagtttctct gctggctgag agttacaacc ctcacgtacg ctacggagct gccatggcac    300

tcggtatcgc ctgtgctggc accggactcc gcgaagctat tgctcttctg gaaccgatgg    360

tgatgttcga tccagtcaat ttcgttcgtc aaggagctct catcgcttct gccatgatct    420

tgatccagca gaccgaacag acctgtccta aagttagttt cttcagacag acttacgctc    480

aggtcatcgc caacaaacat gaggatgtta tggccaaatt cggagctatt ttggctcaag    540

gaattattga cgctggaggc aggaatgtta cattatcact ccagtcgaga acaggacaca    600

ccaatatgtt ggcagtggtc ggaactttgg tgttcaccca gtattggtac tggttccctc    660

tctcccattg tttggctctg gctttcaccc caacttgtgt tatcgccctc aatgaacaac    720

tcaaaatgcc caagttggaa ctgaaatcga atgcaaaacc aagtctctac gcatatccag    780

ctccaatgga agagaaaaag cgcgaagaga gagagaaagt aaccaccgct gttctgagta    840

tcgctgcaag acaacgtggg aaggatcatg aaaagaagca tcgggatgaa aaaaatggat    900

ggggacgaag acaagtctgc agagaaagat gaaaaaaaaa aaaaaaaaaa aaaaaaaaa     959
```

<210> SEQ ID NO 10
<211> LENGTH: 458
<212> TYPE: DNA
<213> ORGANISM: Leptinotarsa decemlineata

<400> SEQUENCE: 10

```
tttttgact tattttttgt tagtgatttt gtattcagat tgtctccgtt cgtaaaaatg     60

ctactgaatc aaatatccat agcaggtgcc gatgactgga gaaatgccgc tcatagcact    120

gggacttcta ttatggcagc agaattcgat ggaggagtaa ttattggtgc tgattcccgt    180

acaactacag gggcgtacat tgcaaatcgt gtaactgaca aactaactaa agtaactgac    240

catatatatt gttgtcgatc tggatcagca gcagatactc aagccattgc tgatattgta    300

tcgtaccatc tgaacttcca tggtatggaa ctaggagaag agccccttgt agaggtgggg    360

gctgctatct tcagggagct ttgctacaac tatagggatt ctctcatggc gggaatccta    420

gttgctggct gggacaaaaa aaaaaaaaaa aaaaaaaa                            458
```

<210> SEQ ID NO 11
<211> LENGTH: 352

```
<212> TYPE: DNA
<213> ORGANISM: Leptinotarsa decemlineata

<400> SEQUENCE: 11

cagttaagaa tatcattcaa ttcctaggtc tccagccagc agaaagaacg gataaggttc     60

ctgaggaaaa atcaactcat actcttttac tagcaggaat gcttcgaggg ggtattgaca    120

ttttagttag ggcaaaacta gccctagctg atggtgtgac tatgcaactg accgtgaggt    180

cacccgatgc tgatgttgct gaacttataa cctcgtctgt aggctaagag aaaagttagc    240

ttggttagat gttcgaaatt atcaggtcat gtgtattata tttgatgtta ttccaatttt    300

aataaatcct cctaatttaa gctaaaaaaa aaaaaaaaaa aaaaaaaaaa aa            352


<210> SEQ ID NO 12
<211> LENGTH: 1407
<212> TYPE: DNA
<213> ORGANISM: Leptinotarsa decemlineata

<400> SEQUENCE: 12

gagtgaaaat atggctggcg caatgttgtt tgaaagagct cagtcagtac cttctcaaca     60

tgataaactg ttaaatttaa aaagaaatga agatgacgat gatcagaaca tcgttaataa    120

agaacaggac atcctcaacc tcggcgaaaa gtacaagaaa gagggtaagg ctaaagaact    180

ggcggaattg gtaaaggcta ctcgtccgtt tctcagcatt ataagcaagg cgaaagctgc    240

gaaactggtc aggtctctgg tcgattattt cctagatttg gaagcaggta tcggaataga    300

agtccaactg tgtaaagaat gtatagagtg ggcaaaagaa gagaaaagga cctttcttcg    360

tcagtctttg gaagcgcgat tgatagcctt gtatttcgat actggtatgt atgccgaggc    420

tctgattctg gaatccacct tgttgaaagg attgaagaag ttggatgaca aaaatttact    480

ggtagaagta cagttgcttg aaagtaagac atatcacgcc ttgagtaacc tgcccaaggc    540

tcgtgccgca ttaacttcag ctcgtacaac agccaattcc atctattgcc ctcctaagat    600

gcaagctgcg cttgaccttc agtctggagt tctgcatgca gctgatgaaa aagacttcaa    660

aactgcctat tcatactttt atgaggcatt tgaagggttt gacagcgtag aatcaccaaa    720

agcgttgaca gctttgaaat atatgcttct ttcaaaaatt atgatcaaca gtccggaaga    780

tgtacaacaa attgtaagcg ggaaattagc catcagatat gctggtcaag acatagaagc    840

aatgaaagct gttgcacgag cttctcacaa gagatccttg gcagattttc agttagcagt    900

gaagcagttc aaacatgaac tagaggatga tgttatcgtc agagcccatt taggaacttt    960

gtatgataat atgttggagc aaaatctgtg caggattata gaaccatatt ccagagtaca   1020

ggtggactat gttgcaaaaa caatcaaact tccaatgtta caagtggaaa agaagctctc   1080

gcagatgatt cttgatgcta aatttcatgg gatattggat caaggagaag gtgttttaat   1140

agtttttgaa gcaactccag tagacaaaac atatgaaatg gccctagaaa caatacaaag   1200

catgagtaaa gtagtagata ccctatatca aaaagctaaa aagctgtcat aggtttgaca   1260

caactaatat aaaactatta aaattattgt attttgatct ttcataaatt ttctctgttt   1320

ggtaatatta cagtttaata taattataat gttttttgg aatataaact aactaaattc   1380

taaaaaaaaa aaaaaaaaaa aaaaaaa                                       1407


<210> SEQ ID NO 13
<211> LENGTH: 821
<212> TYPE: DNA
<213> ORGANISM: Leptinotarsa decemlineata
```

<400> SEQUENCE: 13
ggttgcaagt aatcatggct tcggagcggt atagtttttc gctgacaact tccagtccat 60
ctggaaaact agctcaaatt gaatatgccc tagctgctgt agccgctgga gctccttctg 120
tgggcattaa agcttcaaat ggtgtagtta tcgccacaga aaacaaacat aagtcgatcc 180
tctatgaaga acacagtgtt cataaagttg aaatgattac aaaacatata ggaatgatat 240
attctggtat gggacctgat tatcgcttgt tggtgaaaca agctcgtaaa atggcccaac 300
agtattatct agtttatcaa gagcctatac caacagttca actcgttcaa cgagttgcca 360
ctgttatgca agaatatact cagtccggag gagttaggcc gtttggggtt tcattattga 420
tatgtggttg ggacagtgaa cgaccatact tatttcaatg tgatccatca ggagcttatt 480
ttgcctggaa agctactgcc atgggcaaga atttcatcaa tggaaaaaca tttttggaaa 540
aaagatatag cgaggatttg gaacttgatg acgcagtaca cacagcaatt ctgacgttga 600
aggagagttt tgaaggccaa atgacagcgg acaacattga agtgggaatt tgtgatgaag 660
caggattcag gaggctagat ccctctcatg tgaaggatta cctagctaat attccataag 720
gcatttaggt tatgtaacaa gatttctctt aattttttat gaaactcatg tttcacttga 780
ataaaaccgg atttgaacga aaaaaaaaaa aaaaaaaaaa a 821

<210> SEQ ID NO 14
<211> LENGTH: 474
<212> TYPE: DNA
<213> ORGANISM: Leptinotarsa decemlineata

<400> SEQUENCE: 14
tgaagcaggc caaagaagaa gctcaagacg aaatcgaaaa ataccgtaaa gaacgcgaac 60
gtcaattcag ggagttcgag gccaagcata tgggctccag agaggatgta ccgtccaaaa 120
tcgaagtgga caccaaacgt agaatcgaag agatgaacaa ggctataatc agtcaaaaag 180
aacctgttat ccaagaagtt ctcaacttag tgtacgacat caaacctgaa atccacaaga 240
actaccgcca atagactgtg tgtggttgtt aaaaagtaat tgaattttcc tgtgggaaaa 300
ctaggaatac ctttcaattg ttctgtatag atgttcattc catttattgt atatttaatc 360
tcttaaggca gttcactctt aagttcacag ggtagtggaa tttgtgtact tgtatattgt 420
aagtcaaaat agaaaaaata tattgtgaaa actaaaaaaa aaaaaaaaaa aaaa 474

<210> SEQ ID NO 15
<211> LENGTH: 692
<212> TYPE: DNA
<213> ORGANISM: Leptinotarsa decemlineata

<400> SEQUENCE: 15
gcatgtgaaa atgagttcct tgaagctaca gaagaggctc gccgcctcgg ttatgcgatg 60
tggcaaaaaa aagtatggtt ggatcctaat gaaattaatg aaatcgctaa caccaactca 120
aggcaaaaca tccgtaagtt gatcaaagat ggtctcataa tcaagaaacc agtagcagtg 180
cattcccgtg ctcgagtacg caaaaacaca gaagcccgca ggaagggaag acattgcggt 240
ttcggtaaaa ggaagggtac agcaaatgct cgaatgcccc agaaggaatt atggattcag 300
cgcatgagag ttttgagacg tctcttgaaa aaataccgag aagccaaaaa gatcgacagg 360
catctgtact atgcccttta catgaaagca aagggtaacg tattcaagaa caagagagtc 420
ctcatggaat acatccataa gaagaaggca gagaaggccc gtgccaagat gttggcagac 480
caagccaatg ccaggagatt gaaggtaaaa caagcacgtg aacgtcgtga agaacgtatc 540

-continued gctaccaaga aacaggaagt tctacagaat taccagcggg aagatgaagc ccaagctgct 600
aagaaataag tttattttta tggtaatgac aaataaagtt tgaaattact taaaaaaaaa 660
aataaaaaaa aaaaaaaaaa aaaaaaaaaa aa 692

<210> SEQ ID NO 16
<211> LENGTH: 750
<212> TYPE: DNA
<213> ORGANISM: Leptinotarsa decemlineata

<400> SEQUENCE: 16
aactttctgt accgaaacca aacagctaaa cttccaattg gtttatttag caaaaataga 60
attttttttg aaattcataa ataaagatgt ctgttttgtg tcctgaaatt ccagcgccag 120
gcttttcatt cgagaattgt aaaagaaatg cattgctgga aggcaaggga ttcgctctac 180
caaaagctac taagactggt accaccatcg taggaattac ttataaagat ggagtcattc 240
ttggggccga taccatagcc acagaagata ccacagttgc agacaagaac tctgagaaga 300
ttcactatct tgctccaaat atgtattgtt gtggtgctgg tacagccgcg gatacagaga 360
tgaccactca gatgatctcg tcccaattgg aactccacaa actgcacact aaccgcatcg 420
ccagagtctg cacagctaac cagatgctga agcagtatct gttccgttac cagggctaca 480
tcggtgctgc tcttatcctc ggaggagtcg atgtcgaagg tccccatctc tacatgattt 540
acccccacgg ctctagtgac aacctcccat atggcacgat gggctcgggc tccccggccg 600
ccatagcggt attcgagtcc cgctggagac ccaacttgga ggaggaggaa ggtgtacagc 660
ttgtcagaga cgcgattgct gctggtatct tcaatgattt ggggtctgga tcgaatgttg 720
atgtctgcat cattcggaag ggtctgttg 750

<210> SEQ ID NO 17
<211> LENGTH: 1394
<212> TYPE: DNA
<213> ORGANISM: Leptinotarsa decemlineata

<400> SEQUENCE: 17
ttaaacagtg gctaaagcta aaactattat ttgaaatgtc gtctactcta gaagataaag 60
ctatctggga agatggggaa gaatcattgg gggaggaagt tctgaggatg tcgactgatg 120
aaatagtcag ccggacgcgt ttactcgata atgaaatcaa aataatgaag agcgaagtaa 180
tgagaataaa ccatgaactc caagcccaaa acgaaaaaat caaagaaaac actgaaaaga 240
taaaggtaaa taaaacgcta ccttacttgg tatctaatgt tatagaactg ctagatgtgg 300
accctcaaga ggaagaagaa gacggggcag ttgtagactt ggattctcaa agaaagggaa 360
aatgtgccgt tgtaaaaaca tctactcgtc aaacatattt tctaccagta atcgggctcg 420
ttgatgaaga aaagctcaaa cctggagatt tagtgggtgt gaacaaagat tcttatctta 480
tcctagaaac attaccagcg gagtatgatg caagagtaaa agctatggaa gttgatgaaa 540
gaccaactga acaatactca gacattggtg ggctggacaa acaaatccag gaacttattg 600
aagcagtcgt attgccaatg acccacaagg ataaatttgt taatcttggg attcatccac 660
ctaaaggagt cttgttatat ggacccccag gaactggaaa aactttgttg gctagagcat 720
gtgctgctca gacaaaatca acatttttga aactagctgg accccaatta gttcagatgt 780
tcataggaga tggtgctaaa cttgtaagag atgcttttgc gttagccaag gaaaaggcac 840
cagctataat tttcatcgat gaattggatg ctactggtac gaaacgtttt gattctgaga 900

-continued aggctgggga tcgtgaagta caacgtacaa tgttgggagc ttttgaatca gttggatggg 960
tttagttcaa cagctgatat aaaagtaatt gcagctaccc atcgggttga ttttctagat 1020
cctgctttac tttgatcagg tcggttagat tgtaaaaaag aatttcctcc tccaaaagaa 1080
gaaggtaggg caagaataat gcaaattccc tcaagaaaaa agactgttaa ccccgaagta 1140
aactttgaag aattgggtag atcccctggg ggctttaacg gggtccgggg taaagccgtt 1200
tgttttgaag ccggtttgat agctttggga agaaaagccc ccgctgtttc ccctgaagat 1260
tttttggatg tttttttgga agttcaagcc cagaaaaaag ggaattttaa tttttttttt 1320
taatttcccg cctacagata ataaattttg tttttggtta aaaaaaaaaa aaaaaaaaaa 1380
aaaaaaacaa aaaa 1394

<210> SEQ ID NO 18
<211> LENGTH: 514
<212> TYPE: DNA
<213> ORGANISM: Leptinotarsa decemlineata

<400> SEQUENCE: 18
gacagatgtc gaacccttta tgaaaaattt ttggaatttg gaccagagaa ttgtgtgacc 60
tggatgaaat ttgccgaact agaaacttta ttaggcgaca ttgatcgagc aagggctatt 120
tacgaattgg ctataagtca gcctaggtta gatatgccag agttactttg gaaggcttat 180
atagactttg aaatttctca ggaagaacct gaaaatgcta gacaaatcta tgaaaggctg 240
ctagaaaaaa catcacatgt caaagtatgg ttgtcttatg ccaaatttga acttaacaca 300
caatcagaac ccgacatgaa tgttctgtta tccaggagag tatttgaaag agccaacgag 360
agcctaaaaa attcatctga aaaagaggca agagttctac ttcttgaaaa ctggagggag 420
tttgagaaag cccatggaga tgaaactggt aatgctaaag ttaatagcag gatgcccaaa 480
cgtataaaaa aaaaaaaaaa aaaaaaaaaa aaaa 514

<210> SEQ ID NO 19
<211> LENGTH: 2328
<212> TYPE: DNA
<213> ORGANISM: Leptinotarsa decemlineata

<400> SEQUENCE: 19
atggctacat acgaagagta tatccagcaa aacgaagaca gagacgggat acggttcaca 60
tggaacgttt ggccgtccag cagaatagaa gccacccgtt tggtggtgcc cttggcctgt 120
ctttaccaac ccctgaaaga acgtcccgat cttccaccaa ttcagtacga tccagtgctg 180
tgcactagaa acaattgtcg tgcaatactg aacccactct gccaagtaga ttatcgtgcc 240
aagctttggg tgtgcaactt ctgctttcag aggaacccgt ttccccctca atatgccgcc 300
atttccgagc aacaccaacc agctgagctt atgccaatgt tttccaccat agagtacact 360
attacaagag cacagtgttt acccccgata tatctctatg ttgtcgacac ttgcatggat 420
gaggaagaat tgggttcact caaggactcc ttgcaaatgt ctttgagctt gttgcccccg 480
aatgccttga tagggttgat tacctttggg aagatggtcc aagtgcacga actaggtacc 540
gagggctgca gcaaatctta cgttttccga gggacgaaag acctcacagc taagcaagtt 600
caagagatgt tggaagtggg cagagccgca gtaagtgctc aacctgctcc tcaacaacca 660
ggacaaccca tgaggcctgg agcactccag caagctccta cgccaccagg aagcaggttc 720
cttcaaccca tctcgaaatg cgacatgaac ctcactgatc ttattggaga gttgcaaaga 780
gacccatggc ctgtccacca aggcaaatgc gcccttagat cgaccgggac agctttatcg 840

-continued

```
atagccattg ggttgttgga gtgcacatac gccaatactg gtgccagggt catgctattc    900

gttggaggac cttgctctca aggccctggt caagtcttga atgatgatct gaagcaacct    960

atcagatctc accacgacat ccaaaaagac aatgccaaat acatgaagaa agcaatcaag   1020

cactatgata atttagcgat gagagcagca acgaatggcc actgcgttga catatattca   1080

tgcgctttgg atcagacagg attgatggag atgaaacagt gttgtaattc aacaggggga   1140

catatggtca tgggcgactc gttcaattct tccctgttca agcaaacgtt ccagcgcata   1200

ttttcgaaag atcagaaaaa cgagctgaag atggcattta atggtactct ggaggtcaag   1260

tgttccaggg agttgaaaat tcaaggcggt attggatctt gtgtttcgtt gaatgtgaag   1320

aatcctttgg tttccgacac cgaaatagga atgggtaaca cggtccagtg gaaaatgtgt   1380

acggtaactc caagtactac catggccttg ttcttcgagg tcgtcaacca acattccgct   1440

cccatacctc aagggggaag gggctgcata cagttcatca cgcaatatca gcatgctagt   1500

ggccagaaga ggatccgagt aacgacagtt gctagaaact gggccgatgc ttccgctaat   1560

atacatcatg tcagtgctgg attcgatcag gaggcagccg cagtgataat ggcgaggatg   1620

gcagtttaca gagcggaatc agacgatagc cctgatgttt tgagatgggt cgataggatg   1680

ttgatacgtc tgtgccagaa attcggcgaa tataacaagg acgacccgaa ttcgttccgc   1740

ttgggcgaaa acttcagcct ctacccgcag ttcatgtacc atttgagaag gtcacagttc   1800

ctgcaggtgt ttaacaattc tcccgacgaa acgtccttct acaggcacat gcttatgcgc   1860

gaagacctca cgcagtcgct gatcatgatc cagccgatac tctacagcta cagtttcaat   1920

ggaccaccag aacctgtgct tttggatacg agttccatcc aacccgatag aattctgctc   1980

atggacacgt tcttccagat tctgatattc catggcgaga caatagccca atggcgtaac   2040

ctcaaatatc aggacatgcc tgaatacgag aactttaggc agctgctgca agctccagtg   2100

gacgatgccc aggaaattct tcaaaccagg tttcctatgc cgcgttacat cgatacggaa   2160

caaggaggat cacaggctag attcttgctc tcgaaagtca acccgagtca gactcacaac   2220

aatatgtacg cctacggagg ggacggaggt gctccagttc tcactgatga tgtatcgtta   2280

caagtattca tggatcacct gaaaaaactg gcagtgtcct ctacggct                2328
```

<210> SEQ ID NO 20
<211> LENGTH: 2697
<212> TYPE: DNA
<213> ORGANISM: Leptinotarsa decemlineata

<400> SEQUENCE: 20

```
atgcctcttc gtttagatat caaacgaaag ttaacagccc gttcagacag ggtaaaatgt     60

gtagacctcc atccatctga accatggatg ttatgttctt tatatagtgg caatatcaat    120

gtttggaatt atgaaaatca acaacaagta aaaagtttcg aagtatgtga cctgccagtg    180

agagctgcaa aatttgtccc acgtaaaaac tggatagtca gtggatctga tgatatgcag    240

ataagaatat tcaattacaa cactttagat agaattcatt cctttgaggc acattccgac    300

tatgtgagat gtataatagt tcatccaacc caaccttata ttctgacaag tagcgatgac    360

atgctcatca aattgtggaa ttgggataag gcttgggctt gtcagcaggt ctttgaaggc    420

cactctcatt atatcatgca aatcgccatc aatccaaaag acaacaacac atttgcgagt    480

gcttcactgg accgtacttt gaaagtgtgg caacttggag catcaacagc gaacttcacc    540

cttgaagggc acgagaaagg tgtcaactgt gtggactact atcacggtgg agacaagcca    600
```

-continued

```
tacttgatat cgggagcaga cgatcggttg gttaaaatct gggactatca aaacaaaacg    660

tgtgtccaaa ccttggaagg acacgcccaa aacgtaaccg cggtttgttt ccaccctgaa    720

ctacctgtgg ctctcacagg cagcgaagat ggtaccgtta gagtttggca tacgaataca    780

cacagattag agaattgttt gaattatggg ttcgagagag tgtggaccat ttgttgcttg    840

aagggttcga ataatgtttc tctggggtat gacgagggca gtatattagt gaaagttgga    900

agagaagaac cggcagttag tatggatgcc agtggcggta aaataatttg ggcaaggcac    960

tcggaattac aacaagctaa tttgaaggcg ctgccagaag gtggagaaat aagagatggg   1020

gagcgtttac ctgtctctgt aaaagatatg ggagcatgtg aaatataccc tcaaacaatc   1080

caacataatc cgaatggaag attcgttgta gtatgcggag acggcgaata tatcatttac   1140

acagcgatgg ctctacggaa caaggctttt ggaagcgctc aagagtttgt ctgggctcag   1200

gactccagcg agtatgccat tcgcgagtct ggttccacaa ttcggatatt caaaaacttc   1260

aaagaaagga agaacttcaa gtcggatttc agcgcggaag gaatctacgg gggttttctc   1320

ttggggatta aatcggtgtc cggtttaacg ttttacgatt gggaaacttt ggacttggtg   1380

agacggattg aaatacaacc gagggcggtt tattggtctg acagtggaaa attagtctgt   1440

ctcgcaacgg aggacagcta cttcatcctt tcttatgatt cggagcaagt tcagaaggcc   1500

agggagaaca atcaagtcgc agaggatggc gtagaggccg ctttcgatgt gttgggggaa   1560

atgaacgagt ctgtccgaac aggtctttgg gttggagact gtttcattta tacaaacgcc   1620

gtcaatcgta taaattactt cgttggtggt gaacttgtca cgatagctca tctggaccgt   1680

cctctgtatg tgctggggta tgttcctagg gacgatcgat tgtatctcgt agacaaagaa   1740

ttaggagttg tcagttatca gttgttactg tctgttcttg aatatcaaac ggcagttatg   1800

aggagggact ttcctacagc ggatcgtgtc ctgccttcga ttcccaaaga gcatagaaca   1860

agagttgctc actttttaga aaaacaaggc ttcaagcagc aagccttagc agtgagcact   1920

gatccagagc atcgattcga actcgctgta gccctggaag acctcgatac cgccaaagta   1980

ttagcccagg aagccaacaa tcctcaaaag tggagccaac tagcagagct tgcggcgtca   2040

acaaataatt tacagctagc aaaagagtgt atgcagaagg ctcaggatta tggaggactt   2100

ctcctcctag ccaccagttc tggagatgaa caactagttc aaagcttggg agaactcacg   2160

caagccgaag gaaagcataa cctctccttc ctttcttatt ttctggtggg agatctgccg   2220

aaatgtttgg atatcttggt cagtacggga cgcctacccg aggctgcttt cttcgcacgc   2280

tcgtatctgc cggacagaat atcggaaatt gttgaactgt ggaaggtgaa actgacgtca   2340

attaatgaga aagctggtca gagtctggcg gatccgaaga gctacgagaa tctttttccg   2400

ggtttgcaag aagcgattga aacgcaaaag tatttggagc agcaggatag ggggcttttc   2460

ccggcttcag tatcaacaac gatcgttccc aaccatgaaa ggaatttggt ggcagaggca   2520

cgggcccaga tgaagggtgg tgccgcggtt tttcagcaaa gcaggttact ttctggagaa   2580

aaaacaatat cctttgaaca ggatgaagat gatctagact tagatttgga aggcgttaat   2640

attgacgaca atatagacac aacggatatc aatatcgacg atgatttatt gagcgat      2697
```

<210> SEQ ID NO 21
<211> LENGTH: 558
<212> TYPE: DNA
<213> ORGANISM: Leptinotarsa decemlineata

<400> SEQUENCE: 21

```
gtcgtggaag atagcaggaa agggagacgg agaaggtgag ggaaacatcc tcaagttgga     60
```

gaatcaaatt gccgtcatca agtatgtgct gatatttacg aatatcttgt catggtacat 120
cggaactcaa gttgccggct ttatattcgg tctgtctgga gcgtctgtac tgctggataa 180
cagcgctaga gattcccatt tccagcccag gatccgagaa agtatgcgac gacttatcat 240
gaatgcccat cacgaggaat ccagacaaac actcgccatg attcaggaga atattgcttg 300
ctgtggagct gatggtgcac atgattacct gtctttgcag caaccgctac caagcacttg 360
cagagataca gttactggaa atccctttta tcatggatgc gttgatgagc tgacttggtt 420
tttcgaggag aaatgcggct gggtggccgg acttgtcatg atactttgct tgatccaagt 480
aataaacaca gtcctgtcaa ttatattcct tcaagctctc aagaaagaag agggacaagc 540
tgatacatac agaaaatg 558

<210> SEQ ID NO 22
<211> LENGTH: 320
<212> TYPE: DNA
<213> ORGANISM: Leptinotarsa decemlineata

<400> SEQUENCE: 22
atgtgtgacg aagaggttgc cgcattagtc gtagacaatg gatctggtat gtgcaaagct 60
ggatttgctg gggatgatgc cccccgtgca gttttcccat ccattgttgg tcgtccaaga 120
catcaaggag ttatggtagg aatgggccaa aaggactcgt atgtaggaga tgaagcccaa 180
agcaaaagag gtatccttac cttgaaatac cccattgaac acggtattgt cacaaactgg 240
gatgatatgg agaaaatctg gcaccatacc ttctacaatg aacttcgagt tgcccccgaa 300
gagcaccctg ttttgttgac 320

<210> SEQ ID NO 23
<211> LENGTH: 490
<212> TYPE: DNA
<213> ORGANISM: Leptinotarsa decemlineata

<400> SEQUENCE: 23
ggtaagaatc gtcttttcgt catatccact gtcaaaaagt ttctttttat gagcagcgtg 60
taatggtgga gtagaagttg tttcaactaa cttcccaaga tgcagatctt tgttaaaact 120
ttgactggta agaccatcac tcttgaggtc gaaccttcgg ataccatcga aaatgttaag 180
gctaagattc aagacaagga gggaattcca ccagaccaac tgcgtttaat ttttgctggt 240
aaacaattgg aagatggacg tactttgtcg gactacaata tacaaaagga atctactctt 300
caccttgtat tgcgattgag gggaggtgca aagaaacgta agaagaagaa ttactccacc 360
ccaaaaaaaa atcaagcata agaagaagaa ggtcaagctg gctgtattga aattttataa 420
agtcgaagac aatggtaaaa tccacaggtt gaggcgtgag tgtcctgctg aacaatgcgg 480
agctggtgtc 490

<210> SEQ ID NO 24
<211> LENGTH: 231
<212> TYPE: DNA
<213> ORGANISM: Leptinotarsa decemlineata

<400> SEQUENCE: 24
ccaaacaaga aacgccacga tgcaaatttt cgtaaaaaca ctcacgggta agaccatcac 60
cctcgaggtc gaaccctctg acaccatcga aaacgtcaag gctaagatcc aagacaagga 120
agggatcccc ccagatcagc aaaggttggt cttcgctgga aaacagctcg aagatggtcg 180

-continued aactctttcc gactacaata ttcagaagga gtccaccctc catctcgtcc t 231

<210> SEQ ID NO 25
<211> LENGTH: 571
<212> TYPE: DNA
<213> ORGANISM: Leptinotarsa decemlineata

<400> SEQUENCE: 25
gggaccaaca aaggcttatc ttcgctggaa aacaactgga agatggccga accttatcag 60
attataacat tcagaaagaa tctacacttc acttggttct tcgtctccgt ggtggtatgc 120
agatctttgt caaaactcta actggaaaga ccattacctt agaagtggaa ccatccgata 180
ccattgagaa tgtaaaagcc aaaattcagg acaaggaagg aattcccccca gaccaacaaa 240 gattgatctt cgctggaaaa caacttgaag atggccgaac cttgtcagat tataacattc 300
aaaaagaatc cacactccac ttggttcttc gtctccgtgg tggtatgcag atctttgtca 360
aaactctaac tggaaagaca attaccttgg aagttgaacc atccgacacc atcgagaacg 420
tgaaagctaa aatccaagac aaagagggca ttcccccaga ccaacaaaga ttgatcttcg 480
ctggaaaacg actggaagat ggccgaacct tgtcagatta taacattcag aaagaatcta 540
cgcttcattt ggttcttcgt ctcagaggag g 571

<210> SEQ ID NO 26
<211> LENGTH: 542
<212> TYPE: DNA
<213> ORGANISM: Leptinotarsa decemlineata

<400> SEQUENCE: 26
cttgtttgct ccagtctcga aactacgaga attgaagcca tggaaggttc attgttggaa 60
cccactttat acaccataaa agggattttg atcctggata atgatggaaa cagaatcctg 120
gcaaaatatt acgacaaaac cacattcccc acatcaaaag agcagaaggc atttgagaaa 180
aatctattta acaaaacaca tagagcaaat gcagaaatca tcatgctgga tggattaacc 240
tgcctctata ggagcaatgt ggatttattt ttctatgtta tgggcagctc acacgaaaac 300
gagcttattc ttatgagtat tctcaattgt ctttatgact cagttagcca aatactgagg 360
aaaaatgtgg aaaaacgagc agtactagag tccctggata tagttatgtt agcgctggat 420
gagatatgtg atggaggaat tatccttgat gctgattcga attctgctgt gtcaagggta 480
gctttgagga atgatgatat accaattgga gagcagaccg tagcccaggt ctttcaatct 540
gc 542

<210> SEQ ID NO 27
<211> LENGTH: 747
<212> TYPE: DNA
<213> ORGANISM: Leptinotarsa decemlineata

<400> SEQUENCE: 27
gtatttgaga cctcgctgtc gcaagccctc gtcggtggaa gaggcagcgc ggcagattct 60
gccacaggaa caaataagtt gaacaagata acgcagttga caggttttcg gatcccgttt 120
attcagaagc ttatgtccac gtcaaccagt atgatattgt gctggacgtt ttgatcgtca 180
atcaaactaa tgatactctg caaaattgta ctttggagct ggcgacgttg ggagatctga 240
aacttgtcga aaaacctcag ccagtagttc ttgctcccaa agacttctgt aacatcaaag 300
cccacgtaaa ggttgcttcc actgaaaacg gaatcatctt tggaaacatc gtttatgacg 360
tgacgggcgc ggcctcagac aggaacgtag tcgtcctcaa tgacatccac atcgacatca 420

```
tggactatat tgttccagcg tcttgtaccg attcagaatt tatgaggatg tgggctgaat    480
ttgaatggga aaataaggtg actgtcaaca cacctttgac ggaccttgcg gactacttgg    540
agcacctcat taagagcacc aacatgaaat gcttgacgcc agaaaaggcg ctcagcggtc    600
agtgtggttt catggcagcc aatatgtacg ctaaatccat atttggagaa gacgctttgg    660
ccaatttgag tatagagaaa ccgtttaaca aaccagaagc acctgtagct ggacacatca    720
gaatcagggc taagagtcag ggcatgg                                         747

<210> SEQ ID NO 28
<211> LENGTH: 393
<212> TYPE: DNA
<213> ORGANISM: Leptinotarsa decemlineata

<400> SEQUENCE: 28

ccagcaaacg aagacatcga atcaccccga gatattataa acaaagcatt tagagaaatt     60
tttgaggctg acgaaaacgg gatcaatggg tctctggtgg aaccaccaac tccaacgcag    120
aaaacgtttg atagaccttt ccaagaagat ctaagcgagt tcaactttag aatatatgca    180
gcaacgtatt ttacgaacaa tgccaactat cagttttcaa agaaacctct taaggaatcc    240
ctacattatc ttccgacccc agatgacgtg atcgccgcac aagccttgtg gataaccatc    300
ctcaggttca tgggagacta tccggagccc aaatacgaca attcgacgaa agaaaacgtt    360
cccatcatgc aaatcatctc agagtcgatc ggc                                  393

<210> SEQ ID NO 29
<211> LENGTH: 779
<212> TYPE: DNA
<213> ORGANISM: Leptinotarsa decemlineata

<400> SEQUENCE: 29

ggacgtttgg aggaagccga cgctctcatc caacagctct cttccgacaa ggatcccatc     60
ctcaggcggt cgggcatgta cactatcgcc atggcttact gcagcaccgg acacaaccag    120
gcgatcagga agctgcttca cgttgctgta tccgacgtaa atgatgacgt ccgacgagct    180
gccgtcacgg cgctgggttt cctcttattc agaactcctg aacaatgccc aagcgtagtt    240
tctctgctgg ctgagagtta caaccctcac gtacgctacg gagctgccat ggcactcggt    300
atcgcctgtg ctggcaccgg actccgcgaa gctattgctc ttctggaacc gatggtgatg    360
ttcgatccag tcaatttcgt tcgtcaagga gctctcatcg cttctgccat gatcttgatc    420
cagcagaccg aacagacctg tcctaaagtt agtttcttca gacagactta cgctcaggtc    480
atcgccaaca aacatgagga tgttatggcc aaattcggag ctattttggc tcaaggaatt    540
attgacgctg gaggcaggaa tgttacatta tcactccagt cgagaacagg acacaccaat    600
atgttggcag tggtcggaac tttggtgttc acccagtatt ggtactggtt ccctctctcc    660
cattgtttgg ctctggcttt caccccaact tgtgttatcg ccctcaatga acaactcaaa    720
atgcccaagt tggaactgaa atcgaatgca aaaccaagtc tctacgcata tccagctcc     779

<210> SEQ ID NO 30
<211> LENGTH: 392
<212> TYPE: DNA
<213> ORGANISM: Leptinotarsa decemlineata

<400> SEQUENCE: 30

gttagtgatt ttgtattcag attgtctccg ttcgtaaaaa tgctactgaa tcaaatatcc     60
```

```
atagcaggtg ccgatgactg gagaaatgcc gctcatagca ctgggacttc tattatggca    120

gcagaattcg atggaggagt aattattggt gctgattccc gtacaactac aggggcgtac    180

attgcaaatc gtgtaactga caaactaact aaagtaactg accatatata ttgttgtcga    240

tctggatcag cagcagatac tcaagccatt gctgatattg tatcgtacca tctgaacttc    300

catggtatgg aactaggaga agagcccctt gtagaggtgg gggctgctat cttcagggag    360

ctttgctaca actataggga ttctctcatg gc                                  392


<210> SEQ ID NO 31
<211> LENGTH: 178
<212> TYPE: DNA
<213> ORGANISM: Leptinotarsa decemlineata

<400> SEQUENCE: 31

ctaggtctcc agccagcaga aagaacggat aaggttcctg aggaaaaatc aactcatact     60

cttttactag caggaatgct tcgagggggt attgacattt tagttagggc aaaactagcc    120

ctagctgatg gtgtgactat gcaactgacc gtgaggtcac ccgatgctga tgttgctg      178


<210> SEQ ID NO 32
<211> LENGTH: 559
<212> TYPE: DNA
<213> ORGANISM: Leptinotarsa decemlineata

<400> SEQUENCE: 32

gtaaggctaa agaactggcg gaattggtaa aggctactcg tccgtttctc agcattataa     60

gcaaggcgaa agctgcgaaa ctggtcaggt ctctggtcga ttatttccta gatttggaag    120

caggtatcgg aatagaagtc caactgtgta aagaatgtat agagtgggca aaagaagaga    180

aaaggacctt tcttcgtcag tctttggaag cgcgattgat agccttgtat ttcgatactg    240

gtatgtatgc cgaggctctg attctggaat ccaccttgtt gaaaggattg aagaagttgg    300

atgacaaaaa tttactggta gaagtacagt tgcttgaaag taagacatat cacgccttga    360

gtaacctgcc caaggctcgt gccgcattaa cttcagctcg tacaacagcc aattccatct    420

attgccctcc taagatgcaa gctgcgcttg accttcagtc tggagttctg catgcagctg    480

atgaaaaaga cttcaaaact gcctattcat acttttatga ggcatttgaa gggtttgaca    540

gcgtagaatc accaaaagc                                                 559


<210> SEQ ID NO 33
<211> LENGTH: 586
<212> TYPE: DNA
<213> ORGANISM: Leptinotarsa decemlineata

<400> SEQUENCE: 33

gcttcggagc ggtatagttt ttcgctgaca acttccagtc catctggaaa actagctcaa     60

attgaatatg ccctagctgc tgtagccgct ggagctcctt ctgtgggcat taaagcttca    120

aatggtgtag ttatcgccac agaaaacaaa cataagtcga tcctctatga agaacacagt    180

gttcataaag ttgaaatgat tacaaaacat ataggaatga tatattctgg tatgggacct    240

gattatcgct tgttggtgaa acaagctcgt aaaatggccc aacagtatta tctagtttat    300

caagagccta taccaacagt tcaactcgtt caacgagttg ccactgttat gcaagaatat    360

actcagtccg gaggagttag gccgtttggg gtttcattat tgatatgtgg ttgggacagt    420

gaacgaccat acttatttca atgtgatcca tcaggagctt attttgcctg gaaagctact    480

gccatgggca agaatttcat caatggaaaa acatttttgg aaaaaagata tagcgaggat    540
```

ttggaacttg atgacgcagt acacacagca attctgacgt tgaagg 586

<210> SEQ ID NO 34
<211> LENGTH: 267
<212> TYPE: DNA
<213> ORGANISM: Leptinotarsa decemlineata

<400> SEQUENCE: 34
gctgaagcag gccaaagaag aagctcaaga cgaaatcgaa aaataccgta aagaacgcga 60
acgtcaattc agggagttcg aggccaagca tatgggctcc agagaggatg taccgtccaa 120
aatcgaagtg gacaccaaac gtagaatcga agagatgaac aaggctataa tcagtcaaaa 180
agaacctgtt atccaagaag ttctcaactt agtgtacgac atcaaacctg aaatccacaa 240
gaactaccgc caatagactg tgtgtgg 267

<210> SEQ ID NO 35
<211> LENGTH: 603
<212> TYPE: DNA
<213> ORGANISM: Leptinotarsa decemlineata

<400> SEQUENCE: 35
gcatgtgaaa atgagttcct tgaagctaca gaagaggctc gccgcctcgg ttatgcgatg 60
tggcaaaaaa aagtatggtt ggatcctaat gaaattaatg aaatcgctaa caccaactca 120
aggcaaaaca tccgtaagtt gatcaaagat ggtctcataa tcaagaaacc agtagcagtg 180
cattcccgtg ctcgagtacg caaaaacaca gaagcccgca ggaagggaag acattgcggt 240
ttcggtaaaa ggaagggtac agcaaatgct cgaatgcccc agaaggaatt atggattcag 300
cgcatgagag ttttgagacg tctcttgaaa aaataccgag aagccaaaaa gatcgacagg 360
catctgtact atgccccttta catgaaagca aagggtaacg tattcaagaa caagagagtc 420
ctcatggaat acatccataa gaagaaggca gagaaggccc gtgccaagat gttggcagac 480
caagccaatg ccaggagatt gaaggtaaaa caagcacgtg aacgtcgtga agaacgtatc 540
gctaccaaga aacaggaagt tctacagaat taccagcggg aagatgaagc ccaagctgct 600
aag 603

<210> SEQ ID NO 36
<211> LENGTH: 273
<212> TYPE: DNA
<213> ORGANISM: Leptinotarsa decemlineata

<400> SEQUENCE: 36
gatgtctgtt ttgtgtcctg aaattccagc gccaggcttt tcattcgaga attgtaaaag 60
aaatgcattg ctggaaggca agggattcgc tctaccaaaa gctactaaga ctggtaccac 120
catcgtagga attacttata aagatggagt cattcttggg gccgatacca tagccacaga 180
agataccaca gttgcagaca agaactctga gaagattcac tatcttgctc caaatatgta 240
ttgttgtggt gctggtacag ccgcggatac aga 273

<210> SEQ ID NO 37
<211> LENGTH: 310
<212> TYPE: DNA
<213> ORGANISM: Leptinotarsa decemlineata

<400> SEQUENCE: 37
atgtcgtcta ctctagaaga taaagctatc tgggaagatg ggaagaatc attgggggag 60 gaagttctga ggatgtcgac tgatgaaata gtcagccgga cgcgtttact cgataatgaa 120
atcaaaataa tgaagagcga agtaatgaga ataaaccatg aactccaagc ccaaaacgaa 180
aaaatcaaag aaaacactga aaagataaag gtaaataaaa cgctacctta cttggtatct 240
aatgttatag aactgctaga tgtggaccct caagaggaag aagaagacgg ggcagttgta 300
gacttggatt 310

<210> SEQ ID NO 38
<211> LENGTH: 388
<212> TYPE: DNA
<213> ORGANISM: Leptinotarsa decemlineata

<400> SEQUENCE: 38
ggaatttgga ccagagaatt gtgtgacctg gatgaaattt gccgaactag aaactttatt 60
aggcgacatt gatcgagcaa gggctattta cgaattggct ataagtcagc ctaggttaga 120
tatgccagag ttactttgga aggcttatat agactttgaa atttctcagg aagaacctga 180
aaatgctaga caaatctatg aaaggctgct agaaaaaaca tcacatgtca aagtatggtt 240
gtcttatgcc aaatttgaac ttaacacaca atcagaaccc gacatgaatg ttctgttatc 300
caggagagta tttgaaagag ccaacgagag cctaaaaaat tcatctgaaa aagaggcaag 360
agttctactt cttgaaaact ggagggag 388

<210> SEQ ID NO 39
<211> LENGTH: 1504
<212> TYPE: DNA
<213> ORGANISM: Leptinotarsa decemlineata

<400> SEQUENCE: 39
gcttgttgcc cccgaatgcc ttgatagggt tgattacctt tgggaagatg gtccaagtgc 60
acgaactagg taccgagggc tgcagcaaat cttacgtttt ccgagggacg aaagacctca 120
cagctaagca agttcaagag atgttggaag tgggcagagc cgcagtaagt gctcaacctg 180
ctcctcaaca accaggacaa cccatgaggc ctggagcact ccagcaagct cctacgccac 240
caggaagcag gttccttcaa cccatctcga aatgcgacat gaacctcact gatcttattg 300
gagagttgca aagagaccca tggcctgtcc accaaggcaa atgcgccctt agatcgaccg 360
ggacagcttt atcgatagcc attgggttgt tggagtgcac atacgccaat actggtgcca 420
gggtcatgct attcgttgga ggaccttgct ctcaaggccc tggtcaagtc ttgaatgatg 480
atctgaagca acctatcaga tctcaccacg acatccaaaa agacaatgcc aaatacatga 540
agaaagcaat caagcactat gataatttag cgatgagagc agcaacgaat ggccactgcg 600
ttgacatata ttcatgcgct ttggatcaga caggattgat ggagatgaaa cagtgttgta 660
attcaacagg gggacatatg gtcatgggcg actcgttcaa ttcttccctg ttcaagcaaa 720
cgttccagcg catattttcg aaagatcaga aaaacgagct gaagatggca tttaatggta 780
ctctggaggt caagtgttcc agggagttga aaattcaagg cggtattgga tcttgtgttt 840
cgttgaatgt gaagaatcct ttggtttccg acaccgaaat aggaatgggt aacacggtcc 900
agtggaaaat gtgtacggta actccaagta ctaccatggc cttgttcttc gaggtcgtca 960
accaacattc cgctcccata cctcaagggg gaaggggctg catacagttc atcacgcaat 1020
atcagcatgc tagtggccag aagaggatcc gagtaacgac agttgctaga aactgggccg 1080
atgcttccgc taatatacat catgtcagtg ctggattcga tcaggaggca gccgcagtga 1140
taatggcgag gatggcagtt tacagagcgg aatcagacga tagccctgat gttttgagat 1200

```
gggtcgatag gatgttgata cgtctgtgcc agaaattcgg cgaatataac aaggacgacc   1260

cgaattcgtt ccgcttgggc gaaaacttca gcctctaccc gcagttcatg taccatttga   1320

gaaggtcaca gttcctgcag gtgtttaaca attctcccga cgaaacgtcc ttctacaggc   1380

acatgcttat gcgcgaagac ctcacgcagt cgctgatcat gatccagccg atactctaca   1440

gctacagttt caatggacca ccagaacctg tgcttttgga tacgagttcc atccaacccg   1500

atag                                                                1504
```

<210> SEQ ID NO 40
<211> LENGTH: 967
<212> TYPE: DNA
<213> ORGANISM: Leptinotarsa decemlineata

<400> SEQUENCE: 40

```
gggagcagac gatcggttgg ttaaaatctg ggactatcaa aacaaaacgt gtgtccaaac     60

cttggaagga cacgcccaaa acgtaaccgc ggtttgtttc caccctgaac tacctgtggc    120

tctcacaggc agcgaagatg gtaccgttag agtttggcat acgaatacac acagattaga    180

gaattgtttg aattatgggt tcgagagagt gtggaccatt tgttgcttga agggttcgaa    240

taatgtttct ctggggtatg acgagggcag tatattagtg aaagttggaa gagaagaacc    300

ggcagttagt atggatgcca gtggcggtaa aataatttgg gcaaggcact cggaattaca    360

acaagctaat ttgaaggcgc tgccagaagg tggagaaata agagatgggg agcgtttacc    420

tgtctctgta aaagatatgg gagcatgtga aatataccct caaacaatcc aacataatcc    480

gaatggaaga ttcgttgtag tatgcggaga cggcgaatat atcatttaca cagcgatggc    540

tctacggaac aaggcttttg gaagcgctca agagtttgtc tgggctcagg actccagcga    600

gtatgccatt cgcgagtctg gttccacaat tcggatattc aaaaacttca aagaaaggaa    660

gaacttcaag tcggatttca gcgcggaagg aatctacggg ggttttctct tggggattaa    720

atcggtgtcc ggtttaacgt tttacgattg ggaaactttg gacttggtga gacggattga    780

aatacaaccg agggcggttt attggtctga cagtggaaaa ttagtctgtc tcgcaacgga    840

ggacagctac ttcatccttt cttatgattc ggagcaagtt cagaaggcca gggagaacaa    900

tcaagtcgca gaggatggcg tagaggccgc tttcgatgtg ttgggggaaa tgaacgagtc    960

tgtccga                                                              967
```

<210> SEQ ID NO 41
<211> LENGTH: 43
<212> TYPE: DNA
<213> ORGANISM: Artificial
<220> FEATURE:
<223> OTHER INFORMATION: Primer

<400> SEQUENCE: 41

```
gcgtaatacg actcactata ggtcgtggaa gatagcagga aag                       43
```

<210> SEQ ID NO 42
<211> LENGTH: 31
<212> TYPE: DNA
<213> ORGANISM: Artificial
<220> FEATURE:
<223> OTHER INFORMATION: Primer

<400> SEQUENCE: 42

```
cattttctgt atgtatcagc ttgtccctct t                                    31
```

-continued

<210> SEQ ID NO 43
<211> LENGTH: 26
<212> TYPE: DNA
<213> ORGANISM: Artificial
<220> FEATURE:
<223> OTHER INFORMATION: Primer

<400> SEQUENCE: 43
gtcgtggaag atagcaggaa agggag 26

<210> SEQ ID NO 44
<211> LENGTH: 41
<212> TYPE: DNA
<213> ORGANISM: Artificial
<220> FEATURE:
<223> OTHER INFORMATION: Primer

<400> SEQUENCE: 44
gcgtaatacg actcactata ggcattttct gtatgtatca g 41

<210> SEQ ID NO 45
<211> LENGTH: 44
<212> TYPE: DNA
<213> ORGANISM: Artificial
<220> FEATURE:
<223> OTHER INFORMATION: Primer

<400> SEQUENCE: 45
gcgtaatacg actcactata ggatgtgtga cgaagaggtt gccg 44

<210> SEQ ID NO 46
<211> LENGTH: 24
<212> TYPE: DNA
<213> ORGANISM: Artificial
<220> FEATURE:
<223> OTHER INFORMATION: Primer

<400> SEQUENCE: 46
gtcaacaaaa cagggtgctc ttcg 24

<210> SEQ ID NO 47
<211> LENGTH: 22
<212> TYPE: DNA
<213> ORGANISM: Artificial
<220> FEATURE:
<223> OTHER INFORMATION: Primer

<400> SEQUENCE: 47
atgtgtgacg aagaggttgc cg 22

<210> SEQ ID NO 48
<211> LENGTH: 46
<212> TYPE: DNA
<213> ORGANISM: Artificial
<220> FEATURE:
<223> OTHER INFORMATION: Primer

<400> SEQUENCE: 48
gcgtaatacg actcactata gggtcaacaa aacagggtgc tcttcg 46

<210> SEQ ID NO 49
<211> LENGTH: 41
<212> TYPE: DNA
<213> ORGANISM: Artificial
<220> FEATURE:
<223> OTHER INFORMATION: Primer

<400> SEQUENCE: 49
gcgtaatacg actcactata ggtaagaatc gtcttttcgt c 41

<210> SEQ ID NO 50
<211> LENGTH: 22
<212> TYPE: DNA
<213> ORGANISM: Artificial
<220> FEATURE:
<223> OTHER INFORMATION: Primer

<400> SEQUENCE: 50
gacaccagct ccgcattgtt ca 22

<210> SEQ ID NO 51
<211> LENGTH: 29
<212> TYPE: DNA
<213> ORGANISM: Artificial
<220> FEATURE:
<223> OTHER INFORMATION: Primer

<400> SEQUENCE: 51
ggtaagaatc gtcttttcgt catatccac 29

<210> SEQ ID NO 52
<211> LENGTH: 42
<212> TYPE: DNA
<213> ORGANISM: Artificial
<220> FEATURE:
<223> OTHER INFORMATION: Primer

<400> SEQUENCE: 52
gcgtaatacg actcactata ggacaccagc tccgcattgt tc 42

<210> SEQ ID NO 53
<211> LENGTH: 44
<212> TYPE: DNA
<213> ORGANISM: Artificial
<220> FEATURE:
<223> OTHER INFORMATION: Primer

<400> SEQUENCE: 53
gcgtaatacg actcactata ggccaaacaa gaaacgccac gatg 44

<210> SEQ ID NO 54
<211> LENGTH: 20
<212> TYPE: DNA
<213> ORGANISM: Artificial
<220> FEATURE:
<223> OTHER INFORMATION: Primer

<400> SEQUENCE: 54
aggacgagat ggagggtgga 20

<210> SEQ ID NO 55
<211> LENGTH: 22
<212> TYPE: DNA
<213> ORGANISM: Leptinotarsa decemlineata

<400> SEQUENCE: 55
ccaaacaaga aacgccacga tg 22

<210> SEQ ID NO 56
<211> LENGTH: 42
<212> TYPE: DNA

-continued

<213> ORGANISM: Artificial
<220> FEATURE:
<223> OTHER INFORMATION: Primer

<400> SEQUENCE: 56
gcgtaatacg actcactata ggaggacgag atggagggtg ga 42

<210> SEQ ID NO 57
<211> LENGTH: 43
<212> TYPE: DNA
<213> ORGANISM: Artificial
<220> FEATURE:
<223> OTHER INFORMATION: Primer

<400> SEQUENCE: 57
gcgtaatacg actcactata gggaccaaca aaggcttatc ttc 43

<210> SEQ ID NO 58
<211> LENGTH: 26
<212> TYPE: DNA
<213> ORGANISM: Artificial
<220> FEATURE:
<223> OTHER INFORMATION: Primer

<400> SEQUENCE: 58
cctcctctga gacgaagaac caaatg 26

<210> SEQ ID NO 59
<211> LENGTH: 24
<212> TYPE: DNA
<213> ORGANISM: Artificial
<220> FEATURE:
<223> OTHER INFORMATION: Primer

<400> SEQUENCE: 59
gggaccaaca aaggcttatc ttcg 24

<210> SEQ ID NO 60
<211> LENGTH: 42
<212> TYPE: DNA
<213> ORGANISM: Artificial
<220> FEATURE:
<223> OTHER INFORMATION: Primer

<400> SEQUENCE: 60
gcgtaatacg actcactata ggcctcctct gagacgaaga ac 42

<210> SEQ ID NO 61
<211> LENGTH: 41
<212> TYPE: DNA
<213> ORGANISM: Artificial
<220> FEATURE:
<223> OTHER INFORMATION: Primer

<400> SEQUENCE: 61
gcgtaatacg actcactata ggcttgtttg ctccagtctc g 41

<210> SEQ ID NO 62
<211> LENGTH: 24
<212> TYPE: DNA
<213> ORGANISM: Artificial
<220> FEATURE:
<223> OTHER INFORMATION: Primer

<400> SEQUENCE: 62
gcagattgaa agacctgggc tacg 24

<210> SEQ ID NO 63
<211> LENGTH: 27
<212> TYPE: DNA
<213> ORGANISM: Artificial
<220> FEATURE:
<223> OTHER INFORMATION: Primer

<400> SEQUENCE: 63
cttgtttgct ccagtctcga aactacg 27

<210> SEQ ID NO 64
<211> LENGTH: 40
<212> TYPE: DNA
<213> ORGANISM: Artificial
<220> FEATURE:
<223> OTHER INFORMATION: Primer

<400> SEQUENCE: 64
gcgtaatacg actcactata gggcagattg aaagacctgg 40

<210> SEQ ID NO 65
<211> LENGTH: 41
<212> TYPE: DNA
<213> ORGANISM: Artificial
<220> FEATURE:
<223> OTHER INFORMATION: Primer

<400> SEQUENCE: 65
gcgtaatacg actcactata ggtatttgag acctcgctgt c 41

<210> SEQ ID NO 66
<211> LENGTH: 23
<212> TYPE: DNA
<213> ORGANISM: Artificial
<220> FEATURE:
<223> OTHER INFORMATION: Primer

<400> SEQUENCE: 66
ccatgccctg actcttagcc ctg 23

<210> SEQ ID NO 67
<211> LENGTH: 25
<212> TYPE: DNA
<213> ORGANISM: Artificial
<220> FEATURE:
<223> OTHER INFORMATION: Primer

<400> SEQUENCE: 67
gtatttgaga cctcgctgtc gcaag 25

<210> SEQ ID NO 68
<211> LENGTH: 41
<212> TYPE: DNA
<213> ORGANISM: Artificial
<220> FEATURE:
<223> OTHER INFORMATION: Primer

<400> SEQUENCE: 68
gcgtaatacg actcactata ggccatgccc tgactcttag c 41

<210> SEQ ID NO 69
<211> LENGTH: 47
<212> TYPE: DNA
<213> ORGANISM: Artificial
<220> FEATURE:

-continued

<223> OTHER INFORMATION: Primer

<400> SEQUENCE: 69
gcgtaatacg actcactata ggccagcaaa cgaagacatc gaatcac 47

<210> SEQ ID NO 70
<211> LENGTH: 24
<212> TYPE: DNA
<213> ORGANISM: Artificial
<220> FEATURE:
<223> OTHER INFORMATION: Primer

<400> SEQUENCE: 70
gccgatcgac tctgagatga tttg 24

<210> SEQ ID NO 71
<211> LENGTH: 25
<212> TYPE: DNA
<213> ORGANISM: Artificial
<220> FEATURE:
<223> OTHER INFORMATION: Primer

<400> SEQUENCE: 71
ccagcaaacg aagacatcga atcac 25

<210> SEQ ID NO 72
<211> LENGTH: 46
<212> TYPE: DNA
<213> ORGANISM: Artificial
<220> FEATURE:
<223> OTHER INFORMATION: Primer

<400> SEQUENCE: 72
gcgtaatacg actcactata gggccgatcg actctgagat gatttg 46

<210> SEQ ID NO 73
<211> LENGTH: 41
<212> TYPE: DNA
<213> ORGANISM: Artificial
<220> FEATURE:
<223> OTHER INFORMATION: Primer

<400> SEQUENCE: 73
gcgtaatacg actcactata ggacgtttgg aggaagccga c 41

<210> SEQ ID NO 74
<211> LENGTH: 27
<212> TYPE: DNA
<213> ORGANISM: Artificial
<220> FEATURE:
<223> OTHER INFORMATION: Primer

<400> SEQUENCE: 74
ggagctggat atgcgtagag acttggt 27

<210> SEQ ID NO 75
<211> LENGTH: 21
<212> TYPE: DNA
<213> ORGANISM: Artificial
<220> FEATURE:
<223> OTHER INFORMATION: Primer

<400> SEQUENCE: 75
ggacgtttgg aggaagccga c 21

<210> SEQ ID NO 76
<211> LENGTH: 42
<212> TYPE: DNA
<213> ORGANISM: Artificial
<220> FEATURE:
<223> OTHER INFORMATION: Primer

<400> SEQUENCE: 76
gcgtaatacg actcactata ggagctggat atgcgtagag ac 42

<210> SEQ ID NO 77
<211> LENGTH: 41
<212> TYPE: DNA
<213> ORGANISM: Artificial
<220> FEATURE:
<223> OTHER INFORMATION: Primer

<400> SEQUENCE: 77
gcgtaatacg actcactata ggttagtgat tttgtattca g 41

<210> SEQ ID NO 78
<211> LENGTH: 28
<212> TYPE: DNA
<213> ORGANISM: Artificial
<220> FEATURE:
<223> OTHER INFORMATION: Primer

<400> SEQUENCE: 78
gccatgagag aatccctata gttgtagc 28

<210> SEQ ID NO 79
<211> LENGTH: 30
<212> TYPE: DNA
<213> ORGANISM: Artificial
<220> FEATURE:
<223> OTHER INFORMATION: Primer

<400> SEQUENCE: 79
gttagtgatt ttgtattcag attgtctccg 30

<210> SEQ ID NO 80
<211> LENGTH: 42
<212> TYPE: DNA
<213> ORGANISM: Artificial
<220> FEATURE:
<223> OTHER INFORMATION: Primer

<400> SEQUENCE: 80
gcgtaatacg actcactata ggccatgaga gaatccctat ag 42

<210> SEQ ID NO 81
<211> LENGTH: 41
<212> TYPE: DNA
<213> ORGANISM: Artificial
<220> FEATURE:
<223> OTHER INFORMATION: Primer

<400> SEQUENCE: 81
gcgtaatacg actcactata ggctaggtct ccagccagca g 41

<210> SEQ ID NO 82
<211> LENGTH: 22
<212> TYPE: DNA
<213> ORGANISM: Artificial
<220> FEATURE:
<223> OTHER INFORMATION: Primer -continued

<400> SEQUENCE: 82
cagcaacatc agcatcgggt ga 22

<210> SEQ ID NO 83
<211> LENGTH: 26
<212> TYPE: DNA
<213> ORGANISM: Artificial
<220> FEATURE:
<223> OTHER INFORMATION: Primer

<400> SEQUENCE: 83
ctaggtctcc agccagcaga aagaac 26

<210> SEQ ID NO 84
<211> LENGTH: 43
<212> TYPE: DNA
<213> ORGANISM: Artificial
<220> FEATURE:
<223> OTHER INFORMATION: Primer

<400> SEQUENCE: 84
gcgtaatacg actcactata ggcagcaaca tcagcatcgg gtg 43

<210> SEQ ID NO 85
<211> LENGTH: 41
<212> TYPE: DNA
<213> ORGANISM: Artificial
<220> FEATURE:
<223> OTHER INFORMATION: Primer

<400> SEQUENCE: 85
gcgtaatacg actcactata gggtaaggct aaagaactgg c 41

<210> SEQ ID NO 86
<211> LENGTH: 27
<212> TYPE: DNA
<213> ORGANISM: Artificial
<220> FEATURE:
<223> OTHER INFORMATION: Primer

<400> SEQUENCE: 86
gcttttggtg attctacgct gtcaaac 27

<210> SEQ ID NO 87
<211> LENGTH: 26
<212> TYPE: DNA
<213> ORGANISM: Artificial
<220> FEATURE:
<223> OTHER INFORMATION: Primer

<400> SEQUENCE: 87
gtaaggctaa agaactggcg gaattg 26

<210> SEQ ID NO 88
<211> LENGTH: 42
<212> TYPE: DNA
<213> ORGANISM: Artificial
<220> FEATURE:
<223> OTHER INFORMATION: Primer

<400> SEQUENCE: 88
gcgtaatacg actcactata ggcttttggt gattctacgc tg 42

<210> SEQ ID NO 89
<211> LENGTH: 44

<212> TYPE: DNA
<213> ORGANISM: Artificial
<220> FEATURE:
<223> OTHER INFORMATION: Primer

<400> SEQUENCE: 89
gcgtaatacg actcactata ggcttcggag cggtatagtt tttc 44

<210> SEQ ID NO 90
<211> LENGTH: 28
<212> TYPE: DNA
<213> ORGANISM: Artificial
<220> FEATURE:
<223> OTHER INFORMATION: Primer

<400> SEQUENCE: 90
ccttcaacgt cagaattgct gtgtgtac 28

<210> SEQ ID NO 91
<211> LENGTH: 24
<212> TYPE: DNA
<213> ORGANISM: Artificial
<220> FEATURE:
<223> OTHER INFORMATION: Primer

<400> SEQUENCE: 91
gcttcggagc ggtatagttt ttcg 24

<210> SEQ ID NO 92
<211> LENGTH: 41
<212> TYPE: DNA
<213> ORGANISM: Artificial
<220> FEATURE:
<223> OTHER INFORMATION: Primer

<400> SEQUENCE: 92
gcgtaatacg actcactata ggccttcaac gtcagaattg c 41

<210> SEQ ID NO 93
<211> LENGTH: 46
<212> TYPE: DNA
<213> ORGANISM: Artificial
<220> FEATURE:
<223> OTHER INFORMATION: Primer

<400> SEQUENCE: 93
gcgtaatacg actcactata gggctgaagc aggccaaaga agaagc 46

<210> SEQ ID NO 94
<211> LENGTH: 27
<212> TYPE: DNA
<213> ORGANISM: Artificial
<220> FEATURE:
<223> OTHER INFORMATION: Primer

<400> SEQUENCE: 94
ccacacacag tctattggcg gtagttc 27

<210> SEQ ID NO 95
<211> LENGTH: 24
<212> TYPE: DNA
<213> ORGANISM: Artificial
<220> FEATURE:
<223> OTHER INFORMATION: Primer

<400> SEQUENCE: 95
gctgaagcag gccaaagaag aagc 24

<210> SEQ ID NO 96
<211> LENGTH: 49
<212> TYPE: DNA
<213> ORGANISM: Artificial
<220> FEATURE:
<223> OTHER INFORMATION: Primer

<400> SEQUENCE: 96
gcgtaatacg actcactata ggccacacac agtctattgg cggtagttc 49

<210> SEQ ID NO 97
<211> LENGTH: 43
<212> TYPE: DNA
<213> ORGANISM: Artificial
<220> FEATURE:
<223> OTHER INFORMATION: Primer

<400> SEQUENCE: 97
gcgtaatacg actcactata ggcatgtgaa aatgagttcc ttg 43

<210> SEQ ID NO 98
<211> LENGTH: 25
<212> TYPE: DNA
<213> ORGANISM: Artificial
<220> FEATURE:
<223> OTHER INFORMATION: Primer

<400> SEQUENCE: 98
cttagcagct tgggcttcat cttcc 25

<210> SEQ ID NO 99
<211> LENGTH: 26
<212> TYPE: DNA
<213> ORGANISM: Artificial
<220> FEATURE:
<223> OTHER INFORMATION: Primer

<400> SEQUENCE: 99
gcatgtgaaa atgagttcct tgaagc 26

<210> SEQ ID NO 100
<211> LENGTH: 43
<212> TYPE: DNA
<213> ORGANISM: Artificial
<220> FEATURE:
<223> OTHER INFORMATION: Primer

<400> SEQUENCE: 100
gcgtaatacg actcactata ggcttagcag cttgggcttc atc 43

<210> SEQ ID NO 101
<211> LENGTH: 50
<212> TYPE: DNA
<213> ORGANISM: Artificial
<220> FEATURE:
<223> OTHER INFORMATION: Primer

<400> SEQUENCE: 101
gcgtaatacg actcactata gggatgtctg ttttgtgtcc tgaaattcca 50

<210> SEQ ID NO 102
<211> LENGTH: 22
<212> TYPE: DNA
<213> ORGANISM: Artificial

-continued

<220> FEATURE:
<223> OTHER INFORMATION: Primer

<400> SEQUENCE: 102
tctgtatccg cggctgtacc ag 22

<210> SEQ ID NO 103
<211> LENGTH: 28
<212> TYPE: DNA
<213> ORGANISM: Artificial
<220> FEATURE:
<223> OTHER INFORMATION: Primer

<400> SEQUENCE: 103
gatgtctgtt ttgtgtcctg aaattcca 28

<210> SEQ ID NO 104
<211> LENGTH: 44
<212> TYPE: DNA
<213> ORGANISM: Artificial
<220> FEATURE:
<223> OTHER INFORMATION: Primer

<400> SEQUENCE: 104
gcgtaatacg actcactata ggtctgtatc cgcggctgta ccag 44

<210> SEQ ID NO 105
<211> LENGTH: 56
<212> TYPE: DNA
<213> ORGANISM: Artificial
<220> FEATURE:
<223> OTHER INFORMATION: Primer

<400> SEQUENCE: 105
gcgtaatacg actcactata ggatgtcgtc tactctagaa gataaagcta tctggg 56

<210> SEQ ID NO 106
<211> LENGTH: 24
<212> TYPE: DNA
<213> ORGANISM: Artificial
<220> FEATURE:
<223> OTHER INFORMATION: Primer

<400> SEQUENCE: 106
aatccaagtc tacaactgcc ccgt 24

<210> SEQ ID NO 107
<211> LENGTH: 34
<212> TYPE: DNA
<213> ORGANISM: Artificial
<220> FEATURE:
<223> OTHER INFORMATION: Primer

<400> SEQUENCE: 107
atgtcgtcta ctctagaaga taaagctatc tggg 34

<210> SEQ ID NO 108
<211> LENGTH: 46
<212> TYPE: DNA
<213> ORGANISM: Artificial
<220> FEATURE:
<223> OTHER INFORMATION: Primer

<400> SEQUENCE: 108
gcgtaatacg actcactata ggaatccaag tctacaactg ccccgt 46

<210> SEQ ID NO 109
<211> LENGTH: 41
<212> TYPE: DNA
<213> ORGANISM: Artificial
<220> FEATURE:
<223> OTHER INFORMATION: Primer

<400> SEQUENCE: 109
gcgtaatacg actcactata ggaatttgga ccagagaatt g 41

<210> SEQ ID NO 110
<211> LENGTH: 29
<212> TYPE: DNA
<213> ORGANISM: Artificial
<220> FEATURE:
<223> OTHER INFORMATION: Primer

<400> SEQUENCE: 110
ctccctccag ttttcaagaa gtagaactc 29

<210> SEQ ID NO 111
<211> LENGTH: 27
<212> TYPE: DNA
<213> ORGANISM: Artificial
<220> FEATURE:
<223> OTHER INFORMATION: Primer

<400> SEQUENCE: 111
ggaatttgga ccagagaatt gtgtgac 27

<210> SEQ ID NO 112
<211> LENGTH: 43
<212> TYPE: DNA
<213> ORGANISM: Artificial
<220> FEATURE:
<223> OTHER INFORMATION: Primer

<400> SEQUENCE: 112
gcgtaatacg actcactata ggctccctcc agttttcaag aag 43

<210> SEQ ID NO 113
<211> LENGTH: 41
<212> TYPE: DNA
<213> ORGANISM: Artificial
<220> FEATURE:
<223> OTHER INFORMATION: Primer

<400> SEQUENCE: 113
gcgtaatacg actcactata gggcttgttg cccccgaatg c 41

<210> SEQ ID NO 114
<211> LENGTH: 22
<212> TYPE: DNA
<213> ORGANISM: Artificial
<220> FEATURE:
<223> OTHER INFORMATION: Primer

<400> SEQUENCE: 114
ctatcgggtt ggatggaact cg 22

<210> SEQ ID NO 115
<211> LENGTH: 19
<212> TYPE: DNA
<213> ORGANISM: Artificial
<220> FEATURE:
<223> OTHER INFORMATION: Primer

<400> SEQUENCE: 115
gcttgttgcc cccgaatgc 19

<210> SEQ ID NO 116
<211> LENGTH: 44
<212> TYPE: DNA
<213> ORGANISM: Artificial
<220> FEATURE:
<223> OTHER INFORMATION: Primer

<400> SEQUENCE: 116
gcgtaatacg actcactata ggctatcggg ttggatggaa ctcg 44

<210> SEQ ID NO 117
<211> LENGTH: 42
<212> TYPE: DNA
<213> ORGANISM: Artificial
<220> FEATURE:
<223> OTHER INFORMATION: Primer

<400> SEQUENCE: 117
gcgtaatacg actcactata gggggagcag acgatcggtt gg 42

<210> SEQ ID NO 118
<211> LENGTH: 23
<212> TYPE: DNA
<213> ORGANISM: Artificial
<220> FEATURE:
<223> OTHER INFORMATION: Primer

<400> SEQUENCE: 118
tcggacagac tcgttcattt ccc 23

<210> SEQ ID NO 119
<211> LENGTH: 20
<212> TYPE: DNA
<213> ORGANISM: Artificial
<220> FEATURE:
<223> OTHER INFORMATION: Primer

<400> SEQUENCE: 119
gggagcagac gatcggttgg 20

<210> SEQ ID NO 120
<211> LENGTH: 45
<212> TYPE: DNA
<213> ORGANISM: Artificial
<220> FEATURE:
<223> OTHER INFORMATION: Primer

<400> SEQUENCE: 120
gcgtaatacg actcactata ggtcggacag actcgttcat ttccc 45

<210> SEQ ID NO 121
<211> LENGTH: 837
<212> TYPE: DNA
<213> ORGANISM: Lygus hesperus

<400> SEQUENCE: 121
gaacacggta tcgtcaccaa ctgggacgat atggagaaaa tctggcacca caccttctac 60
aacgagttga gagtcgcccc cgaggaacac cccgtcctcc tgactgaagc ccccctcaac 120
cctaaggcca acagggagaa gatgacccag atcatgttcg aaaccttcaa cacacccgcc 180

```
atgtacgtgg ccatccaggc tgtcctgtcg ctgtacgcct ccggtcgtac cactggtatc    240

gtcctcgact ccggagatgg tgtctcccac accgtcccga tctacgaggg atacgctcty    300

ccccacgcca tcctccgtct cgacttggct ggccgtgact tgaccgacta ccttatgaag    360

atcctcaccg agagaggcta ctccttcacg accaccgccg aaagggagat cgtccgtgac    420

atcaaggaga agctctgcta cgtcgccctc gacttcgagc aggaaatggc caccgccgcg    480

tcctcctcgt ccctcgaaaa gtcctacgag cttcccgacg gtcaagtcat caccatcgga    540

aacgagaggt tcaggtgccc mgaagccctc ttccagcctt ccttcttggg aatggaagcc    600

tgcggtatcc acgaaaccac ttacaactcc atcatgaagt gcgacgtgga catccgtaag    660

gacctgtacg ccaacaccgt gctctctgga ggcaccacca tgtacccagg aatcgccgac    720

aggatgcaga aggaaatcac cgccctcgcc ccatccacca tgaagatcaa gatcatcgct    780

cccccagagc gcaaatactc cgtatggatc ggaggatcca tcctcgcctc cctctcc       837
```

<210> SEQ ID NO 122
<211> LENGTH: 756
<212> TYPE: DNA
<213> ORGANISM: Lygus hesperus

<400> SEQUENCE: 122

```
gagcacggca tcatcaccaa ctgggacgac atggagaaga tctggcacca caccttctac     60

aacgagctcc gcgtcgctcc cgaggagcac cccatcctcc tcacggaggc tcccctcaac    120

cccaaagcca acagggagaa gatgactcag atcatgtttg agaccttcaa caccccgcc    180

atgtacgtcg ccatccaggc cgtmctttcc ctctacgctt ccggtcgtac caccggtatc    240

gtcctcgact ccggagatgg tgtctcccac accgtcccca tctaygaagg ttacgccctt    300

ccycacgcca tcctccgtct ggacttggct ggmcgtgact tgactgacta cctgatgaag    360

atcctcaccg agaggggtta ctctttcacs accaccgctg agagggaaat cgtccgcgac    420

atcaaggaga agctctgcta cgtcgctctg gacttcgagc aggaaatggc caccgccgcc    480

gcctccacct ccctcgagaa gtcctacgag cttcccgacg gacaggtcat caccatcggy    540

aacgagaggt tccgttgccc cgaagccctc ttccagcctt ccttcctggg tatggaatcc    600

tgcggyatcc acgagaccgt ctacaactcc atcatgaagt gcgacgtcga catcaggaaa    660

gacctgtacg ccaacaccgt cctctccgga ggcaccacca tgtaccccgg tatcgccgac    720

aggatgcaga aggaaatcac cgccctcgct ccctcg                              756
```

<210> SEQ ID NO 123
<211> LENGTH: 213
<212> TYPE: DNA
<213> ORGANISM: Lygus hesperus

<400> SEQUENCE: 123

```
atccccccgg atcagcagcg tcttatcttc gccggtaagc aattggaaga tggccgcacc     60

ctttctgact acaacatcca gaaagaatcc accttgcact trgtgctcag gcttcgyggt    120

ggtgccaaga aaaggaagaa gaagaactac tccactccca agaagatcaa gcacaagaag    180

aagaagatta agttggctgt gcttaaatac tac                                 213
```

<210> SEQ ID NO 124
<211> LENGTH: 265
<212> TYPE: DNA
<213> ORGANISM: Lygus hesperus

<400> SEQUENCE: 124
caargchaar atccargaca aggaaggsat ycccccagay cagcagaggt tgatcttcgc 60
tggcaagcag ctcgaagatg gccgcacact ttcygactac aacatccaga aagagtccac 120
ccttcacttg gtcctccgyc tgagaggagg agtcatcgag cccrccctca ggatyttggc 180
tcagaagtac aactgcgaca aratgatctg caggaagtgc tacgctcgtc tccaccccag 240
ggcgaccaac tgtcgcaaga agaaa 265

<210> SEQ ID NO 125
<211> LENGTH: 384
<212> TYPE: DNA
<213> ORGANISM: Lygus hesperus

<400> SEQUENCE: 125
aagaccctca caggaaagac catcactctt gaggtcgagc cttctgacac catcgaaaac 60
gtcaaggcta aaattcaaga caaggaaggt attcctccag atcagcagag attgatcttc 120
gccggcaaac aactcgaaga tggccgtacc ctctctgact acaatattca aaaagagtcc 180
acccttcact tggtgttgag attgcgtgga ggtatgcaaa tctttgtcaa aacattgact 240
ggaaagacca tcacccttga agtcgaaccc tccgacacca tcgaaaatgt caaggccaag 300
atccaggaca aggaaggcat ccccccagat cagcagaggt tgattttcgc tggcaaacaa 360
cttgaagacg gacgtaccct ctcg 384

<210> SEQ ID NO 126
<211> LENGTH: 156
<212> TYPE: DNA
<213> ORGANISM: Lygus hesperus

<400> SEQUENCE: 126
accctgtccg actacaacat acagaaggag tccactcttc acttggtgtt gagattgcgt 60
ggtggtatgc agatcttcgt caagacgttg acaggcaaga ccatcaccct tgaagtcgag 120
ccctctgaca ccatcgaaaa cgtcaaggct aagatc 156

<210> SEQ ID NO 127
<211> LENGTH: 156
<212> TYPE: DNA
<213> ORGANISM: Lygus hesperus

<400> SEQUENCE: 127
accctgtccg actacaacat acagaaggag tcgaccctcc atcttgtcct ccgtctgcgt 60
ggtggtatgc agatttttgt caaaacgctg actggcaaga caatcaccct tgaagtagag 120
ccctctgaca ccatcgaaaa tgtcaaggcg aaaatc 156

<210> SEQ ID NO 128
<211> LENGTH: 141
<212> TYPE: DNA
<213> ORGANISM: Lygus hesperus

<400> SEQUENCE: 128
cacttggtgt tgagattgcg tggtggtatg cagatcttcg tcaaaacctt gaccggcaag 60
acgatcactt tggaagtgga gccctctgac accattgaga atgttaaagc caagatccag 120
gacaaggaag gtatcccccc a 141

<210> SEQ ID NO 129
<211> LENGTH: 138
<212> TYPE: DNA

<213> ORGANISM: Lygus hesperus

<400> SEQUENCE: 129
cttgtactcc gtctgcgtgg tggtatgcag attttcgtga agaccttgac tggcaagacc 60
atcactcttg aggtcgagcc ctctgacacc attgaaaacg tcaaggccaa gatccaggac 120
aaggaaggta tcccccca 138

<210> SEQ ID NO 130
<211> LENGTH: 228
<212> TYPE: DNA
<213> ORGANISM: Lygus hesperus

<400> SEQUENCE: 130
agctcycacg agaacgaact gatcctcatg agcgttctyc agtgtctgta cgactcgaty 60
agtcaaatcc tgaggaaaaa cgtygagaaa cgaacgatat tcgagaacct ggagatcgtc 120
atgctcgcca tggacgagat ctgcgacggt gggatactcc tggaggccga ccctacgtcc 180
gtcgtacagc gagtcgccat ccggaccgat gacatcccct tgggcgaa 228

<210> SEQ ID NO 131
<211> LENGTH: 418
<212> TYPE: DNA
<213> ORGANISM: Lygus hesperus

<400> SEQUENCE: 131
cttgracgta ctcattgtca accagacagc tgacactctt caaaattgca ctctggaatt 60
ggctacactt ggcgacctga aattggtcga gaagccgcaa ccctgcgttt tggcgcctca 120
tgacttctgt aacataaaag ctaacgtcaa agtggcttcc actgaaaacg gaattatttt 180
tggcaacatt gkttacgacg ttagtggagc agcttccgac cgaaacgtcg tcgtcctcaa 240
tgacattcac atcgatatta tggactacat agttcctgca tcttgttctg acactgaatt 300
ccgccaaatg tgggctgaat tcgaatggga aaacaaggta tctgtcaaca ccaacctcac 360
ggacttgcac gagtatttgg cccatttggt caggagcacc aacatgaagt gcttgaca 418

<210> SEQ ID NO 132
<211> LENGTH: 348
<212> TYPE: DNA
<213> ORGANISM: Lygus hesperus

<400> SEQUENCE: 132
gtcctagaca ttgtrgctta ccaactgaat ttctacagaa atgaaacgaa tgaagaaccg 60
accgtcgaaa ttgcggccaa tgtgttccgt gatgtctact acaggtaccg wgaccagttg 120
caggtcggtc tgatcatagc tggatgggay aaagtcaagg gaggacaggt gtacaatatt 180
cctttgggtg ggatggtcat ccgtcaaaag ttctgcatgg gtggttctgg cagcacgttt 240
gtctttggtt tcaccgacac caacttcaag gagaacatga cagaagccga gtgcaagaac 300
ttcttaacra gagctattgg cctygccatc agccgcgacg gttcatct 348

<210> SEQ ID NO 133
<211> LENGTH: 348
<212> TYPE: DNA
<213> ORGANISM: Lygus hesperus

<400> SEQUENCE: 133
gtatcggaaa tggtgacttt ccaactgaat ttatacagaa atgaaacaaa taaagaaccg 60
actgttgaaa tggcggccaa tgtgttccgt gatgtctgct acaggtaccg tgaccagctg 120

-continued

```
caggttggtc tgatcatagc tggatgggat gaagtcaaag gagcacaggt gtacatgatt    180

cctttgggcg ggatggtcat ccgtcagaag ttcgccatga gtggttctgg cagcaccttc    240

atttatggtt tcactgacgc ccacttcaag gagaacatga ccgaagcgga gtgcaagaac    300

ttcttaacca gagctattgg ccttgccatc agccgcgacg gtgcgtct                 348
```

<210> SEQ ID NO 134
<211> LENGTH: 1115
<212> TYPE: DNA
<213> ORGANISM: Lygus hesperus

<400> SEQUENCE: 134

```
tcgcttcatt tgtatctgaa atcagtgatg aattcaaaat cgtcgtcgtc caggctattc     60

gtgcgctctg cctcaagttt cccagaaagc atagtaccct aatgacattc ctgtctgcca    120

tgctccgcga tgaaggtgga ttggagtaca gagcttcgat agctgatacc atcatcacaa    180

tcattgaaga taatcctgaa gctaaagaaa ttggactcgc tcatctctgc gagttcattg    240

aagattgtga gcacgttagt ttggcagtca gaatccttca tctacttggt aaagaaggac    300

cgaaaacaat tcaaccttct cgatacatca gattcattta caatagggtt atccttgaaa    360

tagctgttat tcgggctgct gcagtttctg cccttgctca gtttggagct ctatgtccag    420

atcttctccc caacatcttg gttttgctgg cccgatgcca aatggacact gatgacgaag    480

tgagagatag ggcgacttac tattatcatc tactgaaatt gcaggagaaa ggacttattt    540

tcaattacat tgtcgaccca atgcaggttt gtctggtgag tctcgagaaa tcgttggccc    600

aacatgttca cgataaggta cccactaaat tcgatttgaa gtccgttcca cctgctcctg    660

tcgtgtctac tactgaagac accgcacaag aaacggtacc tgaaggctcc attagttcag    720

ccccaagtaa gatcgctcct ttacaatcaa cagttagtag ctatgcagag aagctgcaag    780

gagttccagg tctacaaagc atacccggga cattattcca tgtatcagaa ccagttgaac    840

tcaccgaatc cgaaactgaa tacgttgtca cgtgcaccaa acttacatac cctcatcacc    900

tcgtgttgca gtttgaatgc aagaacacgt tgagygatca rcttcttgag aatgtcagag    960

ttcwgattga ggccagtgaa ggttacagaa tcgtcaagga aataccgatc tccaagcttc   1020

cttacaacga aacacattgt gcctacgtag tgytgcaatt tccagagcaa ctttccctca   1080

ccgtcackaa tttcggagct acactcagat ttatc                              1115
```

<210> SEQ ID NO 135
<211> LENGTH: 915
<212> TYPE: DNA
<213> ORGANISM: Lygus hesperus

<400> SEQUENCE: 135

```
aaggccaagg wattgggtga actgatccaa gcctccaggc ccttcctgtc tgagatatct     60

aaagcaaaag ctgccaaatt agtcagaact ctggtagatt tcttcctaga tttagaggcc    120

gaaactggaa gagaggttca gctgtgcaag gagtgcatag aatgggccac aaccgagaga    180

agaacgttcc tcaggcaaag tctcgaagct cgactcatcg ctttgtattt cgayacgggc    240

atgtacacgg aagccctcgg tttgggatcg agccttctca aagaactgaa aaaacttgac    300

gacaaaaatc tccttgtrga agtyctgctt ctagagtcga aaacctacca tgcactcagc    360

aatttgtcca aggctagagc agctctcaca tcagcrcgca caacagcaaa ttccatctac    420

tgtccaccta aaatgcaggc agccctggat ctccagtctg gaatacttca tgctgctgat    480
```

```
gaacaagatt tcaaaactgc atattcctat ttctacgaag ctttcgaagg atatgattcg    540
gtagactctc cgaaagcgtt gactgctcta aaatacatgc ttctctcaaa aattatgttg    600
aacactccgg aggatgtaca gcaacttatt tcaggaaaac ttgctttgaa gcatgcaggg    660
cgagacatcg acgccatgaa aaacgtagct aaggcttctg ccaagcggtc ccttgcagat    720
ttccagtcca ctcttgaagg ctacaagaaa gagttgaaag aagacccgat tgtgaaggcc    780
catctgggca ctctctacga caacatgctg gaacaaaatt tgtgtcgtat aatcgaaccc    840
tattcaagag tacaagtgga atacgtctcg aaagccatca aactcccgac tctccaggtg    900
gagaagaagc tctcc                                                     915

<210> SEQ ID NO 136
<211> LENGTH: 537
<212> TYPE: DNA
<213> ORGANISM: Lygus hesperus

<400> SEQUENCE: 136

ttggccgctg tatctgctgg cgccccttcc ataggcatta aagcgcaaaa tggygtggtt     60
ttggcgactg agaacaartt caagtctatt ctctatgaag aacactcgat aaaaaagatt    120
gagatggtcg aagaacayat tggaatggtc tacagtggta tgggacccga ttacaggctg    180
ctagtgaaga gagcgcgcaa gttagctcar cagtacaagt tggtttatgg acagaggata    240
ccgacgcccc aactcgttca aaaggttgcc atggtgatgc aggagtacac gcaatcagga    300
ggcgtacggc cgttcggagt gtcgttactc atytgcgggt gggacgatgg ccgtccracc    360
ttgttccagt gcgatccttc tggcgcctac tttgcctgga aagcaactgc gatggggaag    420
aayttcatca atggaaaaac tttcytggag aagaggtaca ttgaaaccca agacatcgar    480
gacgctgtmc acaccgccat attgaccttg aaagaaggat tcgaaggtca aatggat       537

<210> SEQ ID NO 137
<211> LENGTH: 241
<212> TYPE: DNA
<213> ORGANISM: Lygus hesperus

<400> SEQUENCE: 137

tgcggaagca aagaaaagga aagctcgccg tttgaagcag gccaaggaag aggctcagga     60
ggaaattgaa aggtacaagc aagrcagaga gaagcagttc aaggagttcg aagcccagca    120
catgggctcc agggaggacg ttgctgccag gatagacgct gacactcgtc agagaattga    180
agagatgaca aaagctgtca atgtcaacaa agaacaagtg atccaaagaa tactggaact    240
t                                                                    241

<210> SEQ ID NO 138
<211> LENGTH: 538
<212> TYPE: DNA
<213> ORGANISM: Lygus hesperus

<400> SEQUENCE: 138

cgcctcggtg atgagatgcg gcaagaagaa agtgtggttg gaccctaatg aaatcaacga     60
aatcgccrmc rccaactcta ggcaaaayat ycgtaagctg atcaaggatg gtttgatcat    120
caaaaagcct gtggctgtcc actccagrgc ccgcgtccgt aaaaacacag aagccagacg    180
gaagggtcgt caytgtggct tyggtaagag gaagggtacs gccaacgcca gaatgcctgt    240
gaaggtcctg tgggtsaacm gaatgagrgt cctgcgacgg ctccttaaaa aatacagaga    300
agccaagaag atcgataggc aaatgtacca cgacctttac atgaaagcca aaggtaacgt    360
```

```
cttcaaaaac aagagggtac tgatggactt cattcacaag aagaaggctg aaaaggcgag    420

atcaaagatg ttgaaggacc aggcagaggc gagacgtctc aaggtcaagg aggcgaagaa    480

gaggcgcgag gagaggatcg ccaccaagaa gcaagagatc atgcaggcgt acgcccga      538


<210> SEQ ID NO 139
<211> LENGTH: 657
<212> TYPE: DNA
<213> ORGANISM: Lygus hesperus
<220> FEATURE:
<221> NAME/KEY: misc_feature
<222> LOCATION: (366)..(366)
<223> OTHER INFORMATION: n is a, c, g, or t

<400> SEQUENCE: 139

gagaaatttg aaaatttggg tattcaaccc cccaaggggg ttctgttata tggaccacct     60

ggcactggta agactctcct ggccagagct tgtgctgccc aaaccaaatc caccttcctg    120

aaacttgctg gacctcagtt ggttcaaatg tttattggag acggtgccaa actcgtcagg    180

gacgccttcg ctttggccaa agaaaaagct cctgccatta ttttcatcga cgaattagac    240

gcaattggta cgaaaagatt cgactctgag aaggcaggtg acagagaagt gcagagaact    300

atgttggagt tgctgaacca gctggatggt ttcagttcca cagctgatat caaagttatt    360

gctgcnacta accgtgtgga cattttggac cctgctttgc tacgatcggg tcgtcttgat    420

cgaaaaatcg agttcccaca tcccaacgag gacgccaggg ctcgcatcat gcagatccac    480

tcgcgcaaaa tgaacatcag cgtcgacgtc aatttcgagg aactcgcacg gtccaccgac    540

gacttcaacg gcgctcagtg caaagcagtt tgcgtggaag ctggtatgat cgctcttcgt    600

agaagcgcga gtgtcgtctc ccacgaagac ttcatggatg cgatattgga agtycag       657


<210> SEQ ID NO 140
<211> LENGTH: 276
<212> TYPE: DNA
<213> ORGANISM: Lygus hesperus

<400> SEQUENCE: 140

aacaaaaccc ttccatattt ggtctccaac gtcattgagc tacttgatgt tgacccagaa     60

gagacygagg aagatggtgc tgtggttgat ttggatgcga gaagaaaagg gaagtgcgcc    120

gtgattaaaa catctactag acaaacgtat ttccttccag tcaytggktt ggttgatgcg    180

gaaaaattaa agcctgggga tttggtcgga gtaaataagg attcctattt gattttggaa    240

acccttccag ctgartatga cgctcgagtg aaagct                              276


<210> SEQ ID NO 141
<211> LENGTH: 625
<212> TYPE: DNA
<213> ORGANISM: Lygus hesperus

<400> SEQUENCE: 141

ctaaggccaa cagggagaag atgacccaga tcatgttcga aaccttcaac acacccgcca     60

tgtacgtggc catccaggct gtcctgtcgc tgtacgcctc cggtcgtacc actggtatcg    120

tcctcgactc cggagatggt gtctcccaca ccgtcccgat ctacgaggga tacgctctcc    180

cccacgccat cctccgtctc gacttggctg gccgtgactt gaccgactac cttatgaaga    240

tcctcaccga gagaggctac tccttcacga ccaccgccga aagggagatc gtccgtgaca    300

tcaaggagaa gctctgctac gtcgccctcg acttcgagca ggaaatggcc accgccgcgt    360
```

-continued

```
cctcctcgtc cctcgaaaag tcctacgagc ttcccgacgg tcaagtcatc accatcggaa    420

acgagaggtt caggtgcccc gaagccctct tccagccttc cttcttggga atggaagcct    480

gcggtatcca cgaaaccact tacaactcca tcatgaagtg cgacgtggac atccgtaagg    540

acctgtacgc caacaccgtg ctctctggag gcaccaccat gtacccagga atcgccgaca    600

ggatgcagaa ggaaatcacc gccct                                          625
```

<210> SEQ ID NO 142
<211> LENGTH: 168
<212> TYPE: DNA
<213> ORGANISM: Lygus hesperus

<400> SEQUENCE: 142

```
tgcttgatct tcttgggagt ggagtagttc ttcttcttcc ttttcttggc accaccacga     60

agcctgagca ccaagtgcaa ggtggattct ttctggatgt tgtagtcaga aagggtgcgg    120

ccatcttcca attgcttacc ggcgaagata agacgctgct gatccggg                 168
```

<210> SEQ ID NO 143
<211> LENGTH: 231
<212> TYPE: DNA
<213> ORGANISM: Lygus hesperus

<400> SEQUENCE: 143

```
gctaaaatcc aagacaagga agggattccc ccagaccagc agaggttgat cttcgctggc     60

aagcagctcg aagatggccg cacactttcc gactacaaca tccagaaaga gtccaccctt    120

cacttggtcc tccgtctgag aggaggagtc atcgagccca ccctcaggat cttggctcag    180

aagtacaact gcgacaagat gatctgcagg aagtgctacg ctcgtctcca c             231
```

<210> SEQ ID NO 144
<211> LENGTH: 300
<212> TYPE: DNA
<213> ORGANISM: Lygus hesperus

<400> SEQUENCE: 144

```
cactcttgag gtcgagcctt ctgacaccat cgaaaacgtc aaggctaaaa ttcaagacaa     60

ggaaggtatt cctccagatc agcagagatt gatcttcgcc ggcaaacaac tcgaagatgg    120

ccgtaccctc tctgactaca atattcaaaa agagtccacc cttcacttgg tgttgagatt    180

gcgtggaggt atgcaaatct ttgtcaaaac attgactgga aagaccatca cccttgaagt    240

cgaaccctcc gacaccatcg aaaatgtcaa ggccaagatc caggacaagg aaggcatccc    300
```

<210> SEQ ID NO 145
<211> LENGTH: 172
<212> TYPE: DNA
<213> ORGANISM: Lygus hesperus

<400> SEQUENCE: 145

```
gagcgttctc cagtgtctgt acgactcgat cagtcaaatc ctgaggaaaa acgttgagaa     60

acgaacgata ttcgagaacc tggagatcgt catgctcgcc atggacgaga tctgcgacgg    120

tgggatactc ctggaggccg accctacgtc cgtcgtacag cgagtcgcca tc            172
```

<210> SEQ ID NO 146
<211> LENGTH: 408
<212> TYPE: DNA
<213> ORGANISM: Lygus hesperus

<400> SEQUENCE: 146

```
gaacgtactc attgtcaacc agacagctga cactcttcaa aattgcactc tggaattggc     60

tacacttggc gacctgaaat tggtcgagaa gccgcaaccc tgcgttttgg cgcctcatga    120

cttctgtaac ataaaagcta acgtcaaagt ggcttccact gaaaacggaa ttatttttgg    180

caacattgtt tacgacgtta gtggagcagc ttccgaccga aacgtcgtcg tcctcaatga    240

cattcacatc gatattatgg actacatagt tcctgcatct tgttctgaca ctgaattccg    300

ccaaatgtgg gctgaattcg aatgggaaaa caaggtatct gtcaacacca acctcacgga    360

cttgcacgag tatttggccc atttggtcag gagcaccaac atgaagtg                 408
```

<210> SEQ ID NO 147
<211> LENGTH: 273
<212> TYPE: DNA
<213> ORGANISM: Lygus hesperus

<400> SEQUENCE: 147

```
gaaccgaccg tcgaaattgc ggccaatgtg ttccgtgatg tctactacag gtaccgtgac     60

cagttgcagg tcggtctgat catagctgga tgggataaag tcaagggagg acaggtgtac    120

aatattcctt tgggtgggat ggtcatccgt caaaagttct gcatgggtgg ttctggcagc    180

acgtttgtct ttggtttcac cgacaccaac ttcaaggaga acatgacaga agccgagtgc    240

aagaacttct taacgagagc tattggcctt gcc                                 273
```

<210> SEQ ID NO 148
<211> LENGTH: 1041
<212> TYPE: DNA
<213> ORGANISM: Lygus hesperus

<400> SEQUENCE: 148

```
gtcgtcgtcc aggctattcg tgcgctctgc ctcaagtttc ccagaaagca tagtacccta     60

atgacattcc tgtctgccat gctccgcgat gaaggtggat tggagtacag agcttcgata    120

gctgatacca tcatcacaat cattgaagat aatcctgaag ctaaagaaat tggactcgct    180

catctctgcg agttcattga agattgtgag cacgttagtt tggcagtcag aatccttcat    240

ctacttggta aagaaggacc gaaaacaatt caaccttctc gatacatcag attcatttac    300

aatagggtta tccttgaaat agctgttatt cgggctgctg cagtttctgc ccttgctcag    360

tttggagctc tatgtccaga tcttctcccc aacatcttgg ttttgctggc ccgatgccaa    420

atggacactg atgacgaagt gagagatagg gcgacttact attatcatct actgaaattg    480

caggagaaag gacttatttt caattacatt gtcgacccaa tgcaggtttg tctggtgagt    540

ctcgagaaat cgttggccca acatgttcac gataaggtac ccactaaatt cgatttgaag    600

tccgttccac ctgctcctgt cgtgtctact actgaagaca ccgcacaaga aacggtacct    660

gaaggctcca ttagttcagc cccaagtaag atcgctcctt tacaatcaac agttagtagc    720

tatgcagaga agctgcaagg agttccaggt ctacaaagca tacccgggac attattccat    780

gtatcagaac cagttgaact caccgaatcc gaaactgaat acgttgtcac gtgcaccaaa    840

cttacatacc ctcatcacct cgtgttgcag tttgaatgca agaacacgtt gagtgatcaa    900

cttcttgaga atgtcagagt tcagattgag gccagtgaag gttacagaat cgtcaaggaa    960

ataccgatct ccaagcttcc ttacaacgaa acacattgtg cctacgtagt gctgcaattt   1020

ccagagcaac tttccctcac c                                             1041
```

<210> SEQ ID NO 149

<211> LENGTH: 710
<212> TYPE: DNA
<213> ORGANISM: Lygus hesperus

<400> SEQUENCE: 149
ggtgaactga tccaagcctc caggcccttc ctgtctgaga tatctaaagc aaaagctgcc 60
aaattagtca gaactctggt agatttcttc ctagatttag aggccgaaac tggaagagag 120
gttcagctgt gcaaggagtg catagaatgg gccacaaccg agagaagaac gttcctcagg 180
caaagtctcg aagctcgact catcgctttg tatttcgaca cgggcatgta cacggaagcc 240
ctcggtttgg gatcgagcct tctcaaagaa ctgaaaaaac ttgacgacaa aaatctcctt 300
gtggaagtcc tgcttctaga gtcgaaaacc taccatgcac tcagcaattt gtccaaggct 360
agagcagctc tcacatcagc gcgcacaaca gcaaattcca tctactgtcc acctaaaatg 420
caggcagccc tggatctcca gtctggaata cttcatgctg ctgatgaaca agatttcaaa 480
actgcatatt cctatttcta cgaagctttc gaaggatatg attcggtaga ctctccgaaa 540
gcgttgactg ctctaaaata catgcttctc tcaaaaatta tgttgaacac tccggaggat 600
gtacagcaac ttatttcagg aaaacttgct ttgaagcatg cagggcgaga catcgacgcc 660
atgaaaaacg tagctaaggc ttctgccaag cggtcccttg cagatttcca 710

<210> SEQ ID NO 150
<211> LENGTH: 368
<212> TYPE: DNA
<213> ORGANISM: Lygus hesperus

<400> SEQUENCE: 150
aatggtgtgg ttttggcgac tgagaacaag ttcaagtcta ttctctatga agaacactcg 60
ataaaaaaga ttgagatggt cgaagaacat attggaatgg tctacagtgg tatgggaccc 120
gattacaggc tgctagtgaa gagagcgcgc aagttagctc aacagtacaa gttggtttat 180
ggacagagga taccgacgcc ccaactcgtt caaaaggttg ccatggtgat gcaggagtac 240
acgcaatcag gaggcgtacg gccgttcgga gtgtcgttac tcatctgcgg gtgggacgat 300
ggccgtccga ccttgttcca gtgcgatcct tctggcgcct actttgcctg gaaagcaact 360
gcgatggg 368

<210> SEQ ID NO 151
<211> LENGTH: 235
<212> TYPE: DNA
<213> ORGANISM: Lygus hesperus

<400> SEQUENCE: 151
gcggaagcaa agaaaaggaa agctcgccgt ttgaagcagg ccaaggaaga ggctcaggag 60
gaaattgaaa ggtacaagca agacagagag aagcagttca aggagttcga agcccagcac 120
atgggctcca gggaggacgt tgctgccagg atagacgctg acactcgtca gagaattgaa 180
gagatgacaa aagctgtcaa tgtcaacaaa gaacaagtga tccaaagaat actgg 235

<210> SEQ ID NO 152
<211> LENGTH: 511
<212> TYPE: DNA
<213> ORGANISM: Lygus hesperus

<400> SEQUENCE: 152
ggtgatgaga tgcggcaaga agaaagtgtg gttggaccct aatgaaatca acgaaatcgc 60
caacaccaac tctaggcaaa acatccgtaa gctgatcaag gatggtttga tcatcaaaaa 120
gcctgtggct gtccactcca gagcccgcgt ccgtaaaaac acagaagcca gacggaaggg 180
tcgtcactgt ggcttcggta agaggaaggg taccgccaac gccagaatgc ctgtgaaggt 240
cctgtgggtc aacagaatga gagtcctgcg acggctcctt aaaaaataca gagaagccaa 300
gaagatcgat aggcaaatgt accacgacct ttacatgaaa gccaaaggta acgtcttcaa 360
aaacaagagg gtactgatgg acttcattca caagaagaag gctgaaaagg cgagatcaaa 420
gatgttgaag gaccaggcag aggcgagacg tctcaaggtc aaggaggcga agaagaggcg 480
cgaggagagg atcgccacca agaagcaaga g 511

<210> SEQ ID NO 153
<211> LENGTH: 495
<212> TYPE: DNA
<213> ORGANISM: Lygus hesperus

<400> SEQUENCE: 153
tgtgctgccc aaaccaaatc caccttcctg aaacttgctg gacctcagtt ggttcaaatg 60
tttattggag acggtgccaa actcgtcagg gacgccttcg ctttggccaa agaaaaagct 120
cctgccatta ttttcatcga cgaattagac gcaattggta cgaaaagatt cgactctgag 180
aaggcaggtg acagagaagt gcagagaact atgttggagt tgctgaacca gctggatggt 240
ttcagttcca cagctgatat caaagttatt gctgctacta accgtgtgga cattttggac 300
cctgctttgc tacgatcggg tcgtcttgat cgaaaaatcg agttcccaca tcccaacgag 360
gacgccaggg ctcgcatcat gcagatccac tcgcgcaaaa tgaacatcag cgtcgacgtc 420
aatttcgagg aactcgcacg gtccaccgac gacttcaacg gcgctcagtg caaagcagtt 480
tgcgtggaag ctggt 495

<210> SEQ ID NO 154
<211> LENGTH: 45
<212> TYPE: DNA
<213> ORGANISM: Artificial
<220> FEATURE:
<223> OTHER INFORMATION: Primer

<400> SEQUENCE: 154
gcgtaatacg actcactata ggctaaggcc aacagggaga agatg 45

<210> SEQ ID NO 155
<211> LENGTH: 20
<212> TYPE: DNA
<213> ORGANISM: Artificial
<220> FEATURE:
<223> OTHER INFORMATION: Primer

<400> SEQUENCE: 155
agggcggtga tttccttctg 20

<210> SEQ ID NO 156
<211> LENGTH: 23
<212> TYPE: DNA
<213> ORGANISM: Artificial
<220> FEATURE:
<223> OTHER INFORMATION: Primer

<400> SEQUENCE: 156
ctaaggccaa cagggagaag atg 23

<210> SEQ ID NO 157

-continued

<211> LENGTH: 42
<212> TYPE: DNA
<213> ORGANISM: Artificial
<220> FEATURE:
<223> OTHER INFORMATION: Primer

<400> SEQUENCE: 157
gcgtaatacg actcactata ggagggcggt gatttccttc tg 42

<210> SEQ ID NO 158
<211> LENGTH: 45
<212> TYPE: DNA
<213> ORGANISM: Artificial
<220> FEATURE:
<223> OTHER INFORMATION: Primer

<400> SEQUENCE: 158
gcgtaatacg actcactata ggtgcttgat cttcttggga gtgga 45

<210> SEQ ID NO 159
<211> LENGTH: 20
<212> TYPE: DNA
<213> ORGANISM: Artificial
<220> FEATURE:
<223> OTHER INFORMATION: Primer

<400> SEQUENCE: 159
cccggatcag cagcgtctta 20

<210> SEQ ID NO 160
<211> LENGTH: 23
<212> TYPE: DNA
<213> ORGANISM: Artificial
<220> FEATURE:
<223> OTHER INFORMATION: Primer

<400> SEQUENCE: 160
tgcttgatct tcttgggagt gga 23

<210> SEQ ID NO 161
<211> LENGTH: 42
<212> TYPE: DNA
<213> ORGANISM: Artificial
<220> FEATURE:
<223> OTHER INFORMATION: Primer

<400> SEQUENCE: 161
gcgtaatacg actcactata ggcccggatc agcagcgtct ta 42

<210> SEQ ID NO 162
<211> LENGTH: 45
<212> TYPE: DNA
<213> ORGANISM: Artificial
<220> FEATURE:
<223> OTHER INFORMATION: Primer

<400> SEQUENCE: 162
gcgtaatacg actcactata ggctaaaatc caagacaagg aaggg 45

<210> SEQ ID NO 163
<211> LENGTH: 22
<212> TYPE: DNA
<213> ORGANISM: Artificial
<220> FEATURE:
<223> OTHER INFORMATION: Primer

<400> SEQUENCE: 163
gtggagacga gcgtagcact tc 22

<210> SEQ ID NO 164
<211> LENGTH: 24
<212> TYPE: DNA
<213> ORGANISM: Artificial
<220> FEATURE:
<223> OTHER INFORMATION: Primer

<400> SEQUENCE: 164
gctaaaatcc aagacaagga aggg 24

<210> SEQ ID NO 165
<211> LENGTH: 43
<212> TYPE: DNA
<213> ORGANISM: Artificial
<220> FEATURE:
<223> OTHER INFORMATION: Primer

<400> SEQUENCE: 165
gcgtaatacg actcactata ggtggagacg agcgtagcac ttc 43

<210> SEQ ID NO 166
<211> LENGTH: 45
<212> TYPE: DNA
<213> ORGANISM: Artificial
<220> FEATURE:
<223> OTHER INFORMATION: Primer

<400> SEQUENCE: 166
gcgtaatacg actcactata ggcactcttg aggtcgagcc ttctg 45

<210> SEQ ID NO 167
<211> LENGTH: 20
<212> TYPE: DNA
<213> ORGANISM: Artificial
<220> FEATURE:
<223> OTHER INFORMATION: Primer

<400> SEQUENCE: 167
gggatgcctt ccttgtcctg 20

<210> SEQ ID NO 168
<211> LENGTH: 23
<212> TYPE: DNA
<213> ORGANISM: Artificial
<220> FEATURE:
<223> OTHER INFORMATION: Primer

<400> SEQUENCE: 168
cactcttgag gtcgagcctt ctg 23

<210> SEQ ID NO 169
<211> LENGTH: 42
<212> TYPE: DNA
<213> ORGANISM: Artificial
<220> FEATURE:
<223> OTHER INFORMATION: Primer

<400> SEQUENCE: 169
gcgtaatacg actcactata gggggatgcc ttccttgtcc tg 42

<210> SEQ ID NO 170
<211> LENGTH: 45
<212> TYPE: DNA

<213> ORGANISM: Artificial
<220> FEATURE:
<223> OTHER INFORMATION: Primer

<400> SEQUENCE: 170
gcgtaatacg actcactata gggagcgttc tccagtgtct gtacg 45

<210> SEQ ID NO 171
<211> LENGTH: 20
<212> TYPE: DNA
<213> ORGANISM: Artificial
<220> FEATURE:
<223> OTHER INFORMATION: Primer

<400> SEQUENCE: 171
gatggcgact cgctgtacga 20

<210> SEQ ID NO 172
<211> LENGTH: 23
<212> TYPE: DNA
<213> ORGANISM: Artificial
<220> FEATURE:
<223> OTHER INFORMATION: Primer

<400> SEQUENCE: 172
gagcgttctc cagtgtctgt acg 23

<210> SEQ ID NO 173
<211> LENGTH: 42
<212> TYPE: DNA
<213> ORGANISM: Artificial
<220> FEATURE:
<223> OTHER INFORMATION: Primer

<400> SEQUENCE: 173
gcgtaatacg actcactata gggatggcga ctcgctgtac ga 42

<210> SEQ ID NO 174
<211> LENGTH: 47
<212> TYPE: DNA
<213> ORGANISM: Artificial
<220> FEATURE:
<223> OTHER INFORMATION: Primer

<400> SEQUENCE: 174
gcgtaatacg actcactata ggaacgtact cattgtcaac cagacag 47

<210> SEQ ID NO 175
<211> LENGTH: 23
<212> TYPE: DNA
<213> ORGANISM: Artificial
<220> FEATURE:
<223> OTHER INFORMATION: Primer

<400> SEQUENCE: 175
cacttcatgt tggtgctcct gac 23

<210> SEQ ID NO 176
<211> LENGTH: 26
<212> TYPE: DNA
<213> ORGANISM: Artificial
<220> FEATURE:
<223> OTHER INFORMATION: Primer

<400> SEQUENCE: 176
gaacgtactc attgtcaacc agacag 26

<210> SEQ ID NO 177
<211> LENGTH: 45
<212> TYPE: DNA
<213> ORGANISM: Artificial
<220> FEATURE:
<223> OTHER INFORMATION: Primer

<400> SEQUENCE: 177
gcgtaatacg actcactata ggcacttcat gttggtgctc ctgac 45

<210> SEQ ID NO 178
<211> LENGTH: 42
<212> TYPE: DNA
<213> ORGANISM: Artificial
<220> FEATURE:
<223> OTHER INFORMATION: Primer

<400> SEQUENCE: 178
gcgtaatacg actcactata gggaaccgac cgtcgaaatt gc 42

<210> SEQ ID NO 179
<211> LENGTH: 20
<212> TYPE: DNA
<213> ORGANISM: Artificial
<220> FEATURE:
<223> OTHER INFORMATION: Primer

<400> SEQUENCE: 179
ggcaaggcca atagctctcg 20

<210> SEQ ID NO 180
<211> LENGTH: 20
<212> TYPE: DNA
<213> ORGANISM: Artificial
<220> FEATURE:
<223> OTHER INFORMATION: Primer

<400> SEQUENCE: 180
gaaccgaccg tcgaaattgc 20

<210> SEQ ID NO 181
<211> LENGTH: 42
<212> TYPE: DNA
<213> ORGANISM: Artificial
<220> FEATURE:
<223> OTHER INFORMATION: Primer

<400> SEQUENCE: 181
gcgtaatacg actcactata ggggcaaggc caatagctct cg 42

<210> SEQ ID NO 182
<211> LENGTH: 43
<212> TYPE: DNA
<213> ORGANISM: Artificial
<220> FEATURE:
<223> OTHER INFORMATION: Primer

<400> SEQUENCE: 182
gcgtaatacg actcactata ggtcgtcgtc caggctattc gtg 43

<210> SEQ ID NO 183
<211> LENGTH: 21
<212> TYPE: DNA
<213> ORGANISM: Artificial
<220> FEATURE:

<223> OTHER INFORMATION: Primer

<400> SEQUENCE: 183
ggtgagggaa agttgctctg g 21

<210> SEQ ID NO 184
<211> LENGTH: 22
<212> TYPE: DNA
<213> ORGANISM: Artificial
<220> FEATURE:
<223> OTHER INFORMATION: Primer

<400> SEQUENCE: 184
gtcgtcgtcc aggctattcg tg 22

<210> SEQ ID NO 185
<211> LENGTH: 41
<212> TYPE: DNA
<213> ORGANISM: Artificial
<220> FEATURE:
<223> OTHER INFORMATION: Primer

<400> SEQUENCE: 185
gcgtaatacg actcactata ggtgagggaa agttgctctg g 41

<210> SEQ ID NO 186
<211> LENGTH: 44
<212> TYPE: DNA
<213> ORGANISM: Artificial
<220> FEATURE:
<223> OTHER INFORMATION: Primer

<400> SEQUENCE: 186
gcgtaatacg actcactata ggggtgaact gatccaagcc tcca 44

<210> SEQ ID NO 187
<211> LENGTH: 20
<212> TYPE: DNA
<213> ORGANISM: Artificial
<220> FEATURE:
<223> OTHER INFORMATION: Primer

<400> SEQUENCE: 187
tggaaatctg caagggaccg 20

<210> SEQ ID NO 188
<211> LENGTH: 22
<212> TYPE: DNA
<213> ORGANISM: Artificial
<220> FEATURE:
<223> OTHER INFORMATION: Primer

<400> SEQUENCE: 188
ggtgaactga tccaagcctc ca 22

<210> SEQ ID NO 189
<211> LENGTH: 42
<212> TYPE: DNA
<213> ORGANISM: Artificial
<220> FEATURE:
<223> OTHER INFORMATION: Primer

<400> SEQUENCE: 189
gcgtaatacg actcactata ggtggaaatc tgcaagggac cg 42

<210> SEQ ID NO 190
<211> LENGTH: 44
<212> TYPE: DNA
<213> ORGANISM: Artificial
<220> FEATURE:
<223> OTHER INFORMATION: Primer

<400> SEQUENCE: 190
gcgtaatacg actcactata ggaatggtgt ggttttggcg actg 44

<210> SEQ ID NO 191
<211> LENGTH: 20
<212> TYPE: DNA
<213> ORGANISM: Artificial
<220> FEATURE:
<223> OTHER INFORMATION: Primer

<400> SEQUENCE: 191
cccatcgcag ttgctttcca 20

<210> SEQ ID NO 192
<211> LENGTH: 22
<212> TYPE: DNA
<213> ORGANISM: Artificial
<220> FEATURE:
<223> OTHER INFORMATION: Primer

<400> SEQUENCE: 192
aatggtgtgg ttttggcgac tg 22

<210> SEQ ID NO 193
<211> LENGTH: 42
<212> TYPE: DNA
<213> ORGANISM: Artificial
<220> FEATURE:
<223> OTHER INFORMATION: Primer

<400> SEQUENCE: 193
gcgtaatacg actcactata ggcccatcgc agttgctttc ca 42

<210> SEQ ID NO 194
<211> LENGTH: 44
<212> TYPE: DNA
<213> ORGANISM: Artificial
<220> FEATURE:
<223> OTHER INFORMATION: Primer

<400> SEQUENCE: 194
gcgtaatacg actcactata ggcggaagca aagaaaagga aagc 44

<210> SEQ ID NO 195
<211> LENGTH: 29
<212> TYPE: DNA
<213> ORGANISM: Artificial
<220> FEATURE:
<223> OTHER INFORMATION: Primer

<400> SEQUENCE: 195
ccagtattct ttggatcact tgttctttg 29

<210> SEQ ID NO 196
<211> LENGTH: 23
<212> TYPE: DNA
<213> ORGANISM: Artificial
<220> FEATURE:
<223> OTHER INFORMATION: Primer

<400> SEQUENCE: 196
gcggaagcaa agaaaaggaa agc 23

<210> SEQ ID NO 197
<211> LENGTH: 51
<212> TYPE: DNA
<213> ORGANISM: Artificial
<220> FEATURE:
<223> OTHER INFORMATION: Primer

<400> SEQUENCE: 197
gcgtaatacg actcactata ggccagtatt ctttggatca cttgttcttt g 51

<210> SEQ ID NO 198
<211> LENGTH: 42
<212> TYPE: DNA
<213> ORGANISM: Artificial
<220> FEATURE:
<223> OTHER INFORMATION: Primer

<400> SEQUENCE: 198
gcgtaatacg actcactata ggtgatgaga tgcggcaaga ag 42

<210> SEQ ID NO 199
<211> LENGTH: 22
<212> TYPE: DNA
<213> ORGANISM: Artificial
<220> FEATURE:
<223> OTHER INFORMATION: Primer

<400> SEQUENCE: 199
ctcttgcttc ttggtggcga tc 22

<210> SEQ ID NO 200
<211> LENGTH: 22
<212> TYPE: DNA
<213> ORGANISM: Artificial
<220> FEATURE:
<223> OTHER INFORMATION: Primer

<400> SEQUENCE: 200
ggtgatgaga tgcggcaaga ag 22

<210> SEQ ID NO 201
<211> LENGTH: 44
<212> TYPE: DNA
<213> ORGANISM: Artificial
<220> FEATURE:
<223> OTHER INFORMATION: Primer

<400> SEQUENCE: 201
gcgtaatacg actcactata ggctcttgct tcttggtggc gatc 44

<210> SEQ ID NO 202
<211> LENGTH: 42
<212> TYPE: DNA
<213> ORGANISM: Artificial
<220> FEATURE:
<223> OTHER INFORMATION: Primer

<400> SEQUENCE: 202
gcgtaatacg actcactata ggtgtgctgc ccaaaccaaa tc 42

<210> SEQ ID NO 203
<211> LENGTH: 20

<212> TYPE: DNA
<213> ORGANISM: Artificial
<220> FEATURE:
<223> OTHER INFORMATION: Primer

<400> SEQUENCE: 203
accagcttcc acgcaaactg 20

<210> SEQ ID NO 204
<211> LENGTH: 20
<212> TYPE: DNA
<213> ORGANISM: Artificial
<220> FEATURE:
<223> OTHER INFORMATION: Primer

<400> SEQUENCE: 204
tgtgctgccc aaaccaaatc 20

<210> SEQ ID NO 205
<211> LENGTH: 42
<212> TYPE: DNA
<213> ORGANISM: Artificial
<220> FEATURE:
<223> OTHER INFORMATION: Primer

<400> SEQUENCE: 205
gcgtaatacg actcactata ggaccagctt ccacgcaaac tg 42

<210> SEQ ID NO 206
<211> LENGTH: 193
<212> TYPE: PRT
<213> ORGANISM: Leptinotarsa decemlineata

<400> SEQUENCE: 206

Leu Arg Ile Phe Leu Phe Ala Leu Ser Trp Lys Ile Ala Gly Lys Gly
1 5 10 15

Asp Gly Glu Gly Glu Gly Asn Ile Leu Lys Leu Glu Asn Gln Ile Ala
20 25 30

Val Ile Lys Tyr Val Leu Ile Phe Thr Asn Ile Leu Ser Trp Tyr Ile
35 40 45

Gly Thr Gln Val Ala Gly Phe Ile Phe Gly Leu Ser Gly Ala Ser Val
50 55 60

Leu Leu Asp Asn Ser Ala Arg Asp Ser His Phe Gln Pro Arg Ile Arg
65 70 75 80

Glu Ser Met Arg Arg Leu Ile Met Asn Ala His His Glu Glu Ser Arg
85 90 95

Gln Thr Leu Ala Met Ile Gln Glu Asn Ile Ala Cys Cys Gly Ala Asp
100 105 110

Gly Ala His Asp Tyr Leu Ser Leu Gln Gln Pro Leu Pro Ser Thr Cys
115 120 125

Arg Asp Thr Val Thr Gly Asn Pro Phe Tyr His Gly Cys Val Asp Glu
130 135 140

Leu Thr Trp Phe Phe Glu Glu Lys Cys Gly Trp Val Ala Gly Leu Val
145 150 155 160

Met Ile Leu Cys Leu Ile Gln Val Ile Asn Thr Val Leu Ser Ile Ile
165 170 175

Phe Leu Gln Ala Leu Lys Lys Glu Glu Gly Gln Ala Asp Thr Tyr Arg
180 185 190

Lys

<210> SEQ ID NO 207
<211> LENGTH: 204
<212> TYPE: PRT
<213> ORGANISM: Leptinotarsa decemlineata

<400> SEQUENCE: 207

```
Pro Ile Asn Met Cys Asp Glu Glu Val Ala Ala Leu Val Val Asp Asn
1               5                   10                  15

Gly Ser Gly Met Cys Lys Ala Gly Phe Ala Gly Asp Asp Ala Pro Arg
            20                  25                  30

Ala Val Phe Pro Ser Ile Val Gly Arg Pro Arg His Gln Gly Val Met
        35                  40                  45

Val Gly Met Gly Gln Lys Asp Ser Tyr Val Gly Asp Glu Ala Gln Ser
    50                  55                  60

Lys Arg Gly Ile Leu Thr Leu Lys Tyr Pro Ile Glu His Gly Ile Val
65                  70                  75                  80

Thr Asn Trp Asp Asp Met Glu Lys Ile Trp His His Thr Phe Tyr Asn
                85                  90                  95

Glu Leu Arg Val Ala Pro Glu Glu His Pro Val Leu Leu Thr Glu Ala
            100                 105                 110

Pro Leu Asn Pro Lys Ala Asn Arg Glu Lys Met Thr Gln Ile Met Phe
        115                 120                 125

Glu Thr Phe Asn Thr Pro Ala Met Tyr Val Ala Ile Gln Ala Val Leu
    130                 135                 140

Ser Leu Tyr Ala Ser Gly Arg Thr Thr Gly Ile Val Leu Asp Ser Gly
145                 150                 155                 160

Asp Gly Val Ser His Thr Val Pro Ile Tyr Glu Gly Tyr Ala Leu Pro
                165                 170                 175

His Ala Ile Leu Arg Leu Asp Leu Ala Gly Arg Asp Leu Thr Asp Tyr
            180                 185                 190

Leu Met Lys Ile Leu Thr Glu Arg Gly Tyr Ser Phe
        195                 200
```

<210> SEQ ID NO 208
<211> LENGTH: 96
<212> TYPE: PRT
<213> ORGANISM: Leptinotarsa decemlineata

<400> SEQUENCE: 208

```
Leu Pro Lys Met Gln Ile Phe Val Lys Thr Leu Thr Gly Lys Thr Ile
1               5                   10                  15

Thr Leu Glu Val Glu Pro Ser Asp Thr Ile Glu Asn Val Lys Ala Lys
            20                  25                  30

Ile Gln Asp Lys Glu Gly Ile Pro Pro Asp Gln Leu Arg Leu Ile Phe
        35                  40                  45

Ala Gly Lys Gln Leu Glu Asp Gly Arg Thr Leu Ser Asp Tyr Asn Ile
    50                  55                  60

Gln Lys Glu Ser Thr Leu His Leu Val Leu Arg Leu Arg Gly Gly Ala
65                  70                  75                  80

Lys Lys Arg Lys Lys Lys Asn Tyr Ser Thr Pro Lys Lys Asn Gln Ala
                85                  90                  95
```

<210> SEQ ID NO 209
<211> LENGTH: 87
<212> TYPE: PRT
<213> ORGANISM: Leptinotarsa decemlineata

<400> SEQUENCE: 209

```
Phe Asn Gln Thr Arg Asn Ala Thr Met Gln Ile Phe Val Lys Thr Leu
1               5                   10                  15

Thr Gly Lys Thr Ile Thr Leu Glu Val Glu Pro Ser Asp Thr Ile Glu
            20                  25                  30

Asn Val Lys Ala Lys Ile Gln Asp Lys Glu Gly Ile Pro Pro Asp Gln
        35                  40                  45

Gln Arg Leu Val Phe Ala Gly Lys Gln Leu Glu Asp Gly Arg Thr Leu
    50                  55                  60

Ser Asp Tyr Asn Ile Gln Lys Glu Ser Thr Leu His Leu Val Leu Arg
65                  70                  75                  80

Leu Arg Gly Gly Ile Ile Glu
                85
```

<210> SEQ ID NO 210
<211> LENGTH: 192
<212> TYPE: PRT
<213> ORGANISM: Leptinotarsa decemlineata

<400> SEQUENCE: 210

```
Asp Gln Gln Arg Leu Ile Phe Ala Gly Lys Gln Leu Glu Asp Gly Arg
1               5                   10                  15

Thr Leu Ser Asp Tyr Asn Ile Gln Lys Glu Ser Thr Leu His Leu Val
            20                  25                  30

Leu Arg Leu Arg Gly Gly Met Gln Ile Phe Val Lys Thr Leu Thr Gly
        35                  40                  45

Lys Thr Ile Thr Leu Glu Val Glu Pro Ser Asp Thr Ile Glu Asn Val
    50                  55                  60

Lys Ala Lys Ile Gln Asp Lys Glu Gly Ile Pro Pro Asp Gln Gln Arg
65                  70                  75                  80

Leu Ile Phe Ala Gly Lys Gln Leu Glu Asp Gly Arg Thr Leu Ser Asp
                85                  90                  95

Tyr Asn Ile Gln Lys Glu Ser Thr Leu His Leu Val Leu Arg Leu Arg
            100                 105                 110

Gly Gly Met Gln Ile Phe Val Lys Thr Leu Thr Gly Lys Thr Ile Thr
        115                 120                 125

Leu Glu Val Glu Pro Ser Asp Thr Ile Glu Asn Val Lys Ala Lys Ile
    130                 135                 140

Gln Asp Lys Glu Gly Ile Pro Pro Asp Gln Gln Arg Leu Ile Phe Ala
145                 150                 155                 160

Gly Lys Arg Leu Glu Asp Gly Arg Thr Leu Ser Asp Tyr Asn Ile Gln
                165                 170                 175

Lys Glu Ser Thr Leu His Leu Val Leu Arg Leu Arg Gly Gly Lys Tyr
            180                 185                 190
```

<210> SEQ ID NO 211
<211> LENGTH: 195
<212> TYPE: PRT
<213> ORGANISM: Leptinotarsa decemlineata

<400> SEQUENCE: 211

```
Leu Lys Asn Lys Leu Val Cys Ser Ser Leu Glu Thr Thr Arg Ile Glu
1               5                   10                  15

Ala Met Glu Gly Ser Leu Leu Glu Pro Thr Leu Tyr Thr Ile Lys Gly
            20                  25                  30

Ile Leu Ile Leu Asp Asn Asp Gly Asn Arg Ile Leu Ala Lys Tyr Tyr
```

-continued

```
        35                  40                  45

Asp Lys Thr Thr Phe Pro Thr Ser Lys Glu Gln Lys Ala Phe Glu Lys
    50                  55                  60

Asn Leu Phe Asn Lys Thr His Arg Ala Asn Ala Glu Ile Ile Met Leu
65                  70                  75                  80

Asp Gly Leu Thr Cys Leu Tyr Arg Ser Asn Val Asp Leu Phe Phe Tyr
                85                  90                  95

Val Met Gly Ser Ser His Glu Asn Glu Leu Ile Leu Met Ser Ile Leu
            100                 105                 110

Asn Cys Leu Tyr Asp Ser Val Ser Gln Ile Leu Arg Lys Asn Val Glu
        115                 120                 125

Lys Arg Ala Val Leu Glu Ser Leu Asp Ile Val Met Leu Ala Leu Asp
    130                 135                 140

Glu Ile Cys Asp Gly Gly Ile Ile Leu Asp Ala Asp Ser Asn Ser Ala
145                 150                 155                 160

Val Ser Arg Val Ala Leu Arg Asn Asp Asp Ile Pro Ile Gly Glu Gln
                165                 170                 175

Thr Val Ala Gln Val Phe Gln Ser Ala Lys Glu Gln Leu Lys Trp Ser
            180                 185                 190

Leu Leu Lys
        195


<210> SEQ ID NO 212
<211> LENGTH: 245
<212> TYPE: PRT
<213> ORGANISM: Leptinotarsa decemlineata

<400> SEQUENCE: 212

Val Glu Gln Asp Asn Ala Val Asp Arg Phe Ser Asp Pro Val Tyr Ser
1               5                   10                  15

Glu Ala Tyr Val His Val Asn Gln Tyr Asp Ile Val Leu Asp Val Leu
            20                  25                  30

Ile Val Asn Gln Thr Asn Asp Thr Leu Gln Asn Cys Thr Leu Glu Leu
        35                  40                  45

Ala Thr Leu Gly Asp Leu Lys Leu Val Glu Lys Pro Gln Pro Val Val
    50                  55                  60

Leu Ala Pro Lys Asp Phe Cys Asn Ile Lys Ala His Val Lys Val Ala
65                  70                  75                  80

Ser Thr Glu Asn Gly Ile Ile Phe Gly Asn Ile Val Tyr Asp Val Thr
                85                  90                  95

Gly Ala Ala Ser Asp Arg Asn Val Val Val Leu Asn Asp Ile His Ile
            100                 105                 110

Asp Ile Met Asp Tyr Ile Val Pro Ala Ser Cys Thr Asp Ser Glu Phe
        115                 120                 125

Met Arg Met Trp Ala Glu Phe Glu Trp Glu Asn Lys Val Thr Val Asn
    130                 135                 140

Thr Pro Leu Thr Asp Leu Ala Asp Tyr Leu Glu His Leu Ile Lys Ser
145                 150                 155                 160

Thr Asn Met Lys Cys Leu Thr Pro Glu Lys Ala Leu Ser Gly Gln Cys
                165                 170                 175

Gly Phe Met Ala Ala Asn Met Tyr Ala Lys Ser Ile Phe Gly Glu Asp
            180                 185                 190

Ala Leu Ala Asn Leu Ser Ile Glu Lys Pro Phe Asn Lys Pro Glu Ala
        195                 200                 205
```

```
Pro Val Ala Gly His Ile Arg Ile Arg Ala Lys Ser Gln Gly Met Ala
    210                 215                 220

Leu Ser Leu Gly Asp Lys Ile Asn Met Thr Gln Lys Gly Ile Pro Ser
225                 230                 235                 240

Lys Ile Val Ala Ser
                245


<210> SEQ ID NO 213
<211> LENGTH: 166
<212> TYPE: PRT
<213> ORGANISM: Leptinotarsa decemlineata

<400> SEQUENCE: 213

Glu Lys Pro Ala Asn Glu Asp Ile Glu Ser Pro Arg Asp Ile Ile Asn
1               5                   10                  15

Lys Ala Phe Arg Glu Ile Phe Glu Ala Asp Glu Asn Gly Ile Asn Gly
            20                  25                  30

Ser Leu Val Glu Pro Pro Thr Pro Thr Gln Lys Thr Phe Asp Arg Pro
        35                  40                  45

Phe Gln Glu Asp Leu Ser Glu Phe Asn Phe Arg Ile Tyr Ala Ala Thr
    50                  55                  60

Tyr Phe Thr Asn Asn Ala Asn Tyr Gln Phe Ser Lys Lys Pro Leu Lys
65                  70                  75                  80

Glu Ser Leu His Tyr Leu Pro Thr Pro Asp Asp Val Ile Ala Ala Gln
                85                  90                  95

Ala Leu Trp Ile Thr Ile Leu Arg Phe Met Gly Asp Tyr Pro Glu Pro
            100                 105                 110

Lys Tyr Asp Asn Ser Thr Lys Glu Asn Val Pro Ile Met Gln Ile Ile
        115                 120                 125

Ser Glu Ser Ile Gly Lys Ser Phe Thr Asn Arg Lys Glu Tyr Gln Glu
    130                 135                 140

Ile Leu Lys Glu Glu Lys Asn Met Pro Leu Gln Gln Asn Gln Ala Lys
145                 150                 155                 160

Lys Lys Lys Lys Lys Lys
                165


<210> SEQ ID NO 214
<211> LENGTH: 309
<212> TYPE: PRT
<213> ORGANISM: Leptinotarsa decemlineata

<400> SEQUENCE: 214

Tyr Gly Arg Leu Glu Glu Ala Asp Ala Leu Ile Gln Gln Leu Ser Ser
1               5                   10                  15

Asp Lys Asp Pro Ile Leu Arg Arg Ser Gly Met Tyr Thr Ile Ala Met
            20                  25                  30

Ala Tyr Cys Ser Thr Gly His Asn Gln Ala Ile Arg Lys Leu Leu His
        35                  40                  45

Val Ala Val Ser Asp Val Asn Asp Asp Val Arg Arg Ala Ala Val Thr
    50                  55                  60

Ala Leu Gly Phe Leu Leu Phe Arg Thr Pro Glu Gln Cys Pro Ser Val
65                  70                  75                  80

Val Ser Leu Leu Ala Glu Ser Tyr Asn Pro His Val Arg Tyr Gly Ala
                85                  90                  95

Ala Met Ala Leu Gly Ile Ala Cys Ala Gly Thr Gly Leu Arg Glu Ala
            100                 105                 110
```

-continued

```
Ile Ala Leu Leu Glu Pro Met Val Met Phe Asp Pro Val Asn Phe Val
        115                 120                 125

Arg Gln Gly Ala Leu Ile Ala Ser Ala Met Ile Leu Ile Gln Gln Thr
    130                 135                 140

Glu Gln Thr Cys Pro Lys Val Ser Phe Phe Arg Gln Thr Tyr Ala Gln
145                 150                 155                 160

Val Ile Ala Asn Lys His Glu Asp Val Met Ala Lys Phe Gly Ala Ile
                165                 170                 175

Leu Ala Gln Gly Ile Ile Asp Ala Gly Gly Arg Asn Val Thr Leu Ser
            180                 185                 190

Leu Gln Ser Arg Thr Gly His Thr Asn Met Leu Ala Val Val Gly Thr
        195                 200                 205

Leu Val Phe Thr Gln Tyr Trp Tyr Trp Phe Pro Leu Ser His Cys Leu
    210                 215                 220

Ala Leu Ala Phe Thr Pro Thr Cys Val Ile Ala Leu Asn Glu Gln Leu
225                 230                 235                 240

Lys Met Pro Lys Leu Glu Leu Lys Ser Asn Ala Lys Pro Ser Leu Tyr
                245                 250                 255

Ala Tyr Pro Ala Pro Met Glu Glu Lys Lys Arg Glu Glu Arg Glu Lys
            260                 265                 270

Val Thr Thr Ala Val Leu Ser Ile Ala Ala Arg Gln Arg Gly Lys Asp
        275                 280                 285

His Glu Lys Lys His Arg Asp Glu Lys Asn Gly Trp Gly Arg Arg Gln
    290                 295                 300

Val Cys Arg Glu Arg
305


<210> SEQ ID NO 215
<211> LENGTH: 152
<212> TYPE: PRT
<213> ORGANISM: Leptinotarsa decemlineata

<400> SEQUENCE: 215

Phe Phe Asp Leu Phe Phe Val Ser Asp Phe Val Phe Arg Leu Ser Pro
1               5                   10                  15

Phe Val Lys Met Leu Leu Asn Gln Ile Ser Ile Ala Gly Ala Asp Asp
            20                  25                  30

Trp Arg Asn Ala Ala His Ser Thr Gly Thr Ser Ile Met Ala Ala Glu
        35                  40                  45

Phe Asp Gly Gly Val Ile Ile Gly Ala Asp Ser Arg Thr Thr Thr Gly
    50                  55                  60

Ala Tyr Ile Ala Asn Arg Val Thr Asp Lys Leu Thr Lys Val Thr Asp
65                  70                  75                  80

His Ile Tyr Cys Cys Arg Ser Gly Ser Ala Ala Asp Thr Gln Ala Ile
                85                  90                  95

Ala Asp Ile Val Ser Tyr His Leu Asn Phe His Gly Met Glu Leu Gly
            100                 105                 110

Glu Glu Pro Leu Val Glu Val Gly Ala Ala Ile Phe Arg Glu Leu Cys
        115                 120                 125

Tyr Asn Tyr Arg Asp Ser Leu Met Ala Gly Ile Leu Val Ala Gly Trp
    130                 135                 140

Asp Lys Lys Lys Lys Lys Lys Lys
145                 150


<210> SEQ ID NO 216
```

```
<211> LENGTH: 74
<212> TYPE: PRT
<213> ORGANISM: Leptinotarsa decemlineata

<400> SEQUENCE: 216

Val Lys Asn Ile Ile Gln Phe Leu Gly Leu Gln Pro Ala Glu Arg Thr
1               5                   10                  15

Asp Lys Val Pro Glu Glu Lys Ser Thr His Thr Leu Leu Leu Ala Gly
            20                  25                  30

Met Leu Arg Gly Gly Ile Asp Ile Leu Val Arg Ala Lys Leu Ala Leu
        35                  40                  45

Ala Asp Gly Val Thr Met Gln Leu Thr Val Arg Ser Pro Asp Ala Asp
    50                  55                  60

Val Ala Glu Leu Ile Thr Ser Ser Val Gly
65                  70


<210> SEQ ID NO 217
<211> LENGTH: 416
<212> TYPE: PRT
<213> ORGANISM: Leptinotarsa decemlineata

<400> SEQUENCE: 217

Ser Glu Asn Met Ala Gly Ala Met Leu Phe Glu Arg Ala Gln Ser Val
1               5                   10                  15

Pro Ser Gln His Asp Lys Leu Leu Asn Leu Lys Arg Asn Glu Asp Asp
            20                  25                  30

Asp Asp Gln Asn Ile Val Asn Lys Glu Gln Asp Ile Leu Asn Leu Gly
        35                  40                  45

Glu Lys Tyr Lys Lys Glu Gly Lys Ala Lys Glu Leu Ala Glu Leu Val
    50                  55                  60

Lys Ala Thr Arg Pro Phe Leu Ser Ile Ile Ser Lys Ala Lys Ala Ala
65                  70                  75                  80

Lys Leu Val Arg Ser Leu Val Asp Tyr Phe Leu Asp Leu Glu Ala Gly
                85                  90                  95

Ile Gly Ile Glu Val Gln Leu Cys Lys Glu Cys Ile Glu Trp Ala Lys
            100                 105                 110

Glu Glu Lys Arg Thr Phe Leu Arg Gln Ser Leu Glu Ala Arg Leu Ile
        115                 120                 125

Ala Leu Tyr Phe Asp Thr Gly Met Tyr Ala Glu Ala Leu Ile Leu Glu
    130                 135                 140

Ser Thr Leu Leu Lys Gly Leu Lys Lys Leu Asp Asp Lys Asn Leu Leu
145                 150                 155                 160

Val Glu Val Gln Leu Leu Glu Ser Lys Thr Tyr His Ala Leu Ser Asn
                165                 170                 175

Leu Pro Lys Ala Arg Ala Ala Leu Thr Ser Ala Arg Thr Thr Ala Asn
            180                 185                 190

Ser Ile Tyr Cys Pro Pro Lys Met Gln Ala Ala Leu Asp Leu Gln Ser
        195                 200                 205

Gly Val Leu His Ala Ala Asp Glu Lys Asp Phe Lys Thr Ala Tyr Ser
    210                 215                 220

Tyr Phe Tyr Glu Ala Phe Glu Gly Phe Asp Ser Val Glu Ser Pro Lys
225                 230                 235                 240

Ala Leu Thr Ala Leu Lys Tyr Met Leu Leu Ser Lys Ile Met Ile Asn
                245                 250                 255

Ser Pro Glu Asp Val Gln Gln Ile Val Ser Gly Lys Leu Ala Ile Arg
            260                 265                 270
```

```
Tyr Ala Gly Gln Asp Ile Glu Ala Met Lys Ala Val Ala Arg Ala Ser
        275                 280                 285

His Lys Arg Ser Leu Ala Asp Phe Gln Leu Ala Val Lys Gln Phe Lys
    290                 295                 300

His Glu Leu Glu Asp Asp Val Ile Val Arg Ala His Leu Gly Thr Leu
305                 310                 315                 320

Tyr Asp Asn Met Leu Glu Gln Asn Leu Cys Arg Ile Ile Glu Pro Tyr
                325                 330                 335

Ser Arg Val Gln Val Asp Tyr Val Ala Lys Thr Ile Lys Leu Pro Met
            340                 345                 350

Leu Gln Val Glu Lys Lys Leu Ser Gln Met Ile Leu Asp Ala Lys Phe
        355                 360                 365

His Gly Ile Leu Asp Gln Gly Glu Gly Val Leu Ile Val Phe Glu Ala
    370                 375                 380

Thr Pro Val Asp Lys Thr Tyr Glu Met Ala Leu Glu Thr Ile Gln Ser
385                 390                 395                 400

Met Ser Lys Val Val Asp Thr Leu Tyr Gln Lys Ala Lys Lys Leu Ser
                405                 410                 415


<210> SEQ ID NO 218
<211> LENGTH: 238
<212> TYPE: PRT
<213> ORGANISM: Leptinotarsa decemlineata

<400> SEQUENCE: 218

Leu Gln Val Ile Met Ala Ser Glu Arg Tyr Ser Phe Ser Leu Thr Thr
1               5                   10                  15

Ser Ser Pro Ser Gly Lys Leu Ala Gln Ile Glu Tyr Ala Leu Ala Ala
            20                  25                  30

Val Ala Ala Gly Ala Pro Ser Val Gly Ile Lys Ala Ser Asn Gly Val
        35                  40                  45

Val Ile Ala Thr Glu Asn Lys His Lys Ser Ile Leu Tyr Glu Glu His
    50                  55                  60

Ser Val His Lys Val Glu Met Ile Thr Lys His Ile Gly Met Ile Tyr
65                  70                  75                  80

Ser Gly Met Gly Pro Asp Tyr Arg Leu Leu Val Lys Gln Ala Arg Lys
                85                  90                  95

Met Ala Gln Gln Tyr Tyr Leu Val Tyr Gln Glu Pro Ile Pro Thr Val
            100                 105                 110

Gln Leu Val Gln Arg Val Ala Thr Val Met Gln Glu Tyr Thr Gln Ser
        115                 120                 125

Gly Gly Val Arg Pro Phe Gly Val Ser Leu Leu Ile Cys Gly Trp Asp
    130                 135                 140

Ser Glu Arg Pro Tyr Leu Phe Gln Cys Asp Pro Ser Gly Ala Tyr Phe
145                 150                 155                 160

Ala Trp Lys Ala Thr Ala Met Gly Lys Asn Phe Ile Asn Gly Lys Thr
                165                 170                 175

Phe Leu Glu Lys Arg Tyr Ser Glu Asp Leu Glu Leu Asp Asp Ala Val
            180                 185                 190

His Thr Ala Ile Leu Thr Leu Lys Glu Ser Phe Glu Gly Gln Met Thr
        195                 200                 205

Ala Asp Asn Ile Glu Val Gly Ile Cys Asp Glu Ala Gly Phe Arg Arg
    210                 215                 220

Leu Asp Pro Ser His Val Lys Asp Tyr Leu Ala Asn Ile Pro
```

225 230 235

<210> SEQ ID NO 219
<211> LENGTH: 83
<212> TYPE: PRT
<213> ORGANISM: Leptinotarsa decemlineata

<400> SEQUENCE: 219

Lys Gln Ala Lys Glu Glu Ala Gln Asp Glu Ile Glu Lys Tyr Arg Lys
1 5 10 15

Glu Arg Glu Arg Gln Phe Arg Glu Phe Glu Ala Lys His Met Gly Ser
20 25 30

Arg Glu Asp Val Pro Ser Lys Ile Glu Val Asp Thr Lys Arg Arg Ile
35 40 45

Glu Glu Met Asn Lys Ala Ile Ile Ser Gln Lys Glu Pro Val Ile Gln
50 55 60

Glu Val Leu Asn Leu Val Tyr Asp Ile Lys Pro Glu Ile His Lys Asn
65 70 75 80

Tyr Arg Gln

<210> SEQ ID NO 220
<211> LENGTH: 202
<212> TYPE: PRT
<213> ORGANISM: Leptinotarsa decemlineata

<400> SEQUENCE: 220

Ala Cys Glu Asn Glu Phe Leu Glu Ala Thr Glu Glu Ala Arg Arg Leu
1 5 10 15

Gly Tyr Ala Met Trp Gln Lys Lys Val Trp Leu Asp Pro Asn Glu Ile
20 25 30

Asn Glu Ile Ala Asn Thr Asn Ser Arg Gln Asn Ile Arg Lys Leu Ile
35 40 45

Lys Asp Gly Leu Ile Ile Lys Lys Pro Val Ala Val His Ser Arg Ala
50 55 60

Arg Val Arg Lys Asn Thr Glu Ala Arg Arg Lys Gly Arg His Cys Gly
65 70 75 80

Phe Gly Lys Arg Lys Gly Thr Ala Asn Ala Arg Met Pro Gln Lys Glu
85 90 95

Leu Trp Ile Gln Arg Met Arg Val Leu Arg Arg Leu Leu Lys Lys Tyr
100 105 110

Arg Glu Ala Lys Lys Ile Asp Arg His Leu Tyr Tyr Ala Leu Tyr Met
115 120 125

Lys Ala Lys Gly Asn Val Phe Lys Asn Lys Arg Val Leu Met Glu Tyr
130 135 140

Ile His Lys Lys Lys Ala Glu Lys Ala Arg Ala Lys Met Leu Ala Asp
145 150 155 160

Gln Ala Asn Ala Arg Arg Leu Lys Val Lys Gln Ala Arg Glu Arg Arg
165 170 175

Glu Glu Arg Ile Ala Thr Lys Lys Gln Glu Val Leu Gln Asn Tyr Gln
180 185 190

Arg Glu Asp Glu Ala Gln Ala Ala Lys Lys
195 200

<210> SEQ ID NO 221
<211> LENGTH: 223
<212> TYPE: PRT
<213> ORGANISM: Leptinotarsa decemlineata

<400> SEQUENCE: 221

Ile Lys Met Ser Val Leu Cys Pro Glu Ile Pro Ala Pro Gly Phe Ser
1 5 10 15

Phe Glu Asn Cys Lys Arg Asn Ala Leu Leu Glu Gly Lys Gly Phe Ala
20 25 30

Leu Pro Lys Ala Thr Lys Thr Gly Thr Thr Ile Val Gly Ile Thr Tyr
35 40 45

Lys Asp Gly Val Ile Leu Gly Ala Asp Thr Ile Ala Thr Glu Asp Thr
50 55 60

Thr Val Ala Asp Lys Asn Ser Glu Lys Ile His Tyr Leu Ala Pro Asn
65 70 75 80

Met Tyr Cys Cys Gly Ala Gly Thr Ala Ala Asp Thr Glu Met Thr Thr
85 90 95

Gln Met Ile Ser Ser Gln Leu Glu Leu His Lys Leu His Thr Asn Arg
100 105 110

Ile Ala Arg Val Cys Thr Ala Asn Gln Met Leu Lys Gln Tyr Leu Phe
115 120 125

Arg Tyr Gln Gly Tyr Ile Gly Ala Ala Leu Ile Leu Gly Gly Val Asp
130 135 140

Val Glu Gly Pro His Leu Tyr Met Ile Tyr Pro His Gly Ser Ser Asp
145 150 155 160

Asn Leu Pro Tyr Gly Thr Met Gly Ser Gly Ser Pro Ala Ala Ile Ala
165 170 175

Val Phe Glu Ser Arg Trp Arg Pro Asn Leu Glu Glu Glu Glu Gly Val
180 185 190

Gln Leu Val Arg Asp Ala Ile Ala Ala Gly Ile Phe Asn Asp Leu Gly
195 200 205

Ser Gly Ser Asn Val Asp Val Cys Ile Ile Arg Lys Gly Ser Val
210 215 220

<210> SEQ ID NO 222
<211> LENGTH: 320
<212> TYPE: PRT
<213> ORGANISM: Leptinotarsa decemlineata

<400> SEQUENCE: 222

Lys Gln Trp Leu Lys Leu Lys Leu Leu Phe Glu Met Ser Ser Thr Leu
1 5 10 15

Glu Asp Lys Ala Ile Trp Glu Asp Gly Glu Glu Ser Leu Gly Glu Glu
20 25 30

Val Leu Arg Met Ser Thr Asp Glu Ile Val Ser Arg Thr Arg Leu Leu
35 40 45

Asp Asn Glu Ile Lys Ile Met Lys Ser Glu Val Met Arg Ile Asn His
50 55 60

Glu Leu Gln Ala Gln Asn Glu Lys Ile Lys Glu Asn Thr Glu Lys Ile
65 70 75 80

Lys Val Asn Lys Thr Leu Pro Tyr Leu Val Ser Asn Val Ile Glu Leu
85 90 95

Leu Asp Val Asp Pro Gln Glu Glu Glu Glu Asp Gly Ala Val Val Asp
100 105 110

Leu Asp Ser Gln Arg Lys Gly Lys Cys Ala Val Val Lys Thr Ser Thr
115 120 125

Arg Gln Thr Tyr Phe Leu Pro Val Ile Gly Leu Val Asp Glu Glu Lys
130 135 140

```
Leu Lys Pro Gly Asp Leu Val Gly Val Asn Lys Asp Ser Tyr Leu Ile
145                 150                 155                 160

Leu Glu Thr Leu Pro Ala Glu Tyr Asp Ala Arg Val Lys Ala Met Glu
                165                 170                 175

Val Asp Glu Arg Pro Thr Glu Gln Tyr Ser Asp Ile Gly Gly Leu Asp
            180                 185                 190

Lys Gln Ile Gln Glu Leu Ile Glu Ala Val Val Leu Pro Met Thr His
        195                 200                 205

Lys Asp Lys Phe Val Asn Leu Gly Ile His Pro Pro Lys Gly Val Leu
    210                 215                 220

Leu Tyr Gly Pro Pro Gly Thr Gly Lys Thr Leu Leu Ala Arg Ala Cys
225                 230                 235                 240

Ala Ala Gln Thr Lys Ser Thr Phe Leu Lys Leu Ala Gly Pro Gln Leu
                245                 250                 255

Val Gln Met Phe Ile Gly Asp Gly Ala Lys Leu Val Arg Asp Ala Phe
            260                 265                 270

Ala Leu Ala Lys Glu Lys Ala Pro Ala Ile Ile Phe Ile Asp Glu Leu
        275                 280                 285

Asp Ala Thr Gly Thr Lys Arg Phe Asp Ser Glu Lys Ala Gly Asp Arg
    290                 295                 300

Glu Val Gln Arg Thr Met Leu Gly Ala Phe Glu Ser Val Gly Trp Val
305                 310                 315                 320


<210> SEQ ID NO 223
<211> LENGTH: 171
<212> TYPE: PRT
<213> ORGANISM: Leptinotarsa decemlineata

<400> SEQUENCE: 223

Asp Arg Cys Arg Thr Leu Tyr Glu Lys Phe Leu Glu Phe Gly Pro Glu
1               5                   10                  15

Asn Cys Val Thr Trp Met Lys Phe Ala Glu Leu Glu Thr Leu Leu Gly
            20                  25                  30

Asp Ile Asp Arg Ala Arg Ala Ile Tyr Glu Leu Ala Ile Ser Gln Pro
        35                  40                  45

Arg Leu Asp Met Pro Glu Leu Leu Trp Lys Ala Tyr Ile Asp Phe Glu
    50                  55                  60

Ile Ser Gln Glu Glu Pro Glu Asn Ala Arg Gln Ile Tyr Glu Arg Leu
65                  70                  75                  80

Leu Glu Lys Thr Ser His Val Lys Val Trp Leu Ser Tyr Ala Lys Phe
                85                  90                  95

Glu Leu Asn Thr Gln Ser Glu Pro Asp Met Asn Val Leu Leu Ser Arg
            100                 105                 110

Arg Val Phe Glu Arg Ala Asn Glu Ser Leu Lys Asn Ser Ser Glu Lys
        115                 120                 125

Glu Ala Arg Val Leu Leu Leu Glu Asn Trp Arg Glu Phe Glu Lys Ala
    130                 135                 140

His Gly Asp Glu Thr Gly Asn Ala Lys Val Asn Ser Arg Met Pro Lys
145                 150                 155                 160

Arg Ile Lys Lys Lys Lys Lys Lys Lys Lys Lys
                165                 170


<210> SEQ ID NO 224
<211> LENGTH: 776
<212> TYPE: PRT
```

<213> ORGANISM: Leptinotarsa decemlineata

<400> SEQUENCE: 224

```
Met Ala Thr Tyr Glu Glu Tyr Ile Gln Gln Asn Glu Asp Arg Asp Gly
1               5                   10                  15

Ile Arg Phe Thr Trp Asn Val Trp Pro Ser Ser Arg Ile Glu Ala Thr
            20                  25                  30

Arg Leu Val Val Pro Leu Ala Cys Leu Tyr Gln Pro Leu Lys Glu Arg
        35                  40                  45

Pro Asp Leu Pro Pro Ile Gln Tyr Asp Pro Val Leu Cys Thr Arg Asn
    50                  55                  60

Asn Cys Arg Ala Ile Leu Asn Pro Leu Cys Gln Val Asp Tyr Arg Ala
65                  70                  75                  80

Lys Leu Trp Val Cys Asn Phe Cys Phe Gln Arg Asn Pro Phe Pro Pro
                85                  90                  95

Gln Tyr Ala Ala Ile Ser Glu Gln His Gln Pro Ala Glu Leu Met Pro
            100                 105                 110

Met Phe Ser Thr Ile Glu Tyr Thr Ile Thr Arg Ala Gln Cys Leu Pro
        115                 120                 125

Pro Ile Tyr Leu Tyr Val Val Asp Thr Cys Met Asp Glu Glu Glu Leu
    130                 135                 140

Gly Ser Leu Lys Asp Ser Leu Gln Met Ser Leu Ser Leu Leu Pro Pro
145                 150                 155                 160

Asn Ala Leu Ile Gly Leu Ile Thr Phe Gly Lys Met Val Gln Val His
                165                 170                 175

Glu Leu Gly Thr Glu Gly Cys Ser Lys Ser Tyr Val Phe Arg Gly Thr
            180                 185                 190

Lys Asp Leu Thr Ala Lys Gln Val Gln Glu Met Leu Glu Val Gly Arg
        195                 200                 205

Ala Ala Val Ser Ala Gln Pro Ala Pro Gln Gln Pro Gly Gln Pro Met
    210                 215                 220

Arg Pro Gly Ala Leu Gln Gln Ala Pro Thr Pro Pro Gly Ser Arg Phe
225                 230                 235                 240

Leu Gln Pro Ile Ser Lys Cys Asp Met Asn Leu Thr Asp Leu Ile Gly
                245                 250                 255

Glu Leu Gln Arg Asp Pro Trp Pro Val His Gln Gly Lys Cys Ala Leu
            260                 265                 270

Arg Ser Thr Gly Thr Ala Leu Ser Ile Ala Ile Gly Leu Leu Glu Cys
        275                 280                 285

Thr Tyr Ala Asn Thr Gly Ala Arg Val Met Leu Phe Val Gly Gly Pro
    290                 295                 300

Cys Ser Gln Gly Pro Gly Gln Val Leu Asn Asp Asp Leu Lys Gln Pro
305                 310                 315                 320

Ile Arg Ser His His Asp Ile Gln Lys Asp Asn Ala Lys Tyr Met Lys
                325                 330                 335

Lys Ala Ile Lys His Tyr Asp Asn Leu Ala Met Arg Ala Ala Thr Asn
            340                 345                 350

Gly His Cys Val Asp Ile Tyr Ser Cys Ala Leu Asp Gln Thr Gly Leu
        355                 360                 365

Met Glu Met Lys Gln Cys Cys Asn Ser Thr Gly Gly His Met Val Met
    370                 375                 380

Gly Asp Ser Phe Asn Ser Ser Leu Phe Lys Gln Thr Phe Gln Arg Ile
385                 390                 395                 400
```

-continued

```
Phe Ser Lys Asp Gln Lys Asn Glu Leu Lys Met Ala Phe Asn Gly Thr
                405                 410                 415

Leu Glu Val Lys Cys Ser Arg Glu Leu Lys Ile Gln Gly Gly Ile Gly
            420                 425                 430

Ser Cys Val Ser Leu Asn Val Lys Asn Pro Leu Val Ser Asp Thr Glu
        435                 440                 445

Ile Gly Met Gly Asn Thr Val Gln Trp Lys Met Cys Thr Val Thr Pro
    450                 455                 460

Ser Thr Thr Met Ala Leu Phe Phe Glu Val Val Asn Gln His Ser Ala
465                 470                 475                 480

Pro Ile Pro Gln Gly Gly Arg Gly Cys Ile Gln Phe Ile Thr Gln Tyr
                485                 490                 495

Gln His Ala Ser Gly Gln Lys Arg Ile Arg Val Thr Thr Val Ala Arg
            500                 505                 510

Asn Trp Ala Asp Ala Ser Ala Asn Ile His His Val Ser Ala Gly Phe
        515                 520                 525

Asp Gln Glu Ala Ala Ala Val Ile Met Ala Arg Met Ala Val Tyr Arg
    530                 535                 540

Ala Glu Ser Asp Asp Ser Pro Asp Val Leu Arg Trp Val Asp Arg Met
545                 550                 555                 560

Leu Ile Arg Leu Cys Gln Lys Phe Gly Glu Tyr Asn Lys Asp Asp Pro
                565                 570                 575

Asn Ser Phe Arg Leu Gly Glu Asn Phe Ser Leu Tyr Pro Gln Phe Met
            580                 585                 590

Tyr His Leu Arg Arg Ser Gln Phe Leu Gln Val Phe Asn Asn Ser Pro
        595                 600                 605

Asp Glu Thr Ser Phe Tyr Arg His Met Leu Met Arg Glu Asp Leu Thr
    610                 615                 620

Gln Ser Leu Ile Met Ile Gln Pro Ile Leu Tyr Ser Tyr Ser Phe Asn
625                 630                 635                 640

Gly Pro Pro Glu Pro Val Leu Leu Asp Thr Ser Ser Ile Gln Pro Asp
                645                 650                 655

Arg Ile Leu Leu Met Asp Thr Phe Phe Gln Ile Leu Ile Phe His Gly
            660                 665                 670

Glu Thr Ile Ala Gln Trp Arg Asn Leu Lys Tyr Gln Asp Met Pro Glu
        675                 680                 685

Tyr Glu Asn Phe Arg Gln Leu Leu Gln Ala Pro Val Asp Asp Ala Gln
    690                 695                 700

Glu Ile Leu Gln Thr Arg Phe Pro Met Pro Arg Tyr Ile Asp Thr Glu
705                 710                 715                 720

Gln Gly Gly Ser Gln Ala Arg Phe Leu Leu Ser Lys Val Asn Pro Ser
                725                 730                 735

Gln Thr His Asn Asn Met Tyr Ala Tyr Gly Gly Asp Gly Gly Ala Pro
            740                 745                 750

Val Leu Thr Asp Asp Val Ser Leu Gln Val Phe Met Asp His Leu Lys
        755                 760                 765

Lys Leu Ala Val Ser Ser Thr Ala
    770                 775
```

<210> SEQ ID NO 225
<211> LENGTH: 899
<212> TYPE: PRT
<213> ORGANISM: Leptinotarsa decemlineata

<400> SEQUENCE: 225

```
Met Pro Leu Arg Leu Asp Ile Lys Arg Lys Leu Thr Ala Arg Ser Asp
1               5                   10                  15

Arg Val Lys Cys Val Asp Leu His Pro Ser Glu Pro Trp Met Leu Cys
            20                  25                  30

Ser Leu Tyr Ser Gly Asn Ile Asn Val Trp Asn Tyr Glu Asn Gln Gln
        35                  40                  45

Gln Val Lys Ser Phe Glu Val Cys Asp Leu Pro Val Arg Ala Ala Lys
    50                  55                  60

Phe Val Pro Arg Lys Asn Trp Ile Val Ser Gly Ser Asp Asp Met Gln
65                  70                  75                  80

Ile Arg Ile Phe Asn Tyr Asn Thr Leu Asp Arg Ile His Ser Phe Glu
                85                  90                  95

Ala His Ser Asp Tyr Val Arg Cys Ile Ile Val His Pro Thr Gln Pro
            100                 105                 110

Tyr Ile Leu Thr Ser Ser Asp Asp Met Leu Ile Lys Leu Trp Asn Trp
        115                 120                 125

Asp Lys Ala Trp Ala Cys Gln Gln Val Phe Glu Gly His Ser His Tyr
    130                 135                 140

Ile Met Gln Ile Ala Ile Asn Pro Lys Asp Asn Asn Thr Phe Ala Ser
145                 150                 155                 160

Ala Ser Leu Asp Arg Thr Leu Lys Val Trp Gln Leu Gly Ala Ser Thr
                165                 170                 175

Ala Asn Phe Thr Leu Glu Gly His Glu Lys Gly Val Asn Cys Val Asp
            180                 185                 190

Tyr Tyr His Gly Gly Asp Lys Pro Tyr Leu Ile Ser Gly Ala Asp Asp
        195                 200                 205

Arg Leu Val Lys Ile Trp Asp Tyr Gln Asn Lys Thr Cys Val Gln Thr
    210                 215                 220

Leu Glu Gly His Ala Gln Asn Val Thr Ala Val Cys Phe His Pro Glu
225                 230                 235                 240

Leu Pro Val Ala Leu Thr Gly Ser Glu Asp Gly Thr Val Arg Val Trp
                245                 250                 255

His Thr Asn Thr His Arg Leu Glu Asn Cys Leu Asn Tyr Gly Phe Glu
            260                 265                 270

Arg Val Trp Thr Ile Cys Cys Leu Lys Gly Ser Asn Asn Val Ser Leu
        275                 280                 285

Gly Tyr Asp Glu Gly Ser Ile Leu Val Lys Val Gly Arg Glu Glu Pro
    290                 295                 300

Ala Val Ser Met Asp Ala Ser Gly Gly Lys Ile Ile Trp Ala Arg His
305                 310                 315                 320

Ser Glu Leu Gln Gln Ala Asn Leu Lys Ala Leu Pro Glu Gly Gly Glu
                325                 330                 335

Ile Arg Asp Gly Glu Arg Leu Pro Val Ser Val Lys Asp Met Gly Ala
            340                 345                 350

Cys Glu Ile Tyr Pro Gln Thr Ile Gln His Asn Pro Asn Gly Arg Phe
        355                 360                 365

Val Val Val Cys Gly Asp Gly Glu Tyr Ile Ile Tyr Thr Ala Met Ala
    370                 375                 380

Leu Arg Asn Lys Ala Phe Gly Ser Ala Gln Glu Phe Val Trp Ala Gln
385                 390                 395                 400

Asp Ser Ser Glu Tyr Ala Ile Arg Glu Ser Gly Ser Thr Ile Arg Ile
                405                 410                 415
```

-continued

```
Phe Lys Asn Phe Lys Glu Arg Lys Asn Phe Lys Ser Asp Phe Ser Ala
            420                 425                 430

Glu Gly Ile Tyr Gly Gly Phe Leu Leu Gly Ile Lys Ser Val Ser Gly
        435                 440                 445

Leu Thr Phe Tyr Asp Trp Glu Thr Leu Asp Leu Val Arg Arg Ile Glu
    450                 455                 460

Ile Gln Pro Arg Ala Val Tyr Trp Ser Asp Ser Gly Lys Leu Val Cys
465                 470                 475                 480

Leu Ala Thr Glu Asp Ser Tyr Phe Ile Leu Ser Tyr Asp Ser Glu Gln
                485                 490                 495

Val Gln Lys Ala Arg Glu Asn Asn Gln Val Ala Glu Asp Gly Val Glu
            500                 505                 510

Ala Ala Phe Asp Val Leu Gly Glu Met Asn Glu Ser Val Arg Thr Gly
        515                 520                 525

Leu Trp Val Gly Asp Cys Phe Ile Tyr Thr Asn Ala Val Asn Arg Ile
    530                 535                 540

Asn Tyr Phe Val Gly Gly Glu Leu Val Thr Ile Ala His Leu Asp Arg
545                 550                 555                 560

Pro Leu Tyr Val Leu Gly Tyr Val Pro Arg Asp Asp Arg Leu Tyr Leu
                565                 570                 575

Val Asp Lys Glu Leu Gly Val Val Ser Tyr Gln Leu Leu Leu Ser Val
            580                 585                 590

Leu Glu Tyr Gln Thr Ala Val Met Arg Arg Asp Phe Pro Thr Ala Asp
        595                 600                 605

Arg Val Leu Pro Ser Ile Pro Lys Glu His Arg Thr Arg Val Ala His
    610                 615                 620

Phe Leu Glu Lys Gln Gly Phe Lys Gln Gln Ala Leu Ala Val Ser Thr
625                 630                 635                 640

Asp Pro Glu His Arg Phe Glu Leu Ala Val Ala Leu Glu Asp Leu Asp
                645                 650                 655

Thr Ala Lys Val Leu Ala Gln Glu Ala Asn Asn Pro Gln Lys Trp Ser
            660                 665                 670

Gln Leu Ala Glu Leu Ala Ala Ser Thr Asn Asn Leu Gln Leu Ala Lys
        675                 680                 685

Glu Cys Met Gln Lys Ala Gln Asp Tyr Gly Gly Leu Leu Leu Leu Ala
    690                 695                 700

Thr Ser Ser Gly Asp Glu Gln Leu Val Gln Ser Leu Gly Glu Leu Thr
705                 710                 715                 720

Gln Ala Glu Gly Lys His Asn Leu Ser Phe Leu Ser Tyr Phe Leu Val
                725                 730                 735

Gly Asp Leu Pro Lys Cys Leu Asp Ile Leu Val Ser Thr Gly Arg Leu
            740                 745                 750

Pro Glu Ala Ala Phe Phe Ala Arg Ser Tyr Leu Pro Asp Arg Ile Ser
        755                 760                 765

Glu Ile Val Glu Leu Trp Lys Val Lys Leu Thr Ser Ile Asn Glu Lys
    770                 775                 780

Ala Gly Gln Ser Leu Ala Asp Pro Lys Ser Tyr Glu Asn Leu Phe Pro
785                 790                 795                 800

Gly Leu Gln Glu Ala Ile Glu Thr Gln Lys Tyr Leu Glu Gln Gln Asp
                805                 810                 815

Arg Gly Leu Phe Pro Ala Ser Val Ser Thr Thr Ile Val Pro Asn His
            820                 825                 830

Glu Arg Asn Leu Val Ala Glu Ala Arg Ala Gln Met Lys Gly Gly Ala
```

```
        835                 840                 845

Ala Val Phe Gln Gln Ser Arg Leu Leu Ser Gly Glu Lys Thr Ile Ser
    850                 855                 860

Phe Glu Gln Asp Glu Asp Asp Leu Asp Leu Asp Leu Glu Gly Val Asn
865                 870                 875                 880

Ile Asp Asp Asn Ile Asp Thr Thr Asp Ile Asn Ile Asp Asp Asp Leu
                885                 890                 895

Leu Ser Asp


<210> SEQ ID NO 226
<211> LENGTH: 279
<212> TYPE: PRT
<213> ORGANISM: Lygus hesperus

<400> SEQUENCE: 226

Glu His Gly Ile Val Thr Asn Trp Asp Asp Met Glu Lys Ile Trp His
1               5                   10                  15

His Thr Phe Tyr Asn Glu Leu Arg Val Ala Pro Glu Glu His Pro Val
            20                  25                  30

Leu Leu Thr Glu Ala Pro Leu Asn Pro Lys Ala Asn Arg Glu Lys Met
        35                  40                  45

Thr Gln Ile Met Phe Glu Thr Phe Asn Thr Pro Ala Met Tyr Val Ala
    50                  55                  60

Ile Gln Ala Val Leu Ser Leu Tyr Ala Ser Gly Arg Thr Thr Gly Ile
65                  70                  75                  80

Val Leu Asp Ser Gly Asp Gly Val Ser His Thr Val Pro Ile Tyr Glu
                85                  90                  95

Gly Tyr Ala Leu Pro His Ala Ile Leu Arg Leu Asp Leu Ala Gly Arg
            100                 105                 110

Asp Leu Thr Asp Tyr Leu Met Lys Ile Leu Thr Glu Arg Gly Tyr Ser
        115                 120                 125

Phe Thr Thr Thr Ala Glu Arg Glu Ile Val Arg Asp Ile Lys Glu Lys
    130                 135                 140

Leu Cys Tyr Val Ala Leu Asp Phe Glu Gln Glu Met Ala Thr Ala Ala
145                 150                 155                 160

Ser Ser Ser Ser Leu Glu Lys Ser Tyr Glu Leu Pro Asp Gly Gln Val
                165                 170                 175

Ile Thr Ile Gly Asn Glu Arg Phe Arg Cys Pro Glu Ala Leu Phe Gln
            180                 185                 190

Pro Ser Phe Leu Gly Met Glu Ala Cys Gly Ile His Glu Thr Thr Tyr
        195                 200                 205

Asn Ser Ile Met Lys Cys Asp Val Asp Ile Arg Lys Asp Leu Tyr Ala
    210                 215                 220

Asn Thr Val Leu Ser Gly Gly Thr Thr Met Tyr Pro Gly Ile Ala Asp
225                 230                 235                 240

Arg Met Gln Lys Glu Ile Thr Ala Leu Ala Pro Ser Thr Met Lys Ile
                245                 250                 255

Lys Ile Ile Ala Pro Pro Glu Arg Lys Tyr Ser Val Trp Ile Gly Gly
            260                 265                 270

Ser Ile Leu Ala Ser Leu Ser
        275


<210> SEQ ID NO 227
<211> LENGTH: 252
<212> TYPE: PRT
```

<213> ORGANISM: Lygus hesperus

<400> SEQUENCE: 227

Glu His Gly Ile Ile Thr Asn Trp Asp Asp Met Glu Lys Ile Trp His
1               5                   10                  15

His Thr Phe Tyr Asn Glu Leu Arg Val Ala Pro Glu Glu His Pro Ile
            20                  25                  30

Leu Leu Thr Glu Ala Pro Leu Asn Pro Lys Ala Asn Arg Glu Lys Met
        35                  40                  45

Thr Gln Ile Met Phe Glu Thr Phe Asn Thr Pro Ala Met Tyr Val Ala
    50                  55                  60

Ile Gln Ala Val Leu Ser Leu Tyr Ala Ser Gly Arg Thr Thr Gly Ile
65                  70                  75                  80

Val Leu Asp Ser Gly Asp Gly Val Ser His Thr Val Pro Ile Tyr Glu
                85                  90                  95

Gly Tyr Ala Leu Pro His Ala Ile Leu Arg Leu Asp Leu Ala Gly Arg
            100                 105                 110

Asp Leu Thr Asp Tyr Leu Met Lys Ile Leu Thr Glu Arg Gly Tyr Ser
        115                 120                 125

Phe Thr Thr Thr Ala Glu Arg Glu Ile Val Arg Asp Ile Lys Glu Lys
    130                 135                 140

Leu Cys Tyr Val Ala Leu Asp Phe Glu Gln Glu Met Ala Thr Ala Ala
145                 150                 155                 160

Ala Ser Thr Ser Leu Glu Lys Ser Tyr Glu Leu Pro Asp Gly Gln Val
                165                 170                 175

Ile Thr Ile Gly Asn Glu Arg Phe Arg Cys Pro Glu Ala Leu Phe Gln
            180                 185                 190

Pro Ser Phe Leu Gly Met Glu Ser Cys Gly Ile His Glu Thr Val Tyr
        195                 200                 205

Asn Ser Ile Met Lys Cys Asp Val Asp Ile Arg Lys Asp Leu Tyr Ala
    210                 215                 220

Asn Thr Val Leu Ser Gly Gly Thr Thr Met Tyr Pro Gly Ile Ala Asp
225                 230                 235                 240

Arg Met Gln Lys Glu Ile Thr Ala Leu Ala Pro Ser
                245                 250

<210> SEQ ID NO 228
<211> LENGTH: 71
<212> TYPE: PRT
<213> ORGANISM: Lygus hesperus

<400> SEQUENCE: 228

Ile Pro Pro Asp Gln Gln Arg Leu Ile Phe Ala Gly Lys Gln Leu Glu
1               5                   10                  15

Asp Gly Arg Thr Leu Ser Asp Tyr Asn Ile Gln Lys Glu Ser Thr Leu
            20                  25                  30

His Leu Val Leu Arg Leu Arg Gly Gly Ala Lys Lys Arg Lys Lys Lys
        35                  40                  45

Asn Tyr Ser Thr Pro Lys Lys Ile Lys His Lys Lys Lys Lys Ile Lys
    50                  55                  60

Leu Ala Val Leu Lys Tyr Tyr
65                  70

<210> SEQ ID NO 229
<211> LENGTH: 88
<212> TYPE: PRT

```
<213> ORGANISM: Lygus hesperus
<220> FEATURE:
<221> NAME/KEY: misc_feature
<222> LOCATION: (55)..(55)
<223> OTHER INFORMATION: Xaa can be any naturally occurring amino acid

<400> SEQUENCE: 229

Lys Ala Lys Ile Gln Asp Lys Glu Gly Ile Pro Pro Asp Gln Gln Arg
1               5                   10                  15

Leu Ile Phe Ala Gly Lys Gln Leu Glu Asp Gly Arg Thr Leu Ser Asp
            20                  25                  30

Tyr Asn Ile Gln Lys Glu Ser Thr Leu His Leu Val Leu Arg Leu Arg
        35                  40                  45

Gly Gly Val Ile Glu Pro Xaa Leu Arg Ile Leu Ala Gln Lys Tyr Asn
    50                  55                  60

Cys Asp Lys Met Ile Cys Arg Lys Cys Tyr Ala Arg Leu His Pro Arg
65                  70                  75                  80

Ala Thr Asn Cys Arg Lys Lys Lys
                85


<210> SEQ ID NO 230
<211> LENGTH: 128
<212> TYPE: PRT
<213> ORGANISM: Lygus hesperus

<400> SEQUENCE: 230

Lys Thr Leu Thr Gly Lys Thr Ile Thr Leu Glu Val Glu Pro Ser Asp
1               5                   10                  15

Thr Ile Glu Asn Val Lys Ala Lys Ile Gln Asp Lys Glu Gly Ile Pro
            20                  25                  30

Pro Asp Gln Gln Arg Leu Ile Phe Ala Gly Lys Gln Leu Glu Asp Gly
        35                  40                  45

Arg Thr Leu Ser Asp Tyr Asn Ile Gln Lys Glu Ser Thr Leu His Leu
    50                  55                  60

Val Leu Arg Leu Arg Gly Gly Met Gln Ile Phe Val Lys Thr Leu Thr
65                  70                  75                  80

Gly Lys Thr Ile Thr Leu Glu Val Glu Pro Ser Asp Thr Ile Glu Asn
                85                  90                  95

Val Lys Ala Lys Ile Gln Asp Lys Glu Gly Ile Pro Pro Asp Gln Gln
            100                 105                 110

Arg Leu Ile Phe Ala Gly Lys Gln Leu Glu Asp Gly Arg Thr Leu Ser
        115                 120                 125


<210> SEQ ID NO 231
<211> LENGTH: 52
<212> TYPE: PRT
<213> ORGANISM: Lygus hesperus

<400> SEQUENCE: 231

Thr Leu Ser Asp Tyr Asn Ile Gln Lys Glu Ser Thr Leu His Leu Val
1               5                   10                  15

Leu Arg Leu Arg Gly Gly Met Gln Ile Phe Val Lys Thr Leu Thr Gly
            20                  25                  30

Lys Thr Ile Thr Leu Glu Val Glu Pro Ser Asp Thr Ile Glu Asn Val
        35                  40                  45

Lys Ala Lys Ile
    50
```

<210> SEQ ID NO 232
<211> LENGTH: 47
<212> TYPE: PRT
<213> ORGANISM: Lygus hesperus

<400> SEQUENCE: 232

His Leu Val Leu Arg Leu Arg Gly Gly Met Gln Ile Phe Val Lys Thr
1 5 10 15

Leu Thr Gly Lys Thr Ile Thr Leu Glu Val Glu Pro Ser Asp Thr Ile
20 25 30

Glu Asn Val Lys Ala Lys Ile Gln Asp Lys Glu Gly Ile Pro Pro
35 40 45

<210> SEQ ID NO 233
<211> LENGTH: 46
<212> TYPE: PRT
<213> ORGANISM: Lygus hesperus

<400> SEQUENCE: 233

Leu Val Leu Arg Leu Arg Gly Gly Met Gln Ile Phe Val Lys Thr Leu
1 5 10 15

Thr Gly Lys Thr Ile Thr Leu Glu Val Glu Pro Ser Asp Thr Ile Glu
20 25 30

Asn Val Lys Ala Lys Ile Gln Asp Lys Glu Gly Ile Pro Pro
35 40 45

<210> SEQ ID NO 234
<211> LENGTH: 76
<212> TYPE: PRT
<213> ORGANISM: Lygus hesperus

<400> SEQUENCE: 234

Ser Ser His Glu Asn Glu Leu Ile Leu Met Ser Val Leu Gln Cys Leu
1 5 10 15

Tyr Asp Ser Ile Ser Gln Ile Leu Arg Lys Asn Val Glu Lys Arg Thr
20 25 30

Ile Phe Glu Asn Leu Glu Ile Val Met Leu Ala Met Asp Glu Ile Cys
35 40 45

Asp Gly Gly Ile Leu Leu Glu Ala Asp Pro Thr Ser Val Val Gln Arg
50 55 60

Val Ala Ile Arg Thr Asp Asp Ile Pro Leu Gly Glu
65 70 75

<210> SEQ ID NO 235
<211> LENGTH: 139
<212> TYPE: PRT
<213> ORGANISM: Lygus hesperus
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid

<400> SEQUENCE: 235

Leu Xaa Val Leu Ile Val Asn Gln Thr Ala Asp Thr Leu Gln Asn Cys
1 5 10 15

Thr Leu Glu Leu Ala Thr Leu Gly Asp Leu Lys Leu Val Glu Lys Pro
20 25 30

Gln Pro Cys Val Leu Ala Pro His Asp Phe Cys Asn Ile Lys Ala Asn

```
        35                  40                  45

Val Lys Val Ala Ser Thr Glu Asn Gly Ile Ile Phe Gly Asn Ile Xaa
    50                  55                  60

Tyr Asp Val Ser Gly Ala Ala Ser Asp Arg Asn Val Val Val Leu Asn
65                  70                  75                  80

Asp Ile His Ile Asp Ile Met Asp Tyr Ile Val Pro Ala Ser Cys Ser
                85                  90                  95

Asp Thr Glu Phe Arg Gln Met Trp Ala Glu Phe Glu Trp Glu Asn Lys
            100                 105                 110

Val Ser Val Asn Thr Asn Leu Thr Asp Leu His Glu Tyr Leu Ala His
        115                 120                 125

Leu Val Arg Ser Thr Asn Met Lys Cys Leu Thr
    130                 135


<210> SEQ ID NO 236
<211> LENGTH: 116
<212> TYPE: PRT
<213> ORGANISM: Lygus hesperus

<400> SEQUENCE: 236

Val Leu Asp Ile Val Ala Tyr Gln Leu Asn Phe Tyr Arg Asn Glu Thr
1               5                   10                  15

Asn Glu Glu Pro Thr Val Glu Ile Ala Ala Asn Val Phe Arg Asp Val
            20                  25                  30

Tyr Tyr Arg Tyr Arg Asp Gln Leu Gln Val Gly Leu Ile Ile Ala Gly
        35                  40                  45

Trp Asp Lys Val Lys Gly Gly Gln Val Tyr Asn Ile Pro Leu Gly Gly
    50                  55                  60

Met Val Ile Arg Gln Lys Phe Cys Met Gly Gly Ser Gly Ser Thr Phe
65                  70                  75                  80

Val Phe Gly Phe Thr Asp Thr Asn Phe Lys Glu Asn Met Thr Glu Ala
                85                  90                  95

Glu Cys Lys Asn Phe Leu Thr Arg Ala Ile Gly Leu Ala Ile Ser Arg
            100                 105                 110

Asp Gly Ser Ser
        115


<210> SEQ ID NO 237
<211> LENGTH: 116
<212> TYPE: PRT
<213> ORGANISM: Lygus hesperus

<400> SEQUENCE: 237

Val Ser Glu Met Val Thr Phe Gln Leu Asn Leu Tyr Arg Asn Glu Thr
1               5                   10                  15

Asn Lys Glu Pro Thr Val Glu Met Ala Ala Asn Val Phe Arg Asp Val
            20                  25                  30

Cys Tyr Arg Tyr Arg Asp Gln Leu Gln Val Gly Leu Ile Ile Ala Gly
        35                  40                  45

Trp Asp Glu Val Lys Gly Ala Gln Val Tyr Met Ile Pro Leu Gly Gly
    50                  55                  60

Met Val Ile Arg Gln Lys Phe Ala Met Ser Gly Ser Gly Ser Thr Phe
65                  70                  75                  80

Ile Tyr Gly Phe Thr Asp Ala His Phe Lys Glu Asn Met Thr Glu Ala
                85                  90                  95

Glu Cys Lys Asn Phe Leu Thr Arg Ala Ile Gly Leu Ala Ile Ser Arg
```

```
            100                 105                 110

Asp Gly Ala Ser
        115


<210> SEQ ID NO 238
<211> LENGTH: 371
<212> TYPE: PRT
<213> ORGANISM: Lygus hesperus
<220> FEATURE:
<221> NAME/KEY: misc_feature
<222> LOCATION: (321)..(321)
<223> OTHER INFORMATION: Xaa can be any naturally occurring amino acid

<400> SEQUENCE: 238

Ala Ser Phe Val Ser Glu Ile Ser Asp Glu Phe Lys Ile Val Val Val
1               5                   10                  15

Gln Ala Ile Arg Ala Leu Cys Leu Lys Phe Pro Arg Lys His Ser Thr
            20                  25                  30

Leu Met Thr Phe Leu Ser Ala Met Leu Arg Asp Glu Gly Gly Leu Glu
        35                  40                  45

Tyr Arg Ala Ser Ile Ala Asp Thr Ile Ile Thr Ile Ile Glu Asp Asn
    50                  55                  60

Pro Glu Ala Lys Glu Ile Gly Leu Ala His Leu Cys Glu Phe Ile Glu
65                  70                  75                  80

Asp Cys Glu His Val Ser Leu Ala Val Arg Ile Leu His Leu Leu Gly
                85                  90                  95

Lys Glu Gly Pro Lys Thr Ile Gln Pro Ser Arg Tyr Ile Arg Phe Ile
            100                 105                 110

Tyr Asn Arg Val Ile Leu Glu Ile Ala Val Ile Arg Ala Ala Ala Val
        115                 120                 125

Ser Ala Leu Ala Gln Phe Gly Ala Leu Cys Pro Asp Leu Leu Pro Asn
    130                 135                 140

Ile Leu Val Leu Leu Ala Arg Cys Gln Met Asp Thr Asp Asp Glu Val
145                 150                 155                 160

Arg Asp Arg Ala Thr Tyr Tyr Tyr His Leu Leu Lys Leu Gln Glu Lys
                165                 170                 175

Gly Leu Ile Phe Asn Tyr Ile Val Asp Pro Met Gln Val Cys Leu Val
            180                 185                 190

Ser Leu Glu Lys Ser Leu Ala Gln His Val His Asp Lys Val Pro Thr
        195                 200                 205

Lys Phe Asp Leu Lys Ser Val Pro Pro Ala Pro Val Val Ser Thr Thr
    210                 215                 220

Glu Asp Thr Ala Gln Glu Thr Val Pro Glu Gly Ser Ile Ser Ser Ala
225                 230                 235                 240

Pro Ser Lys Ile Ala Pro Leu Gln Ser Thr Val Ser Ser Tyr Ala Glu
                245                 250                 255

Lys Leu Gln Gly Val Pro Gly Leu Gln Ser Ile Pro Gly Thr Leu Phe
            260                 265                 270

His Val Ser Glu Pro Val Glu Leu Thr Glu Ser Glu Thr Glu Tyr Val
        275                 280                 285

Val Thr Cys Thr Lys Leu Thr Tyr Pro His His Leu Val Leu Gln Phe
    290                 295                 300

Glu Cys Lys Asn Thr Leu Ser Asp Gln Leu Leu Glu Asn Val Arg Val
305                 310                 315                 320

Xaa Ile Glu Ala Ser Glu Gly Tyr Arg Ile Val Lys Glu Ile Pro Ile
                325                 330                 335
```

```
Ser Lys Leu Pro Tyr Asn Glu Thr His Cys Ala Tyr Val Val Leu Gln
            340                 345                 350

Phe Pro Glu Gln Leu Ser Leu Thr Val Thr Asn Phe Gly Ala Thr Leu
        355                 360                 365

Arg Phe Ile
    370


<210> SEQ ID NO 239
<211> LENGTH: 305
<212> TYPE: PRT
<213> ORGANISM: Lygus hesperus
<220> FEATURE:
<221> NAME/KEY: misc_feature
<222> LOCATION: (4)..(4)
<223> OTHER INFORMATION: Xaa can be any naturally occurring amino acid

<400> SEQUENCE: 239

Lys Ala Lys Xaa Leu Gly Glu Leu Ile Gln Ala Ser Arg Pro Phe Leu
1               5                   10                  15

Ser Glu Ile Ser Lys Ala Lys Ala Ala Lys Leu Val Arg Thr Leu Val
            20                  25                  30

Asp Phe Phe Leu Asp Leu Glu Ala Glu Thr Gly Arg Glu Val Gln Leu
        35                  40                  45

Cys Lys Glu Cys Ile Glu Trp Ala Thr Thr Glu Arg Arg Thr Phe Leu
    50                  55                  60

Arg Gln Ser Leu Glu Ala Arg Leu Ile Ala Leu Tyr Phe Asp Thr Gly
65                  70                  75                  80

Met Tyr Thr Glu Ala Leu Gly Leu Gly Ser Ser Leu Leu Lys Glu Leu
                85                  90                  95

Lys Lys Leu Asp Asp Lys Asn Leu Leu Val Glu Val Leu Leu Leu Glu
            100                 105                 110

Ser Lys Thr Tyr His Ala Leu Ser Asn Leu Ser Lys Ala Arg Ala Ala
        115                 120                 125

Leu Thr Ser Ala Arg Thr Thr Ala Asn Ser Ile Tyr Cys Pro Pro Lys
    130                 135                 140

Met Gln Ala Ala Leu Asp Leu Gln Ser Gly Ile Leu His Ala Ala Asp
145                 150                 155                 160

Glu Gln Asp Phe Lys Thr Ala Tyr Ser Tyr Phe Tyr Glu Ala Phe Glu
                165                 170                 175

Gly Tyr Asp Ser Val Asp Ser Pro Lys Ala Leu Thr Ala Leu Lys Tyr
            180                 185                 190

Met Leu Leu Ser Lys Ile Met Leu Asn Thr Pro Glu Asp Val Gln Gln
        195                 200                 205

Leu Ile Ser Gly Lys Leu Ala Leu Lys His Ala Gly Arg Asp Ile Asp
    210                 215                 220

Ala Met Lys Asn Val Ala Lys Ala Ser Ala Lys Arg Ser Leu Ala Asp
225                 230                 235                 240

Phe Gln Ser Thr Leu Glu Gly Tyr Lys Lys Glu Leu Lys Glu Asp Pro
                245                 250                 255

Ile Val Lys Ala His Leu Gly Thr Leu Tyr Asp Asn Met Leu Glu Gln
            260                 265                 270

Asn Leu Cys Arg Ile Ile Glu Pro Tyr Ser Arg Val Gln Val Glu Tyr
        275                 280                 285

Val Ser Lys Ala Ile Lys Leu Pro Thr Leu Gln Val Glu Lys Lys Leu
    290                 295                 300
```

Ser
305

<210> SEQ ID NO 240
<211> LENGTH: 179
<212> TYPE: PRT
<213> ORGANISM: Lygus hesperus

<400> SEQUENCE: 240

```
Leu Ala Ala Val Ser Ala Gly Ala Pro Ser Ile Gly Ile Lys Ala Gln
1               5                   10                  15

Asn Gly Val Val Leu Ala Thr Glu Asn Lys Phe Lys Ser Ile Leu Tyr
            20                  25                  30

Glu Glu His Ser Ile Lys Lys Ile Glu Met Val Glu Glu His Ile Gly
        35                  40                  45

Met Val Tyr Ser Gly Met Gly Pro Asp Tyr Arg Leu Leu Val Lys Arg
    50                  55                  60

Ala Arg Lys Leu Ala Gln Gln Tyr Lys Leu Val Tyr Gly Gln Arg Ile
65                  70                  75                  80

Pro Thr Pro Gln Leu Val Gln Lys Val Ala Met Val Met Gln Glu Tyr
                85                  90                  95

Thr Gln Ser Gly Gly Val Arg Pro Phe Gly Val Ser Leu Leu Ile Cys
            100                 105                 110

Gly Trp Asp Asp Gly Arg Pro Thr Leu Phe Gln Cys Asp Pro Ser Gly
        115                 120                 125

Ala Tyr Phe Ala Trp Lys Ala Thr Ala Met Gly Lys Asn Phe Ile Asn
    130                 135                 140

Gly Lys Thr Phe Leu Glu Lys Arg Tyr Ile Glu Thr Gln Asp Ile Glu
145                 150                 155                 160

Asp Ala Val His Thr Ala Ile Leu Thr Leu Lys Glu Gly Phe Glu Gly
                165                 170                 175

Gln Met Asp
```

<210> SEQ ID NO 241
<211> LENGTH: 80
<212> TYPE: PRT
<213> ORGANISM: Lygus hesperus
<220> FEATURE:
<221> NAME/KEY: misc_feature
<222> LOCATION: (28)..(28)
<223> OTHER INFORMATION: Xaa can be any naturally occurring amino acid

<400> SEQUENCE: 241

```
Ala Glu Ala Lys Lys Arg Lys Ala Arg Arg Leu Lys Gln Ala Lys Glu
1               5                   10                  15

Glu Ala Gln Glu Glu Ile Glu Arg Tyr Lys Gln Xaa Arg Glu Lys Gln
            20                  25                  30

Phe Lys Glu Phe Glu Ala Gln His Met Gly Ser Arg Glu Asp Val Ala
        35                  40                  45

Ala Arg Ile Asp Ala Asp Thr Arg Gln Arg Ile Glu Glu Met Thr Lys
    50                  55                  60

Ala Val Asn Val Asn Lys Glu Gln Val Ile Gln Arg Ile Leu Glu Leu
65                  70                  75                  80
```

<210> SEQ ID NO 242
<211> LENGTH: 179
<212> TYPE: PRT
<213> ORGANISM: Lygus hesperus
<220> FEATURE:

<221> NAME/KEY: misc_feature
<222> LOCATION: (23)..(24)
<223> OTHER INFORMATION: Xaa can be any naturally occurring amino acid

<400> SEQUENCE: 242

```
Ala Ser Val Met Arg Cys Gly Lys Lys Lys Val Trp Leu Asp Pro Asn
1               5                   10                  15

Glu Ile Asn Glu Ile Ala Xaa Xaa Asn Ser Arg Gln Asn Ile Arg Lys
            20                  25                  30

Leu Ile Lys Asp Gly Leu Ile Ile Lys Lys Pro Val Ala Val His Ser
        35                  40                  45

Arg Ala Arg Val Arg Lys Asn Thr Glu Ala Arg Arg Lys Gly Arg His
    50                  55                  60

Cys Gly Phe Gly Lys Arg Lys Gly Thr Ala Asn Ala Arg Met Pro Val
65                  70                  75                  80

Lys Val Leu Trp Val Asn Arg Met Arg Val Leu Arg Arg Leu Leu Lys
                85                  90                  95

Lys Tyr Arg Glu Ala Lys Lys Ile Asp Arg Gln Met Tyr His Asp Leu
            100                 105                 110

Tyr Met Lys Ala Lys Gly Asn Val Phe Lys Asn Lys Arg Val Leu Met
        115                 120                 125

Asp Phe Ile His Lys Lys Lys Ala Glu Lys Ala Arg Ser Lys Met Leu
    130                 135                 140

Lys Asp Gln Ala Glu Ala Arg Arg Leu Lys Val Lys Glu Ala Lys Lys
145                 150                 155                 160

Arg Arg Glu Glu Arg Ile Ala Thr Lys Lys Gln Glu Ile Met Gln Ala
                165                 170                 175

Tyr Ala Arg
```

<210> SEQ ID NO 243
<211> LENGTH: 219
<212> TYPE: PRT
<213> ORGANISM: Lygus hesperus

<400> SEQUENCE: 243

```
Glu Lys Phe Glu Asn Leu Gly Ile Gln Pro Pro Lys Gly Val Leu Leu
1               5                   10                  15

Tyr Gly Pro Pro Gly Thr Gly Lys Thr Leu Leu Ala Arg Ala Cys Ala
            20                  25                  30

Ala Gln Thr Lys Ser Thr Phe Leu Lys Leu Ala Gly Pro Gln Leu Val
        35                  40                  45

Gln Met Phe Ile Gly Asp Gly Ala Lys Leu Val Arg Asp Ala Phe Ala
    50                  55                  60

Leu Ala Lys Glu Lys Ala Pro Ala Ile Ile Phe Ile Asp Glu Leu Asp
65                  70                  75                  80

Ala Ile Gly Thr Lys Arg Phe Asp Ser Glu Lys Ala Gly Asp Arg Glu
                85                  90                  95

Val Gln Arg Thr Met Leu Glu Leu Leu Asn Gln Leu Asp Gly Phe Ser
            100                 105                 110

Ser Thr Ala Asp Ile Lys Val Ile Ala Ala Thr Asn Arg Val Asp Ile
        115                 120                 125

Leu Asp Pro Ala Leu Leu Arg Ser Gly Arg Leu Asp Arg Lys Ile Glu
    130                 135                 140

Phe Pro His Pro Asn Glu Asp Ala Arg Ala Arg Ile Met Gln Ile His
145                 150                 155                 160
```

```
Ser Arg Lys Met Asn Ile Ser Val Asp Val Asn Phe Glu Glu Leu Ala
                165                 170                 175

Arg Ser Thr Asp Asp Phe Asn Gly Ala Gln Cys Lys Ala Val Cys Val
            180                 185                 190

Glu Ala Gly Met Ile Ala Leu Arg Arg Ser Ala Ser Val Val Ser His
        195                 200                 205

Glu Asp Phe Met Asp Ala Ile Leu Glu Val Gln
    210                 215


<210> SEQ ID NO 244
<211> LENGTH: 92
<212> TYPE: PRT
<213> ORGANISM: Lygus hesperus
<220> FEATURE:
<221> NAME/KEY: misc_feature
<222> LOCATION: (55)..(55)
<223> OTHER INFORMATION: Xaa can be any naturally occurring amino acid

<400> SEQUENCE: 244

Asn Lys Thr Leu Pro Tyr Leu Val Ser Asn Val Ile Glu Leu Leu Asp
1               5                   10                  15

Val Asp Pro Glu Glu Thr Glu Glu Asp Gly Ala Val Val Asp Leu Asp
            20                  25                  30

Ala Arg Arg Lys Gly Lys Cys Ala Val Ile Lys Thr Ser Thr Arg Gln
        35                  40                  45

Thr Tyr Phe Leu Pro Val Xaa Gly Leu Val Asp Ala Glu Lys Leu Lys
    50                  55                  60

Pro Gly Asp Leu Val Gly Val Asn Lys Asp Ser Tyr Leu Ile Leu Glu
65                  70                  75                  80

Thr Leu Pro Ala Glu Tyr Asp Ala Arg Val Lys Ala
                85                  90


<210> SEQ ID NO 245
<211> LENGTH: 258
<212> TYPE: DNA
<213> ORGANISM: Artificial
<220> FEATURE:
<223> OTHER INFORMATION: GFP

<400> SEQUENCE: 245

agatacccag atcatatgaa acggcatgac tttttcaaga gtgccatgcc cgaaggttat      60

gtacaggaaa gaactatatt tttcaaagat gacgggaact acaagacacg taagtttaaa     120

cagttcggta ctaactaacc atacatattt aaattttcag gtgctgaagt caagtttgaa     180

ggtgataccc ttgttaatag aatcgagtta aaaggtattg attttaaaga agatggaaac     240

attcttggac acaaattg                                                   258


<210> SEQ ID NO 246
<211> LENGTH: 46
<212> TYPE: DNA
<213> ORGANISM: Artificial
<220> FEATURE:
<223> OTHER INFORMATION: Primer

<400> SEQUENCE: 246

gcgtaatacg actcactata ggagataccc agatcatatg aaacgg                     46


<210> SEQ ID NO 247
<211> LENGTH: 24
<212> TYPE: DNA
<213> ORGANISM: Artificial
```

<220> FEATURE:
<223> OTHER INFORMATION: Primer

<400> SEQUENCE: 247
caatttgtgt ccaagaatgt ttcc 24

<210> SEQ ID NO 248
<211> LENGTH: 24
<212> TYPE: DNA
<213> ORGANISM: Artificial
<220> FEATURE:
<223> OTHER INFORMATION: Primer

<400> SEQUENCE: 248
agatacccag atcatatgaa acgg 24

<210> SEQ ID NO 249
<211> LENGTH: 46
<212> TYPE: DNA
<213> ORGANISM: Artificial
<220> FEATURE:
<223> OTHER INFORMATION: Primer

<400> SEQUENCE: 249
gcgtaatacg actcactata ggcaatttgt gtccaagaat gtttcc 46

<210> SEQ ID NO 250
<211> LENGTH: 170
<212> TYPE: DNA
<213> ORGANISM: Artificial
<220> FEATURE:
<223> OTHER INFORMATION: Intron

<400> SEQUENCE: 250
ctcgagcctg agagaaaagc atgaagtata cccataacta acccattagt tatgcattta 60
tgttatatct attcatgctt ctactttaga taatcaatca ccaaacaatg agaatctcaa 120
cggtcgcaat aatgttcatg aaaatgtagt gtgtacactt accttctaga 170

<210> SEQ ID NO 251
<211> LENGTH: 2752
<212> TYPE: DNA
<213> ORGANISM: Lygus hesperus

<400> SEQUENCE: 251
gaagtgacgt gtgacgtgtt cttttgccta tgtcaaatta ttgcatgtcc gtgattttct 60
tcgtaatttt gttccaaaaa ctctaaattc ccatgtgatt tcttctacgg cgaagcccca 120
ggaaaaaaga atgacgacct acgaggagtt cattcaacag agcgaggagc gcgacggtat 180
caggttcact tggaacgtct ggccatcaag tcgcatcgaa gccaccaggt tggtcgtacc 240
cgtaggatgt ctctatcaac cactaaaaga acgcacggat cttccagcta ttcaatacga 300
tcccgttcta tgcactagga atacctgtag agccatactc aacccgatgt gccaagtaaa 360
ctatagggca aagttgtggg tgtgtaactt ctgtttccag aggaatccgt tcccaccaca 420
atacgccgca atttccgagc agcatcagcc tgctgagttg attccatcat tctcaactat 480
agagtatact atatctagag ctcaattttt gcctcctata ttcctattgg tggtggatac 540
gtgtttggat gatgacgagc taggagctct gaaagattcg ttacaaacgt ctctatcttt 600
gctaccaacc aactccctag ttggtctgat cacgtttggt aaaatggtcc aagttcacga 660
acttgggtgt gaaggttgtt cccggagcta cgtgttcaga ggcaccaagg atttgacgtc 720
caagcaagta caggacatgc ttgggatcgg aaaggtttcc gcttctcctc agcaacagca 780
gcaaagggca atgggcggtc agcagccatt ccccaccaat cggttcattc agccgattca 840
aagttgtgac atgagcctca ccgacttgtt gggcgaaatg cagcgtgatc catggccagt 900
gggtcagggt aagcgacctc ttagatcaac gggtgctgct ctagctattg ccattgggtt 960
gttggagtgc tcctacccca acacgggagc aaaagtcatg ttgttccttg gtggcccttg 1020
ttcccaaggg cctggtcaag ttgtcaatga tgacctgagg gaacctatcc gctctcatca 1080
tgacatccag aaagataatg cccgctacat gaaaaaagcc attaaacatt acgattcttt 1140
ggcattgaga gcagccacta atgggcattc agtagacatt tattcctgtg ctttagatca 1200
gacaggtttg gcggaaatga agcaatgttg caattctact gggggtcata tggtgatggg 1260
tgacaccttc aactccactt tgttcaaaca gacgttccag agggtgctct cccgtgatca 1320
aaaaggcgaa ttcaaaatgg ctttcaatgg cgtagttgaa gtcaaaacct cccgagagct 1380
aaaagttatg ggagccattg ggccttgcgt ttcattgaat acgaaaggtc cgtgtgttag 1440
tgaaactgac atagggcttg gaggaacttg ccagtggaag ttctgcacat ttaaccaaaa 1500
taccactgct gccatgttct ttgaggtagt aaaccaacac gctgctccta tccctcaagg 1560
tggaagagga tgtatacagt tcataactca ataccagcat gcgtcgggcc aaaggcgcat 1620
ccgagtaacc actgtagcca ggaattgggc tgatgcgact accaacatgc accatgttag 1680
tgcaggattt gatcaggaag ctggagcggt actcatggcc aggatggtcg ttcacagagc 1740
tgaaactgat gatggacctg atgtcatgag atgggctgat cgcatgttga ttcgtctttg 1800
ccagaaattc ggcgagtaca acaaggatga tccaaatagt ttccgcctcc cagaaaactt 1860
ctcgctttac ccacagttca tgtatcactt gagaaggtcc caattcttgc aggtattcaa 1920
caacagccca gacgaaacgt cgtactatcg tcacatcttg atgcgggaag atttgtcgca 1980
gagcttgatc atgattcagc cgatcctgta cagttacagt ttcaacggtc cagaaccagt 2040
ccttttggac acttccagca ttcaacctga tcggatcctg ctgatggaca ccttcttcca 2100
aatcctcatc ttccacggcg agaccatcgc ccagtggcgt gcccaaaggt accaggacct 2160
acctgaatat gagaacttca agcagctcct acaggctcct gtagacgatg ctaaggaaat 2220
cctgcacact cggttcccca tgccgaggta cattgacacc gaacagggcg gatcacaagc 2280
tagattcctt ctctccaaag tcaacccatc ccaaactcac aacaacatgt acggctatgg 2340
aggggaattt ggagcccctg tgctcactga tgatgtttcc ctccaagtct tcatggaaca 2400
ccttaaaaag ctagccgttt catttactgc ctagatgttt attcccagct caaaaatcca 2460
tttagaaaag aagcctgttt tttttcagta tcaaattcac aatttttttt tgttaatatt 2520
ttcgtgcaat gagtgaaata cttacacttt attgatcact ttgttttgga ccatagtaaa 2580 catttttttca tttttttacca ccttactaag aatgaagtat ttgggtaaat ttacgttgca 2640
aattatattt aaaattattg tttatatcaa tgggtatatt tttaattaaa tcgttgatac 2700
attgattttg tattagctca ttaagttatt aaaaataaat ttatatatta cc 2752

<210> SEQ ID NO 252
<211> LENGTH: 3191
<212> TYPE: DNA
<213> ORGANISM: Lygus hesperus

<400> SEQUENCE: 252
gatctgataa gagattgatg tggtttagtt tgtttgacgt agatttgtaa cattttgatt 60
ccgaatttaa ttgatatttc tcacaatgcc tctcaaattg gacatcaaga gaaagctgtc 120

-continued

```
tgctcgatca gaccgtgtga aatgtgtcga tctgcaccca actgagccgt ggatgttggc    180
ttctctctac aacggaaacg ttcacatttg gaaccacgaa actcaacagc ttctgaaatc    240
cttcgaagta tgcgagcttc caatcagggc tgcagttttc gtaccgagga agaactgggt    300
ggtcacaggc tcggacgaca tgcacgttcg tgtcttcaac tacaacactc tcgagcgtgt    360
acattccttc gaggcccatt ctgattattt gagatgcatc atcgtacatc ctacacagcc    420
ttacatattg acgtgcagcg atgacatgct gatcaagctg tggaactggg aaaaaaattg    480
gctatgccag caagtcttcg aaagccacac ccattacgtc atgcagatcg tgctgaaccc    540
gaaggataac aacactttcg cctctgcctc gctcgaccac accctcaaag tgtggcagtt    600
ggactctgca gcggccaact tcactttgga cggacacgaa aaaggagtta actgcgtcga    660
ctactaccac ggaggagata agccgtatct catctctggc gcggacgatc acatggtcaa    720
aatatgggat taccagaaca aaacgtgcgt tcagactttg gagggacacg ctcaaaatat    780
aactgcagtt tgcctccaca ctgaactacc aatcgcaatt actggctcgg aagatggaac    840
cgttcgcttg tggcactcag caacctatcg acttgaatcg tccttgaact acggctttga    900
aagagtatgg gccatacgct gtctcaaagg ctcaaaccac attgctcttg ggtacgacga    960
gggttccatt atggtcaagg ttggtcgaga agaaccggcc atttccatgg atgttaatgg   1020
agaaaaaatt gtttgggctc gacattctga aatccagcag gtcaatttga agtctctcat   1080
gactgacgag agtgaaattc gcgatgggga gaaactccca gtagcagcta aagacatggg   1140
tccctgcgaa gttttcccgc aaagcatcgc ccacaacccc aatgggaggt ttgtggttgt   1200
ttgcggtgat ggagaataca tcatctacac tgccatggct ttgcgtaata aaagtttcgg   1260
ttccgcccaa gagttcgtct gggcccagga ctcttctgac tacgccatcc gcgaagggac   1320
gtctaccgtc cgacttttca ggcagttcaa ggaaaggaag aacttcaagc ctgaatttgg   1380
agctgaaggt atttttgggg gacagcttct cggagttagg actgtaactg gactgtccct   1440
ctacgactgg gaaactttgg agttgatcag aagcatcgac attcaagcga aagcgccgta   1500
ctggtccgaa gcagggcatc tcttggcaat cgttactgac gacagttact atctcttgaa   1560
attcgaccag agcgccatct cgacgtccac ccctggaact gacggctacg aagatgcctt   1620
tgagctcgtc ggtgaagtca atgatactgt caagaccgga ttgtgggttg gtgactgttt   1680
catctacaca aatgccgttt gtcggatcaa ctactacgtt ggtggtgaga tcgtcaccgt   1740
ggctcacctc gacactacaa tgtacctcct aggatacgtg gcccgccaga acctgctgta   1800
cctgtgcgac aagcatcata acatcatttg ttacacgttg cttctgtctg tcctcgaata   1860
tcagactgct gtgatgagga gagactttga aactgctgac cgagttttgc ccactattcc   1920
tgttcagcat cgctcaagag ttgctcattt cctggaaaaa cagggcttca aaaggcaagc   1980
tctggctgtg tccacggatg ccgagcacaa gtttgaactt gcgcttcagc tcagtgattt   2040
ggaagcagca gtcggcctag cgagggaaat cggcagcaaa gccaagtggg tgcaggtcgc   2100
agagttggcg atgtcagagg ccaagctagg actcgctcag atgtgcttgc atcaggcaca   2160
gcactacgga ggacttctgc tcctgtcaac ttctgccgga aatgtggaca tgatggagaa   2220
actggcagaa agctcgctgt ccgatggcaa aaacaacgtc tcgttcctca cttacttcct   2280
gatgggtaac gtggaaaagt gtctccaaat cctcatcgat actggaagaa ttccggaagc   2340
agctttcttc gcccggacct atatgcctaa agaagtgtct cgcgtggtcg acatgtggaa   2400
aaccctttct aaggacaaga cggggcaatc gctcgctgac ccagcccaat acccgaatct   2460
```

-continued

```
attccccaag cacaccgagg ctctgaaagc cgaacagttc atgaagaagg aattgactca   2520

aaggattccc gcctcgtcgc acaaggatat aaaacccaac tacgaaagga atgccattga   2580

agaaatgaaa gaagccgaag caaacggtct gttcacgtat gatcctccag tggctcctgc   2640

cagtatcaac aatctaattg atgtttctga accggcgaat cgatctgagc ccagcccgtc   2700

tgaaatcttc tccgaagcgc ccgtcgtgtc caagatgacc agcgacgctc ggccgctggt   2760

cgcgccagtt ccgcctgccg cgagacctca aaaacggccg tcggccttcg atgatgacga   2820

cctcgaattg gaaatcgaaa atatgaattt ggatgacatc gatgctagtg atttgaacga   2880

agaagacctc cttatagatt agggatcatt gttttatcta tttaaaatta ctttatttat   2940

caattataat ccacataatt aagtattatc gtacatgaaa gtgaattcca aatattttta   3000

tgggtggtat tctgttctca cgttttcatt cggttgccaa tctgatgtaa ataaatggaa   3060

aactataaaa tgcaatattt atatgaagtt aggctgtcac tattttagaa taagattctt   3120

ggatgatgta tcaattattg tgttccataa gtttaggttg ttatttccta ataaacgttt   3180

attacagcct c                                                        3191
```

<210> SEQ ID NO 253
<211> LENGTH: 859
<212> TYPE: DNA
<213> ORGANISM: Lygus hesperus

<400> SEQUENCE: 253

```
aagcagtggt atcaacgcag agtacttttt tttttttttt tttttttttt ctttctgaaa     60

gtgtggttct cttcgtccga ccatgagttc gctcaaactg cagaagaggc tcgccgcctc    120

ggtgatgaga tgcggcaaga agaaagtgtg gttggaccct aatgaaatca acgaaatcgc    180

caacaccaac tctaggcaaa acatccgtaa gctgatcaag gatggtttga tcatcaaaaa    240

gcctgtggct gtccactcca gagcccgcgt ccgtaaaaac acagaagcca gacggaaggg    300

tcgtcattgt ggcttcggta agaggaaggg taccgccaac gccagaatgc ctgtgaaggt    360

cctgtgggtc aacagaatga gagtcctgcg acggctcctt aaaaaataca gagaagccaa    420

gaagatcgat aggcaaatgt accacgacct ttacatgaaa gccaaaggta acgtcttcaa    480

aaacaagagg gtactgatgg acttcattca caagaagaag gctgaaaagg cgagatcaaa    540

gatgttgaag gaccaggcag aggcgagacg tttcaaggtc aaggaggcga agaagaggcg    600

cgaggagagg atcgccacca agaagcaaga gatcatgcag gcgtacgccc gagaagacga    660

ggctgccgtc aaaaagtgat ctcgcccccct ccgtttttaa attttaaaca aaaaacgtat    720

tttgtacaaa aatttacaaa aaaaaaaaaa aaaaaaaaaa aaaaaaaaaa aaaagtactc    780

tgcgttgata ccactgcttg ccctctattg agtcgaaaaa aaaaaaaaaa aaaaaagtac    840

tctgcgttga taccactgc                                                 859
```

<210> SEQ ID NO 254
<211> LENGTH: 1145
<212> TYPE: DNA
<213> ORGANISM: Lygus hesperus

<400> SEQUENCE: 254

```
tgggttgttg gagtgctcct accccaacac gggagcaaaa gtcatgttgt tccttggtgg     60

cccttgttcc caagggcctg gtcaagttgt caatgatgac ctgagggaac ctatccgctc    120

tcatcatgac atccagaaag ataatgcccg ctacatgaaa aaagccatta aacattacga    180

ttctttggca ttgagagcag ccactaatgg gcattcagta gacatttatt cctgtgcttt    240
```

agatcagaca ggtttggcgg aaatgaagca atgttgcaat tctactgggg gtcatatggt 300
gatgggtgac accttcaact ccactttgtt caaacagacg ttccagaggg tgctctcccg 360
tgatcaaaaa ggcgaattca aaatggcttt caatggcgta gttgaagtca aaacctcccg 420
agagctaaaa gttatgggag ccattgggcc ttgcgtttca ttgaatacga aaggtccgtg 480
tgttagtgaa actgacatag ggcttggagg aacttgccag tggaagttct gcacatttaa 540
ccaaaatacc actgctgcca tgttctttga ggtagtaaac caacacgctg ctcctatccc 600
tcaaggtgga agaggatgta tacagttcat aactcaatac cagcatgcgt cgggccaaag 660
gcgcatccga gtaaccactg tagccaggaa ttgggctgat gcgactacca acatgcacca 720
tgttagtgca ggatttgatc aggaagctgg agcggtactc atggccagga tggtcgttca 780
cagagctgaa actgatgatg gacctgatgt catgagatgg gctgatcgca tgttgattcg 840
tctttgccag aaattcggcg agtacaacaa ggatgatcca aatagtttcc gcctcccaga 900
aaacttctcg ctttacccac agttcatgta tcacttgaga aggtcccaat tcttgcaggt 960
attcaacaac agcccagacg aaacgtcgta ctatcgtcac atcttgatgc gggaagattt 1020
gtcgcagagc ttgatcatga ttcagccgat cctgtacagt tacagtttca acggtccaga 1080
accagtcctt ttggacactt ccagcattca acctgatcgg atcctgctga tggacacctt 1140
cttcc 1145

<210> SEQ ID NO 255
<211> LENGTH: 350
<212> TYPE: DNA
<213> ORGANISM: Lygus hesperus

<400> SEQUENCE: 255
gagactttga aactgctgac cgagttttgc ccactattcc tgttcagcat cgctcaagag 60
ttgctcattt cctggaaaaa cagggcttca aaaggcaagc tctggctgtg tccacggatg 120
ccgagcacaa gtttgaactt gcgcttcagc tcagtgattt ggaagcagca gtcggcctag 180
cgagggaaat cggcagcaaa gccaagtggg tgcaggtcgc agagttggcg atgtcagagg 240
ccaagctagg actcgctcag atgtgcttgc atcaggcaca gcactacgga ggacttctgc 300
tcctgtcaac ttctgccgga aatgtggaca tgatggagaa actggccgaa 350

<210> SEQ ID NO 256
<211> LENGTH: 407
<212> TYPE: DNA
<213> ORGANISM: Lygus hesperus

<400> SEQUENCE: 256
cgaggcccat tctgattatt tgagatgcat catcgtacat cctacacagc cttacatatt 60
gacgtgcagc gatgacatgc tgatcaagct gtggaactgg gaaaaaaatt ggctatgcca 120
gcaagtcttc gaaagccaca cccattacgt catgcagatc gtgctgaacc cgaaggataa 180
caacactttc gcctctgcct cgctcgacca caccctcaaa gtgtggcagt tggactctgc 240
agcggccaac ttcactttgg acggacacga aaaaggagtt aactgcgtcg actactacca 300
cggaggagat aagccgtatc tcatctctgg cgcggacgat cacatggtca aaatatggga 360
ttaccagaac aaaacgtgcg ttcagacttt ggagggacac gctcaaa 407

<210> SEQ ID NO 257
<211> LENGTH: 44
<212> TYPE: DNA

<213> ORGANISM: Artificial
<220> FEATURE:
<223> OTHER INFORMATION: Primer

<400> SEQUENCE: 257
gcgtaatacg actcactata ggtgggttgt tggagtgctc ctac 44

<210> SEQ ID NO 258
<211> LENGTH: 22
<212> TYPE: DNA
<213> ORGANISM: Artificial
<220> FEATURE:
<223> OTHER INFORMATION: Primer

<400> SEQUENCE: 258
ggaagaaggt gtccatcagc ag 22

<210> SEQ ID NO 259
<211> LENGTH: 22
<212> TYPE: DNA
<213> ORGANISM: Artificial
<220> FEATURE:
<223> OTHER INFORMATION: Primer

<400> SEQUENCE: 259
tgggttgttg gagtgctcct ac 22

<210> SEQ ID NO 260
<211> LENGTH: 44
<212> TYPE: DNA
<213> ORGANISM: Artificial
<220> FEATURE:
<223> OTHER INFORMATION: Primer

<400> SEQUENCE: 260
gcgtaatacg actcactata ggggaagaag gtgtccatca gcag 44

<210> SEQ ID NO 261
<211> LENGTH: 45
<212> TYPE: DNA
<213> ORGANISM: Artificial
<220> FEATURE:
<223> OTHER INFORMATION: Primer

<400> SEQUENCE: 261
gcgtaatacg actcactata gggagacttt gaaactgctg accga 45

<210> SEQ ID NO 262
<211> LENGTH: 20
<212> TYPE: DNA
<213> ORGANISM: Artificial
<220> FEATURE:
<223> OTHER INFORMATION: Primer

<400> SEQUENCE: 262
ttcggccagt ttctccatca 20

<210> SEQ ID NO 263
<211> LENGTH: 23
<212> TYPE: DNA
<213> ORGANISM: Artificial
<220> FEATURE:
<223> OTHER INFORMATION: Primer

<400> SEQUENCE: 263
gagactttga aactgctgac cga 23

<210> SEQ ID NO 264
<211> LENGTH: 40
<212> TYPE: DNA
<213> ORGANISM: Artificial
<220> FEATURE:
<223> OTHER INFORMATION: Primer

<400> SEQUENCE: 264
gcgtaatacg actcactata ggttcggcca gtttctccat 40

<210> SEQ ID NO 265
<211> LENGTH: 44
<212> TYPE: DNA
<213> ORGANISM: Artificial
<220> FEATURE:
<223> OTHER INFORMATION: Primer

<400> SEQUENCE: 265
gcgtaatacg actcactata ggcgaggccc attctgatta tttg 44

<210> SEQ ID NO 266
<211> LENGTH: 20
<212> TYPE: DNA
<213> ORGANISM: Artificial
<220> FEATURE:
<223> OTHER INFORMATION: Primer

<400> SEQUENCE: 266
tttgagcgtg tccctccaaa 20

<210> SEQ ID NO 267
<211> LENGTH: 22
<212> TYPE: DNA
<213> ORGANISM: Artificial
<220> FEATURE:
<223> OTHER INFORMATION: Primer

<400> SEQUENCE: 267
cgaggcccat tctgattatt tg 22

<210> SEQ ID NO 268
<211> LENGTH: 42
<212> TYPE: DNA
<213> ORGANISM: Artificial
<220> FEATURE:
<223> OTHER INFORMATION: Primer

<400> SEQUENCE: 268
gcgtaatacg actcactata ggtttgagcg tgtccctcca aa 42

<210> SEQ ID NO 269
<211> LENGTH: 767
<212> TYPE: PRT
<213> ORGANISM: Lygus hesperus

<400> SEQUENCE: 269

```
Met Thr Thr Tyr Glu Glu Phe Ile Gln Gln Ser Glu Glu Arg Asp Gly
1               5                   10                  15

Ile Arg Phe Thr Trp Asn Val Trp Pro Ser Ser Arg Ile Glu Ala Thr
            20                  25                  30

Arg Leu Val Val Pro Val Gly Cys Leu Tyr Gln Pro Leu Lys Glu Arg
        35                  40                  45

Thr Asp Leu Pro Ala Ile Gln Tyr Asp Pro Val Leu Cys Thr Arg Asn
```

-continued

```
    50                  55                  60

Thr Cys Arg Ala Ile Leu Asn Pro Met Cys Gln Val Asn Tyr Arg Ala
65                  70                  75                  80

Lys Leu Trp Val Cys Asn Phe Cys Phe Gln Arg Asn Pro Phe Pro Pro
                85                  90                  95

Gln Tyr Ala Ala Ile Ser Glu Gln His Gln Pro Ala Glu Leu Ile Pro
            100                 105                 110

Ser Phe Ser Thr Ile Glu Tyr Thr Ile Ser Arg Ala Gln Phe Leu Pro
        115                 120                 125

Pro Ile Phe Leu Leu Val Val Asp Thr Cys Leu Asp Asp Asp Glu Leu
    130                 135                 140

Gly Ala Leu Lys Asp Ser Leu Gln Thr Ser Leu Ser Leu Leu Pro Thr
145                 150                 155                 160

Asn Ser Leu Val Gly Leu Ile Thr Phe Gly Lys Met Val Gln Val His
                165                 170                 175

Glu Leu Gly Cys Glu Gly Cys Ser Arg Ser Tyr Val Phe Arg Gly Thr
            180                 185                 190

Lys Asp Leu Thr Ser Lys Gln Val Gln Asp Met Leu Gly Ile Gly Lys
        195                 200                 205

Val Ser Ala Ser Pro Gln Gln Gln Gln Gln Arg Ala Met Gly Gly Gln
    210                 215                 220

Gln Pro Phe Pro Thr Asn Arg Phe Ile Gln Pro Ile Gln Ser Cys Asp
225                 230                 235                 240

Met Ser Leu Thr Asp Leu Leu Gly Glu Met Gln Arg Asp Pro Trp Pro
                245                 250                 255

Val Gly Gln Gly Lys Arg Pro Leu Arg Ser Thr Gly Ala Ala Leu Ala
            260                 265                 270

Ile Ala Ile Gly Leu Leu Glu Cys Ser Tyr Pro Asn Thr Gly Ala Lys
        275                 280                 285

Val Met Leu Phe Leu Gly Gly Pro Cys Ser Gln Gly Pro Gly Gln Val
    290                 295                 300

Val Asn Asp Asp Leu Arg Glu Pro Ile Arg Ser His His Asp Ile Gln
305                 310                 315                 320

Lys Asp Asn Ala Arg Tyr Met Lys Lys Ala Ile Lys His Tyr Asp Ser
                325                 330                 335

Leu Ala Leu Arg Ala Ala Thr Asn Gly His Ser Val Asp Ile Tyr Ser
            340                 345                 350

Cys Ala Leu Asp Gln Thr Gly Leu Ala Glu Met Lys Gln Cys Cys Asn
        355                 360                 365

Ser Thr Gly Gly His Met Val Met Gly Asp Thr Phe Asn Ser Thr Leu
    370                 375                 380

Phe Lys Gln Thr Phe Gln Arg Val Leu Ser Arg Asp Gln Lys Gly Glu
385                 390                 395                 400

Phe Lys Met Ala Phe Asn Gly Val Val Glu Val Lys Thr Ser Arg Glu
                405                 410                 415

Leu Lys Val Met Gly Ala Ile Gly Pro Cys Val Ser Leu Asn Thr Lys
            420                 425                 430

Gly Pro Cys Val Ser Glu Thr Asp Ile Gly Leu Gly Gly Thr Cys Gln
        435                 440                 445

Trp Lys Phe Cys Thr Phe Asn Gln Asn Thr Thr Ala Ala Met Phe Phe
    450                 455                 460

Glu Val Val Asn Gln His Ala Ala Pro Ile Pro Gln Gly Gly Arg Gly
465                 470                 475                 480
```

```
Cys Ile Gln Phe Ile Thr Gln Tyr Gln His Ala Ser Gly Gln Arg Arg
                485                 490                 495

Ile Arg Val Thr Thr Val Ala Arg Asn Trp Ala Asp Ala Thr Thr Asn
            500                 505                 510

Met His His Val Ser Ala Gly Phe Asp Gln Glu Ala Gly Ala Val Leu
        515                 520                 525

Met Ala Arg Met Val Val His Arg Ala Glu Thr Asp Asp Gly Pro Asp
    530                 535                 540

Val Met Arg Trp Ala Asp Arg Met Leu Ile Arg Leu Cys Gln Lys Phe
545                 550                 555                 560

Gly Glu Tyr Asn Lys Asp Asp Pro Asn Ser Phe Arg Leu Pro Glu Asn
                565                 570                 575

Phe Ser Leu Tyr Pro Gln Phe Met Tyr His Leu Arg Arg Ser Gln Phe
            580                 585                 590

Leu Gln Val Phe Asn Asn Ser Pro Asp Glu Thr Ser Tyr Tyr Arg His
        595                 600                 605

Ile Leu Met Arg Glu Asp Leu Ser Gln Ser Leu Ile Met Ile Gln Pro
    610                 615                 620

Ile Leu Tyr Ser Tyr Ser Phe Asn Gly Pro Glu Pro Val Leu Leu Asp
625                 630                 635                 640

Thr Ser Ser Ile Gln Pro Asp Arg Ile Leu Leu Met Asp Thr Phe Phe
                645                 650                 655

Gln Ile Leu Ile Phe His Gly Glu Thr Ile Ala Gln Trp Arg Ala Gln
            660                 665                 670

Arg Tyr Gln Asp Leu Pro Glu Tyr Glu Asn Phe Lys Gln Leu Leu Gln
        675                 680                 685

Ala Pro Val Asp Asp Ala Lys Glu Ile Leu His Thr Arg Phe Pro Met
    690                 695                 700

Pro Arg Tyr Ile Asp Thr Glu Gln Gly Gly Ser Gln Ala Arg Phe Leu
705                 710                 715                 720

Leu Ser Lys Val Asn Pro Ser Gln Thr His Asn Asn Met Tyr Gly Tyr
                725                 730                 735

Gly Gly Glu Phe Gly Ala Pro Val Leu Thr Asp Asp Val Ser Leu Gln
            740                 745                 750

Val Phe Met Glu His Leu Lys Lys Leu Ala Val Ser Phe Thr Ala
        755                 760                 765


<210> SEQ ID NO 270
<211> LENGTH: 938
<212> TYPE: PRT
<213> ORGANISM: Lygus hesperus

<400> SEQUENCE: 270

Met Pro Leu Lys Leu Asp Ile Lys Arg Lys Leu Ser Ala Arg Ser Asp
1               5                   10                  15

Arg Val Lys Cys Val Asp Leu His Pro Thr Glu Pro Trp Met Leu Ala
            20                  25                  30

Ser Leu Tyr Asn Gly Asn Val His Ile Trp Asn His Glu Thr Gln Gln
        35                  40                  45

Leu Leu Lys Ser Phe Glu Val Cys Glu Leu Pro Ile Arg Ala Ala Val
    50                  55                  60

Phe Val Pro Arg Lys Asn Trp Val Val Thr Gly Ser Asp Asp Met His
65                  70                  75                  80

Val Arg Val Phe Asn Tyr Asn Thr Leu Glu Arg Val His Ser Phe Glu
```

-continued

```
                85                  90                  95

Ala His Ser Asp Tyr Leu Arg Cys Ile Ile Val His Pro Thr Gln Pro
            100                 105                 110

Tyr Ile Leu Thr Cys Ser Asp Asp Met Leu Ile Lys Leu Trp Asn Trp
        115                 120                 125

Glu Lys Asn Trp Leu Cys Gln Gln Val Phe Glu Ser His Thr His Tyr
    130                 135                 140

Val Met Gln Ile Val Leu Asn Pro Lys Asp Asn Asn Thr Phe Ala Ser
145                 150                 155                 160

Ala Ser Leu Asp His Thr Leu Lys Val Trp Gln Leu Asp Ser Ala Ala
                165                 170                 175

Ala Asn Phe Thr Leu Asp Gly His Glu Lys Gly Val Asn Cys Val Asp
            180                 185                 190

Tyr Tyr His Gly Gly Asp Lys Pro Tyr Leu Ile Ser Gly Ala Asp Asp
        195                 200                 205

His Met Val Lys Ile Trp Asp Tyr Gln Asn Lys Thr Cys Val Gln Thr
    210                 215                 220

Leu Glu Gly His Ala Gln Asn Ile Thr Ala Val Cys Leu His Thr Glu
225                 230                 235                 240

Leu Pro Ile Ala Ile Thr Gly Ser Glu Asp Gly Thr Val Arg Leu Trp
                245                 250                 255

His Ser Ala Thr Tyr Arg Leu Glu Ser Ser Leu Asn Tyr Gly Phe Glu
            260                 265                 270

Arg Val Trp Ala Ile Arg Cys Leu Lys Gly Ser Asn His Ile Ala Leu
        275                 280                 285

Gly Tyr Asp Glu Gly Ser Ile Met Val Lys Val Gly Arg Glu Glu Pro
    290                 295                 300

Ala Ile Ser Met Asp Val Asn Gly Glu Lys Ile Val Trp Ala Arg His
305                 310                 315                 320

Ser Glu Ile Gln Gln Val Asn Leu Lys Ser Leu Met Thr Asp Glu Ser
                325                 330                 335

Glu Ile Arg Asp Gly Glu Lys Leu Pro Val Ala Ala Lys Asp Met Gly
            340                 345                 350

Pro Cys Glu Val Phe Pro Gln Ser Ile Ala His Asn Pro Asn Gly Arg
        355                 360                 365

Phe Val Val Val Cys Gly Asp Gly Glu Tyr Ile Ile Tyr Thr Ala Met
    370                 375                 380

Ala Leu Arg Asn Lys Ser Phe Gly Ser Ala Gln Glu Phe Val Trp Ala
385                 390                 395                 400

Gln Asp Ser Ser Asp Tyr Ala Ile Arg Glu Gly Thr Ser Thr Val Arg
                405                 410                 415

Leu Phe Arg Gln Phe Lys Glu Arg Lys Asn Phe Lys Pro Glu Phe Gly
            420                 425                 430

Ala Glu Gly Ile Phe Gly Gly Gln Leu Leu Gly Val Arg Thr Val Thr
        435                 440                 445

Gly Leu Ser Leu Tyr Asp Trp Glu Thr Leu Glu Leu Ile Arg Ser Ile
    450                 455                 460

Asp Ile Gln Ala Lys Ala Pro Tyr Trp Ser Glu Ala Gly His Leu Leu
465                 470                 475                 480

Ala Ile Val Thr Asp Asp Ser Tyr Tyr Leu Leu Lys Phe Asp Gln Ser
                485                 490                 495

Ala Ile Ser Thr Ser Thr Pro Gly Thr Asp Gly Tyr Glu Asp Ala Phe
            500                 505                 510
```

-continued

```
Glu Leu Val Gly Glu Val Asn Asp Thr Val Lys Thr Gly Leu Trp Val
        515                 520                 525

Gly Asp Cys Phe Ile Tyr Thr Asn Ala Val Cys Arg Ile Asn Tyr Tyr
    530                 535                 540

Val Gly Gly Glu Ile Val Thr Val Ala His Leu Asp Thr Thr Met Tyr
545                 550                 555                 560

Leu Leu Gly Tyr Val Ala Arg Gln Asn Leu Leu Tyr Leu Cys Asp Lys
                565                 570                 575

His His Asn Ile Ile Cys Tyr Thr Leu Leu Leu Ser Val Leu Glu Tyr
            580                 585                 590

Gln Thr Ala Val Met Arg Arg Asp Phe Glu Thr Ala Asp Arg Val Leu
        595                 600                 605

Pro Thr Ile Pro Val Gln His Arg Ser Arg Val Ala His Phe Leu Glu
    610                 615                 620

Lys Gln Gly Phe Lys Arg Gln Ala Leu Ala Val Ser Thr Asp Ala Glu
625                 630                 635                 640

His Lys Phe Glu Leu Ala Leu Gln Leu Ser Asp Leu Glu Ala Ala Val
                645                 650                 655

Gly Leu Ala Arg Glu Ile Gly Ser Lys Ala Lys Trp Val Gln Val Ala
            660                 665                 670

Glu Leu Ala Met Ser Glu Ala Lys Leu Gly Leu Ala Gln Met Cys Leu
        675                 680                 685

His Gln Ala Gln His Tyr Gly Gly Leu Leu Leu Leu Ser Thr Ser Ala
    690                 695                 700

Gly Asn Val Asp Met Met Glu Lys Leu Ala Glu Ser Ser Leu Ser Asp
705                 710                 715                 720

Gly Lys Asn Asn Val Ser Phe Leu Thr Tyr Phe Leu Met Gly Asn Val
                725                 730                 735

Glu Lys Cys Leu Gln Ile Leu Ile Asp Thr Gly Arg Ile Pro Glu Ala
            740                 745                 750

Ala Phe Phe Ala Arg Thr Tyr Met Pro Lys Glu Val Ser Arg Val Val
        755                 760                 765

Asp Met Trp Lys Thr Leu Ser Lys Asp Lys Thr Gly Gln Ser Leu Ala
    770                 775                 780

Asp Pro Ala Gln Tyr Pro Asn Leu Phe Pro Lys His Thr Glu Ala Leu
785                 790                 795                 800

Lys Ala Glu Gln Phe Met Lys Lys Glu Leu Thr Gln Arg Ile Pro Ala
                805                 810                 815

Ser Ser His Lys Asp Ile Lys Pro Asn Tyr Glu Arg Asn Ala Ile Glu
            820                 825                 830

Glu Met Lys Glu Ala Glu Ala Asn Gly Leu Phe Thr Tyr Asp Pro Pro
        835                 840                 845

Val Ala Pro Ala Ser Ile Asn Asn Leu Ile Asp Val Ser Glu Pro Ala
    850                 855                 860

Asn Arg Ser Glu Pro Ser Pro Ser Glu Ile Phe Ser Glu Ala Pro Val
865                 870                 875                 880

Val Ser Lys Met Thr Ser Asp Ala Arg Pro Leu Val Ala Pro Val Pro
                885                 890                 895

Pro Ala Ala Arg Pro Gln Lys Arg Pro Ser Ala Phe Asp Asp Asp Asp
            900                 905                 910

Leu Glu Leu Glu Ile Glu Asn Met Asn Leu Asp Asp Ile Asp Ala Ser
        915                 920                 925
```

Asp Leu Asn Glu Glu Asp Leu Leu Ile Asp
    930                 935

<210> SEQ ID NO 271
<211> LENGTH: 198
<212> TYPE: PRT
<213> ORGANISM: Lygus hesperus

<400> SEQUENCE: 271

Met Ser Ser Leu Lys Leu Gln Lys Arg Leu Ala Ala Ser Val Met Arg
1               5                   10                  15

Cys Gly Lys Lys Lys Val Trp Leu Asp Pro Asn Glu Ile Asn Glu Ile
            20                  25                  30

Ala Asn Thr Asn Ser Arg Gln Asn Ile Arg Lys Leu Ile Lys Asp Gly
        35                  40                  45

Leu Ile Ile Lys Lys Pro Val Ala Val His Ser Arg Ala Arg Val Arg
    50                  55                  60

Lys Asn Thr Glu Ala Arg Arg Lys Gly Arg His Cys Gly Phe Gly Lys
65                  70                  75                  80

Arg Lys Gly Thr Ala Asn Ala Arg Met Pro Val Lys Val Leu Trp Val
                85                  90                  95

Asn Arg Met Arg Val Leu Arg Arg Leu Leu Lys Lys Tyr Arg Glu Ala
            100                 105                 110

Lys Lys Ile Asp Arg Gln Met Tyr His Asp Leu Tyr Met Lys Ala Lys
        115                 120                 125

Gly Asn Val Phe Lys Asn Lys Arg Val Leu Met Asp Phe Ile His Lys
    130                 135                 140

Lys Lys Ala Glu Lys Ala Arg Ser Lys Met Leu Lys Asp Gln Ala Glu
145                 150                 155                 160

Ala Arg Arg Phe Lys Val Lys Glu Ala Lys Lys Arg Arg Glu Glu Arg
                165                 170                 175

Ile Ala Thr Lys Lys Gln Glu Ile Met Gln Ala Tyr Ala Arg Glu Asp
            180                 185                 190

Glu Ala Ala Val Lys Lys
        195

<210> SEQ ID NO 272
<211> LENGTH: 311
<212> TYPE: DNA
<213> ORGANISM: Artificial
<220> FEATURE:
<223> OTHER INFORMATION: GUS

<400> SEQUENCE: 272
ccagcgtatc gtgctgcgtt tcgatgcggt cactcattac ggcaaagtgt gatggagcat 60
cagggcggct atacgccatt tgaagccgat gtcacgccgt atgttattgc cgggaaaagt 120
gtacgtatct gaaatcaaaa aactcgacgg cctgtgggca ttcagtctgg atcgcgaaaa 180
ctgtggaatt gatccagcgc cgtcgtcggt gaacaggtat ggaatttcgc cgattttgcg 240
acctcgcaag gcatattcgg gtgaaggtta tctctatgaa ctgtgcgtca cagccaaaag 300
ccagacagag t 311

<210> SEQ ID NO 273
<211> LENGTH: 596
<212> TYPE: DNA
<213> ORGANISM: Lygus hesperus

<400> SEQUENCE: 273

```
gtgtagtgca tggtgttact gaaagtttgg taacgcccta gcgcaaacat gcagattttc     60

gtcaaaaccc tcacgggtaa gaccatcacc cttgaggtcg agccttctga taccatcgag    120

aatgtgaagg ctaagatcca ggacaaggag ggaatccccc cggatcagca gcgtcttatc    180

ttcgccggta agcaattgga agatggccgc accctttctg actacaacat ccagaaagaa    240

tccaccttgc acttggtgct caggcttcgt ggtggtgcca agaaaaggaa gaagaagaac    300

tactccactc ccaagaagat caagcacaag aagaagaaga ttaagttggc tgtgcttaaa    360

tactacaagg ttgacgagaa cggcaaaatc agccgattga ggagggagtg tccgtcagag    420

caatgcggtg ccggtgtttt catggctgcc atggaagata ggcattactg tggaaagtgc    480

agttacactc ttgtttttaa taaacccgag gagaaataaa ttttttaaa tataatgtta     540

cgccgttaaa atacacattt gaacggttaa aaaaaaaaaa aaaaaaaaaa aaaaaa        596
```

<210> SEQ ID NO 274
<211> LENGTH: 603
<212> TYPE: DNA
<213> ORGANISM: Lygus hesperus

<400> SEQUENCE: 274

```
ttacttgcgt tactcaggat tgtcgctaaa attgttgaat tttcgttttg ttcatcatag     60

gtgaacgatg caaattttcg tcaaaaccct cacgggtaaa actattaccc tcgaagttga    120

gccttcggac actatcgaaa atgtcaaagc taaaatccaa gacaaggaag ggattccccc    180

agaccagcag aggttgatct tcgctggcaa gcagctcgaa gatggccgca cactttccga    240

ctacaacatc cagaaagagt ccacccttca cttggtcctc cgtttgagag gaggagtcat    300

cgagcccacc ctcaggatct tggctcagaa gtacaactgc gacaagatga tttgcaggaa    360

gtgctacgct cgtctccacc ccagggcgac caactgtcgc aagaagaaat gcggacacac    420

caacaacatc cgccccaaga agaagctgaa gtaaactata atttcccttt gggaaccatc    480

cttcaagggg gttccctctc accaatattt ttttcttttt tcatggacaa aatcctgatg    540

ttaactttca aggataaata aaatcaagag tttaaaaaaa aaaaaaaaaa aaaaaaaaaa    600

aaa                                                                  603
```

<210> SEQ ID NO 275
<211> LENGTH: 3278
<212> TYPE: DNA
<213> ORGANISM: Lygus hesperus

<400> SEQUENCE: 275

```
gataacgccg cggagcttta tgcttgtctt gtctcatttt ccgtgttttt cgtataaatt     60

gggaatttgt tcgtgatatt tgtggttttg aaatattaaa aacaacttgc aaaactatca    120

acattcacgg taaagatggg gatggtcgta gagcagccat gttactcgct gatcaatttt    180

gcggcggact cggagccagt tagcgaaatg cagctgaaac aagattttga atctgggagc    240

acagctcaga aagttgaagc tctcaagaaa acgattcaca tgatttccaa cggcgagcgt    300

ttaccgggtc ttctgatgca tatcatcaga ttcattctgc cttcccagga ccacacgatc    360

aaaaagttgc tgctaatatt ctgggagatc gttcctaaaa cttaccccga tggaaaactg    420

cttcaagaaa tgatacttgt ttgcgacgcc tacagaaagg atttacaaca ccccaatgag    480

ttcgtgcgcg ggtcgacttt gagattcctc tgcaaattga aggagccaga acttctggaa    540

ccgctgatgc ctgccattcg gtcgtgcctc gagcacagag tgtcttacgt ccgcaggaac    600
```

-continued

```
gctgtccttg ccattttcac gatctacaag aatttcgaat ttctaatccc tgatgctccc    660
gaactcattg ccaatttcct cgacggagag caagatatgt cttgcaaaag gaatgccttc    720
ttgatgctcc tccacgctga ccaagacaga gcactctcct atcttgcttc ttgtctggac    780
caagtcacca gctttggcga catcctccag cttgtcatcg ttgaattgat ttacaaggtt    840
tgtcatgcga atccctcaga acgttctcgg ttcattaggt gcatatacaa cctattgaat    900
tcaagcagcc ctgctgtccg atatgaagct gctggtacgc tgataaccct gtccaacgca    960
cctactgcca tcaaggctgc tgcatcatgc tacattgatc taatcatcaa ggaaagcgat   1020
aacaacgtca aactgatcgt cctcgatcgc ctggtcgccc tcaaagacat cccgacgtac   1080
gaaagagtct tgcaggatct cgtcatggac atcctccgcg tcttggccag cccggatatg   1140
gaagtcagga agaaggcttt gaatctcgct cttgatctta caacttcgcg ttgtgtcgaa   1200
gaagtagttt tgatgctgaa gaaagaggtt gccaaaactc ataacttgtc cgagcacgag   1260
gaaacaggaa aatataggca actccttgtg agaactctgc actcttgcag catgaaattc   1320
cctgatgtgg ctgcttcagt catcccagtg ctcatggaat tttgtctga ctccaacgag    1380
ctcgcttccc aagacgtcct tattttcgta agggaagcca ttcacaaatt tgaaaatctg   1440
aggaacacaa tcattgagaa attgcttgaa gcttttccgt ccataaagtt cgtcaaagtc   1500
catcgtgctg cgttgtggat attaggagag tacgctgctt ccatcgatga cgtcagagct   1560
gtcatgaaac aaattaaaca gaatttgggt gaggttccta tggtggaaga tgaaatgaag   1620
cgggccgctg gagagaagac ggaagagtca tctgaacaga acagcggggg tgcaatgccg   1680
tcaagcgctt ccaaactagt aacgtctgat gggacctatg cttctcagtc tgtgttcagc   1740
actgtatcca catccaaaaa agaggaccga ccacctttga ggcagtatct gattgatggt   1800
gattatttta ttggctccac catcgcgtcc actttggtga aactttctct gaagtttgac   1860
aacttggaat ccaacacggc tgcgcagaac gaattctgca atgaatgcat gctgatcatc   1920
gcttgcaccc tccatcttgg aagatctggc ctttgcacaa agaatttgaa taacgacgac   1980
gctgagagga tgctgttttg tcttcgagtt ctttgggatg gaagcccaac cattgagaag   2040
atttttactc aagaatgccg agaagctctt gcgtctatgc ttaccgctca acaccatgag   2100
gaaatcgcct tgaataaggc caaagaaaag accgcacatc tcatccacgt agacgaccca   2160
gtctcattcc tgcaattatc atctctgaga aactctgaac ttggttctga aaacgtgttc   2220
gagctaagtc ttactcaggc gcttggtggt cccaccagtg gtggctcctc caactcggac   2280
ctcttcttct ctgccagcaa gctcaacaaa gtcacgcagc ttactggctt ttctgaccct   2340
gtctacgctg aagcttacgt ccaagtcaac cagtatgata tcgtcttgga cgtactcatt   2400
gtcaaccaga cagctgacac tcttcaaaat tgcactctgg aattggctac acttggcgac   2460
ctgaaattgg tcgagaagcc gcaaccctgc gttttggcgc ctcatgactt ctgtaacata   2520
aaagctaacg tcaaagtggc ttccactgaa aacggaatta tttttggcaa cattgtttac   2580
gacgttagtg gagcagcttc cgaccgaaac gtcgtcgtcc tcaatgacat tcacatcgat   2640
attatggact acatagttcc tgcatcttgt tctgacactg aattccgcca aatgtgggct   2700
gaattcgaat gggaaaacaa ggtatctgtc aacaccaacc tcacggactt gcacgagtat   2760
ttggcccatt tggtcaggag caccaacatg aagtgcttga caccagagaa agcgctctgc   2820
ggtcaatgtg ggttcatggc tgccaacatg tatgcgcgct cgattttcgg agaagatgcg   2880
ttggcgaacc tgagcatcga gaaacccttc aacaagcctg atgcacctgt cactggacac   2940
atccgcatcc gagccaaaag ccagggaatg gcactcagtt tgggagacaa aatcaacatg   3000
```

acccagaaga gaccgcagaa aatgtacggt gcctaagccc tcatagatcc caccacctcg 3060
gttcaacttt ccatttcctt tgtgagagca ccctactgct tacctgcgcc acactgcaag 3120
taaacttggc ttcggcctcc tatttatcat attttacggt attctttgtt atcgaaatat 3180
ttatgcatat tatattattg gcatttcgtt atcccaattc attcaataaa tatatagatt 3240
aatttactaa aaaaaaaaaa aaaaaaaaaa aaaaaaaa 3278

<210> SEQ ID NO 276
<211> LENGTH: 806
<212> TYPE: DNA
<213> ORGANISM: Lygus hesperus

<400> SEQUENCE: 276
tccttcgcct gttggatttt tggtcgctcc acttttcccc atacatacgt tttgtcagga 60
aacttctgta aaggtttgtt cgagtaattg attatggcga gtcaaactca aggaatccaa 120
cagctcctcg cagctgagaa acgagccgcc gagaaggttg cggaagcaaa gaaaaggaaa 180
gctcgccgtt tgaagcaggc caaggaagag gctcaggagg aaattgaaag gtacaagcaa 240
gacagagaga agcagttcaa ggagttcgaa gcccagcaca tgggctccag ggaggacgtt 300
gctgccagga tagacgctga cactcgtcag agaattgaag agatgacaaa agctgtcaat 360
gtcaacaaag aacaagtgat ccaaagaata ctggaacttg tgtacgacat cagacctgaa 420
atgcacaaga attaccgtcc taccttgtag aaaaatgtac attaaacgca ttatactgaa 480
ttaaattcaa tatattgaac aaatcattat tataatatcg agtatttttg aattctgtga 540
tggtttttgt tgtcaaaatt atttgccact cgaggcttgt atccctacaa atgttgtagg 600
ttagctgtac ttcctgtgtg ctgcacacaa tgaataaatt cagtagaatt acattccacg 660
attctatttc tgttaatact attgttgttt ttttccgtgt ttttacgaaa cccattctgt 720
gaaatggaac ttgtatgtat cataactaac ccaaatacat tattagacta actagtaaaa 780
aaaaaaaaaa aaaaaaaaaa aaaaaa 806

<210> SEQ ID NO 277
<211> LENGTH: 717
<212> TYPE: DNA
<213> ORGANISM: Lygus hesperus

<400> SEQUENCE: 277
aaagtgtggt tctcttcgtc cgaccatgag ttcgctcaaa ctgcagaaga ggctcgccgc 60
ctcggtgatg agatgcggca agaagaaagt gtggttggac cctaatgaaa tcaacgaaat 120
cgccaacacc aactctaggc aaaacatccg taagctgatc aaggatggtt tgatcatcaa 180
aaagcctgtg gctgtccact ccagagcccg cgtccgtaaa aacacagaag ccagacggaa 240
gggtcgtcat tgtggcttcg gtaagaggaa gggtaccgcc aacgccagaa tgcctgtgaa 300
ggtcctgtgg gtcaacagaa tgagagtcct gcgacggctc cttaaaaaat acagagaagc 360
caagaagatc gataggcaaa tgtaccacga cctttacatg aaagccaaag gtaacgtctt 420
caaaaacaag agggtactga tggacttcat tcacaagaag aaggctgaaa aggcgagatc 480
aaagatgttg aaggaccagg cagaggcgag acgtttcaag gtcaaggagg cgaagaagag 540
gcgcgaggag aggatcgcca ccaagaagca agagatcatg caggcgtacg cccgagaaga 600
cgaggctgcc gtcaaaaagt gatctcgccc cctccgtttt taaattttaa acaaaaaacg 660
tattttgtac aaaaatttac aaaaaaaaaa aaaaaaaaaa aaaaaaaaaa aaaaaaa 717

<210> SEQ ID NO 278
<211> LENGTH: 2304
<212> TYPE: DNA
<213> ORGANISM: Lygus hesperus

<400> SEQUENCE: 278
atgacgacct acgaggagtt cattcaacag agcgaggagc gcgacggtat caggttcact 60
tggaacgtct ggccatcaag tcgcatcgaa gccaccaggt tggtcgtacc cgtaggatgt 120
ctctatcaac cactaaaaga acgcacggat cttccagcta ttcaatacga tcccgttcta 180
tgcactagga atacctgtag agccatactc aacccgatgt gccaagtaaa ctatagggca 240
aagttgtggg tgtgtaactt ctgtttccag aggaatccgt tcccaccaca atacgccgca 300
atttccgagc agcatcagcc tgctgagttg attccatcat tctcaactat agagtatact 360
atatctagag ctcaattttt gcctcctata ttcctattgg tggtggatac gtgtttggat 420
gatgacgagc taggagctct gaaagattcg ttacaaacgt ctctatcttt gctaccaacc 480
aactccctag ttggtctgat cacgtttggt aaaatggtcc aagttcacga acttgggtgt 540
gaaggttgtt cccggagcta cgtgttcaga ggcaccaagg atttgacgtc caagcaagta 600
caggacatgc ttgggatcgg aaaggtttcc gcttctcctc agcaacagca gcaaagggca 660
atgggcggtc agcagccatt ccccaccaat cggttcattc agccgattca aagttgtgac 720
atgagcctca ccgacttgtt gggcgaaatg cagcgtgatc catggccagt gggtcagggt 780
aagcgacctc ttagatcaac gggtgctgct ctagctattg ccattgggtt gttggagtgc 840
tcctacccca acacgggagc aaaagtcatg ttgttccttg gtggcccttg ttcccaaggg 900
cctggtcaag ttgtcaatga tgacctgagg gaacctatcc gctctcatca tgacatccag 960
aaagataatg cccgctacat gaaaaaagcc attaaacatt acgattcttt ggcattgaga 1020
gcagccacta atgggcattc agtagacatt tattcctgtg ctttagatca gacaggtttg 1080
gcggaaatga agcaatgttg caattctact gggggtcata tggtgatggg tgacaccttc 1140
aactccactt tgttcaaaca gacgttccag agggtgctct cccgtgatca aaaaggcgaa 1200
ttcaaaatgg ctttcaatgg cgtagttgaa gtcaaaacct cccgagagct aaaagttatg 1260
ggagccattg ggccttgcgt ttcattgaat acgaaaggtc cgtgtgttag tgaaactgac 1320
atagggcttg gaggaacttg ccagtggaag ttctgcacat ttaaccaaaa taccactgct 1380
gccatgttct ttgaggtagt aaaccaacac gctgctccta tccctcaagg tggaagagga 1440
tgtatacagt tcataactca ataccagcat gcgtcgggcc aaaggcgcat ccgagtaacc 1500
actgtagcca ggaattgggc tgatgcgact accaacatgc accatgttag tgcaggattt 1560
gatcaggaag ctggagcggt actcatggcc aggatggtcg ttcacagagc tgaaactgat 1620
gatggacctg atgtcatgag atgggctgat cgcatgttga ttcgtctttg ccagaaattc 1680
ggcgagtaca acaaggatga tccaaatagt ttccgcctcc cagaaaactt ctcgctttac 1740
ccacagttca tgtatcactt gagaaggtcc caattcttgc aggtattcaa caacagccca 1800
gacgaaacgt cgtactatcg tcacatcttg atgcgggaag atttgtcgca gagcttgatc 1860
atgattcagc cgatcctgta cagttacagt ttcaacggtc cagaaccagt ccttttggac 1920
acttccagca ttcaacctga tcggatcctg ctgatggaca ccttcttcca aatcctcatc 1980
ttccacggcg agaccatcgc ccagtggcgt gcccaaaggt accaggacct acctgaatat 2040
gagaacttca agcagctcct acaggctcct gtagacgatg ctaaggaaat cctgcacact 2100
cggttcccca tgccgaggta cattgacacc gaacagggcg gatcacaagc tagattcctt 2160
ctctccaaag tcaacccatc ccaaactcac aacaacatgt acggctatgg aggggaattt 2220
ggagcccctg tgctcactga tgatgtttcc ctccaagtct tcatggaaca ccttaaaaag 2280
ctagccgttt catttactgc ctag 2304

<210> SEQ ID NO 279
<211> LENGTH: 2962
<212> TYPE: DNA
<213> ORGANISM: Lygus hesperus

<400> SEQUENCE: 279
atgtggttta atttgtttga cgtaaatttg taacattttg attccgaatt taattgatat 60
ttcgccctta tgcctctcag attggacatc aagagaaagc tgtctgctcg atcagaccgt 120
gtgaaatgtg tcgatctgca cccaactgag ccgtggatgt tggcttctct ctacaacgga 180
aacgtacaca tttggaacca cgaaactcaa cagcttctga aatccttcga agtatgcgag 240
cttccaatca gggctgcagt tttcgtaccg aggaagaact gggtggtcac aggctcggac 300
gacatgcacg ttcgtgtctt caactacaac actctcgagc gtgtacattc cttcgaggcc 360
cattctgatt atttgagatg catcatcgta catcctacac agccttacat attgacgtgc 420
agcgatgaca tgctgatcaa gctgtggaac tgggaaaaaa actggctatg ccagcaagtc 480
ttcgaaagcc acacccatta cgtcatgcag atcgtgctga acccgaagga taacaatact 540
ttcgcctctg cctcgctcga ccacaccctc aaagtgtggc agttgggatc agcagcggcc 600
aacttcactt tggacggaca cgaaaaagga gtgaactgcg tcgactacta ccacggagga 660
gataagcctt atctcatctc tggcgcggac gatcacatgg tcaaaatatg ggattaccag 720
aacaaaacgt gcgtccagac tttggaggga cacgctcaaa atataactgc agtttgcttc 780
cacactgaac taccaatcgc aattactggc tcggaagacg gaaccgttcg cttgtggcac 840
tcagccacct atcgacttga atcgtccttg aactacggct ttgaaagagt atggaccata 900
cgctgtctca aaggctcaaa ccacattgct cttgggtacg acgagggttc cattatggtc 960
aaagttggtc gagaagaacc ggccatttcc atggatgtta atggagaaaa aattgtttgg 1020
gctcgacatt ctgaaatcca gcaggtcaat ttgaagtctc tcatgactga cgagagtgaa 1080
attcgcgatg gggagaaact cccagtagca gctaaagaca tgggtccctg cgaagttttc 1140
ccacaaagca tcgcccacaa ccccaatgga agatttgtgg ttgtttgcgg tgatggagaa 1200
tacatcatct acactgccat ggctttgcgt aataaaagtt tcggttccgc ccaagagttc 1260
gtctgggccc aggactcttc tgactacgcc atccgcgaag ggacgtctac cgtccgactt 1320
ttcaggcagt tcaaggaaag gaagaacttc aagcctgaat ttggagctga aggtattttt 1380
gggggacagc ttctcggagt taggactgta actggactgt ccctctacga ctgggaaact 1440
ttggagttga tcagaagcat cgacattcaa gcgaaagcgc cgtactggtc cgaagcaggg 1500
catctcttgg caatcgttac tgacgacagt tactatctct tgaaattcga ccagagcgcc 1560
atctcgacgt ccacccctgg aactgacggc tacgaagatg cctttgagct cgtcggtgaa 1620
gtcaatgata ctgtcaagac cggattgtgg gttggtgact gtttcatcta cacaaacgcc 1680
gtttgtcgga tcaactacta cgtaggtggt gagatcgtca ccgtggctca cctcgacact 1740
acaatgtacc tcctaggata cgtggcccgc cagaacctgc tgtacctgtg cgacaagcat 1800
cataacatca tttgttacac gttgcttctg tctgtcctcg aatatcagac tgctgtgatg 1860
aggagagact ttgaaactgc tgaccgagtt ttgcccacta ttcctgttca gcatcgctca 1920

```
agagttgctc atttcctgga aaaacagggc ttcaaaaggc aagctctggc tgtgtccacg   1980
gatgccgagc acaagtttga acttgcgctt cagctcagtg atttggaagc agcagtcggc   2040
ctagcgaggg aaatcggcag caaagccaag tgggtgcagg tcgccgagtt ggcgatgtca   2100
gaggccaagc taggactcgc tcagatgtgc ttgcatcagg cacagcacta cggaggactt   2160
ctgctcctgt caacttctgc cggaaatgtg gacatgatgg agaaactggc cgaaagctcg   2220
ctgtccgatg gcaaaaacaa cgtctcgttc ctcacttact tcctgatggg taacgtggaa   2280
aagtgtctcc aaatcctcat cgatactgga agaattccgg aagcagcttt cttcgcccgg   2340
acctatatgc ctaaagaagt gtctcgcgtg gtcgacatgt ggaaaaccct ttctaaggac   2400
aagacggggc aatcgctcgc tgacccagcc caatacccga atctattccc caagcacacc   2460
gaggctctga aagccgaaca gttcatgaag aaggaattga ctcaaaggat tcccgcctcg   2520
tcgcacaagg atataaaacc caactacgaa aggaatgcca ttgaagaaat gaaagaagcc   2580
gaagcaaacg gtctgttcac gtatgatcct ccagtggctc ctgccagtat caacaatcta   2640
attgatgttt ctgaaccggc gaatcgatct gagcccagcc cgtctgaaat cttctccgaa   2700
gcgcccgccg tgtccaagat gaccagcgac gctcggccgc tggtcgcgcc agttccgcct   2760
gccgcgagac ctcaaaaacg gccgtcggcc ttcgatgatg acgacctcga attggaaatc   2820
gaaaatatga atttggatga catcgatgct agtgatttga acgaagaaga cctccttata   2880
gattagggat cattgtttta tctatttaaa attactttat ttatcaatta taatccacat   2940
aattaagtat tatcgtacat ga                                             2962
```

<210> SEQ ID NO 280
<211> LENGTH: 1184
<212> TYPE: DNA
<213> ORGANISM: Lygus hesperus

<400> SEQUENCE: 280

```
ggtcggtgga cgaggtcgag aactcttcta gagtcagagt ctgatgtgca cacaatcatc     60
ctggagttga gtcaggccga ttttcctagt gaatgtcaat gtttttctca acgtaaccag    120
ggtcagcttc ctccttaagt ttatttaggt ttacagtgaa aaaatgagtt tcttcagcaa    180
agtgttcgga gggaagaaag atgacaaggg ccctacggct tcggaagcga ttcagaaact    240
ccgcgagact gaagacatgc tagtgaagaa acaggaatat ttggaaacca aaattgaagc    300
tgaaatgaag attatcaaaa agaatgggac ggccaacagg cgtgtatcta tacaagctct    360
aaagaagaaa aagcggtttg aaaaacaact tcaacagatt gatggaactc tgtcgacgat    420
tgaaatgcag agagaagcct tggaatcagc caatactagt tccaaggttg tacaaactat    480
gaaattagct gctgatacac tgaagacagc tcatcagcac atggacgttg atcaagtaca    540
tgacatgatg gatgaaatcg ccgaacagca tgaagcagcg aaggaaatat cagaagccat    600
atctaatcca gttgcttttg gaaacgacat agacgaggat gaactcgaga gggaattaga    660
agaattagaa cagcaagaac tggatagaga acttcttgga acccatactc ctgctgctga    720
tcatttgccg gatgtacctg ctaccattcc agttccacat aaaccaaagc aaactgttgc    780
tgatgaagat gatgatttga agcaacttca ggaatgggca acctaaattg cttgtggtct    840
atcaaagatg ctgcgttact aaatttttga tatgaaaatg tattattctt atgtttattg    900
tttgttccaa agctagaagc attttgaaga atacctacgt gcatatttca gctcaggaat    960
ttttaaaacg agagttgtgt aaataggtct atgtaatgct taataatatt ccaagttcac   1020
taaaactact cattataaca ggaaaaaaaa aagatattct tatactttca atgatgaagt   1080
```

```
ttatttagag ccaccattta ttttcgatga gagaacagaa aatagatcct ctcaataaat   1140

aagttcgata caataaaaaa aaaaaaaaaa aaaaaaaaaa aaaa                    1184


<210> SEQ ID NO 281
<211> LENGTH: 156
<212> TYPE: PRT
<213> ORGANISM: Lygus hesperus

<400> SEQUENCE: 281

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Ala Lys Lys Arg
65                  70                  75                  80

Lys Lys Lys Asn Tyr Ser Thr Pro Lys Lys Ile Lys His Lys Lys Lys
                85                  90                  95

Lys Ile Lys Leu Ala Val Leu Lys Tyr Tyr Lys Val Asp Glu Asn Gly
            100                 105                 110

Lys Ile Ser Arg Leu Arg Arg Glu Cys Pro Ser Glu Gln Cys Gly Ala
        115                 120                 125

Gly Val Phe Met Ala Ala Met Glu Asp Arg His Tyr Cys Gly Lys Cys
    130                 135                 140

Ser Tyr Thr Leu Val Phe Asn Lys Pro Glu Glu Lys
145                 150                 155


<210> SEQ ID NO 282
<211> LENGTH: 128
<212> TYPE: PRT
<213> ORGANISM: Lygus hesperus

<400> SEQUENCE: 282

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Val Ile Glu Pro
65                  70                  75                  80

Thr Leu Arg Ile Leu Ala Gln Lys Tyr Asn Cys Asp Lys Met Ile Cys
                85                  90                  95

Arg Lys Cys Tyr Ala Arg Leu His Pro Arg Ala Thr Asn Cys Arg Lys
            100                 105                 110

Lys Lys Cys Gly His Thr Asn Asn Ile Arg Pro Lys Lys Lys Leu Lys
        115                 120                 125


<210> SEQ ID NO 283
<211> LENGTH: 966
<212> TYPE: PRT
```

<213> ORGANISM: Lygus hesperus

<400> SEQUENCE: 283

Met Gly Met Val Val Glu Gln Pro Cys Tyr Ser Leu Ile Asn Phe Ala
1 5 10 15

Ala Asp Ser Glu Pro Val Ser Glu Met Gln Leu Lys Gln Asp Phe Glu
20 25 30

Ser Gly Ser Thr Ala Gln Lys Val Glu Ala Leu Lys Lys Thr Ile His
35 40 45

Met Ile Ser Asn Gly Glu Arg Leu Pro Gly Leu Leu Met His Ile Ile
50 55 60

Arg Phe Ile Leu Pro Ser Gln Asp His Thr Ile Lys Lys Leu Leu Leu
65 70 75 80

Ile Phe Trp Glu Ile Val Pro Lys Thr Tyr Pro Asp Gly Lys Leu Leu
85 90 95

Gln Glu Met Ile Leu Val Cys Asp Ala Tyr Arg Lys Asp Leu Gln His
100 105 110

Pro Asn Glu Phe Val Arg Gly Ser Thr Leu Arg Phe Leu Cys Lys Leu
115 120 125

Lys Glu Pro Glu Leu Leu Glu Pro Leu Met Pro Ala Ile Arg Ser Cys
130 135 140

Leu Glu His Arg Val Ser Tyr Val Arg Arg Asn Ala Val Leu Ala Ile
145 150 155 160

Phe Thr Ile Tyr Lys Asn Phe Glu Phe Leu Ile Pro Asp Ala Pro Glu
165 170 175

Leu Ile Ala Asn Phe Leu Asp Gly Glu Gln Asp Met Ser Cys Lys Arg
180 185 190

Asn Ala Phe Leu Met Leu Leu His Ala Asp Gln Asp Arg Ala Leu Ser
195 200 205

Tyr Leu Ala Ser Cys Leu Asp Gln Val Thr Ser Phe Gly Asp Ile Leu
210 215 220

Gln Leu Val Ile Val Glu Leu Ile Tyr Lys Val Cys His Ala Asn Pro
225 230 235 240

Ser Glu Arg Ser Arg Phe Ile Arg Cys Ile Tyr Asn Leu Leu Asn Ser
245 250 255

Ser Ser Pro Ala Val Arg Tyr Glu Ala Ala Gly Thr Leu Ile Thr Leu
260 265 270

Ser Asn Ala Pro Thr Ala Ile Lys Ala Ala Ala Ser Cys Tyr Ile Asp
275 280 285

Leu Ile Ile Lys Glu Ser Asp Asn Asn Val Lys Leu Ile Val Leu Asp
290 295 300

Arg Leu Val Ala Leu Lys Asp Ile Pro Thr Tyr Glu Arg Val Leu Gln
305 310 315 320

Asp Leu Val Met Asp Ile Leu Arg Val Leu Ala Ser Pro Asp Met Glu
325 330 335

Val Arg Lys Lys Ala Leu Asn Leu Ala Leu Asp Leu Thr Thr Ser Arg
340 345 350

Cys Val Glu Glu Val Val Leu Met Leu Lys Lys Glu Val Ala Lys Thr
355 360 365

His Asn Leu Ser Glu His Glu Glu Thr Gly Lys Tyr Arg Gln Leu Leu
370 375 380

Val Arg Thr Leu His Ser Cys Ser Met Lys Phe Pro Asp Val Ala Ala
385 390 395 400

```
Ser Val Ile Pro Val Leu Met Glu Phe Leu Ser Asp Ser Asn Glu Leu
                405                 410                 415

Ala Ser Gln Asp Val Leu Ile Phe Val Arg Glu Ala Ile His Lys Phe
            420                 425                 430

Glu Asn Leu Arg Asn Thr Ile Ile Glu Lys Leu Leu Glu Ala Phe Pro
        435                 440                 445

Ser Ile Lys Phe Val Lys Val His Arg Ala Ala Leu Trp Ile Leu Gly
    450                 455                 460

Glu Tyr Ala Ala Ser Ile Asp Asp Val Arg Ala Val Met Lys Gln Ile
465                 470                 475                 480

Lys Gln Asn Leu Gly Glu Val Pro Met Val Glu Asp Glu Met Lys Arg
                485                 490                 495

Ala Ala Gly Glu Lys Thr Glu Glu Ser Ser Glu Gln Asn Ser Gly Gly
            500                 505                 510

Ala Met Pro Ser Ser Ala Ser Lys Leu Val Thr Ser Asp Gly Thr Tyr
        515                 520                 525

Ala Ser Gln Ser Val Phe Ser Thr Val Ser Thr Ser Lys Lys Glu Asp
    530                 535                 540

Arg Pro Pro Leu Arg Gln Tyr Leu Ile Asp Gly Asp Tyr Phe Ile Gly
545                 550                 555                 560

Ser Thr Ile Ala Ser Thr Leu Val Lys Leu Ser Leu Lys Phe Asp Asn
                565                 570                 575

Leu Glu Ser Asn Thr Ala Ala Gln Asn Glu Phe Cys Asn Glu Cys Met
            580                 585                 590

Leu Ile Ile Ala Cys Thr Leu His Leu Gly Arg Ser Gly Leu Cys Thr
        595                 600                 605

Lys Asn Leu Asn Asn Asp Asp Ala Glu Arg Met Leu Phe Cys Leu Arg
    610                 615                 620

Val Leu Trp Asp Gly Ser Pro Thr Ile Glu Lys Ile Phe Thr Gln Glu
625                 630                 635                 640

Cys Arg Glu Ala Leu Ala Ser Met Leu Thr Ala Gln His His Glu Glu
                645                 650                 655

Ile Ala Leu Asn Lys Ala Lys Glu Lys Thr Ala His Leu Ile His Val
            660                 665                 670

Asp Asp Pro Val Ser Phe Leu Gln Leu Ser Ser Leu Arg Asn Ser Glu
        675                 680                 685

Leu Gly Ser Glu Asn Val Phe Glu Leu Ser Leu Thr Gln Ala Leu Gly
    690                 695                 700

Gly Pro Thr Ser Gly Gly Ser Ser Asn Ser Asp Leu Phe Phe Ser Ala
705                 710                 715                 720

Ser Lys Leu Asn Lys Val Thr Gln Leu Thr Gly Phe Ser Asp Pro Val
                725                 730                 735

Tyr Ala Glu Ala Tyr Val Gln Val Asn Gln Tyr Asp Ile Val Leu Asp
            740                 745                 750

Val Leu Ile Val Asn Gln Thr Ala Asp Thr Leu Gln Asn Cys Thr Leu
        755                 760                 765

Glu Leu Ala Thr Leu Gly Asp Leu Lys Leu Val Glu Lys Pro Gln Pro
    770                 775                 780

Cys Val Leu Ala Pro His Asp Phe Cys Asn Ile Lys Ala Asn Val Lys
785                 790                 795                 800

Val Ala Ser Thr Glu Asn Gly Ile Ile Phe Gly Asn Ile Val Tyr Asp
                805                 810                 815

Val Ser Gly Ala Ala Ser Asp Arg Asn Val Val Val Leu Asn Asp Ile
```

820 825 830

His Ile Asp Ile Met Asp Tyr Ile Val Pro Ala Ser Cys Ser Asp Thr
835 840 845

Glu Phe Arg Gln Met Trp Ala Glu Phe Glu Trp Glu Asn Lys Val Ser
850 855 860

Val Asn Thr Asn Leu Thr Asp Leu His Glu Tyr Leu Ala His Leu Val
865 870 875 880

Arg Ser Thr Asn Met Lys Cys Leu Thr Pro Glu Lys Ala Leu Cys Gly
885 890 895

Gln Cys Gly Phe Met Ala Ala Asn Met Tyr Ala Arg Ser Ile Phe Gly
900 905 910

Glu Asp Ala Leu Ala Asn Leu Ser Ile Glu Lys Pro Phe Asn Lys Pro
915 920 925

Asp Ala Pro Val Thr Gly His Ile Arg Ile Arg Ala Lys Ser Gln Gly
930 935 940

Met Ala Leu Ser Leu Gly Asp Lys Ile Asn Met Thr Gln Lys Arg Pro
945 950 955 960

Gln Lys Met Tyr Gly Ala
965

<210> SEQ ID NO 284
<211> LENGTH: 118
<212> TYPE: PRT
<213> ORGANISM: Lygus hesperus

<400> SEQUENCE: 284

Met Ala Ser Gln Thr Gln Gly Ile Gln Gln Leu Leu Ala Ala Glu Lys
1 5 10 15

Arg Ala Ala Glu Lys Val Ala Glu Ala Lys Lys Arg Lys Ala Arg Arg
20 25 30

Leu Lys Gln Ala Lys Glu Glu Ala Gln Glu Glu Ile Glu Arg Tyr Lys
35 40 45

Gln Asp Arg Glu Lys Gln Phe Lys Glu Phe Glu Ala Gln His Met Gly
50 55 60

Ser Arg Glu Asp Val Ala Ala Arg Ile Asp Ala Asp Thr Arg Gln Arg
65 70 75 80

Ile Glu Glu Met Thr Lys Ala Val Asn Val Asn Lys Glu Gln Val Ile
85 90 95

Gln Arg Ile Leu Glu Leu Val Tyr Asp Ile Arg Pro Glu Met His Lys
100 105 110

Asn Tyr Arg Pro Thr Leu
115

<210> SEQ ID NO 285
<211> LENGTH: 198
<212> TYPE: PRT
<213> ORGANISM: Lygus hesperus

<400> SEQUENCE: 285

Met Ser Ser Leu Lys Leu Gln Lys Arg Leu Ala Ala Ser Val Met Arg
1 5 10 15

Cys Gly Lys Lys Lys Val Trp Leu Asp Pro Asn Glu Ile Asn Glu Ile
20 25 30

Ala Asn Thr Asn Ser Arg Gln Asn Ile Arg Lys Leu Ile Lys Asp Gly
35 40 45

Leu Ile Ile Lys Lys Pro Val Ala Val His Ser Arg Ala Arg Val Arg

```
    50                  55                  60

Lys Asn Thr Glu Ala Arg Arg Lys Gly Arg His Cys Gly Phe Gly Lys
65                  70                  75                  80

Arg Lys Gly Thr Ala Asn Ala Arg Met Pro Val Lys Val Leu Trp Val
                85                  90                  95

Asn Arg Met Arg Val Leu Arg Arg Leu Leu Lys Lys Tyr Arg Glu Ala
            100                 105                 110

Lys Lys Ile Asp Arg Gln Met Tyr His Asp Leu Tyr Met Lys Ala Lys
        115                 120                 125

Gly Asn Val Phe Lys Asn Lys Arg Val Leu Met Asp Phe Ile His Lys
    130                 135                 140

Lys Lys Ala Glu Lys Ala Arg Ser Lys Met Leu Lys Asp Gln Ala Glu
145                 150                 155                 160

Ala Arg Arg Phe Lys Val Lys Glu Ala Lys Lys Arg Arg Glu Glu Arg
                165                 170                 175

Ile Ala Thr Lys Lys Gln Glu Ile Met Gln Ala Tyr Ala Arg Glu Asp
            180                 185                 190

Glu Ala Ala Val Lys Lys
        195


<210> SEQ ID NO 286
<211> LENGTH: 767
<212> TYPE: PRT
<213> ORGANISM: Lygus hesperus

<400> SEQUENCE: 286

Met Thr Thr Tyr Glu Glu Phe Ile Gln Gln Ser Glu Glu Arg Asp Gly
1               5                   10                  15

Ile Arg Phe Thr Trp Asn Val Trp Pro Ser Ser Arg Ile Glu Ala Thr
            20                  25                  30

Arg Leu Val Val Pro Val Gly Cys Leu Tyr Gln Pro Leu Lys Glu Arg
        35                  40                  45

Thr Asp Leu Pro Ala Ile Gln Tyr Asp Pro Val Leu Cys Thr Arg Asn
    50                  55                  60

Thr Cys Arg Ala Ile Leu Asn Pro Met Cys Gln Val Asn Tyr Arg Ala
65                  70                  75                  80

Lys Leu Trp Val Cys Asn Phe Cys Phe Gln Arg Asn Pro Phe Pro Pro
                85                  90                  95

Gln Tyr Ala Ala Ile Ser Glu Gln His Gln Pro Ala Glu Leu Ile Pro
            100                 105                 110

Ser Phe Ser Thr Ile Glu Tyr Thr Ile Ser Arg Ala Gln Phe Leu Pro
        115                 120                 125

Pro Ile Phe Leu Leu Val Val Asp Thr Cys Leu Asp Asp Asp Glu Leu
    130                 135                 140

Gly Ala Leu Lys Asp Ser Leu Gln Thr Ser Leu Ser Leu Leu Pro Thr
145                 150                 155                 160

Asn Ser Leu Val Gly Leu Ile Thr Phe Gly Lys Met Val Gln Val His
                165                 170                 175

Glu Leu Gly Cys Glu Gly Cys Ser Arg Ser Tyr Val Phe Arg Gly Thr
            180                 185                 190

Lys Asp Leu Thr Ser Lys Gln Val Gln Asp Met Leu Gly Ile Gly Lys
        195                 200                 205

Val Ser Ala Ser Pro Gln Gln Gln Gln Gln Arg Ala Met Gly Gly Gln
    210                 215                 220
```

-continued

```
Gln Pro Phe Pro Thr Asn Arg Phe Ile Gln Pro Ile Gln Ser Cys Asp
225                 230                 235                 240

Met Ser Leu Thr Asp Leu Leu Gly Glu Met Gln Arg Asp Pro Trp Pro
                245                 250                 255

Val Gly Gln Gly Lys Arg Pro Leu Arg Ser Thr Gly Ala Ala Leu Ala
            260                 265                 270

Ile Ala Ile Gly Leu Leu Glu Cys Ser Tyr Pro Asn Thr Gly Ala Lys
        275                 280                 285

Val Met Leu Phe Leu Gly Gly Pro Cys Ser Gln Gly Pro Gly Gln Val
    290                 295                 300

Val Asn Asp Asp Leu Arg Glu Pro Ile Arg Ser His His Asp Ile Gln
305                 310                 315                 320

Lys Asp Asn Ala Arg Tyr Met Lys Lys Ala Ile Lys His Tyr Asp Ser
                325                 330                 335

Leu Ala Leu Arg Ala Ala Thr Asn Gly His Ser Val Asp Ile Tyr Ser
            340                 345                 350

Cys Ala Leu Asp Gln Thr Gly Leu Ala Glu Met Lys Gln Cys Cys Asn
        355                 360                 365

Ser Thr Gly Gly His Met Val Met Gly Asp Thr Phe Asn Ser Thr Leu
    370                 375                 380

Phe Lys Gln Thr Phe Gln Arg Val Leu Ser Arg Asp Gln Lys Gly Glu
385                 390                 395                 400

Phe Lys Met Ala Phe Asn Gly Val Val Glu Val Lys Thr Ser Arg Glu
                405                 410                 415

Leu Lys Val Met Gly Ala Ile Gly Pro Cys Val Ser Leu Asn Thr Lys
            420                 425                 430

Gly Pro Cys Val Ser Glu Thr Asp Ile Gly Leu Gly Gly Thr Cys Gln
        435                 440                 445

Trp Lys Phe Cys Thr Phe Asn Gln Asn Thr Thr Ala Ala Met Phe Phe
    450                 455                 460

Glu Val Val Asn Gln His Ala Ala Pro Ile Pro Gln Gly Gly Arg Gly
465                 470                 475                 480

Cys Ile Gln Phe Ile Thr Gln Tyr Gln His Ala Ser Gly Gln Arg Arg
                485                 490                 495

Ile Arg Val Thr Thr Val Ala Arg Asn Trp Ala Asp Ala Thr Thr Asn
            500                 505                 510

Met His His Val Ser Ala Gly Phe Asp Gln Glu Ala Gly Ala Val Leu
        515                 520                 525

Met Ala Arg Met Val Val His Arg Ala Glu Thr Asp Asp Gly Pro Asp
    530                 535                 540

Val Met Arg Trp Ala Asp Arg Met Leu Ile Arg Leu Cys Gln Lys Phe
545                 550                 555                 560

Gly Glu Tyr Asn Lys Asp Asp Pro Asn Ser Phe Arg Leu Pro Glu Asn
                565                 570                 575

Phe Ser Leu Tyr Pro Gln Phe Met Tyr His Leu Arg Arg Ser Gln Phe
            580                 585                 590

Leu Gln Val Phe Asn Asn Ser Pro Asp Glu Thr Ser Tyr Tyr Arg His
        595                 600                 605

Ile Leu Met Arg Glu Asp Leu Ser Gln Ser Leu Ile Met Ile Gln Pro
    610                 615                 620

Ile Leu Tyr Ser Tyr Ser Phe Asn Gly Pro Glu Pro Val Leu Leu Asp
625                 630                 635                 640

Thr Ser Ser Ile Gln Pro Asp Arg Ile Leu Leu Met Asp Thr Phe Phe
```

-continued

```
                645                 650                 655

Gln Ile Leu Ile Phe His Gly Glu Thr Ile Ala Gln Trp Arg Ala Gln
            660                 665                 670

Arg Tyr Gln Asp Leu Pro Glu Tyr Glu Asn Phe Lys Gln Leu Leu Gln
        675                 680                 685

Ala Pro Val Asp Asp Ala Lys Glu Ile Leu His Thr Arg Phe Pro Met
    690                 695                 700

Pro Arg Tyr Ile Asp Thr Glu Gln Gly Gly Ser Gln Ala Arg Phe Leu
705                 710                 715                 720

Leu Ser Lys Val Asn Pro Ser Gln Thr His Asn Asn Met Tyr Gly Tyr
                725                 730                 735

Gly Gly Glu Phe Gly Ala Pro Val Leu Thr Asp Asp Val Ser Leu Gln
            740                 745                 750

Val Phe Met Glu His Leu Lys Lys Leu Ala Val Ser Phe Thr Ala
        755                 760                 765


<210> SEQ ID NO 287
<211> LENGTH: 938
<212> TYPE: PRT
<213> ORGANISM: Lygus hesperus

<400> SEQUENCE: 287

Met Pro Leu Arg Leu Asp Ile Lys Arg Lys Leu Ser Ala Arg Ser Asp
1               5                   10                  15

Arg Val Lys Cys Val Asp Leu His Pro Thr Glu Pro Trp Met Leu Ala
            20                  25                  30

Ser Leu Tyr Asn Gly Asn Val His Ile Trp Asn His Glu Thr Gln Gln
        35                  40                  45

Leu Leu Lys Ser Phe Glu Val Cys Glu Leu Pro Ile Arg Ala Ala Val
    50                  55                  60

Phe Val Pro Arg Lys Asn Trp Val Val Thr Gly Ser Asp Asp Met His
65                  70                  75                  80

Val Arg Val Phe Asn Tyr Asn Thr Leu Glu Arg Val His Ser Phe Glu
                85                  90                  95

Ala His Ser Asp Tyr Leu Arg Cys Ile Ile Val His Pro Thr Gln Pro
            100                 105                 110

Tyr Ile Leu Thr Cys Ser Asp Asp Met Leu Ile Lys Leu Trp Asn Trp
        115                 120                 125

Glu Lys Asn Trp Leu Cys Gln Gln Val Phe Glu Ser His Thr His Tyr
    130                 135                 140

Val Met Gln Ile Val Leu Asn Pro Lys Asp Asn Asn Thr Phe Ala Ser
145                 150                 155                 160

Ala Ser Leu Asp His Thr Leu Lys Val Trp Gln Leu Gly Ser Ala Ala
                165                 170                 175

Ala Asn Phe Thr Leu Asp Gly His Glu Lys Gly Val Asn Cys Val Asp
            180                 185                 190

Tyr Tyr His Gly Gly Asp Lys Pro Tyr Leu Ile Ser Gly Ala Asp Asp
        195                 200                 205

His Met Val Lys Ile Trp Asp Tyr Gln Asn Lys Thr Cys Val Gln Thr
    210                 215                 220

Leu Glu Gly His Ala Gln Asn Ile Thr Ala Val Cys Phe His Thr Glu
225                 230                 235                 240

Leu Pro Ile Ala Ile Thr Gly Ser Glu Asp Gly Thr Val Arg Leu Trp
                245                 250                 255
```

-continued

```
His Ser Ala Thr Tyr Arg Leu Glu Ser Ser Leu Asn Tyr Gly Phe Glu
            260                 265                 270

Arg Val Trp Thr Ile Arg Cys Leu Lys Gly Ser Asn His Ile Ala Leu
        275                 280                 285

Gly Tyr Asp Glu Gly Ser Ile Met Val Lys Val Gly Arg Glu Glu Pro
    290                 295                 300

Ala Ile Ser Met Asp Val Asn Gly Glu Lys Ile Val Trp Ala Arg His
305                 310                 315                 320

Ser Glu Ile Gln Gln Val Asn Leu Lys Ser Leu Met Thr Asp Glu Ser
                325                 330                 335

Glu Ile Arg Asp Gly Glu Lys Leu Pro Val Ala Ala Lys Asp Met Gly
            340                 345                 350

Pro Cys Glu Val Phe Pro Gln Ser Ile Ala His Asn Pro Asn Gly Arg
        355                 360                 365

Phe Val Val Val Cys Gly Asp Gly Glu Tyr Ile Ile Tyr Thr Ala Met
    370                 375                 380

Ala Leu Arg Asn Lys Ser Phe Gly Ser Ala Gln Glu Phe Val Trp Ala
385                 390                 395                 400

Gln Asp Ser Ser Asp Tyr Ala Ile Arg Glu Gly Thr Ser Thr Val Arg
                405                 410                 415

Leu Phe Arg Gln Phe Lys Glu Arg Lys Asn Phe Lys Pro Glu Phe Gly
            420                 425                 430

Ala Glu Gly Ile Phe Gly Gly Gln Leu Leu Gly Val Arg Thr Val Thr
        435                 440                 445

Gly Leu Ser Leu Tyr Asp Trp Glu Thr Leu Glu Leu Ile Arg Ser Ile
    450                 455                 460

Asp Ile Gln Ala Lys Ala Pro Tyr Trp Ser Glu Ala Gly His Leu Leu
465                 470                 475                 480

Ala Ile Val Thr Asp Asp Ser Tyr Tyr Leu Leu Lys Phe Asp Gln Ser
                485                 490                 495

Ala Ile Ser Thr Ser Thr Pro Gly Thr Asp Gly Tyr Glu Asp Ala Phe
            500                 505                 510

Glu Leu Val Gly Glu Val Asn Asp Thr Val Lys Thr Gly Leu Trp Val
        515                 520                 525

Gly Asp Cys Phe Ile Tyr Thr Asn Ala Val Cys Arg Ile Asn Tyr Tyr
    530                 535                 540

Val Gly Gly Glu Ile Val Thr Val Ala His Leu Asp Thr Thr Met Tyr
545                 550                 555                 560

Leu Leu Gly Tyr Val Ala Arg Gln Asn Leu Leu Tyr Leu Cys Asp Lys
                565                 570                 575

His His Asn Ile Ile Cys Tyr Thr Leu Leu Leu Ser Val Leu Glu Tyr
            580                 585                 590

Gln Thr Ala Val Met Arg Arg Asp Phe Glu Thr Ala Asp Arg Val Leu
        595                 600                 605

Pro Thr Ile Pro Val Gln His Arg Ser Arg Val Ala His Phe Leu Glu
    610                 615                 620

Lys Gln Gly Phe Lys Arg Gln Ala Leu Ala Val Ser Thr Asp Ala Glu
625                 630                 635                 640

His Lys Phe Glu Leu Ala Leu Gln Leu Ser Asp Leu Glu Ala Ala Val
                645                 650                 655

Gly Leu Ala Arg Glu Ile Gly Ser Lys Ala Lys Trp Val Gln Val Ala
            660                 665                 670

Glu Leu Ala Met Ser Glu Ala Lys Leu Gly Leu Ala Gln Met Cys Leu
```

```
        675                 680                 685

His Gln Ala Gln His Tyr Gly Gly Leu Leu Leu Leu Ser Thr Ser Ala
    690                 695                 700

Gly Asn Val Asp Met Met Glu Lys Leu Ala Glu Ser Ser Leu Ser Asp
705                 710                 715                 720

Gly Lys Asn Asn Val Ser Phe Leu Thr Tyr Phe Leu Met Gly Asn Val
                725                 730                 735

Glu Lys Cys Leu Gln Ile Leu Ile Asp Thr Gly Arg Ile Pro Glu Ala
            740                 745                 750

Ala Phe Phe Ala Arg Thr Tyr Met Pro Lys Glu Val Ser Arg Val Val
        755                 760                 765

Asp Met Trp Lys Thr Leu Ser Lys Asp Lys Thr Gly Gln Ser Leu Ala
    770                 775                 780

Asp Pro Ala Gln Tyr Pro Asn Leu Phe Pro Lys His Thr Glu Ala Leu
785                 790                 795                 800

Lys Ala Glu Gln Phe Met Lys Lys Glu Leu Thr Gln Arg Ile Pro Ala
                805                 810                 815

Ser Ser His Lys Asp Ile Lys Pro Asn Tyr Glu Arg Asn Ala Ile Glu
            820                 825                 830

Glu Met Lys Glu Ala Glu Ala Asn Gly Leu Phe Thr Tyr Asp Pro Pro
        835                 840                 845

Val Ala Pro Ala Ser Ile Asn Asn Leu Ile Asp Val Ser Glu Pro Ala
    850                 855                 860

Asn Arg Ser Glu Pro Ser Pro Ser Glu Ile Phe Ser Glu Ala Pro Ala
865                 870                 875                 880

Val Ser Lys Met Thr Ser Asp Ala Arg Pro Leu Val Ala Pro Val Pro
                885                 890                 895

Pro Ala Ala Arg Pro Gln Lys Arg Pro Ser Ala Phe Asp Asp Asp Asp
            900                 905                 910

Leu Glu Leu Glu Ile Glu Asn Met Asn Leu Asp Asp Ile Asp Ala Ser
        915                 920                 925

Asp Leu Asn Glu Glu Asp Leu Leu Ile Asp
    930                 935


<210> SEQ ID NO 288
<211> LENGTH: 220
<212> TYPE: PRT
<213> ORGANISM: Lygus hesperus

<400> SEQUENCE: 288

Met Ser Phe Phe Ser Lys Val Phe Gly Gly Lys Lys Asp Asp Lys Gly
1               5                   10                  15

Pro Thr Ala Ser Glu Ala Ile Gln Lys Leu Arg Glu Thr Glu Asp Met
            20                  25                  30

Leu Val Lys Lys Gln Glu Tyr Leu Glu Thr Lys Ile Glu Ala Glu Met
        35                  40                  45

Lys Ile Ile Lys Lys Asn Gly Thr Ala Asn Arg Arg Val Ser Ile Gln
    50                  55                  60

Ala Leu Lys Lys Lys Lys Arg Phe Glu Lys Gln Leu Gln Gln Ile Asp
65                  70                  75                  80

Gly Thr Leu Ser Thr Ile Glu Met Gln Arg Glu Ala Leu Glu Ser Ala
                85                  90                  95

Asn Thr Ser Ser Lys Val Val Gln Thr Met Lys Leu Ala Ala Asp Thr
            100                 105                 110
```

-continued

```
Leu Lys Thr Ala His Gln His Met Asp Val Asp Gln Val His Asp Met
        115                 120                 125

Met Asp Glu Ile Ala Glu Gln His Glu Ala Ala Lys Glu Ile Ser Glu
    130                 135                 140

Ala Ile Ser Asn Pro Val Ala Phe Gly Asn Asp Ile Asp Glu Asp Glu
145                 150                 155                 160

Leu Glu Arg Glu Leu Glu Glu Leu Glu Gln Gln Glu Leu Asp Arg Glu
                165                 170                 175

Leu Leu Gly Thr His Thr Pro Ala Ala Asp His Leu Pro Asp Val Pro
            180                 185                 190

Ala Thr Ile Pro Val Pro His Lys Pro Lys Gln Thr Val Ala Asp Glu
        195                 200                 205

Asp Asp Asp Leu Lys Gln Leu Gln Glu Trp Ala Thr
    210                 215                 220
```